United States Patent
Kim et al.

(10) Patent No.: US 10,361,373 B2
(45) Date of Patent: Jul. 23, 2019

(54) CONDENSED-CYCLIC COMPOUND AND ORGANIC LIGHT EMITTING DEVICE COMPRISING THE SAME

(71) Applicant: SAMSUNG DISPLAY CO., LTD., Yongin-si, Gyeonggi-do (KR)

(72) Inventors: Kwanghyun Kim, Yongin-si (KR); Jongwoo Kim, Yongin-si (KR); Jeonga Oh, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 177 days.

(21) Appl. No.: 15/061,710

(22) Filed: Mar. 4, 2016

(65) Prior Publication Data

US 2017/0062720 A1    Mar. 2, 2017

(30) Foreign Application Priority Data

Aug. 28, 2015 (KR) .................. 10-2015-0121827

(51) Int. Cl.
     *H01L 51/50*      (2006.01)
     *H01L 51/00*      (2006.01)
     (Continued)

(52) U.S. Cl.
     CPC .......... *H01L 51/006* (2013.01); *C07D 319/24* (2013.01); *C07D 405/12* (2013.01);
     (Continued)

(58) Field of Classification Search
None
See application file for complete search history.

(56) References Cited

U.S. PATENT DOCUMENTS

| | | |
|---|---|---|
| 2007/0129555 A1 | 6/2007 | Kai et al. |
| 2009/0153031 A1 | 6/2009 | Kai et al. |
| | (Continued) | |

FOREIGN PATENT DOCUMENTS

| | | |
|---|---|---|
| CN | 103483312 A | 1/2014 |
| CN | 104844587 A | 8/2015 |
| | (Continued) | |

OTHER PUBLICATIONS

Partial English translation of relevant parts of JP 2014-231505 A, dated Dec. 11, 2014, 15 pages, listed above.
(Continued)

*Primary Examiner* — Gregory D Clark
(74) *Attorney, Agent, or Firm* — Lewis Roca Rothgerber Chrisitie LLP

(57) ABSTRACT

The present disclosure provides a condensed-cyclic compound represented by Formula 1, in which one selected from $R_1$ to $R_8$ is a monoamine represented by Formula 2:

Formula 1

Formula 2

(Continued)

The condensed-cyclic compound represented by Formula 1 may act as a hole transport material having a suitable energy level and band-gap. Further, the condensed-cyclic compound represented by Formula 1 has a fused core, and accordingly may have a high glass transition temperature (Tg), high melting point, and improved resistance to high temperatures. Therefore an organic light-emitting device including the condensed-cyclic compound represented by Formula 1 may retain high durability during storing and/or driving.

15 Claims, 1 Drawing Sheet

(51) Int. Cl.
    *C07D 405/14*     (2006.01)
    *C07D 319/24*     (2006.01)
    *C07D 405/12*     (2006.01)
    *C07D 407/12*     (2006.01)
    *C07D 407/14*     (2006.01)
    *C07D 409/12*     (2006.01)

(52) U.S. Cl.
    CPC .......... *C07D 405/14* (2013.01); *C07D 407/12* (2013.01); *C07D 407/14* (2013.01); *C07D 409/12* (2013.01); *H01L 51/0052* (2013.01); *H01L 51/0061* (2013.01); *H01L 51/0072* (2013.01); *H01L 51/0073* (2013.01); *H01L 51/0074* (2013.01); *H01L 51/0058* (2013.01); *H01L 51/5056* (2013.01)

(56) References Cited

U.S. PATENT DOCUMENTS

| | | | |
|---|---|---|---|
| 2011/0240979 A1* | 10/2011 | Kim | C07D 487/04 257/40 |
| 2014/0239279 A1 | 8/2014 | Park et al. | |
| 2015/0137111 A1 | 5/2015 | Ryu et al. | |
| 2015/0162542 A1 | 6/2015 | Ryu et al. | |
| 2015/0179953 A1 | 6/2015 | Mujica-Fernaud et al. | |
| 2016/0322584 A1 | 11/2016 | Li et al. | |

FOREIGN PATENT DOCUMENTS

| | | | |
|---|---|---|---|
| JP | 2011-178742 A | 9/2011 | |
| JP | 2014-231505 A | 12/2014 | |
| JP | 2015-109370 A | 6/2015 | |
| KR | 10-2006-0127181 | 12/2006 | |
| KR | 10-2008-0037699 A | 4/2008 | |
| KR | 10-2011-0119206 | 11/2011 | |
| KR | 10-2012-0042633 | 5/2012 | |
| KR | 10-2014-0025120 | 3/2014 | |
| KR | 10-2014-0042554 | 4/2014 | |
| KR | 10-2014-0068772 | 6/2014 | |
| KR | 10-2014-0108117 A | 9/2014 | |
| KR | 10-2014-0134884 A | 11/2014 | |
| KR | 10-2014-0145428 A | 12/2014 | |
| KR | 10-2015-0036721 A | 4/2015 | |
| KR | 10-2015-0077263 | 7/2015 | |
| KR | 2015-0102735 | * 7/2015 | ............ C09K 11/06 |
| KR | 10-2015-0102734 | 9/2015 | |
| WO | WO 2011/136482 A1 | 11/2011 | |
| WO | WO 2012/026780 A1 | 3/2012 | |
| WO | WO 2012/157474 A1 | 11/2012 | |
| WO | WO 2014/200260 A1 | 12/2014 | |

OTHER PUBLICATIONS

Partial English translation of relevant parts of KR 10-2015-0077263, dated Jul. 7, 2015, 12 pages, listed above.
EPO Partial Search Report dated Jan. 19, 2017, for corresponding European Patent Application No. 16179781.6 (7 pages).
Abstract for Japanese Patent Publication No. 2014-141416, dated Aug. 7, 2014 Corresponding to PCT Publication No. 2012/157474 A1, dated Nov. 22, 2012, 1 Page.
KIPO Office Action dated Feb. 13, 2017, for corresponding Korean Patent Application No. 10-2015-0121827 (15 pages).

* cited by examiner

10

| 190 |
| --- |
| 150 |
| 110 |

CONDENSED-CYCLIC COMPOUND AND ORGANIC LIGHT EMITTING DEVICE COMPRISING THE SAME

CROSS-REFERENCE TO RELATED APPLICATION

This application claims priority to and the benefit of Korean Patent Application No. 10-2015-0121827, filed on Aug. 28, 2015, in the Korean Intellectual Property Office, the entire content of which is incorporated herein by reference.

BACKGROUND

1. Field

One or more aspects of example embodiments are related to a condensed-cyclic compound and an organic light-emitting device including the same.

2. Description of the Related Art

Organic light-emitting devices (OLEDs) are self-emission devices that have wide viewing angles, high contrast ratios, and short response times. In addition, OLEDs exhibit high luminances, low driving voltages, and fast response speed characteristics, and produce full-color images.

An OLED may include a first electrode on a substrate, and a hole transport region, an emission layer, an electron transport region, and a second electrode sequentially positioned on the first electrode. Holes provided from the first electrode may move toward the emission layer through the hole transport region, and electrons provided from the second electrode may move toward the emission layer through the electron transport region. The holes and the electrons may recombine in the emission layer to produce excitons. These excitons change (e.g., decay or transition) from an excited state to a ground state to thereby generate light.

The above information disclosed in this Background section is included only to enhance understanding of the background of the present disclosure, and may therefore contain information that does not form the prior art that is already known in this country to a person of ordinary skill in the art.

SUMMARY

One or more aspects of example embodiments are directed toward a condensed-cyclic compound and an organic light-emitting device including the same.

Additional aspects will be set forth in part in the description which follows and, in part, will be apparent from the description, or may be learned by practice of the presented embodiments.

One or more aspects of example embodiments provide a condensed-cyclic compound represented by Formula 1:

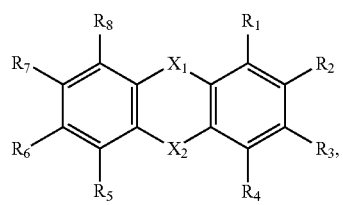

Formula 1

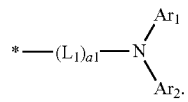

Formula 2

In Formulae 1 and 2, $X_1$ and $X_2$ may each independently be selected from O and S, $L_1$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 may be an integer selected from 0 to 3, and when a1 is 2 or more, each $L_1$ moiety may be independently selected from the above groups, $Ar_1$ and $Ar_2$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_1$ to $R_8$ may each independently be selected from a group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), one selected from $R_1$ to $R_8$ is a group represented by Formula 2, and at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si$(Q_{11})(Q_{12})(Q_{13})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si$(Q_{21})(Q_{22})(Q_{23})$; and —Si$(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, $C_1$-$C_{60}$ heteroaryl group, a monovalent non-aromatic condensed polycyclic group, and a monovalent non-aromatic condensed heteropolycyclic group.

According to one or more example embodiments of the present disclosure, an organic light-emitting device includes: a first electrode; a second electrode facing the first electrode; and an organic layer between the first electrode and the second electrode, wherein the organic layer includes an emission layer and at least one of the condensed-cyclic compounds described above.

BRIEF DESCRIPTION OF THE DRAWING

These and/or other aspects will become apparent and more readily appreciated from the following description of the example embodiments, taken in conjunction with the accompanying drawing, which illustrates a schematic cross-sectional view of an organic light-emitting device, according to one or more embodiments of the present disclosure.

DETAILED DESCRIPTION

Reference will now be made in more detail to example embodiments, examples of which are illustrated in the accompanying drawing, wherein like reference numerals refer to like elements throughout. In this regard, the present example embodiments may have different forms and should not be construed as being limited to the descriptions set forth herein. Accordingly, the example embodiments are merely described below, by referring to the drawing, to explain aspects of the present description. As used herein, the term "and/or" includes any and all combinations of one or more of the associated listed items. Expressions such as "at least one of", "one of", "at least one selected from", and "one selected from" when preceding a list of elements, modify the entire list of elements and do not modify the individual elements of the list.

In the drawing, the thickness of layers, films, panels, regions, etc., may be exaggerated for clarity. Like reference numerals designate like elements throughout the specification. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

A condensed-cyclic compound may be represented by Formula 1:

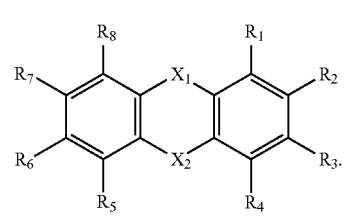

Formula 1

In Formula 1, $X_1$ and $X_2$ may each independently be selected from O and S. In some embodiments, $X_1$ and $X_2$ may each be O, but embodiments of the present disclosure are not limited thereto.

In Formula 1, $R_1$ to $R_8$ may each independently be selected from a group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

In Formula 1, one selected from $R_1$ to $R_8$ may be a group represented by Formula 2:

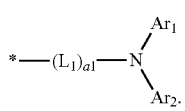

Formula 2

In Formula 2, $L_1$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, in Formula 2, $L_1$ may be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

According to an embodiment, in Formula 2, $L_1$ may be selected from the group represented by Formulae 3-1 to 3-41:

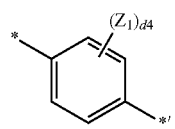

Formula 3-1

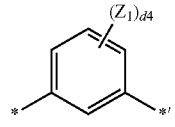

Formula 3-2

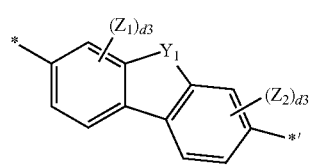

Formula 3-3

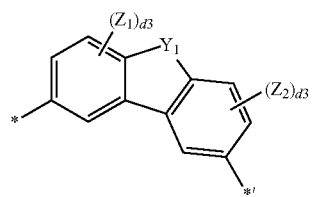

Formula 3-4

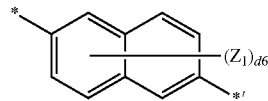

Formula 3-5

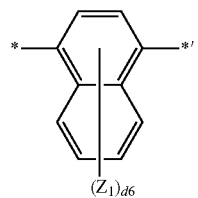

Formula 3-6

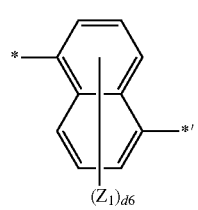

Formula 3-7

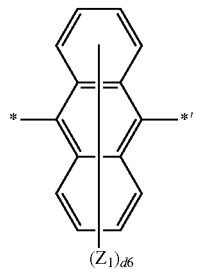

Formula 3-8

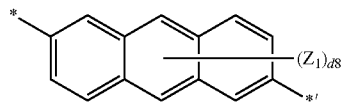

Formula 3-9

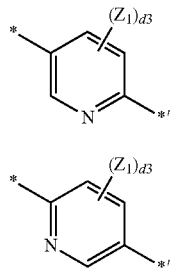

Formula 3-10

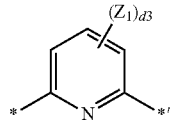

Formula 3-11

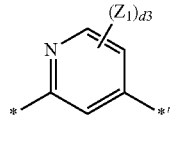

Formula 3-12

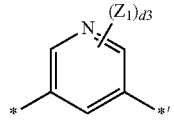

Formula 3-13

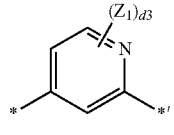

Formula 3-14

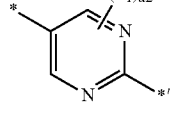

Formula 3-15

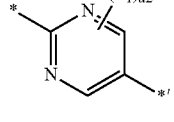

Formula 3-16

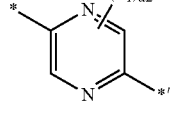

Formula 3-17

Formula 3-18

-continued
Formula 3-19
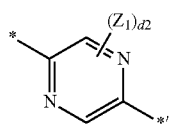
Formula 3-20
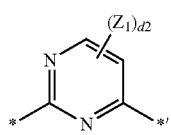
Formula 3-21
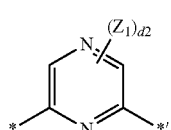
Formula 3-22
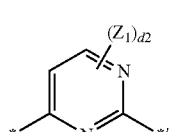
Formula 3-23
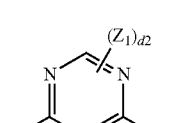
Formula 3-24
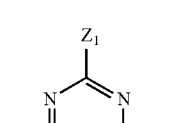
Formula 3-25
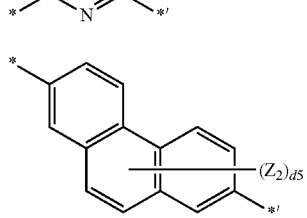
Formula 3-26
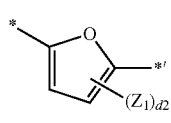
Formula 3-27
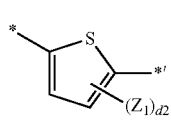
Formula 3-28
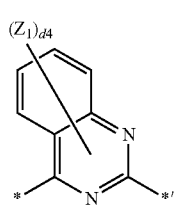
-continued
Formula 3-29
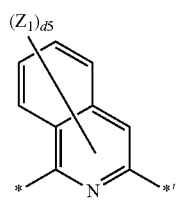
Formula 3-30
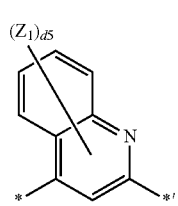
Formula 3-31
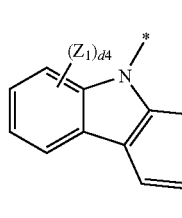
Formula 3-32
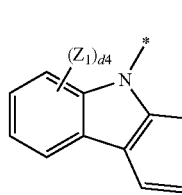
Formula 3-33
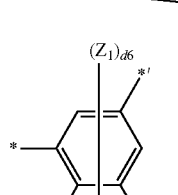
Formula 3-34
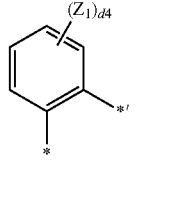
Formula 3-35
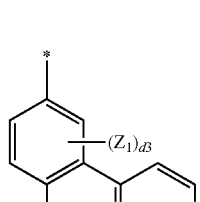

-continued

Formula 3-36
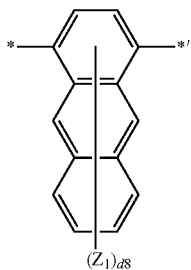

Formula 3-37
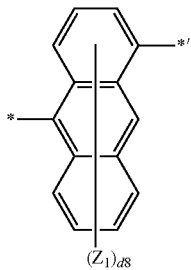

Formula 3-38
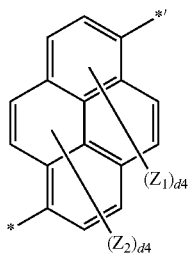

Formula 3-39
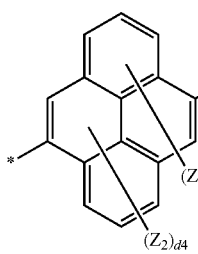

Formula 3-40
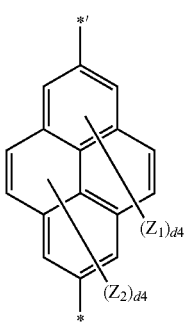

Formula 3-41
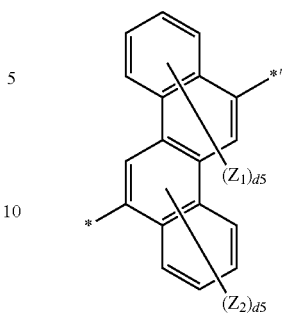

In Formulae 3-1 to 3-41, $Y_1$ may be selected from O, S, $C(Z_3)(Z_4)$, $N(Z_5)$, and $Si(Z_6)(Z_7)$, and $Z_1$ to $Z_7$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{33})(Q_{34})(Q_{35})$, wherein $Q_{33}$ to $Q_{35}$ may each independently be selected from a $C_1$-$C_{10}$ alkyl group, a $C_1$-$C_{10}$ alkoxy group, a phenyl group, a biphenyl group, a terphenyl group, and a naphthyl group, d2 may be an integer selected from 1 and 2, d3 may be an integer selected from 1 to 3, d4 may be an integer selected from 1 to 4, d5 may be an integer selected from 1 to 5, d6 may be an integer selected from 1 to 6, d8 may be an integer selected from 1 to 8, and

* and *' each indicate a binding site to an adjacent atom.

In some embodiments, in Formula 2, $L_1$ may be selected from:

a phenylene group, a naphthylene group, a fluorenylene group, a benzofuranylene group, a pyridinylene group, a pyrimidinylene group, and a triazinylene group; and a phenylene group, a naphthylene group, a fluorenylene group, a benzofuranylene group, a pyridinylene group, a pyrimidinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

In Formula 2, a1 may be an integer selected from 0 to 3. a1 in Formula 2 indicates the number of $L_1$ moieties. When a1 is 2 or more, each $L_1$ moiety may be independently selected from the above groups. In some embodiments, when a1 is 0, *-$(L_1)_{a1}$-*' may be a single bond. In some embodiments, a1 may be selected from 0, 1, and 2, but embodiments of the present disclosure are not limited thereto.

According to an embodiment, in Formula 2, *-$(L_1)_{a1}$-*' may be selected from a single bond and the group represented by Formulae 4-1 to Formula 4-36, but embodiments of the present disclosure are not limited thereto:

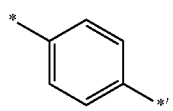
Formula 4-1

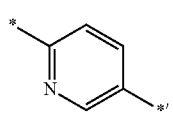
Formula 4-2

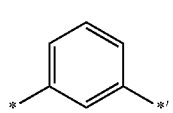
Formula 4-3

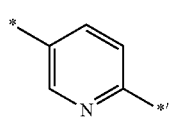
Formula 4-4

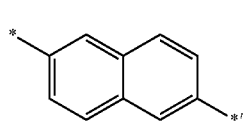
Formula 4-5

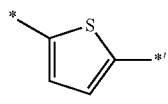
Formula 4-6

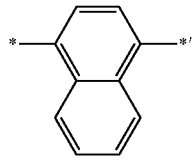
Formula 4-7

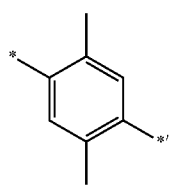
Formula 4-8

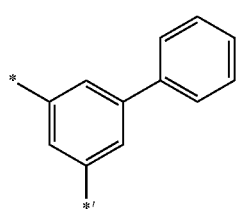
Formula 4-9

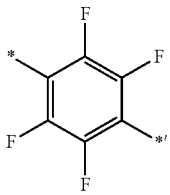
Formula 4-10

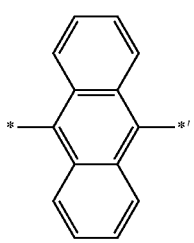
Formula 4-11

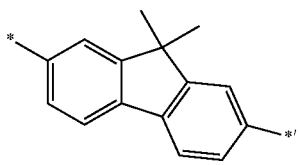
Formula 4-12

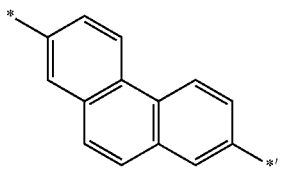
Formula 13

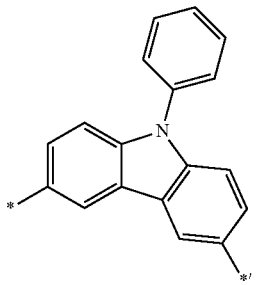
Formula 14

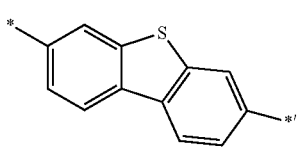
Formula 15

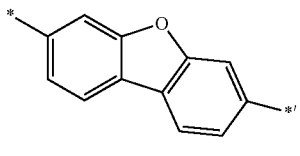
Formula 4-16

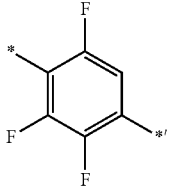
Formula 4-17

-continued
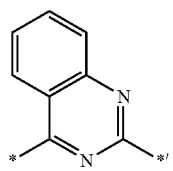
Formula 4-18
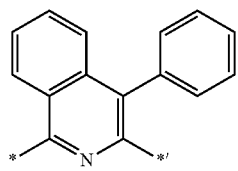
Formula 4-19
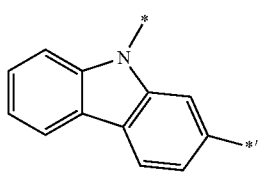
Formula 4-20
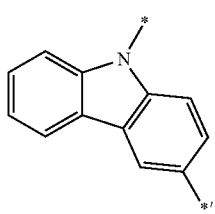
Formula 4-21
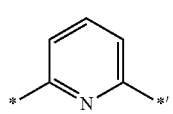
Formula 4-22
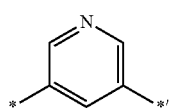
Formula 4-23
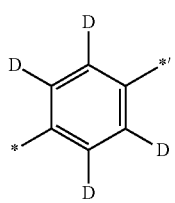
Formula 4-24
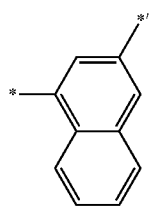
Formula 4-25
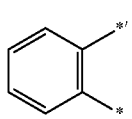
Formula 4-26
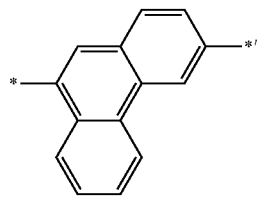
Formula 4-27
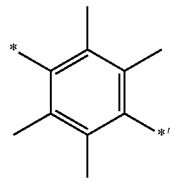
Formula 4-28
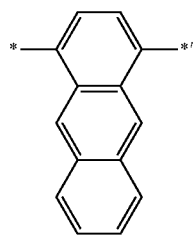
Formula 4-29
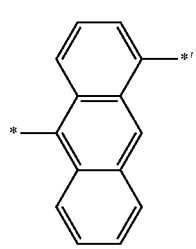
Formula 4-30
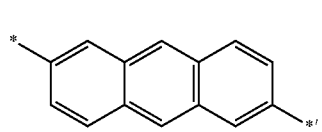
Formula 4-31
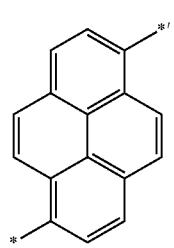
Formula 4-32
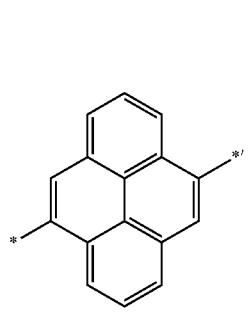
Formula 4-33

-continued

Formula 4-34

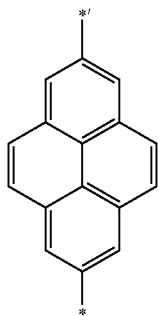

Formula 4-35

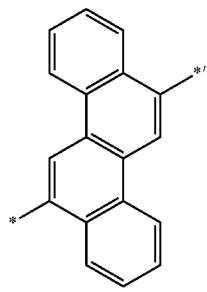

Formula 4-36

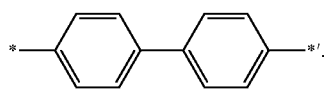

In Formulae 4-1 to 4-36, * and *' each indicate a binding site to an adjacent atom.

In Formula 2, $Ar_1$ and $Ar_2$ may each independently be selected from a substituted or unsubstituted $C_3$-$C_{10}$ cycloalkyl group, a substituted or unsubstituted $C_1$-$C_{10}$heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 2, $Ar_1$ and $Ar_2$ may each independently be selected from:

a substituted or unsubstituted phenyl group, a substituted or unsubstituted biphenyl group, a substituted or unsubstituted terphenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted benzofluorenyl group, a substituted or unsubstituted dibenzofluorenyl group, a substituted or unsubstituted phenalenyl group, a substituted or unsubstituted phenanthrenyl group, a substituted or unsubstituted anthracenyl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pentacenyl group, a substituted or unsubstituted rubicenyl group, a substituted or unsubstituted coronenyl group, a substituted or unsubstituted ovalenyl group, a substituted or unsubstituted pyrrolyl group, a substituted or unsubstituted thiophenyl group, a substituted or unsubstituted furanyl group, a substituted or unsubstituted imidazolyl group, a substituted or unsubstituted pyrazolyl group, a substituted or unsubstituted thiazolyl group, a substituted or unsubstituted isothiazolyl group, a substituted or unsubstituted oxazolyl group, a substituted or unsubstituted isoxazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzimidazolyl group, a substituted or unsubstituted benzofuranyl group, a substituted or unsubstituted benzothiophenyl group, a substituted or unsubstituted isobenzothiazolyl group, a substituted or unsubstituted benzoxazolyl group, a substituted or unsubstituted isobenzoxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzocarbazolyl group, a substituted or unsubstituted dibenzocarbazolyl group, a substituted or unsubstituted thiadiazolyl group, a substituted or unsubstituted imidazopyridinyl group, a substituted or unsubstituted imidazopyrimidinyl group, a substituted or unsubstituted benzoxanthenyl group, a substituted or unsubstituted dibenzodioxinyl group, and —Si($Q_1$)($Q_2$)($Q_3$), and at least one substituent of the substituted phenyl group, substituted biphenyl group, substituted terphenyl group, substituted pentalenyl group, substituted indenyl group, substituted naphthyl group, substituted azulenyl group, substituted heptalenyl group, substituted indacenyl group, substituted acenaphthyl group, substituted fluorenyl group, substituted spiro-fluorenyl group, substituted benzofluorenyl group, substituted dibenzofluorenyl group, substituted phenalenyl group, substituted phenanthrenyl group, substituted anthracenyl group, substituted fluoranthenyl group, substituted triphenylenyl group, substituted pyrenyl group, substituted chrysenyl group, substituted naphthacenyl group, substituted picenyl group, substituted perylenyl group, substituted pentaphenyl group, substituted hexacenyl group, substituted pentacenyl group, substituted rubicenyl group, substituted coronenyl group, substituted ovalenyl group, substituted pyrrolyl group, substituted thiophenyl group, substituted furanyl group, substituted imidazolyl group, substituted pyrazolyl group, substituted thiazolyl group, substituted isothiazolyl group, substituted oxazolyl group, substituted isoxazolyl group, substituted pyridinyl group, substituted pyrazinyl group, substituted pyrimidinyl group, substituted pyridazinyl group, substituted isoindolyl group, substituted indolyl group, substituted indazolyl group, substituted purinyl group, substituted quinolinyl group, substituted isoquinolinyl group, substituted benzoquinolinyl group, substituted phthalazinyl group, substituted naphthyridinyl group, substituted quinoxalinyl group, substituted quinazolinyl group, substituted cinnolinyl group, substituted carbazolyl group, substituted phenanthridinyl group, substituted acridinyl group, substituted phenanthrolinyl group, substituted phenazinyl group, substituted benzimidazolyl group, substituted benzofuranyl group, substituted benzothiophenyl group, substituted isobenzothiazolyl group, substituted benzoxazolyl group, substituted isobenzoxazolyl group, substituted triazolyl group, substituted tetrazolyl group, substituted oxadiazolyl group, substituted triazinyl group, substituted benzocarbazolyl group, substituted dibenzocarbazolyl group, substituted thiadiazolyl group, substituted imidazopyridinyl group, substituted imidazopyrimidinyl group, substituted benzoxanthenyl group, and substituted dibenzodioxinyl group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —Si($Q_{31}$)($Q_{32}$)($Q_{33}$), wherein $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group.

In some embodiments, in Formula 2, $Ar_1$ and $Ar_2$ may each independently be selected from the group represented by Formulae 5-1 to 5-79:

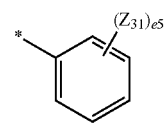

Formula 5-1

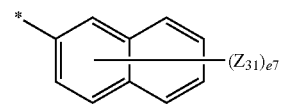

Formula 5-2

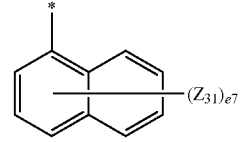

Formula 5-3

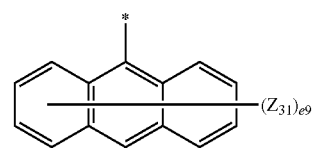

Formula 5-4

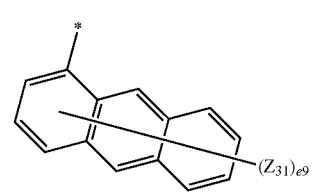

Formula 5-5

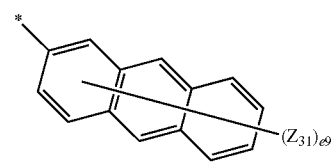

Formula 5-6

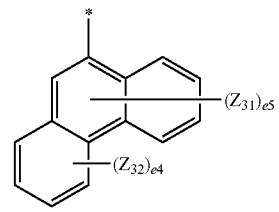

Formula 5-7

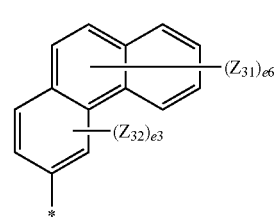

Formula 5-8

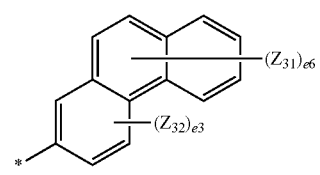

Formula 5-9

-continued

Formula 5-10

Formula 5-11

Formula 5-12

Formula 5-19

Formula 5-20

Formula 5-21

Formula 5-22

Formula 5-23

Formula 5-24

Formula 5-25

Formula 5-26

Formula 5-27

Formula 5-28

Formula 5-29

Formula 5-30

Formula 5-31

Formula 5-32

Formula 5-33

-continued
Formula 5-34
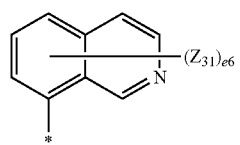
Formula 5-35
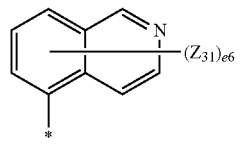
Formula 5-36
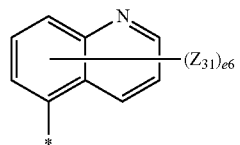
Formula 5-37
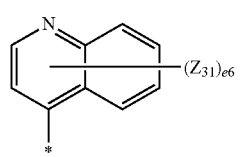
Formula 5-38
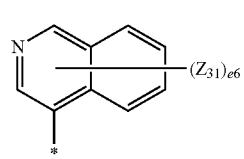
Formula 5-39
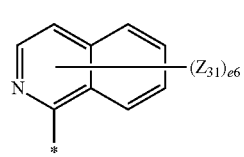
Formula 5-40
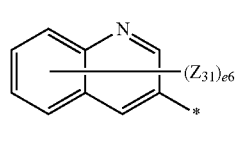
Formula 5-41
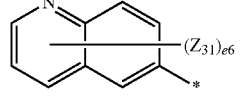
Formula 5-42
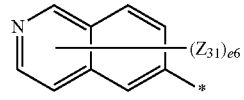
Formula 5-43
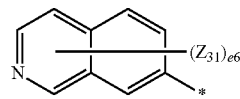
Formula 5-44
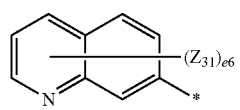
Formula 5-45
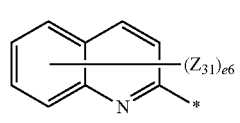
-continued
Formula 5-46
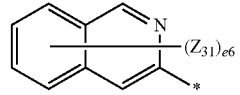
Formula 5-47
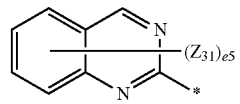
Formula 5-48
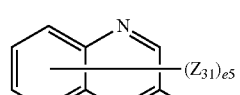
Formula 5-49
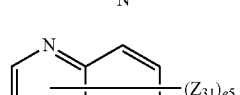
Formula 5-50
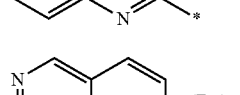
Formula 5-51
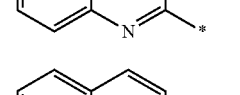
Formula 5-52
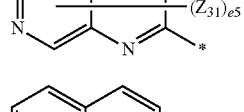
Formula 5-53
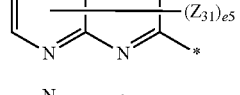
Formula 5-54
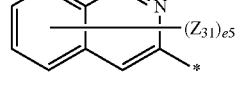
Formula 5-55
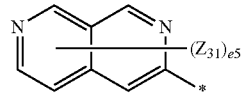
Formula 5-56
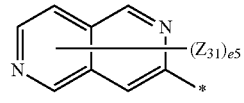
Formula 5-57
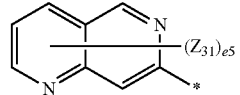
Formula 5-58
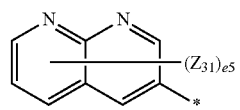
Formula 5-59
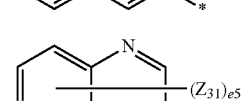

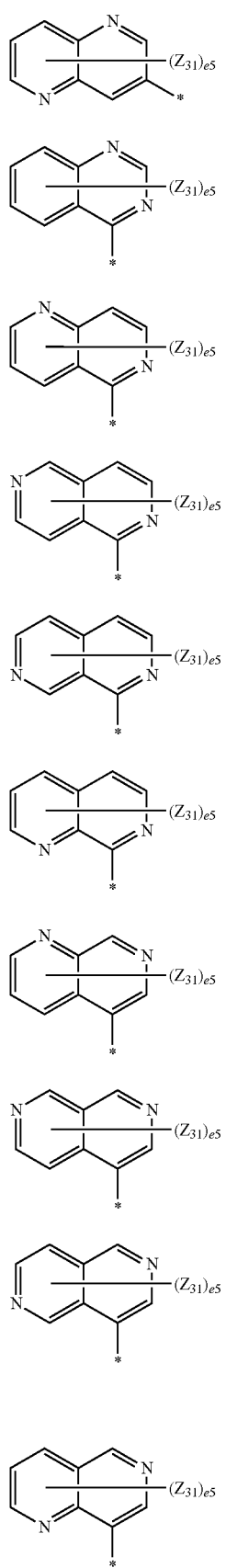
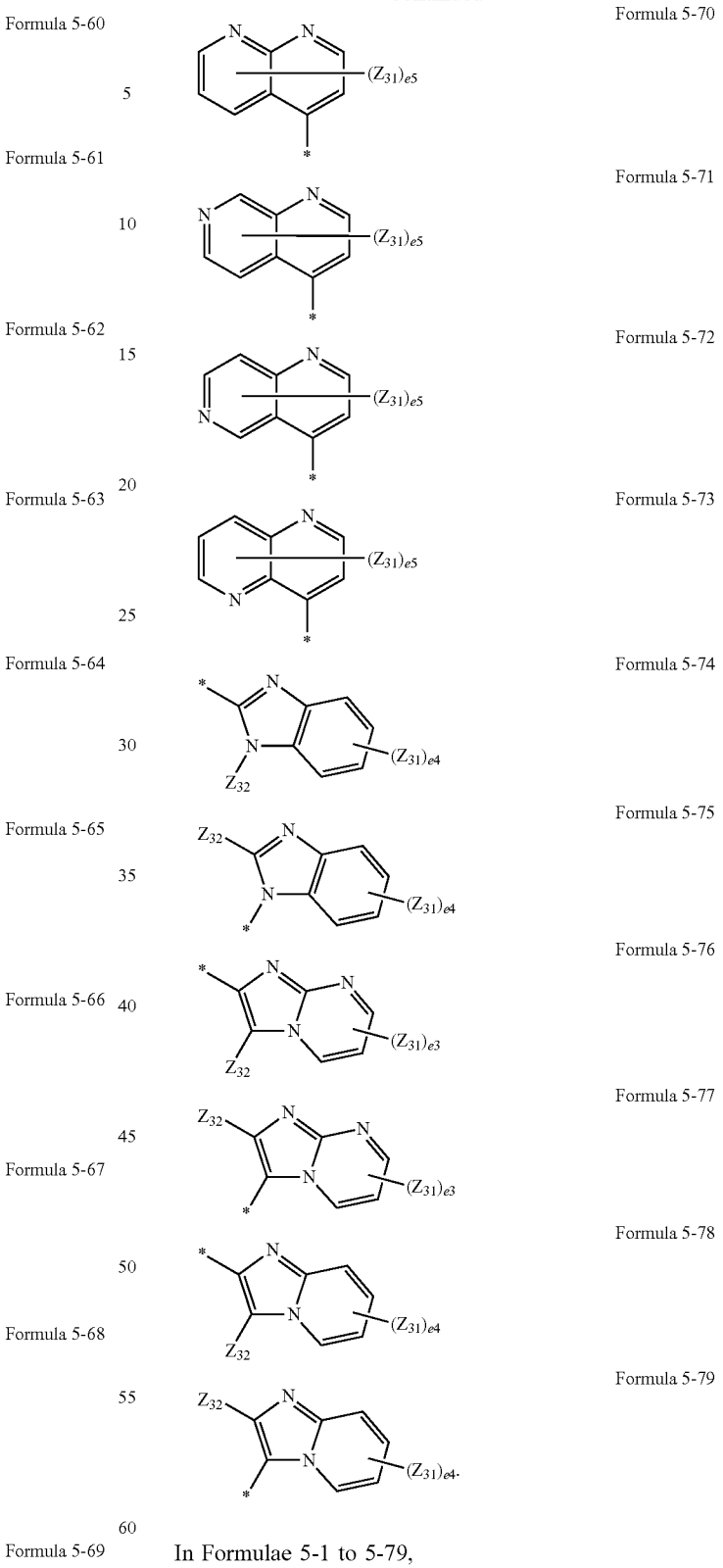
In Formulae 5-1 to 5-79,
Y$_{31}$ and Y$_{32}$ may each independently be selected from O, S, C(Z$_{33}$)(Z$_{34}$), N(Z$_{35}$), and Si(Z$_{36}$)(Z$_{37}$),
Z$_{31}$ to Z$_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a biphenyl group, a terphenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and a pyridinyl group; and —Si($Q_{31}$)($Q_{32}$)($Q_{33}$), and $Z_{33}$ and $Z_{34}$ may be optionally linked (e.g., coupled) to each other to form a saturated or unsaturated ring, wherein $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group, e2 may be an integer selected from 1 and 2,
e3 may be an integer selected from 1 to 3,
e4 may be an integer selected from 1 to 4,
e5 may be an integer selected from 1 to 5,
e6 may be an integer selected from 1 to 6,
e7 may be an integer selected from 1 to 7,
e8 may be an integer selected from 1 to 8,
e9 may be an integer selected from 1 to 9, and
* indicates a binding site to an adjacent atom.

In some embodiments, in Formula 2, $Ar_1$ and $Ar_2$ may each independently be selected from the group represented by Formulae 6-1 to 6-54:

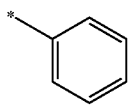

Formula 6-1

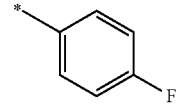

Formula 6-2

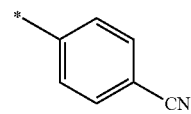

Formula 6-3

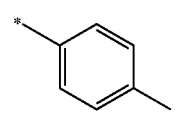

Formula 6-4

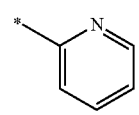

Formula 6-5

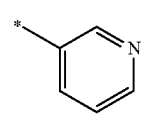

Formula 6-6

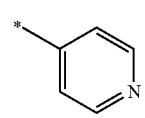

Formula 6-7

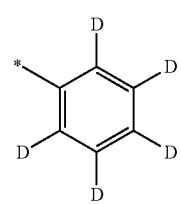

Formula 6-8

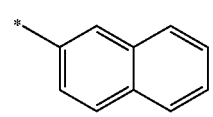

Formula 6-9

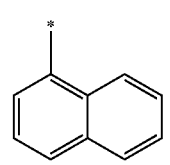

Formula 6-10

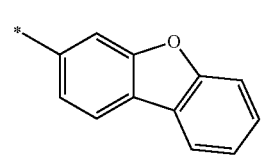

Formula 6-11

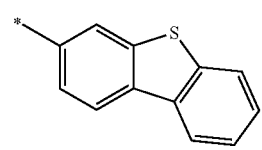

Formula 6-12

-continued
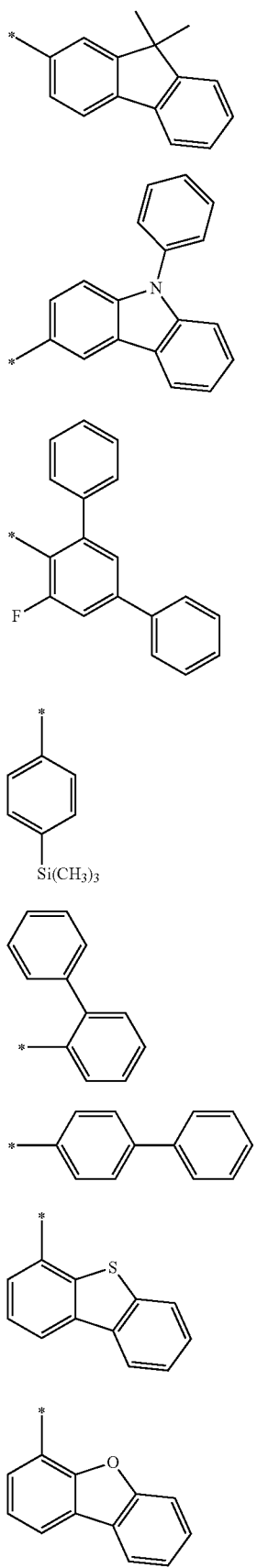
Formula 6-13
Formula 6-14
Formula 6-15
Formula 6-16
Formula 6-17
Formula 6-18
Formula 6-19
Formula 6-20
-continued
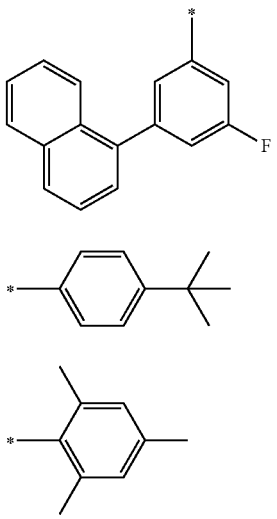
Formula 6-21
Formula 6-22
Formula 6-23
Formula 6-24
Formula 6-25
Formula 6-26
Formula 6-27
Formula 6-28
Formula 6-29

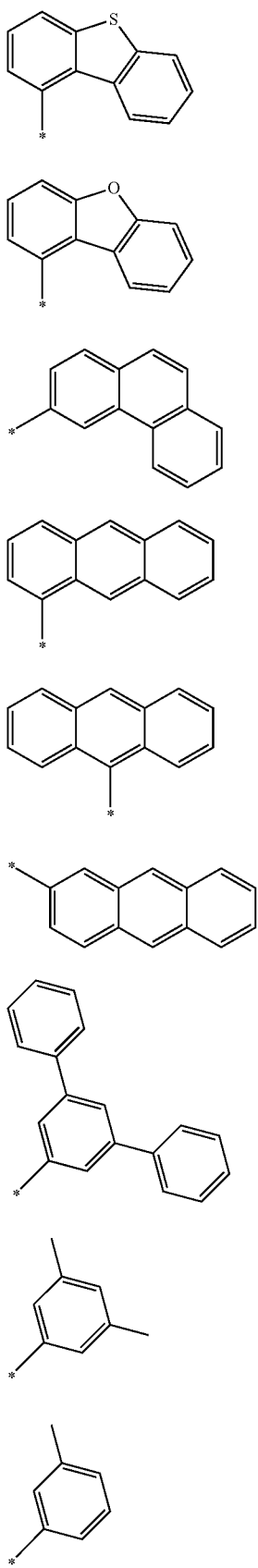
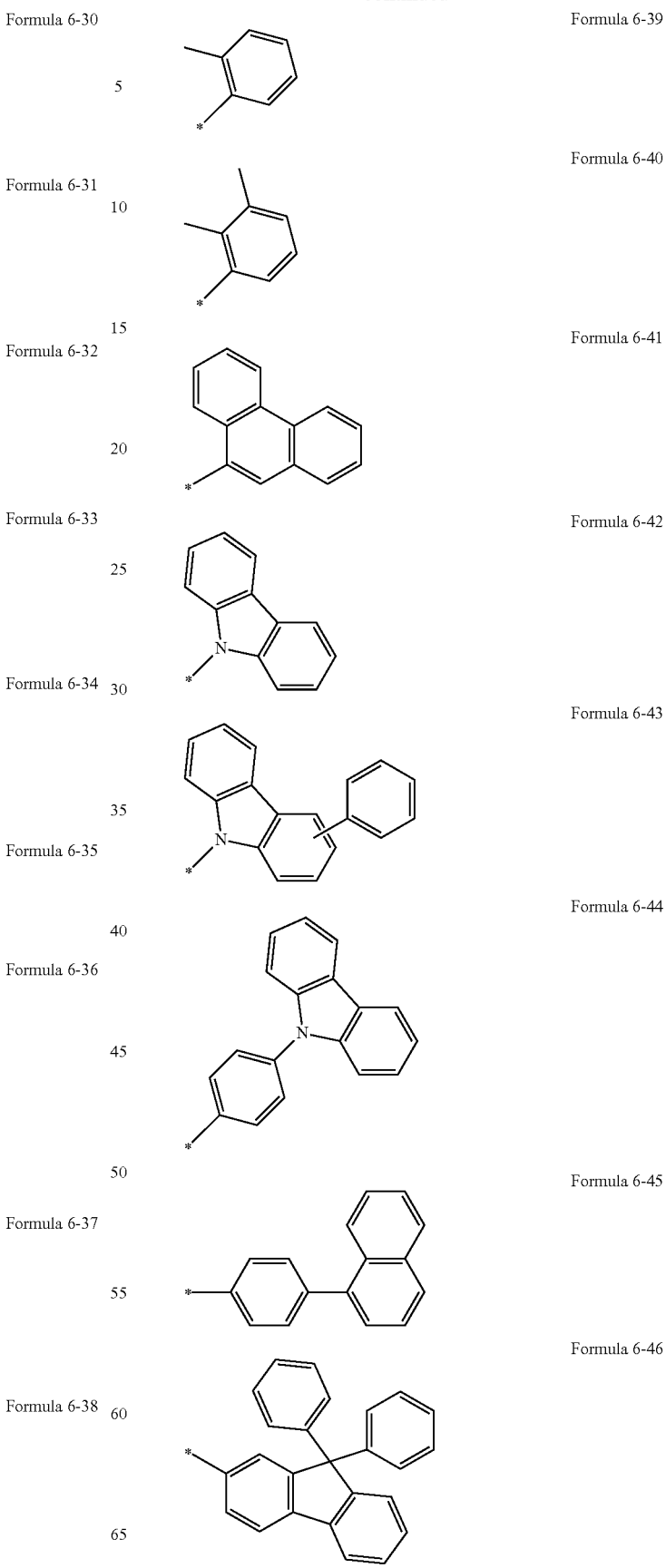

-continued

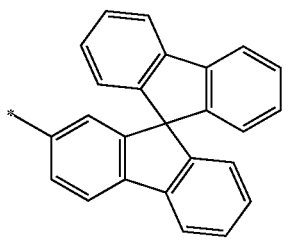
Formula 6-47

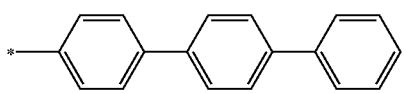
Formula 6-48

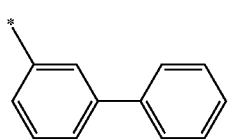
Formula 6-49

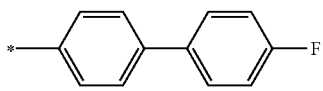
Formula 6-50

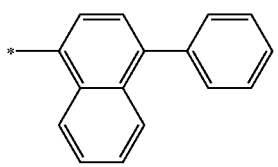
Formula 6-51

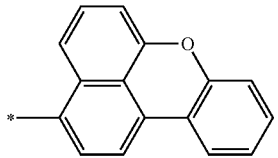
Formula 6-52

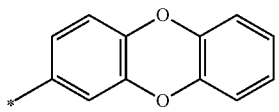
Formula 6-53

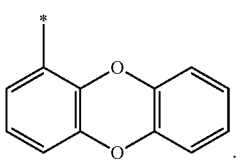
Formula 6-54

In Formulae 6-1 to 6-54, * indicates a binding site to an adjacent atom.

In Formula 1, $R_1$ to $R_8$ may each independently be selected from:

a group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In some embodiments, in Formula 1, $R_1$ to $R_8$ may each independently be selected from:

a group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a biphenyl group, a terphenyl group, a naphthyl group, a pyridinyl group, a pyrimidinyl group, and a triazinyl group;

a phenyl group, a biphenyl group, a terphenyl group, a naphthyl group, a pyridinyl group, a pyrimidinyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formula 1, one selected from $R_1$ to $R_8$ may be a group represented by Formula 2. In some embodiments, in Formula 1, one selected from $R_3$ and $R_4$ may be a group represented by Formula 2.

In some embodiments, the condensed-cyclic compound represented by Formula 1 may be further represented by one of Formulae 1A and 1B:

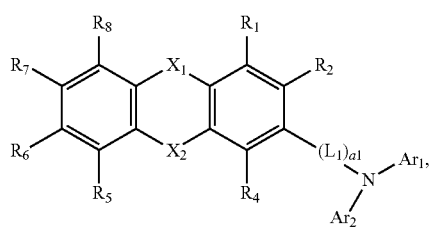

Formula 1A

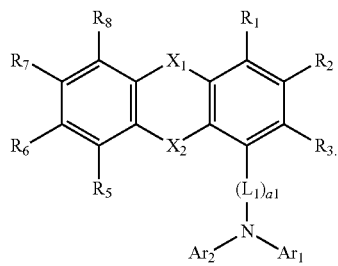

Formula 1B

In Formulae 1A and 1B, $X_1$, $X_2$, $L_1$, a1, $Ar_1$, $Ar_2$, and $R_1$ to $R_8$ may each be the same as described earlier herein.

In some embodiments, in Formulae 1A and 1B, $X_1$ and $X_2$ may each independently be selected from O and S, $L_1$ may be selected from the group represented by Formulae 3-1 to 3-41, a1 may be selected from 0, 1, and 2, $Ar_1$ and $Ar_2$ may each independently be selected from the group represented by Formulae 5-1 to 5-79, and $R_1$ to $R_8$ may each independently be selected from:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a biphenyl group, a terphenyl group, a naphthyl group, a pyridinyl group, a pyrimidinyl group, and a triazinyl group;

a phenyl group, a biphenyl group, a terphenyl group, a naphthyl group, a pyridinyl group, a pyrimidinyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In some embodiments, in Formulae 1A and 1B, $X_1$ and $X_2$ may be O, $R_1$ to $R_8$ may be hydrogen,

*-($L_1$)$_{a1}$-*' may be selected from a single bond and the group represented by Formulae 4-1 to 4-36, and $Ar_1$ and $Ar_2$ may each independently be selected from the group represented by Formulae 6-1 to 6-54.

In some embodiments, the condensed-cyclic compound represented by Formula 1 may be represented by one of Compounds 1 to 117, but embodiments of the present disclosure are not limited thereto:

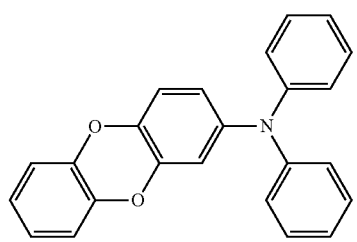

1

2

3
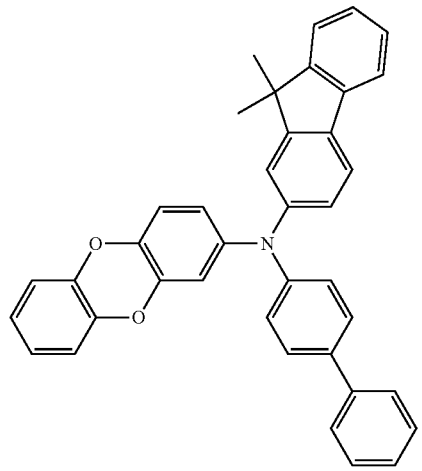
4
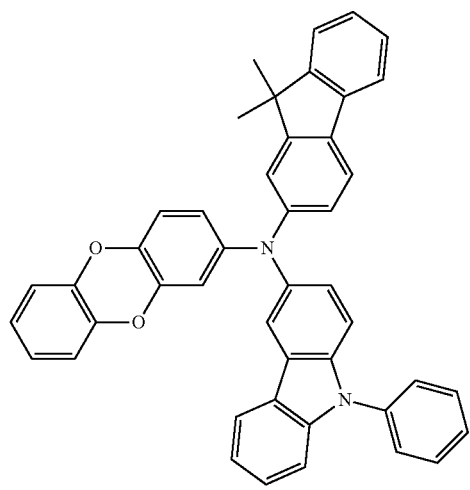
5
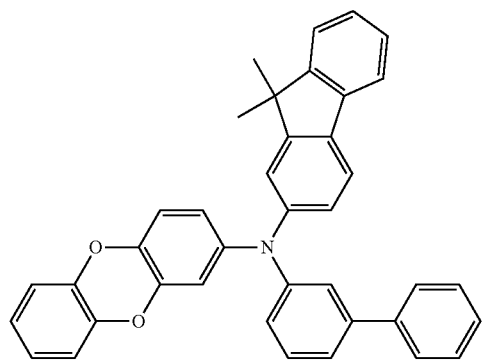
6
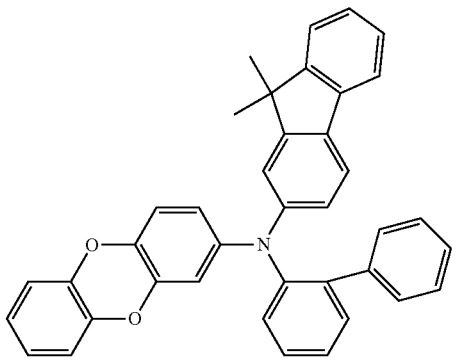
7
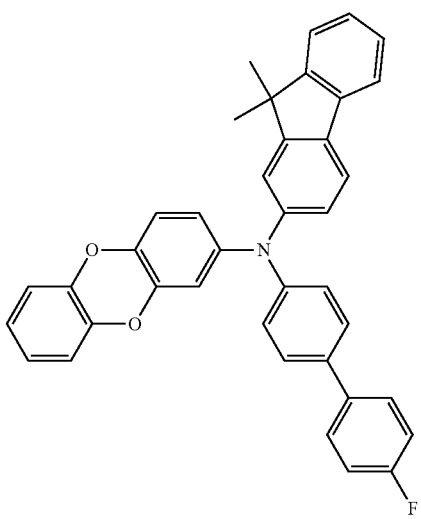
8
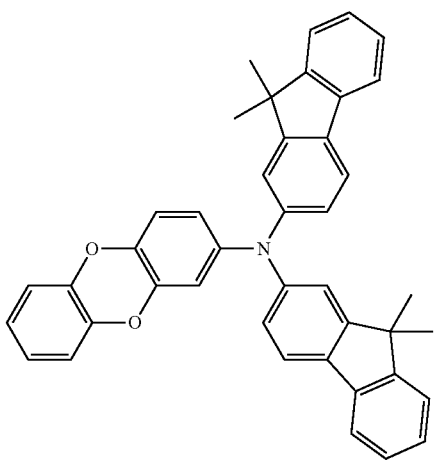

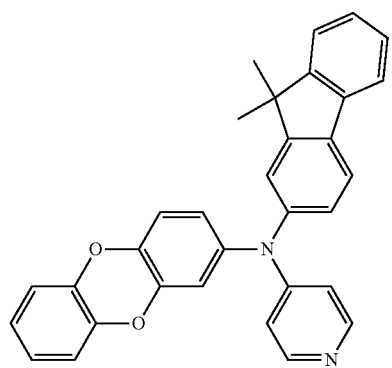
9
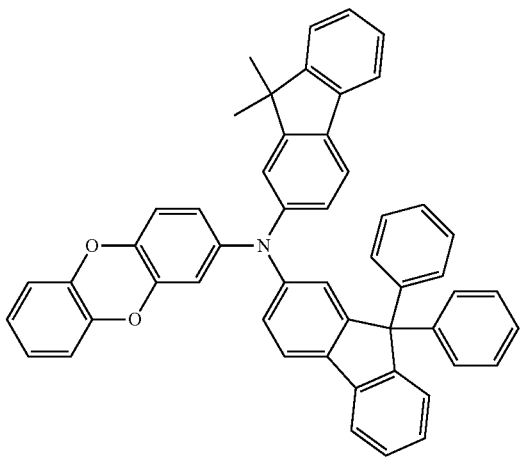
12
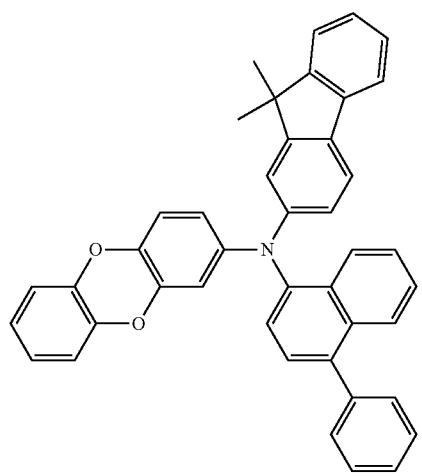
10
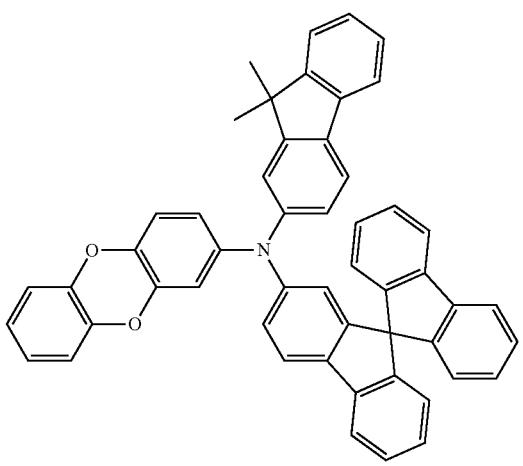
13
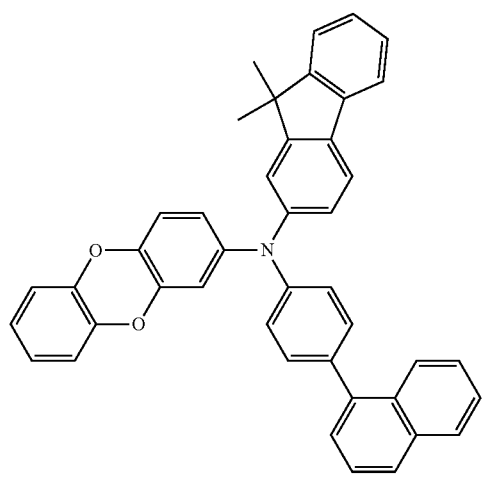
11
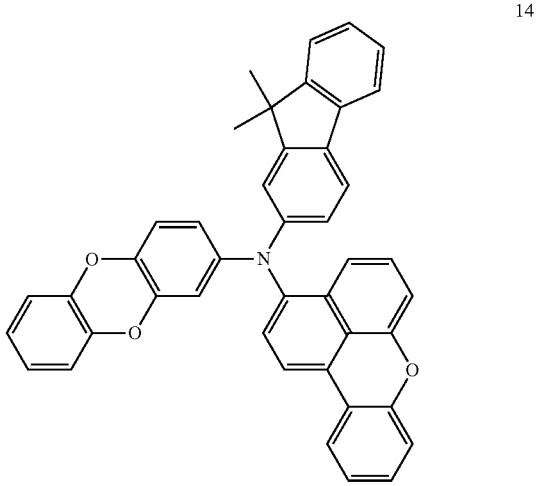
14

15
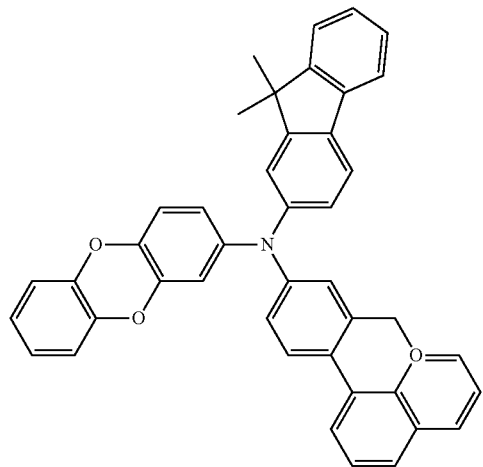
16
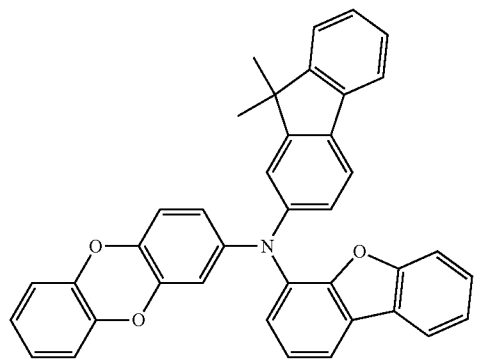
17
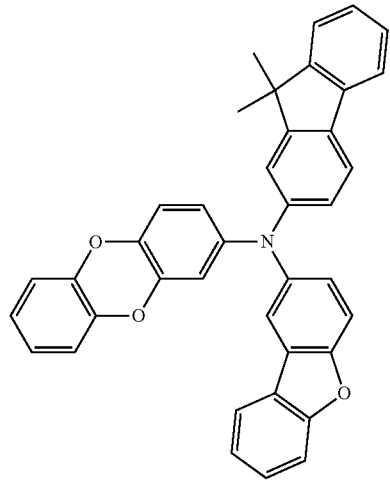
18
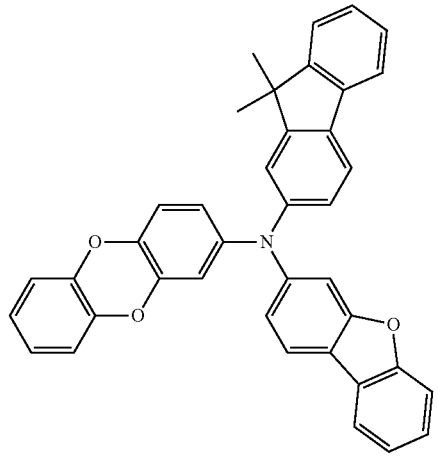
19
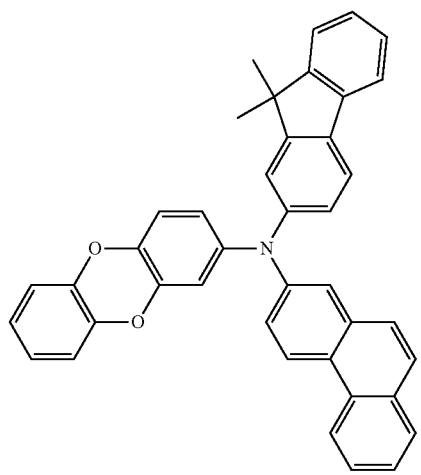
20
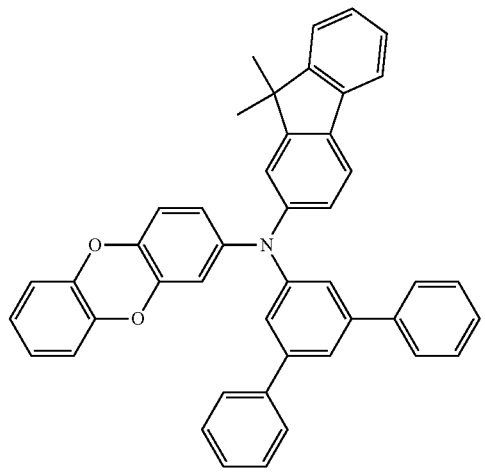

21
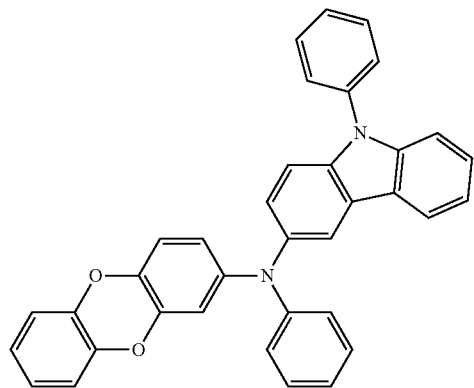
22
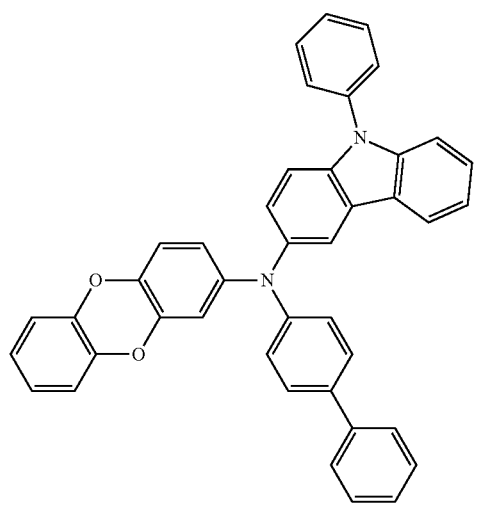
23
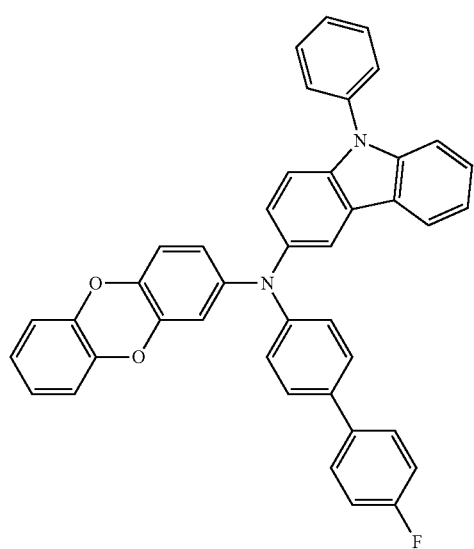
24
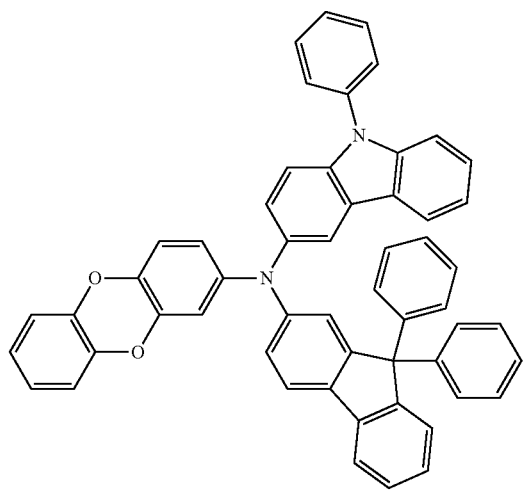
25
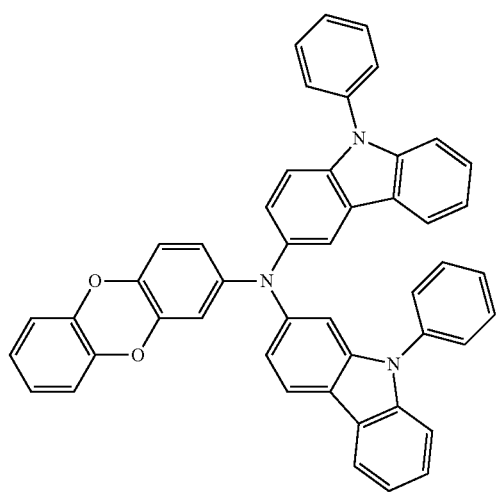
26
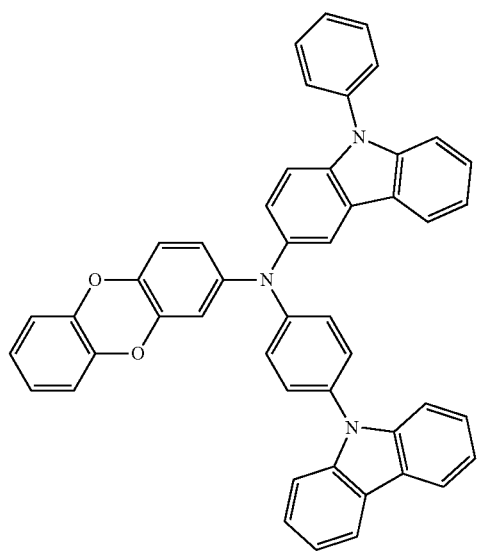

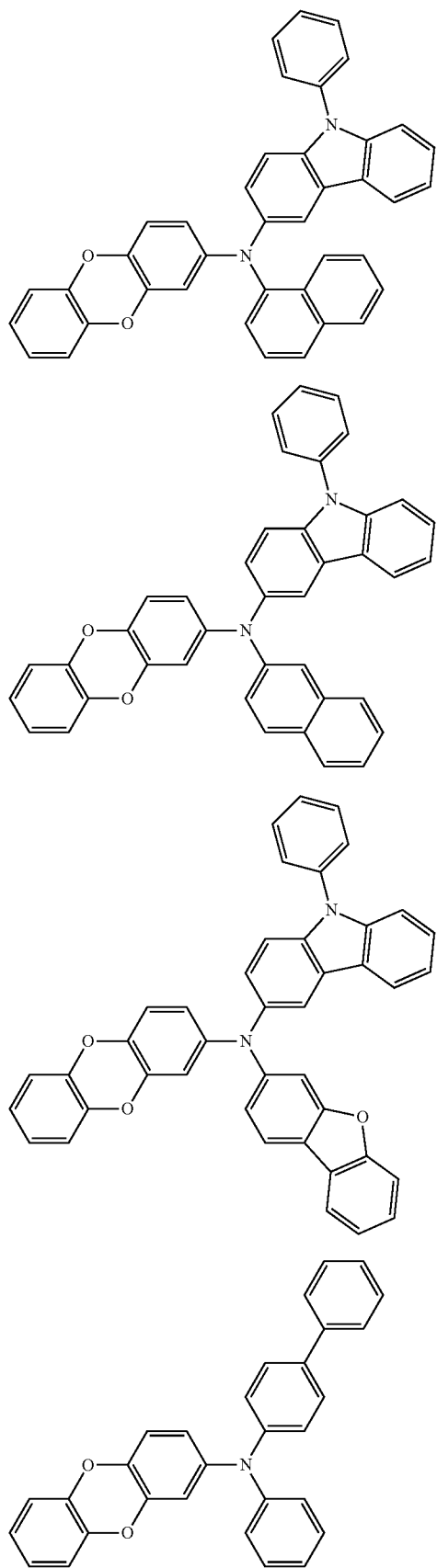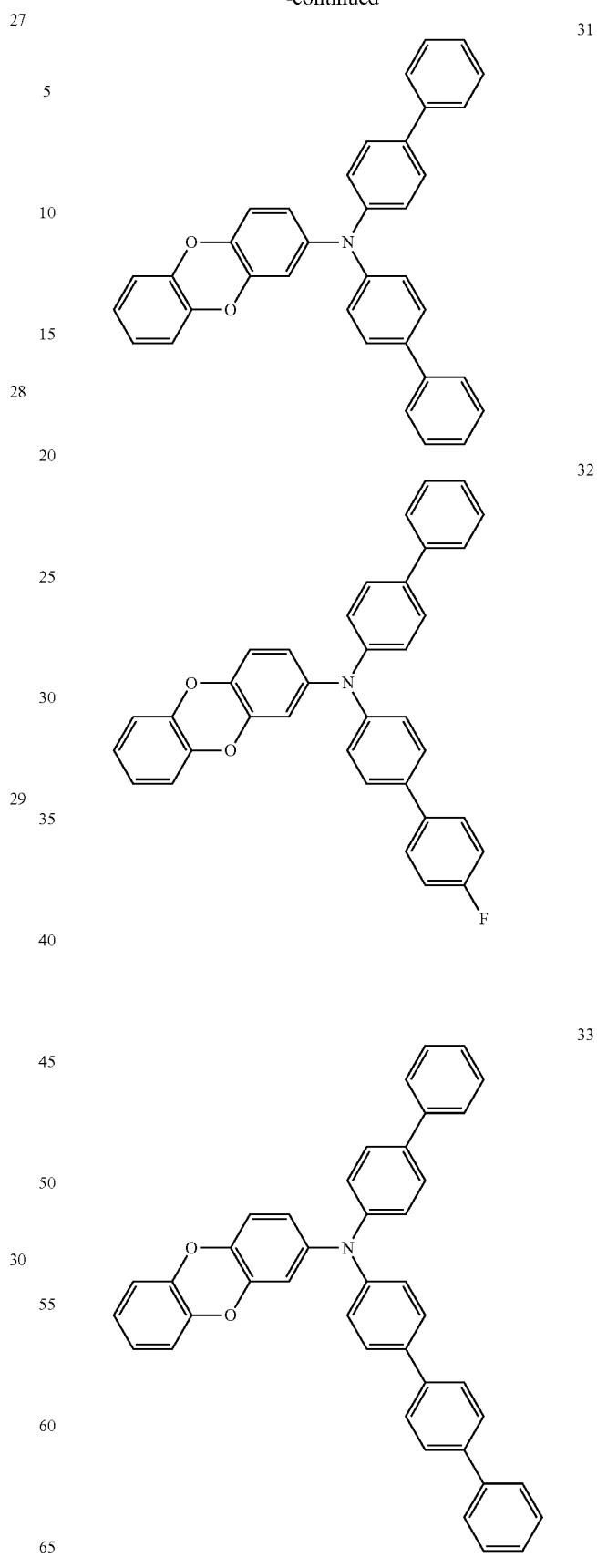

34
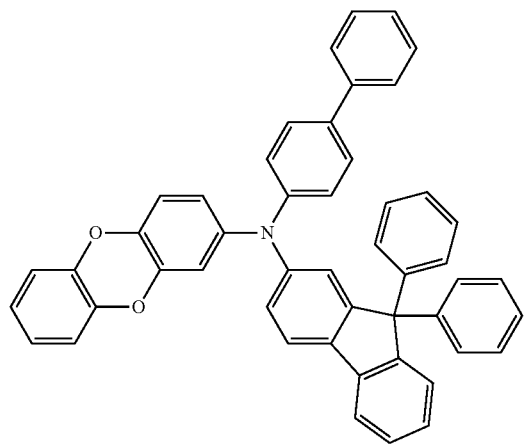
35
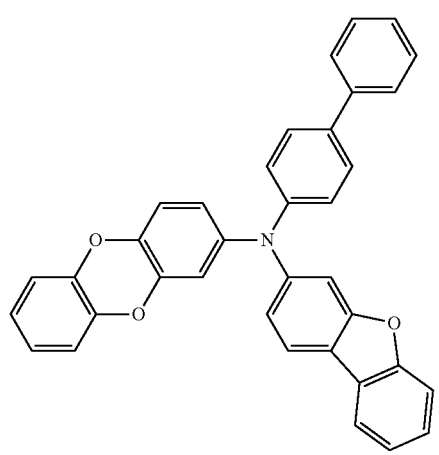
36
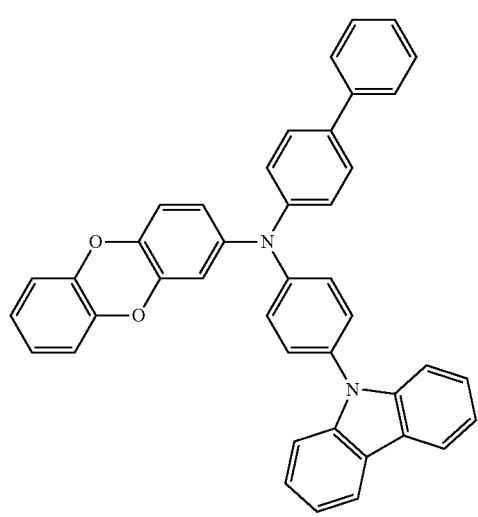
37
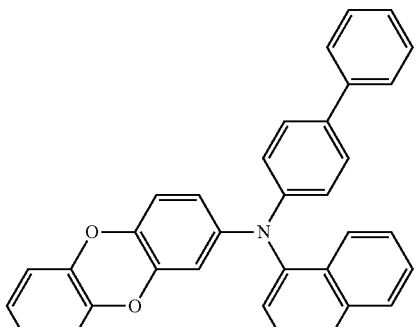
38
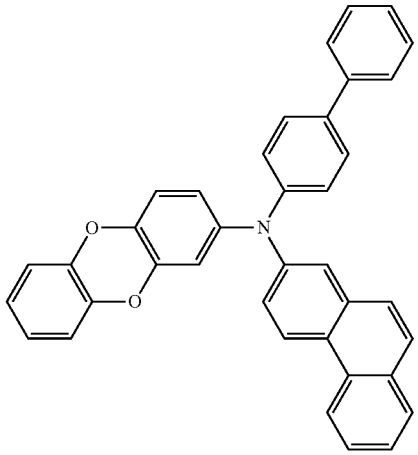
39
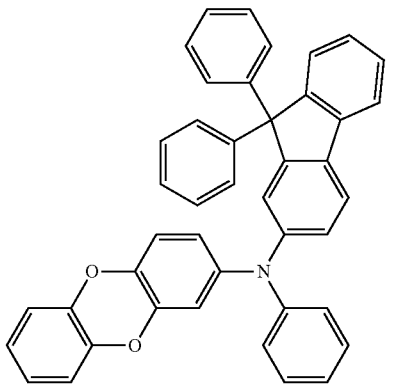
40
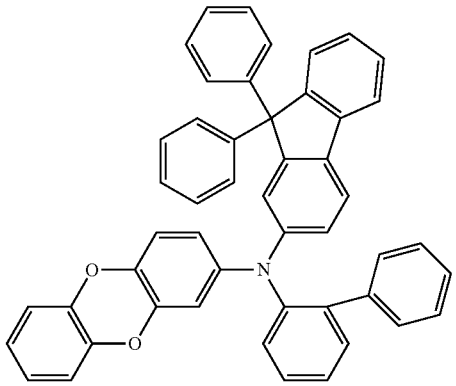

41
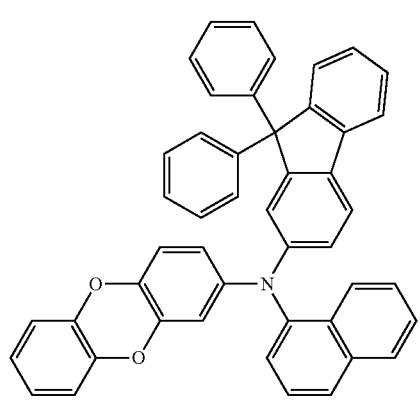
42
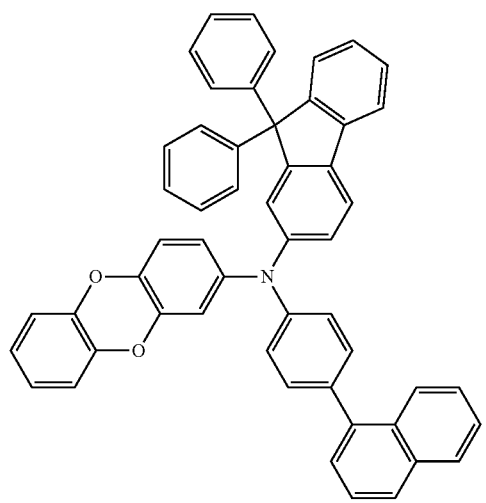
43
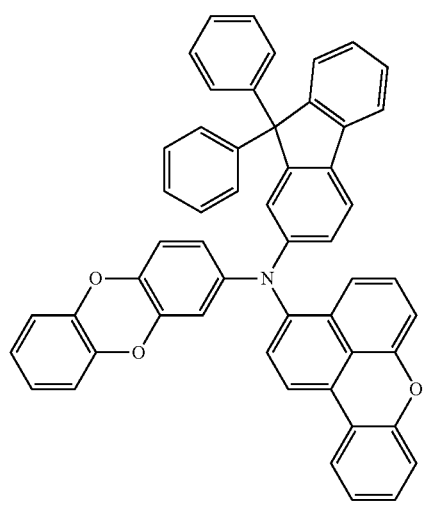
44
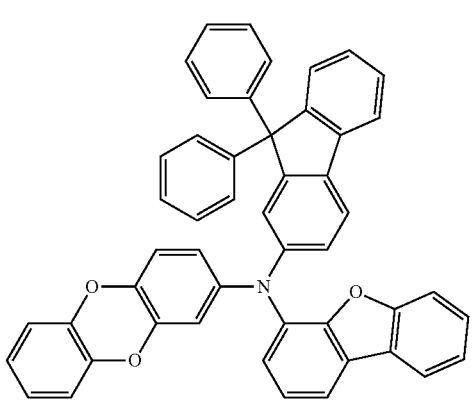
45
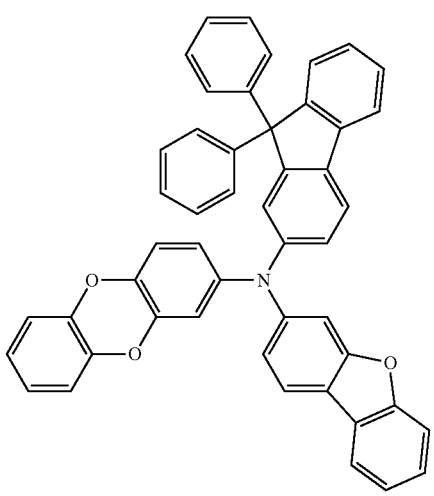
46
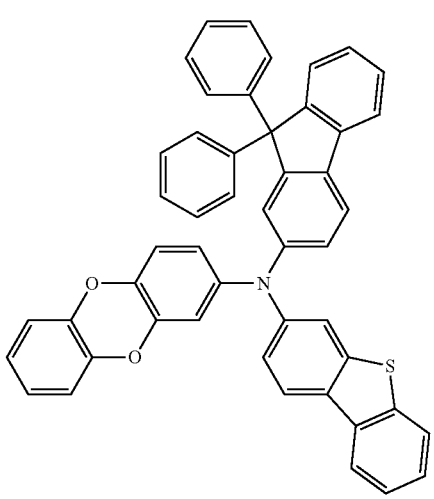

47
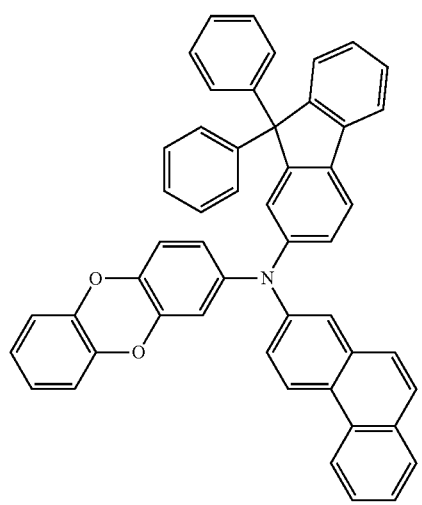
48
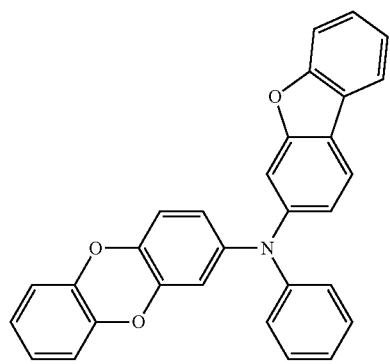
49
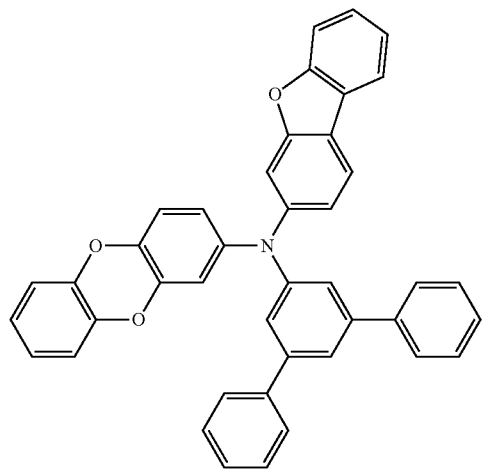
50
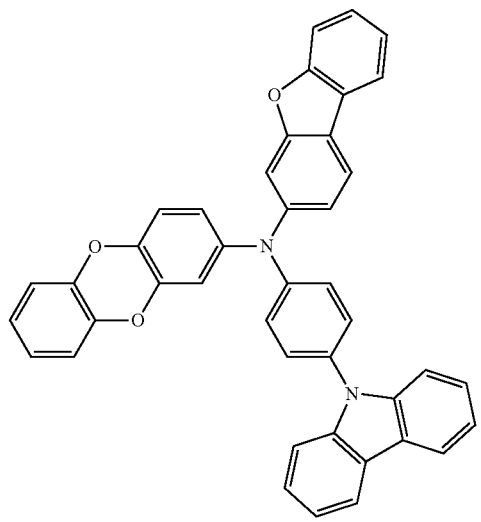
51
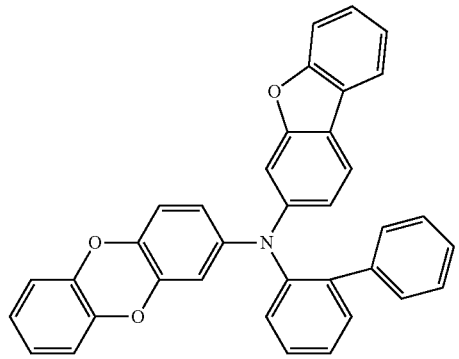
52
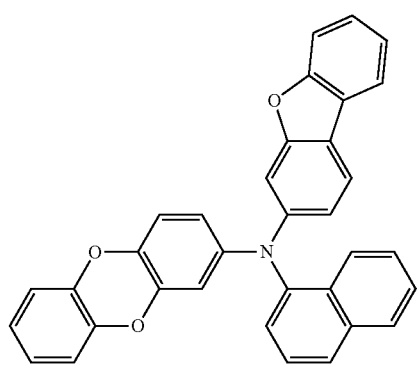
53
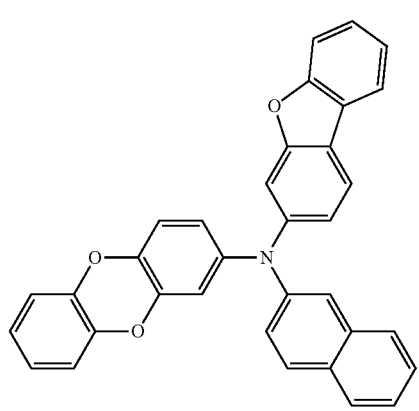

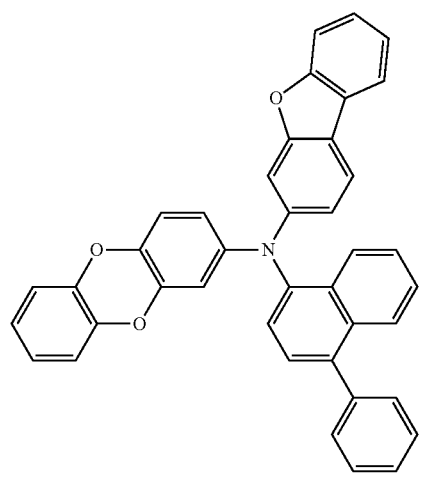
54
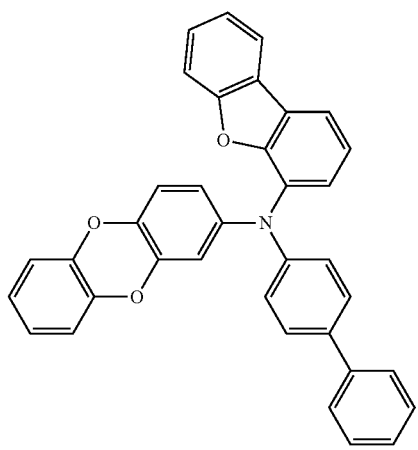
57
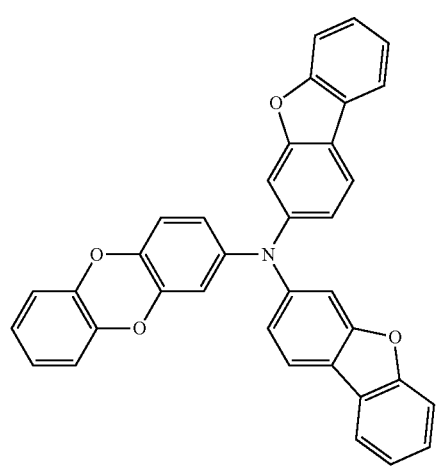
55
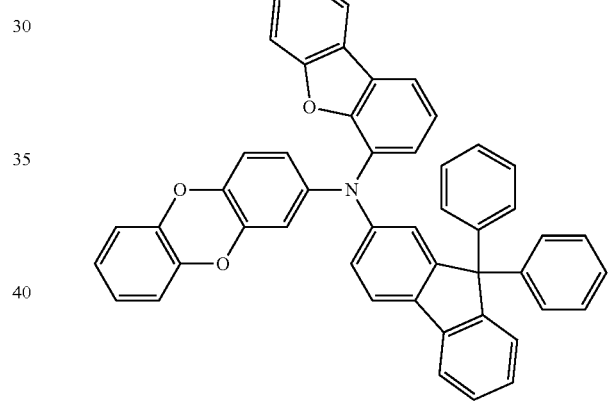
58
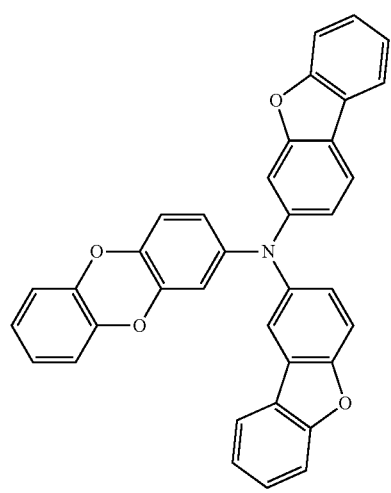
56
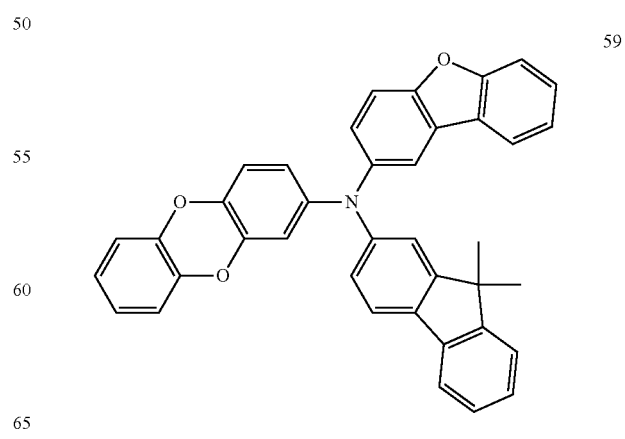
59

60
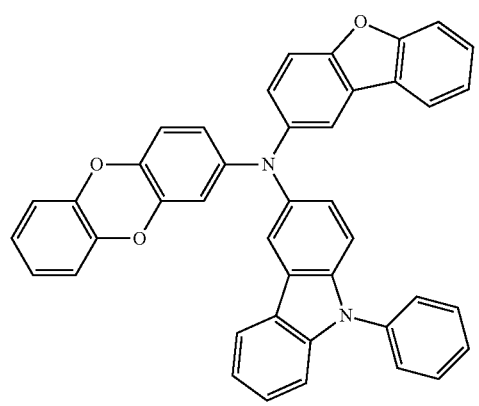
61
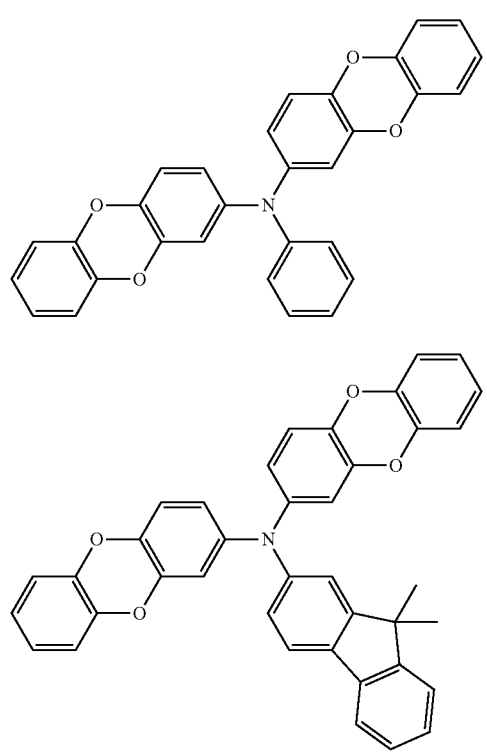
62
63
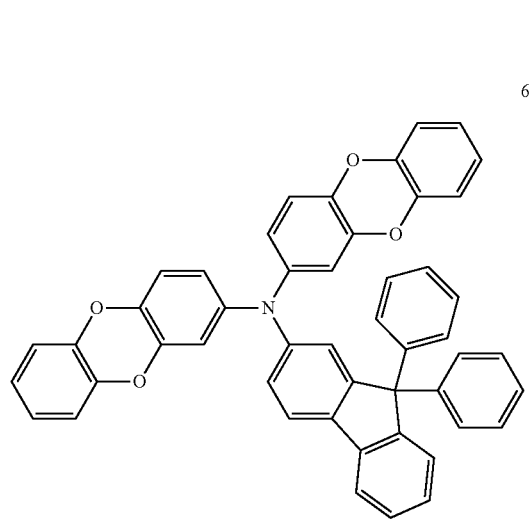
64
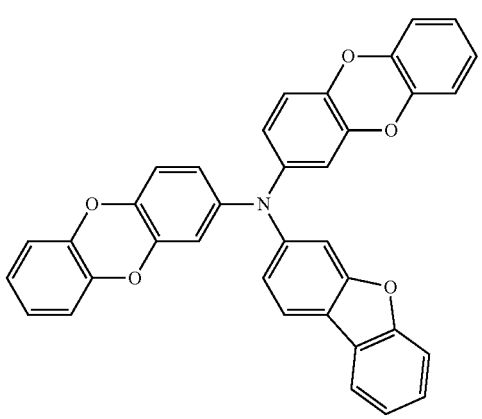
65
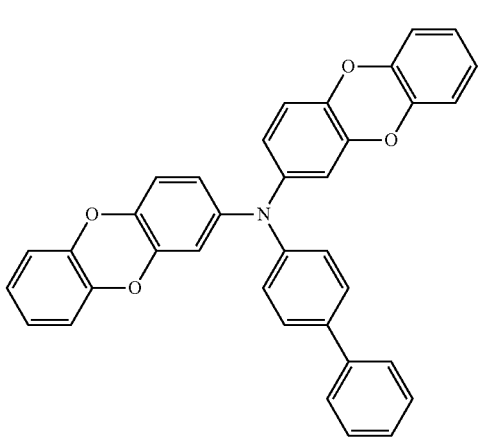
66
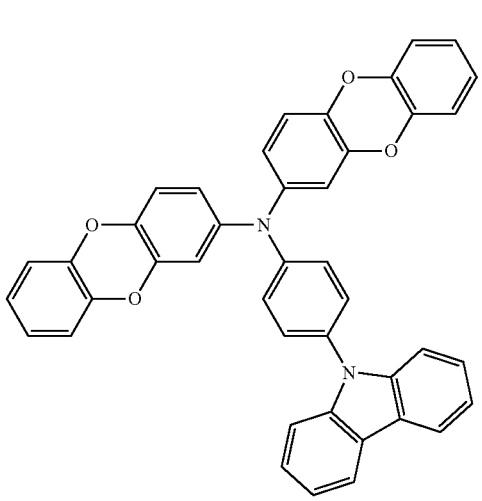

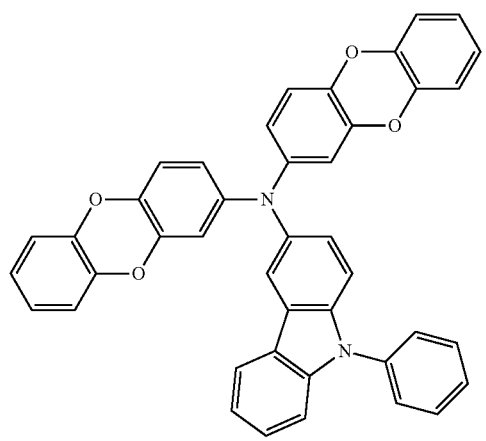
67
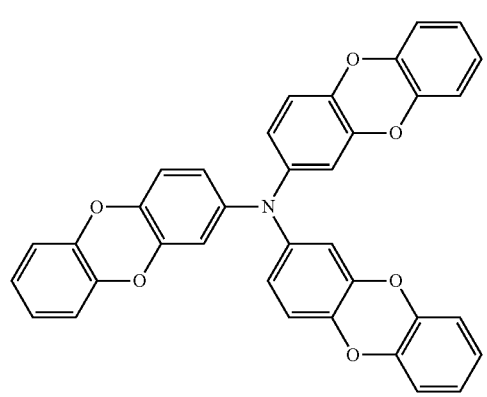
68
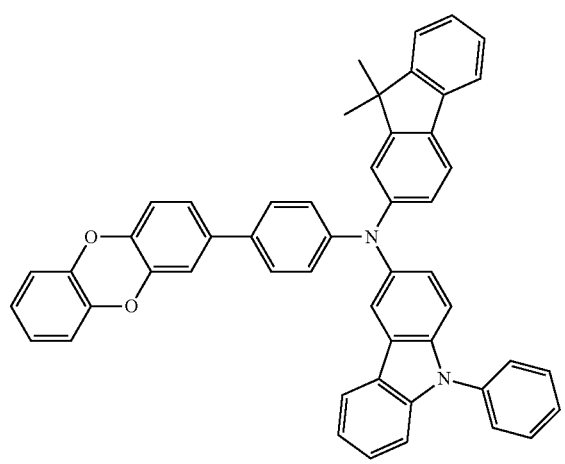
69
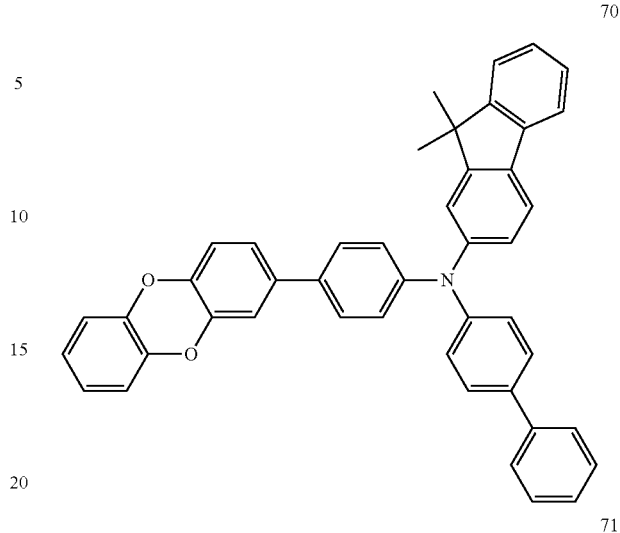
70
71
72

73
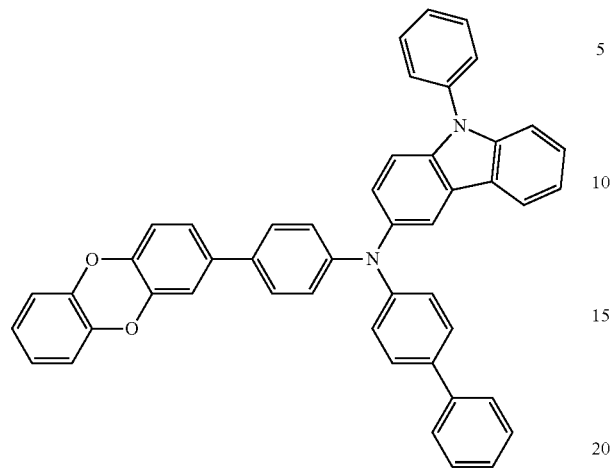
76
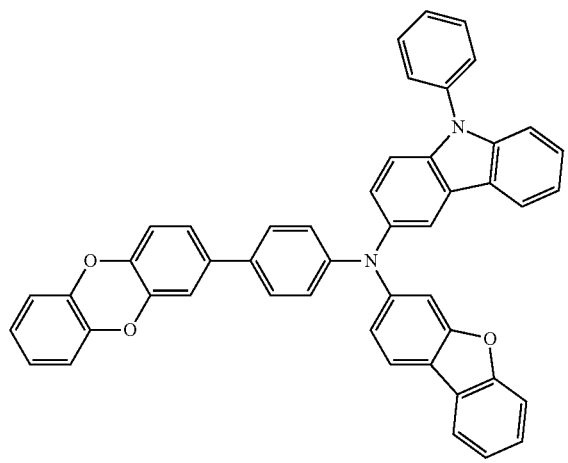
74
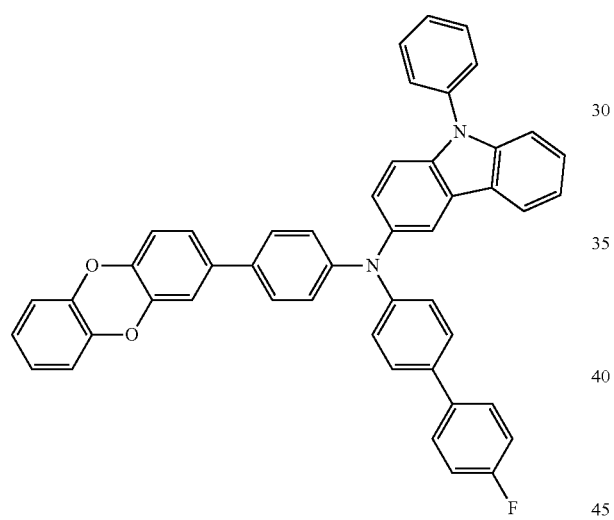
77
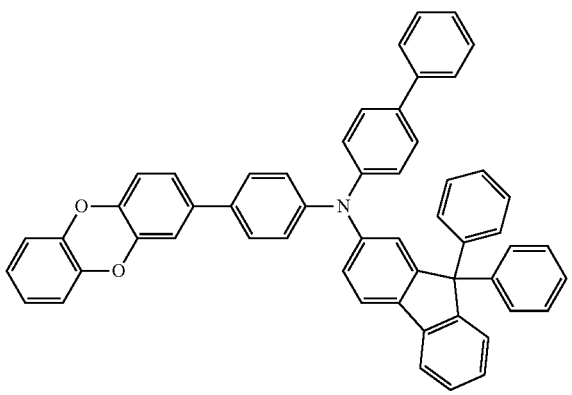
75
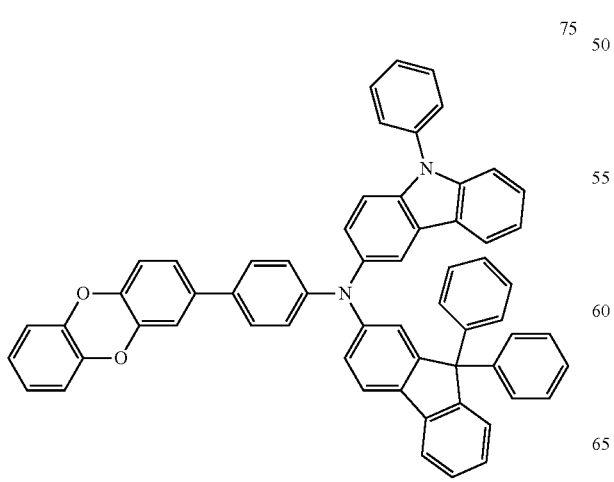
78
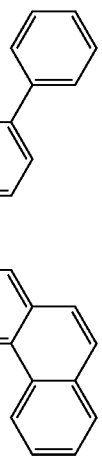

79
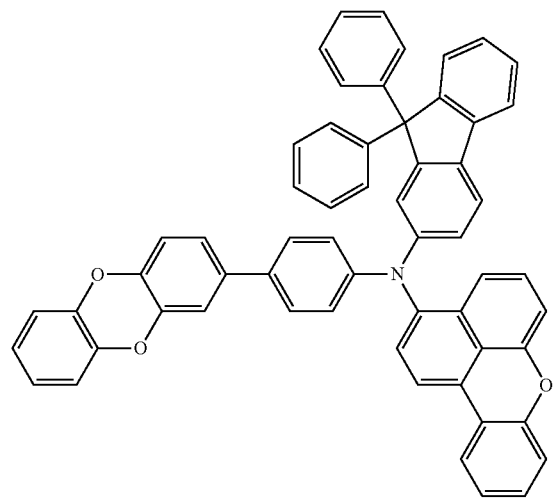
82
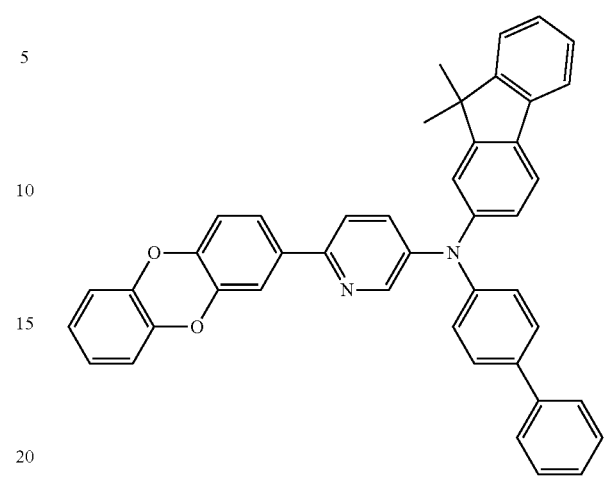
80
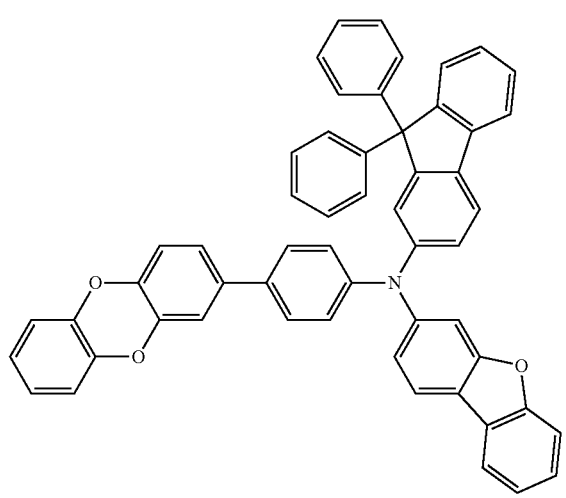
83
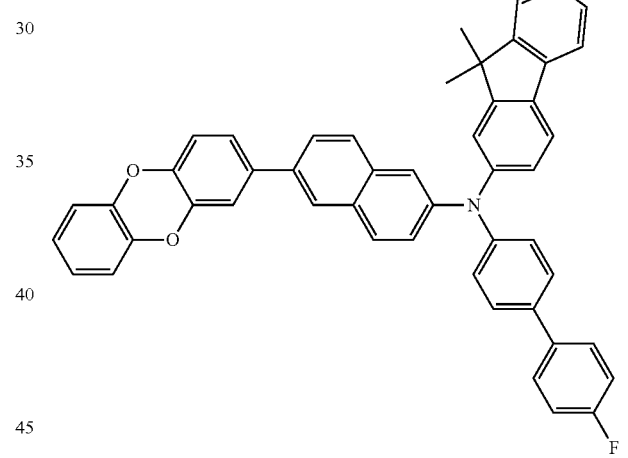
81
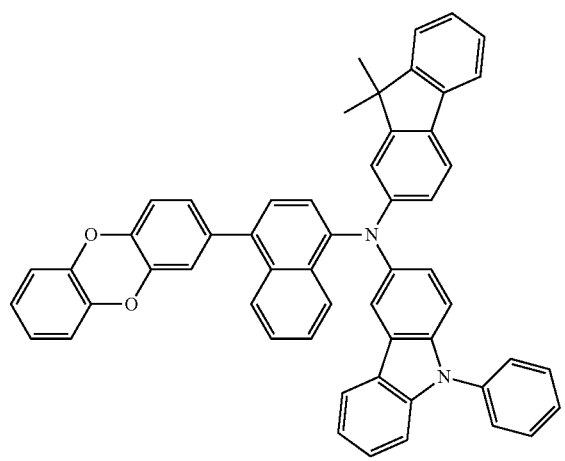
84
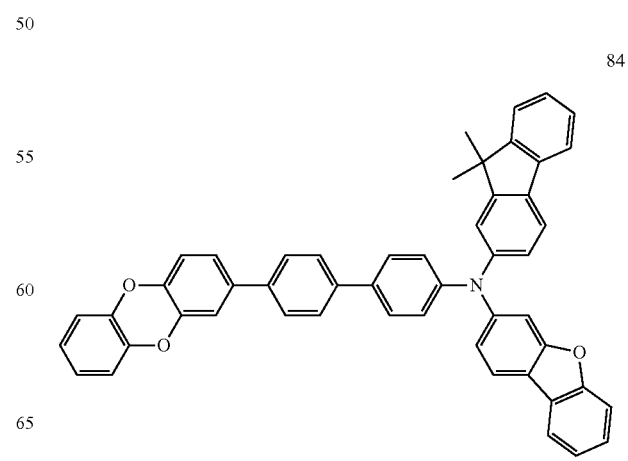

85
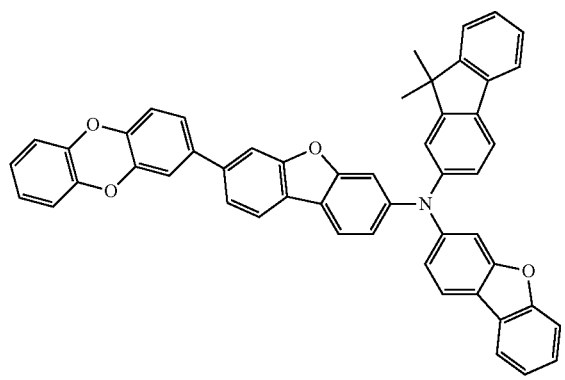
86
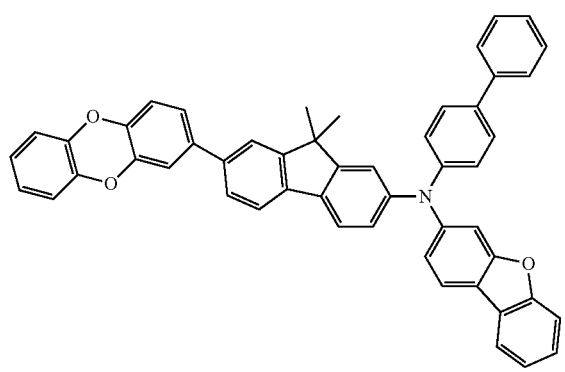
87
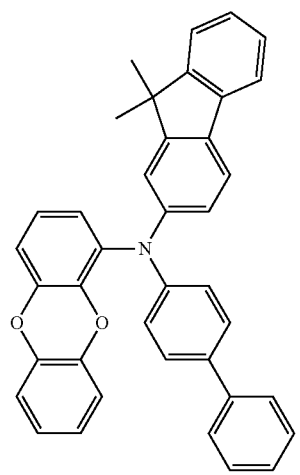
88
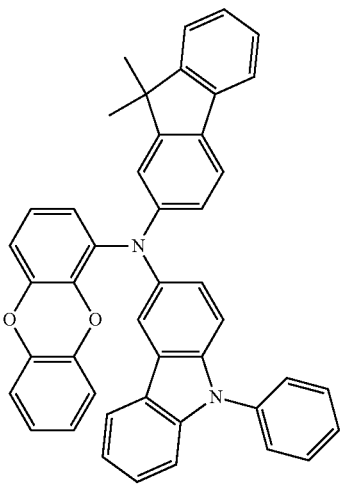
89
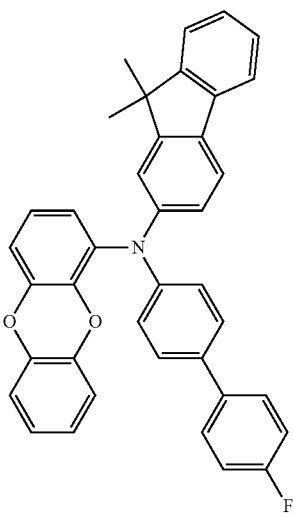
90
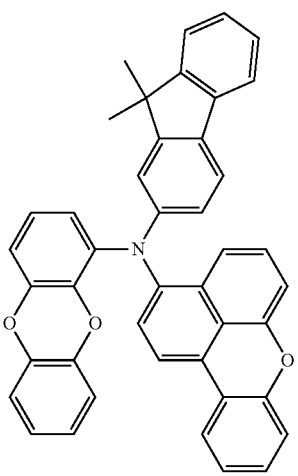

91
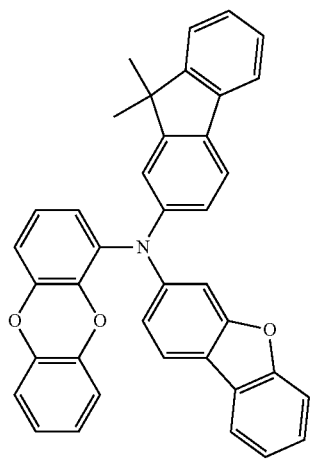
92
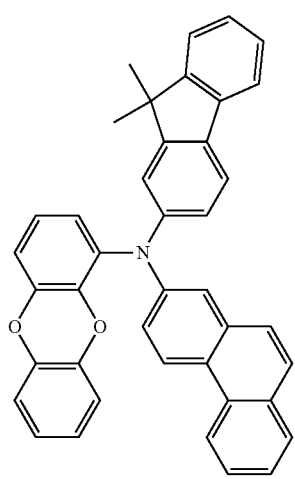
93
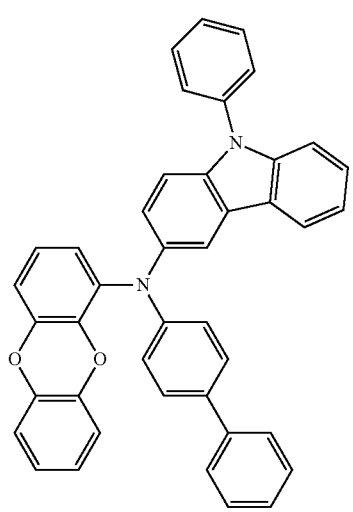
94
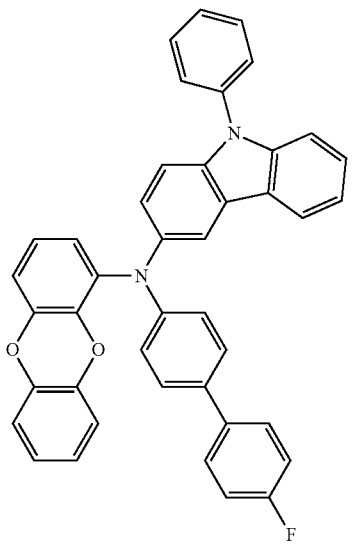
95
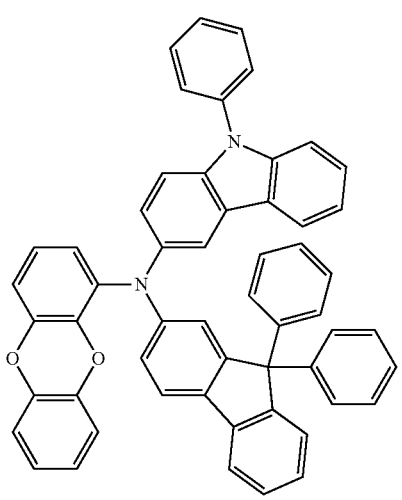
96
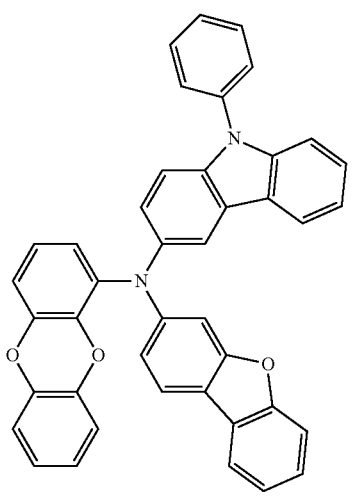

97
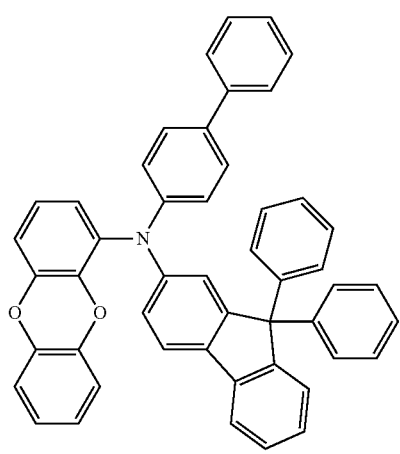
98
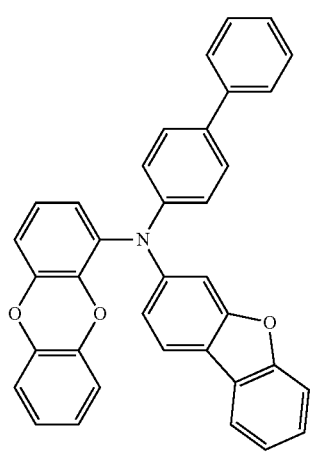
99
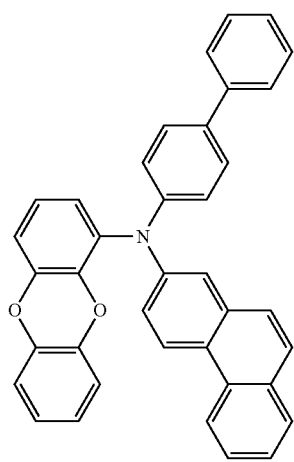
100
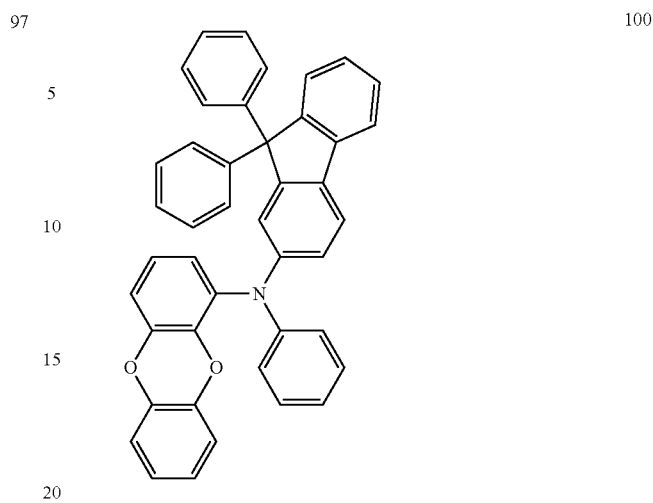
101
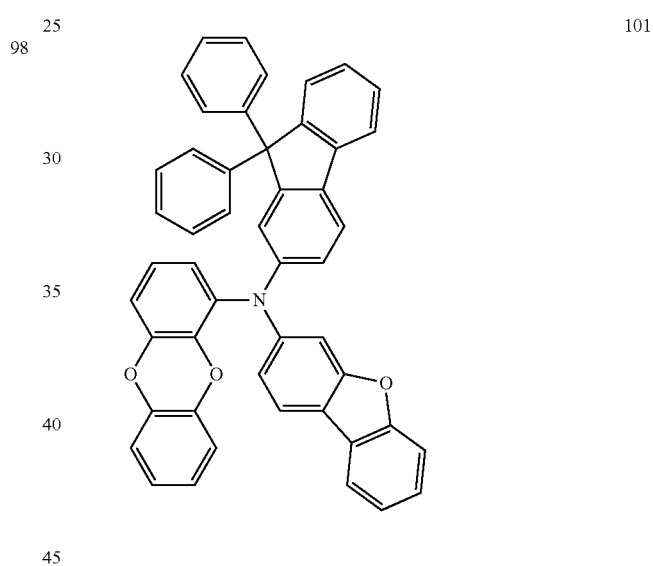
102
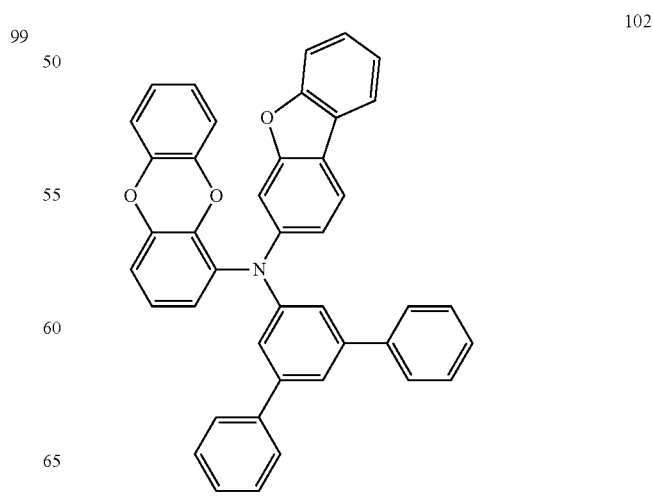

| 69 -continued | 70 -continued |
|---|---|
| 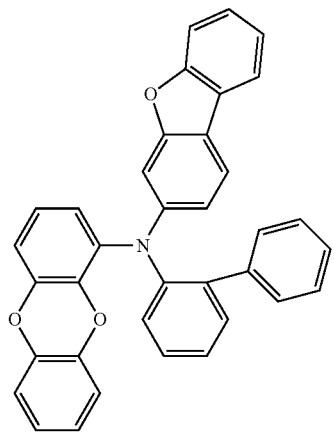 | 103 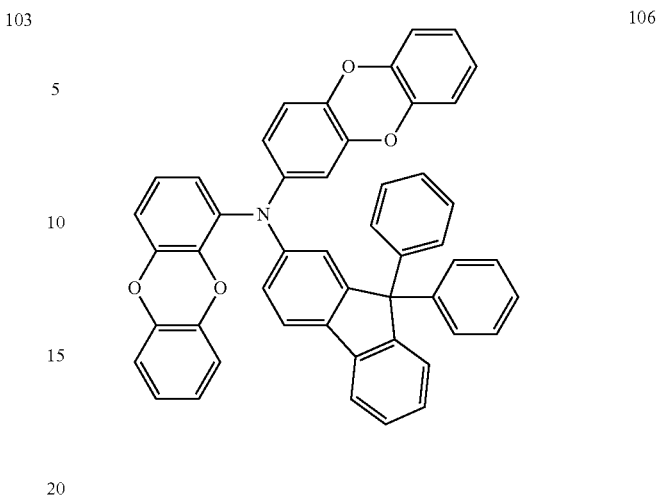 106 |
| 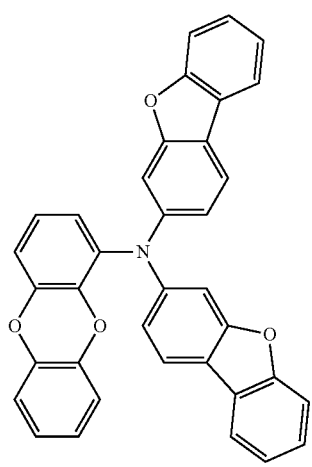 104 | 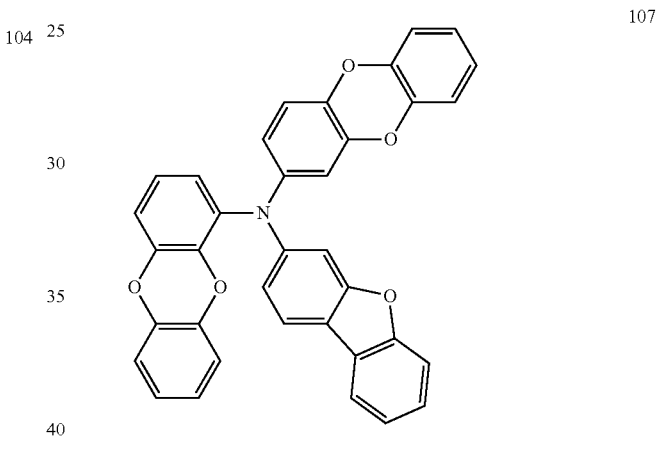 107 |
| 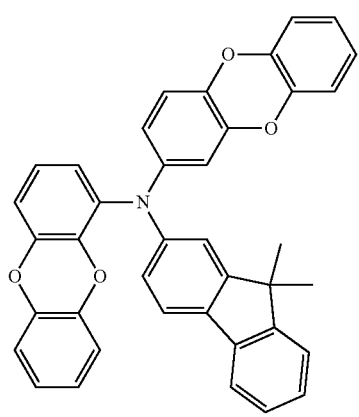 105 | 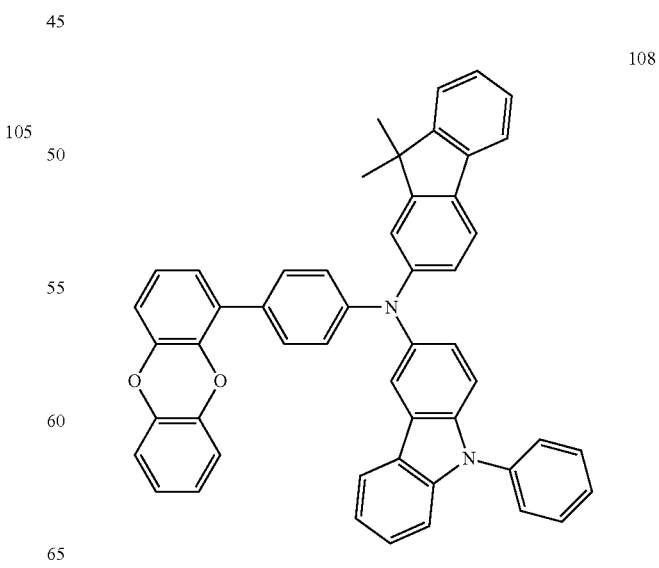 108 |

109
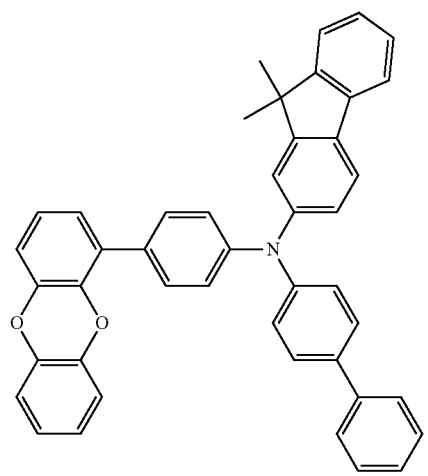
110
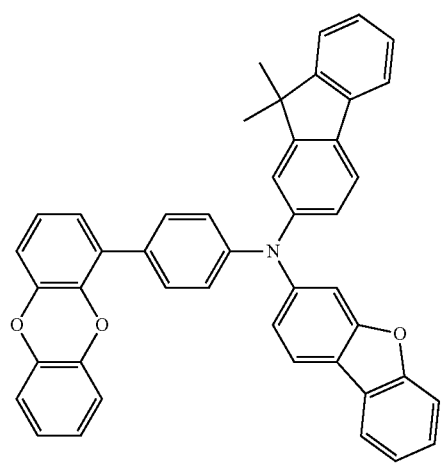
111
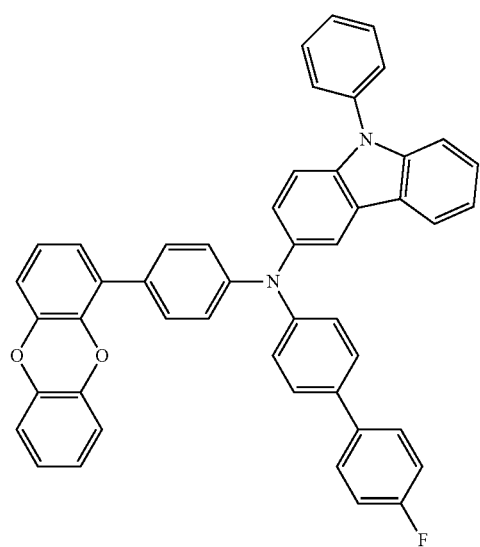
112
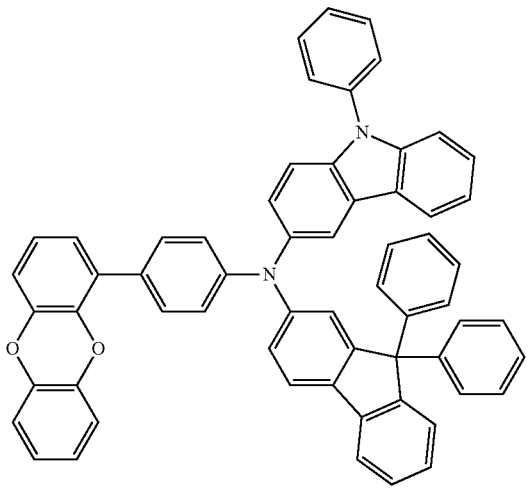
113
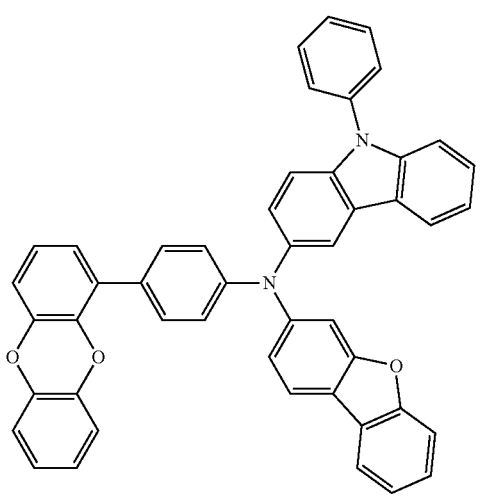
114
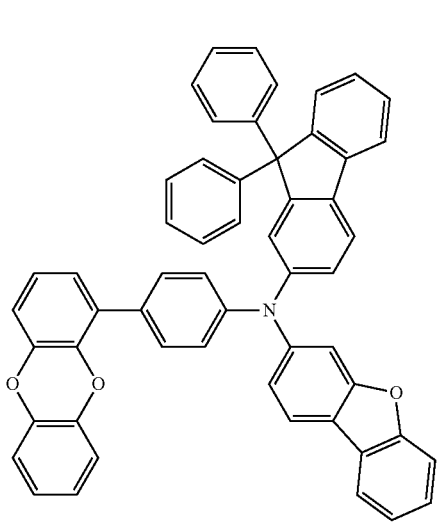

-continued

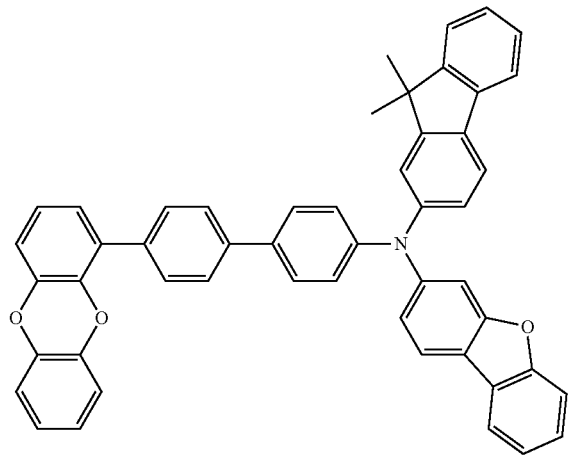
115

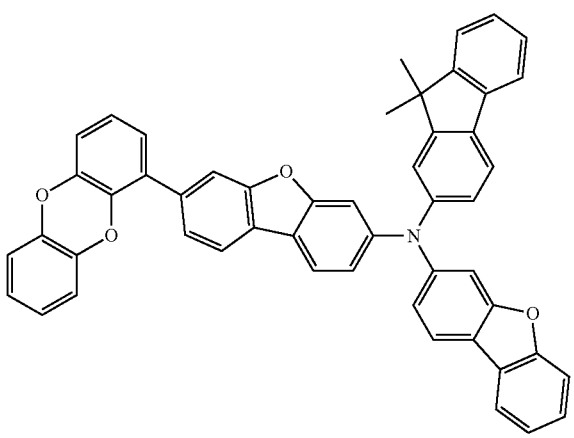
116

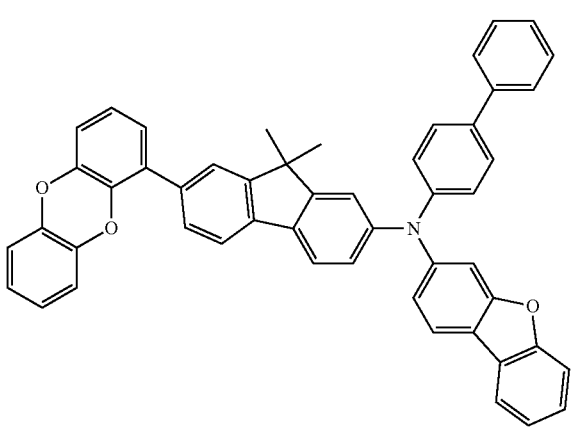
117

Since the condensed-cyclic compound represented by Formula 1 includes a condensed ring core represented by Formula 1', the condensed-cyclic compound represented by Formula 1 may have a high glass transition temperature (Tg) and/or a high melting point. Accordingly, an organic light-emitting device may have improved heat resistance to Joule heating generated in an organic layer of the organic light-emitting device and between the organic layer and an electrode, and/or an improved resistance to high temperatures. Therefore an organic light-emitting device including the condensed-cyclic compound represented by Formula 1 may retain high durability during storing and/or driving.

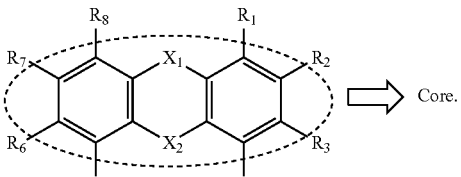

Formula 1'

In some embodiments, in the condensed-cyclic compound represented by Formula 1, $X_1$ and $X_2$ may each independently be selected from O and S. The electron donating abilities of dibenzo-dioxane may facilitate hole injection and transfer thereby provide excellent hole transfer characteristics. Further, in the condensed-cyclic compound represented by Formula 1, at least one selected from $R_1$ to $R_8$ may be a monoamine-based compound, which is represented by Formula 2. Thus the condensed-cyclic compound represented by Formula 1 may act as a hole transport material having a suitable energy level and band-gap. Accordingly, an organic light-emitting device including the condensed-cyclic compound may have improved efficiency and/or a long lifespan.

The condensed-cyclic compound represented by Formula 1 may be synthesized using a suitable organic synthetic method. Methods of synthesizing the condensed-cyclic compound should be readily apparent to those of ordinary skill in the art by referring to examples used herein.

At least one of the condensed-cyclic compounds represented by Formula 1 may be included between a pair of electrodes in an organic light-emitting device. For example, the condensed-cyclic compound may be included in a hole transport region (e.g., in a hole transport layer). In some embodiments, the condensed-cyclic compound may be included in an emission layer. Accordingly, aspects of embodiments of the present disclosure provide an organic light-emitting device including a first electrode; a second electrode facing the first electrode; and an organic layer between the first electrode and the second electrode that may include an emission layer; wherein the organic layer may include at least one condensed-cyclic compound represented by Formula 1.

As used herein, the expression "the (organic layer) includes at least one condensed-cyclic compound" may refer to "the (organic layer) may include one condensed-cyclic compound represented by Formula 1 and/or two different condensed-cyclic compounds represented by Formula 1".

For example, the organic layer may include only Compound 1 as the condensed-cyclic compound. In this regard, Compound 1 may be included in the hole transport layer of the organic light-emitting device. In some embodiments, the organic layer may include Compound 1 and Compound 2 as condensed-cyclic compounds. In these embodiments, Compound 1 and Compound 2 may be in the same layer (for example, both Compound 1 and Compound 2 may be in a hole transport layer), and/or in different layers (for example, Compound 1 may be in a hole transport layer and Compound 2 may be in an emission layer).

The organic layer may include i) a hole transport region between the first electrode (anode) and the emission layer, including at least one selected from a hole injection layer, a hole transport layer, a buffer layer, and an electron blocking layer and ii) an electron transport region between the emission layer and the second electrode (cathode) that includes at least one selected from a hole blocking layer, an electron transport layer, and an electron injection layer. At least one selected from the hole transport region and the emission layer may include at least one condensed-cyclic compound represented by Formula 1. In some embodiments, the hole transport region may include a hole transport layer, wherein the hole transport layer may include the at least one condensed-cyclic compound represented by Formula 1.

As used herein, the term "organic layer" may refer to a single layer and/or a plurality of layers between the first electrode and the second electrode in an organic light-emitting device. The "organic layer" may include other materials besides an organic material.

The drawing illustrates a schematic view of an organic light-emitting device 10, according to an embodiment of the present disclosure. The organic light-emitting device 10 may include a first electrode 110, an organic layer 150, and a second electrode 190.

Hereinafter, a structure and a method of manufacturing the organic light-emitting device according to an embodiment of the present disclosure will each be described with reference to the drawing.

Referring to the drawing, a substrate may be under the first electrode 110 or on the second electrode 190. The substrate may be a glass substrate and/or a transparent plastic substrate, each with excellent mechanical strength, thermal stability, transparency, surface smoothness, ease of handling, and/or water resistance.

The first electrode 110 may be formed by depositing and/or sputtering a material for forming the first electrode on the substrate. When the first electrode 110 is an anode, the material for the first electrode may be selected from materials with a high work function that facilitate hole injection. The first electrode 110 may be a reflective electrode, a semi-transmissive electrode, and/or a transmissive electrode. The material for the first electrode 110 may be a transparent and highly conductive material. Non-limiting examples of such a material may include indium tin oxide (ITO), indium zinc oxide (IZO), tin oxide ($SnO_2$), and zinc oxide (ZnO). When the first electrode 110 is a semi-transmissive electrode and/or a reflective electrode, at least one selected from magnesium (Mg), aluminum (Al), aluminum-lithium (Al—Li), calcium (Ca), magnesium-indium (Mg—In), and/or magnesium-silver (Mg—Ag) may be used as a material for forming the first electrode.

The first electrode 110 may have a single-layer structure, and/or a multi-layer structure including a plurality of layers. For example, the first electrode 110 may have a triple-layer structure of ITO/Ag/ITO, but embodiments of the present disclosure are not limited thereto.

The organic layer 150 may be on the first electrode 110. The organic layer 150 may include an emission layer.

The organic layer 150 may further include a hole transport region between the first electrode and the emission layer and/or an electron transport region between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but embodiments of the present disclosure are not limited thereto.

The hole transport region may have a single-layered structure including a single material, a single-layered structure including a plurality of different materials, and/or a multi-layered structure having a plurality of layers including a plurality of different materials.

For example, the hole transport region may have a single-layered structure formed of a plurality of different materials, a structure of hole injection layer/hole transport layer, a structure of hole injection layer/hole transport layer/buffer layer, a structure of hole injection layer/buffer layer, a structure of hole transport layer/buffer layer, and/or a structure of hole injection layer/hole transport layer/electron blocking layer, wherein layers of each structure are sequentially stacked on the first electrode 110 in the stated order, but embodiments of the present disclosure are not limited thereto.

When the hole transport region includes a hole injection layer, the hole injection layer may be formed on the first electrode 110 using one or more suitable methods, for example, vacuum deposition, spin coating, casting, a Langmuir-Blodgett (LB) method, ink-jet printing, laser printing, and/or laser-induced thermal imaging (LITI).

When the hole injection layer is formed by vacuum deposition, the vacuum deposition may be performed at a temperature of about 100° C. to about 500° C., at a vacuum degree of about $10^{-8}$ Torr to about $10^{-3}$ Torr, and at a vacuum deposition rate of about 0.01 Angstroms per second (Å/sec) to about 100 Å/sec, depending on the compound for forming the hole injection layer, and the structure of the hole injection layer to be formed.

When a hole injection layer is formed by spin coating, the spin coating may be performed at a coating rate of about 2,000 revolutions per minute (rpm) to about 5,000 rpm, and at a temperature of about 80° C. to 200° C., depending on the compound for forming the hole injection layer and the structure of a hole injection layer to be formed.

When the hole transport region includes a hole transport layer, the hole transport layer may be formed on the first electrode 110 and/or on the hole injection layer using one or more suitable methods, such as vacuum deposition, spin coating, casting, an LB method, ink-jet printing, laser printing, and/or LITI. When the hole transport layer is formed by vacuum deposition and/or spin coating, the conditions for vacuum deposition and coating may be similar to the vacuum deposition and coating conditions used for forming the hole injection layer.

The hole transport region may include the condensed-cyclic compound represented by Formula 1. In some embodiments, the hole transport region may include a hole transport layer, wherein the hole transport layer may include the condensed-cyclic compound represented by Formula 1.

In some embodiments, the hole transport region may include at least one selected from m-MTDATA, TDATA, 2-TNATA, NPB, β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylene dioxythiophene)/poly(4-styrenesulfonate) (PEDOT/PSS), polyaniline/camphor sulfonic acid (PANI/CSA), (polyaniline)/poly (4-styrenesulfonate) (PANI/PSS), a compound represented by Formula 201 below, and a compound represented by Formula 202:

-continued
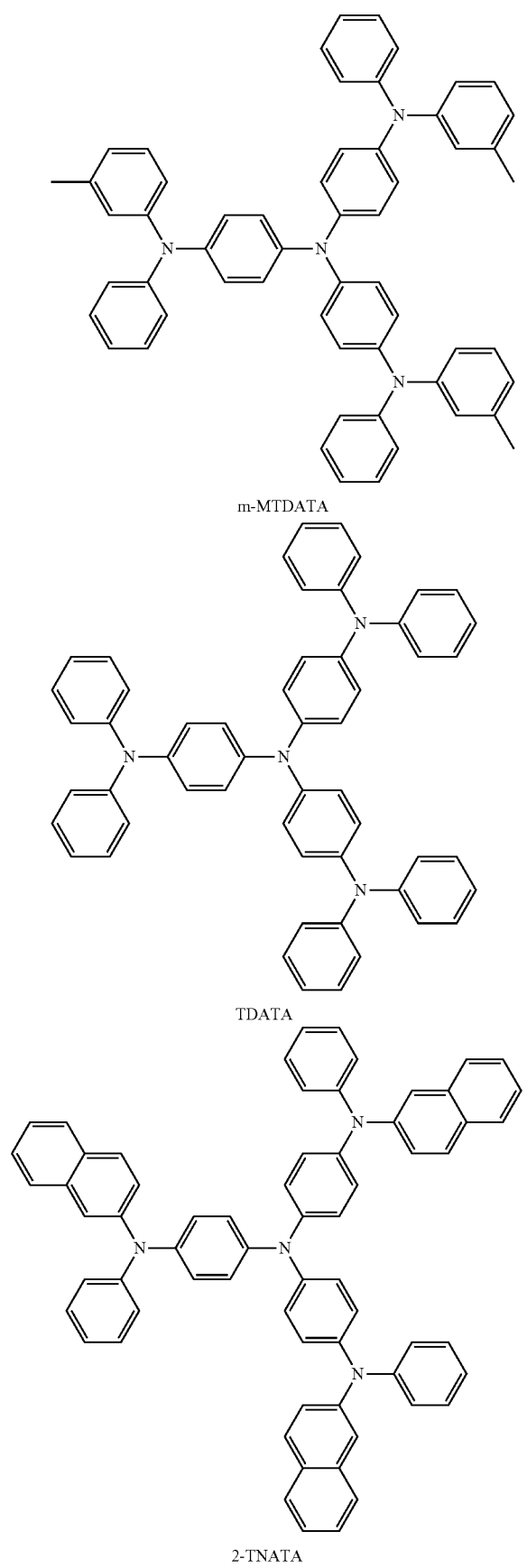
m-MTDATA
TDATA
2-TNATA
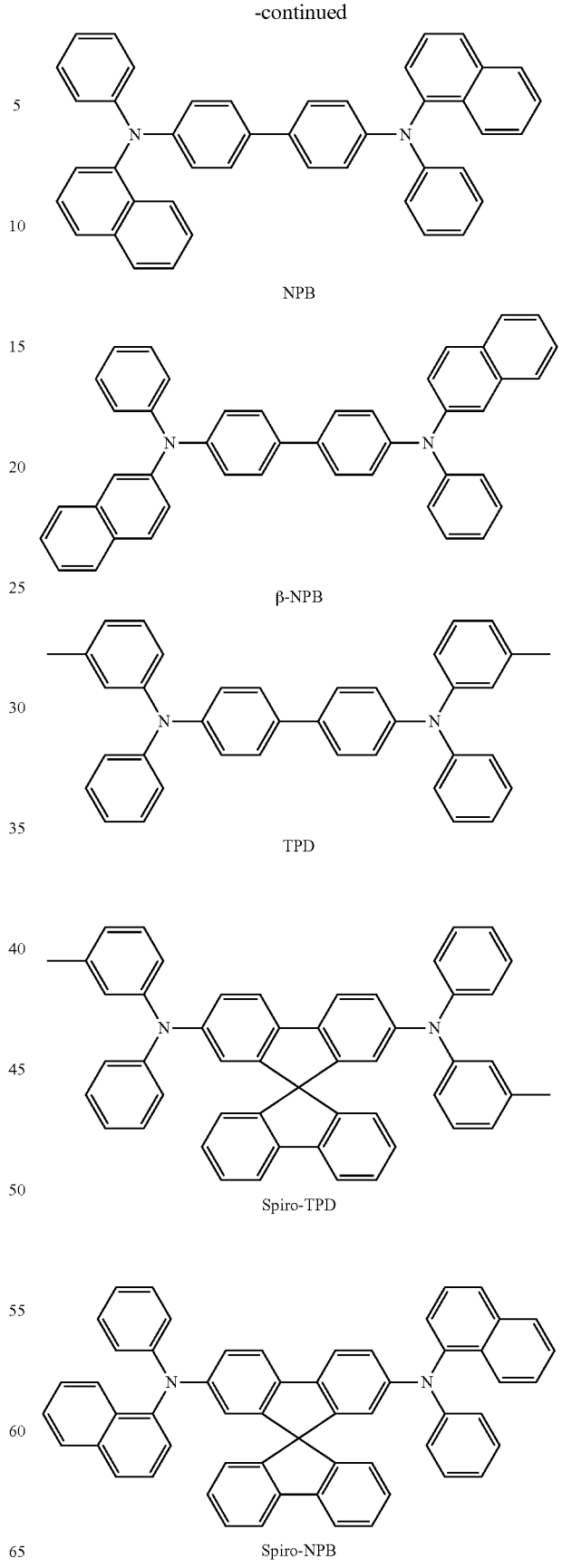
NPB
β-NPB
TPD
Spiro-TPD
Spiro-NPB -continued

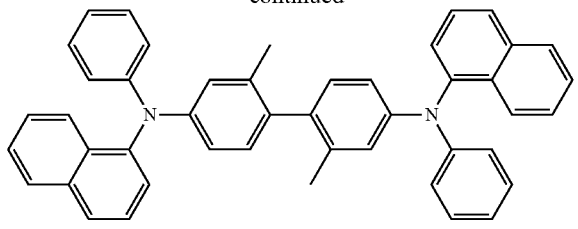

methylated NPB

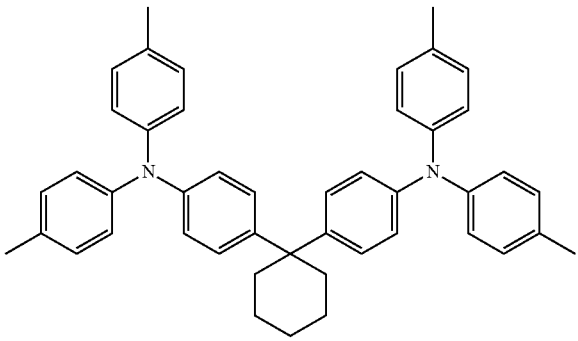

TAPC

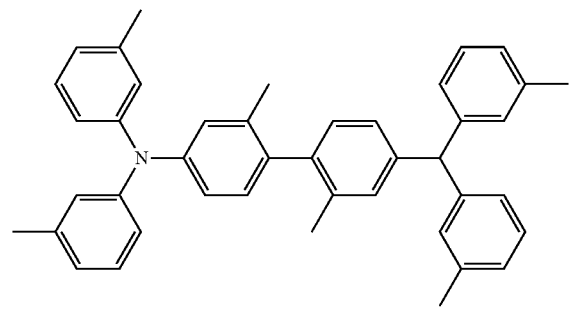

HMTPD

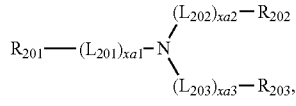

Formula 201

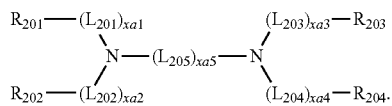

Formula 202

In Formulae 201 and 202, $L_{201}$ to $L_{205}$ may each independently be selected from the same groups described herein in connection with $L_1$, xa1 to xa4 may each independently be selected from 0, 1, 2, and 3, xa5 may be selected from 1, 2, 3, 4, and 5, and $R_{201}$ to $R_{204}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may each independently be selected from:
a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may each independently be selected from 0, 1, and 2, xa5 may be selected from 1, 2, and 3, and $R_{201}$ to $R_{204}$ may each independently be selected from:
a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments are not limited thereto.

The compound represented by Formula 201 may be further represented by Formula 201A:

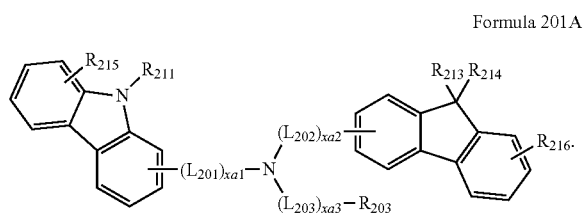

Formula 201A

In some embodiments, the compound represented by Formula 201 may be further represented by Formula 201A-1, but embodiments of the present disclosure are not limited thereto:

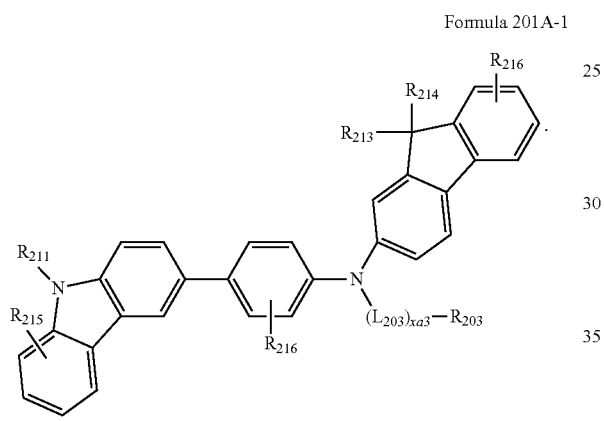

Formula 201A-1

In some embodiments, the compound represented by Formula 202 may be further represented by Formula 202A, but embodiments of the present disclosure are not limited thereto:

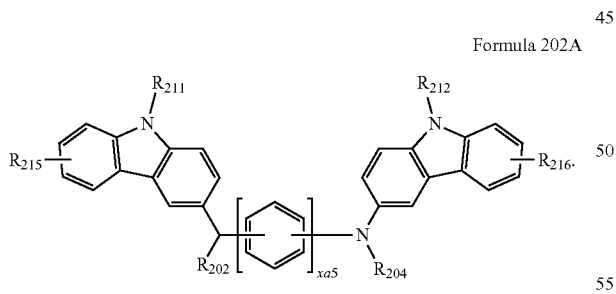

Formula 202A

In Formulae 201A, 201A-1, and 202A, $L_{201}$ to $L_{203}$, xa1 to xa3, xa5, and $R_{202}$ to $R_{204}$ may each be the same as described earlier herein. $R_{211}$ and $R_{212}$ may be the same as described earlier herein in connection with $R_{203}$; and $R_{213}$ to $R_{216}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201 and the compound represented by Formula 202 may be selected from Compounds HT1 to HT20, but embodiments of the present disclosure are not limited thereto:

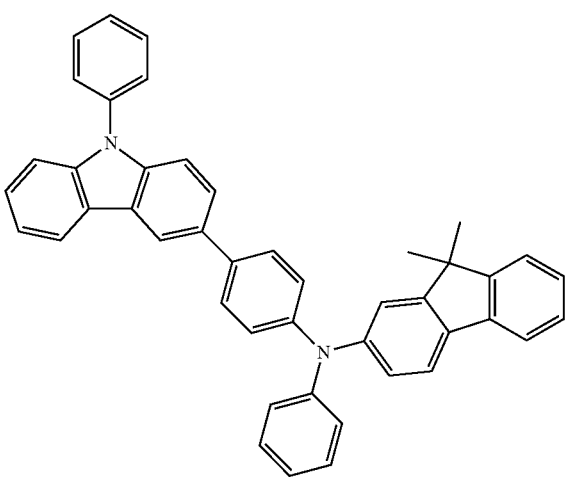

HT1

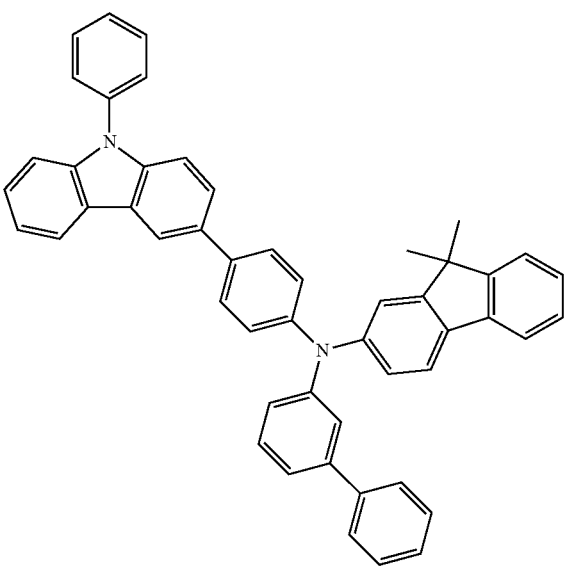

HT2

HT3
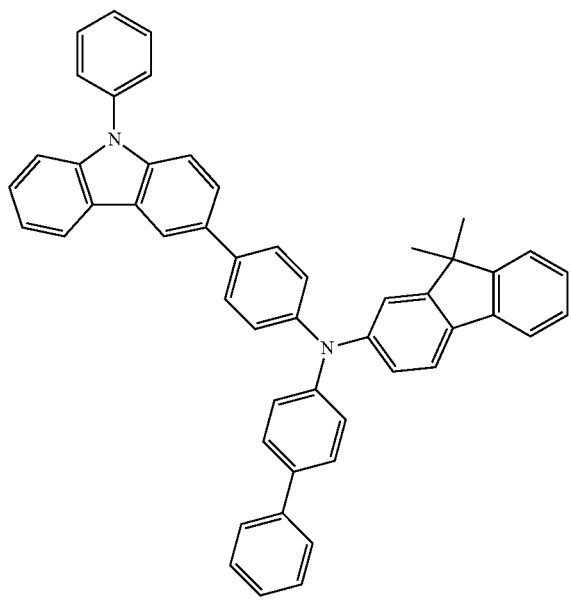
HT5
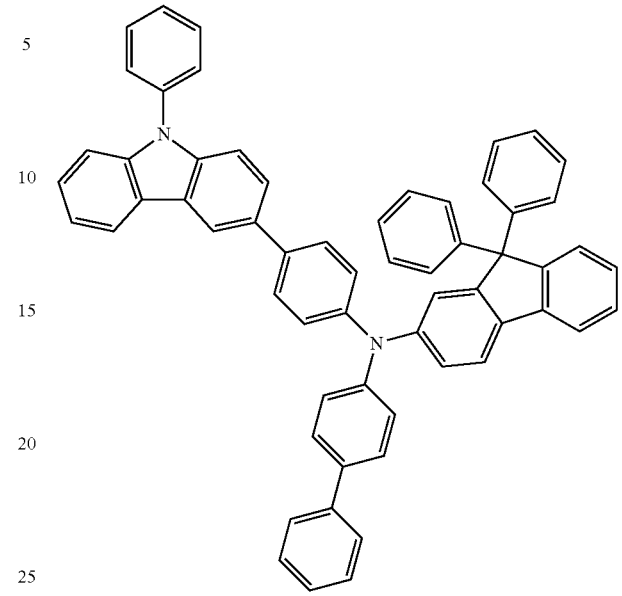
HT4
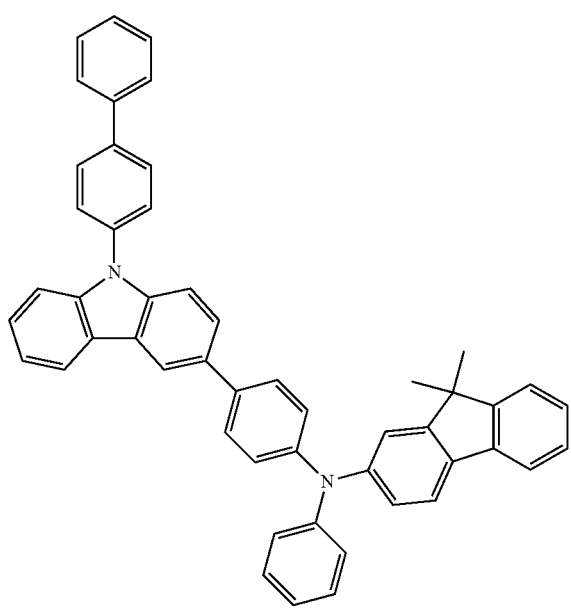
HT6
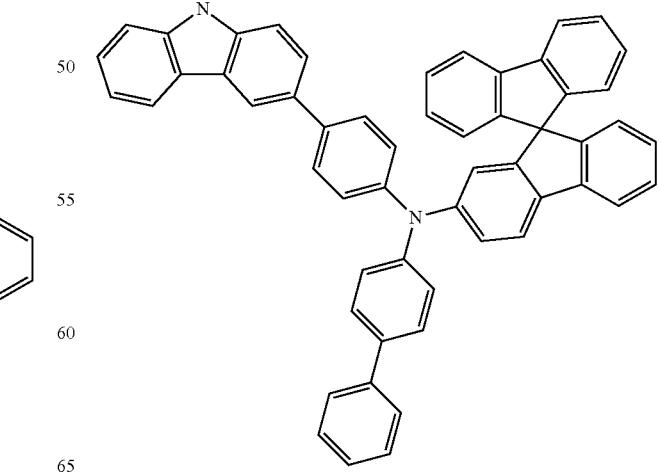

HT7
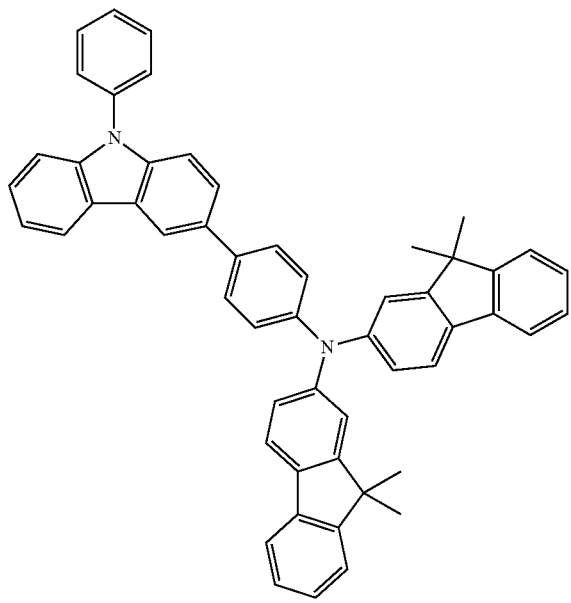
HT9
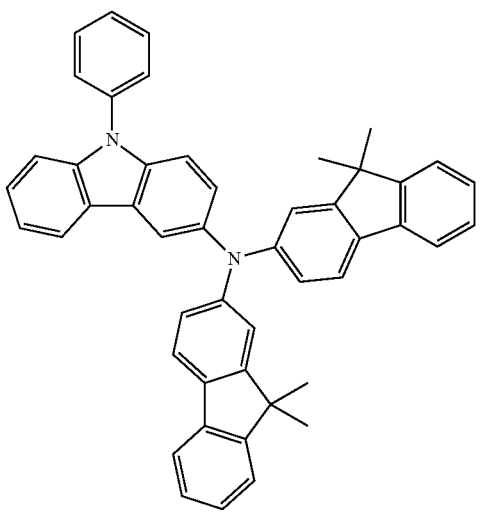
HT8
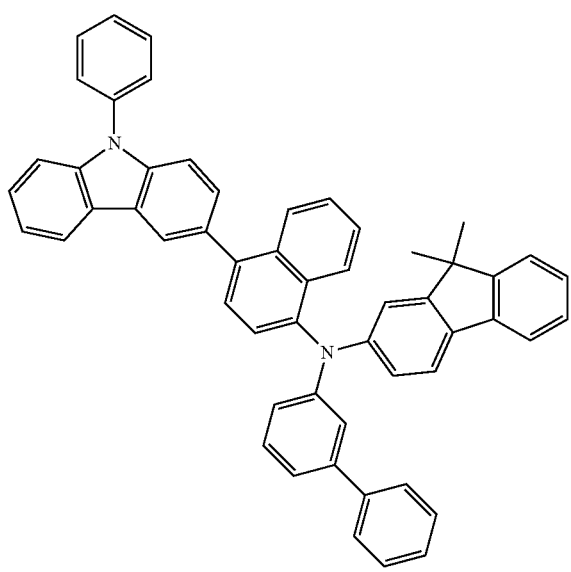
HT10
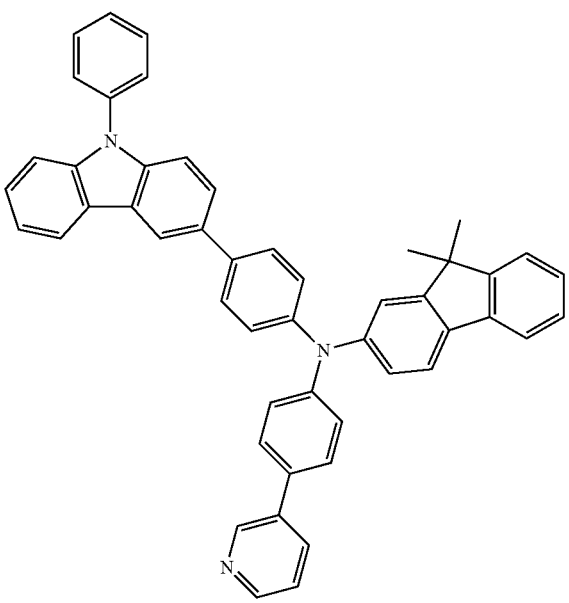

HT11
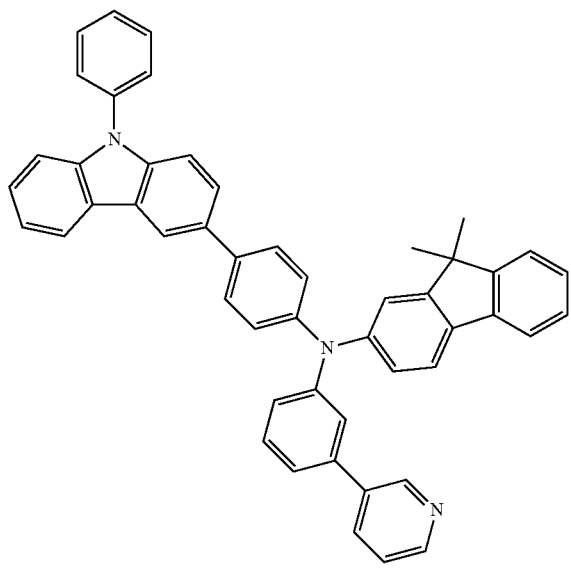
HT12
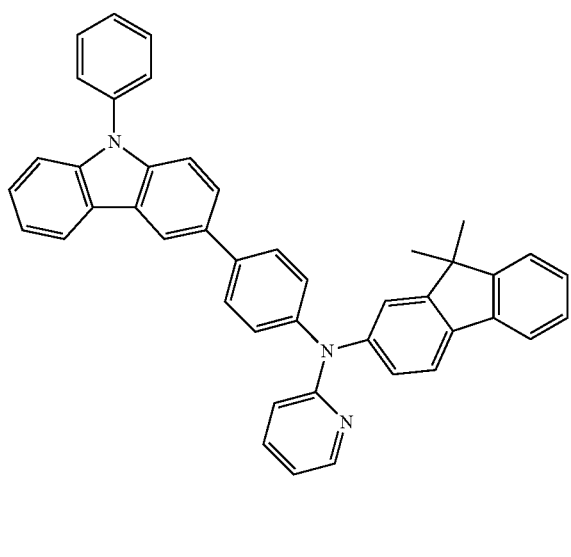
HT13
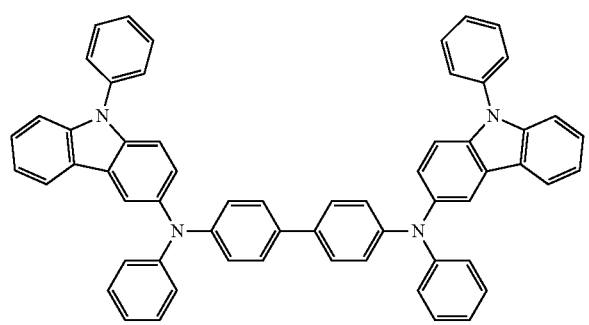
HT14
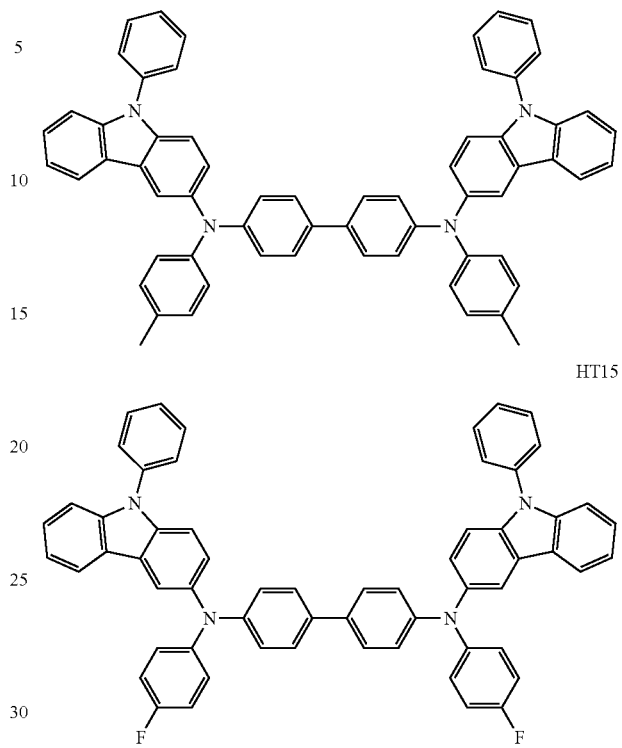
HT15
HT16
HT17
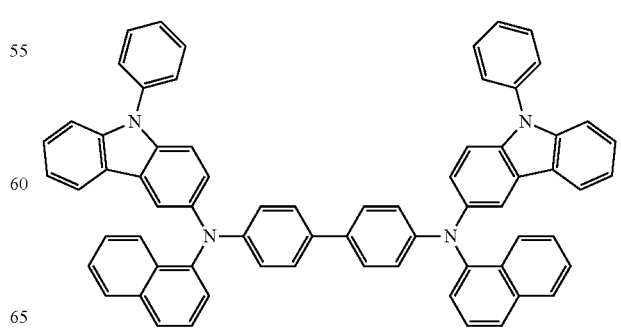

-continued

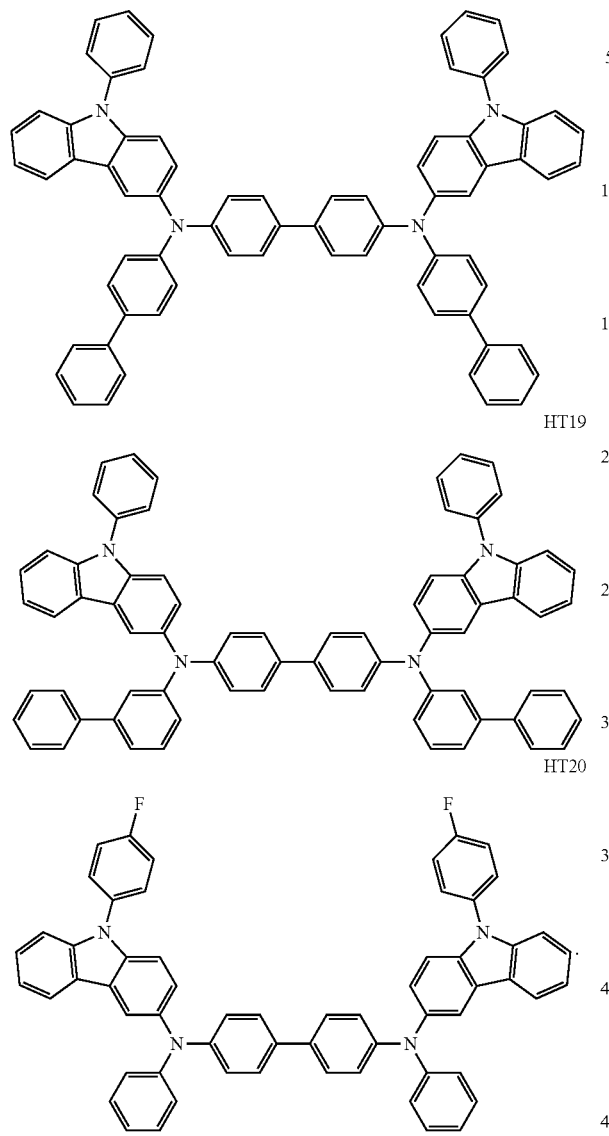

HT18

HT19

HT20

The thickness of the hole transport region may be about 100 Å to about 10,000 Å, and in some embodiments, about 100 Å to about 1,000 Å. When the hole transport region includes a hole injection layer and a hole transport layer, the thickness of the hole injection layer may be about 100 Å to about 10,000 Å, and in some embodiments, about 100 Å to about 1,000 Å; the thickness of the hole transport layer may be about 50 Å to about 2,000 Å, and in some embodiments, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include a charge-generating material in addition to the abovementioned materials to improve conductive properties. The charge-generating material may be homogeneously and/or non-homogeneously dispersed throughout the hole transport region.

The charge-generating material may be, for example, a p-dopant. The p-dopant may be selected from a quinone derivative, a metal oxide, and a cyano group-containing compound, but embodiments of the present disclosure are not limited thereto. Non-limiting examples of the p-dopant may include quinone derivatives (such as tetracyanoquinonedimethane (TCNQ) and/or 2,3,5,6-tetrafluoro-tetracyano-1,4-benzoquinonedimethane (F4-TCNQ)); metal oxides (such as a tungsten oxide and/or a molybdenum oxide); and Compound HT-D1, but embodiments of the present disclosure are not limited thereto:

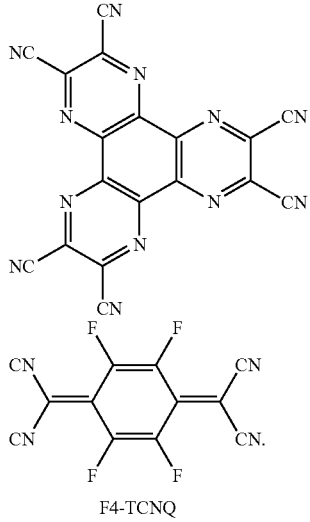

Compound HT-D1

F4-TCNQ

The hole transport region may further include, in addition to the hole injection layer and the hole transport layer, at least one selected from a buffer layer and an electron blocking layer. Since the buffer layer may compensate for an optical resonance distance according to a wavelength of light emitted from the emission layer (e.g., be used to adjust the optical resonance distance to match the wavelength of light emitted from the emission layer), the light-emission efficiency of the resulting organic light-emitting device may be improved. Materials included in the hole transport region may be used as materials in the buffer layer. In some embodiments, the electron blocking layer prevents or reduces injection of electrons from the electron transport region.

An emission layer may be formed on the first electrode 110 and/or on the hole transport region using one or more suitable methods, such as vacuum deposition, spin coating, casting, an LB method, ink-jet printing, laser printing, and/or LITI. When the emission layer is formed by vacuum deposition and/or spin coating, the deposition and coating conditions used for the emission layer may be similar to the deposition and coating conditions used for the hole injection layer.

When the organic light-emitting device 10 is a full color organic light-emitting device, the emission layer may be patterned into a red emission layer, a green emission layer, and/or a blue emission layer, according to a sub-pixel. In some embodiments, the emission layer may have a stacked structure of a red emission layer, a green emission layer, and a blue emission layer, and/or may include a red-light emission material, a green-light emission material, and a blue-light emission material, which are mixed with each other in a single layer to emit white light.

The emission layer may include a host and/or a dopant. The host may include at least one selected from an anthracene-based compound, arylamine-based compound, and a styryl-based compound.

In some embodiments, the host may further include a compound represented by Formula 301:

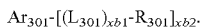

Ar$_{301}$-[(L$_{301}$)$_{xb1}$-R$_{301}$]$_{xb2}$.  Formula 301

In Formula 301,

Ar$_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si(Q$_{301}$)(Q$_{302}$)(Q$_{303}$), wherein Q$_{301}$ to Q$_{303}$ may be each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group, L$_{301}$ may be the same as described herein in connection with L$_1$, R$_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

In some embodiments, in Formula 301,

L$_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and R$_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments are not limited thereto.

In some embodiment, the host may include a compound represented by Formula 301A:

Formula 301A

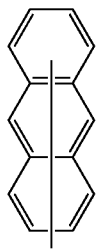

$[(L_{301})_{xb1}$—$R_{301}]_{xb2}$.

In Formula 301A, $L_{301}$, $R_{301}$, xb1, and xb2 may each be the same as described herein in connection with Formula 301.

The compound represented by Formula 301 may include at least one compound selected from Compounds H1 to H42, but embodiments of the present disclosure are not limited thereto:

H1

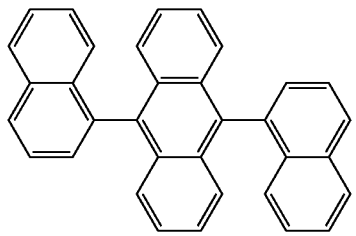

H2

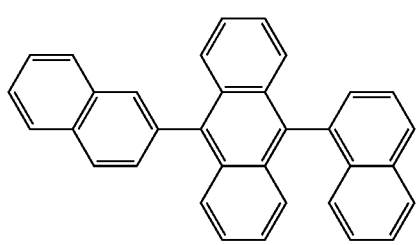

H3

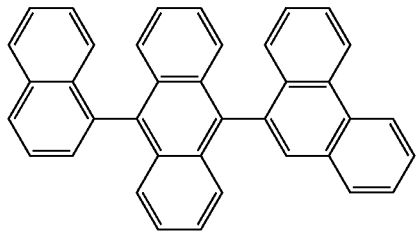

H4

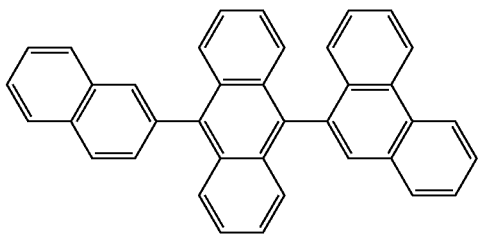

H5

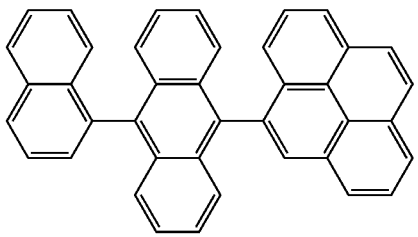

H6

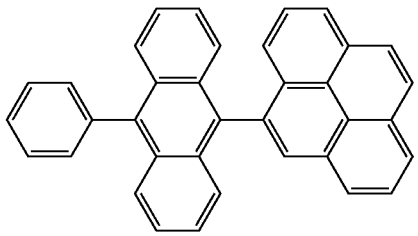

H7

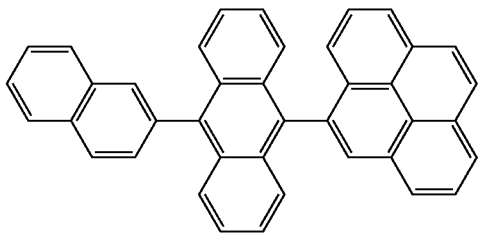

H8

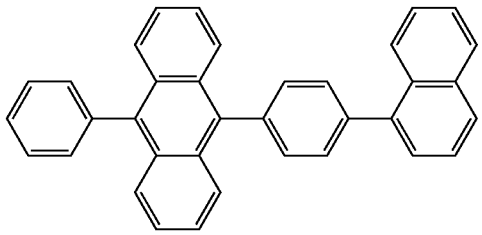

H9

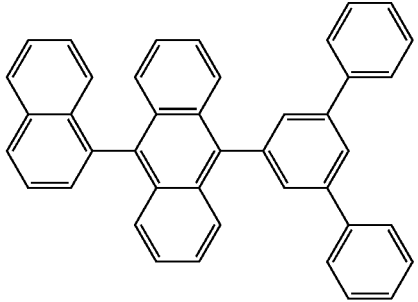

H10
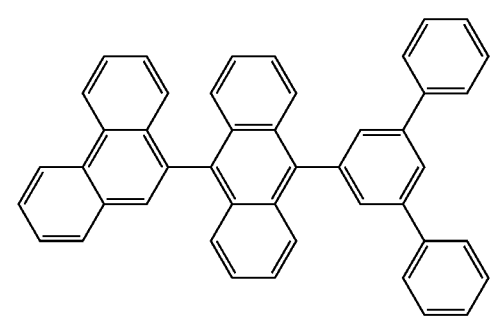
H11
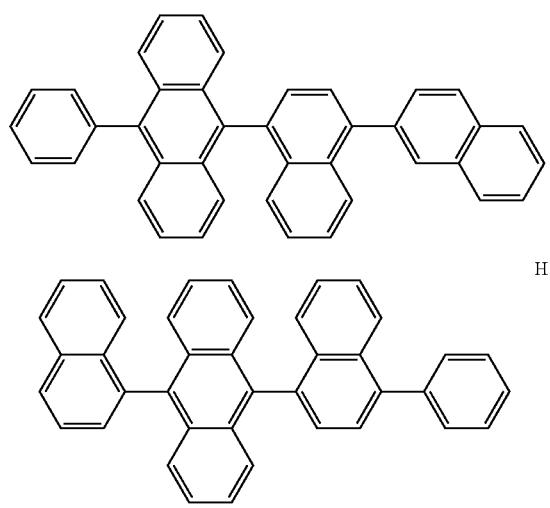
H12
H13
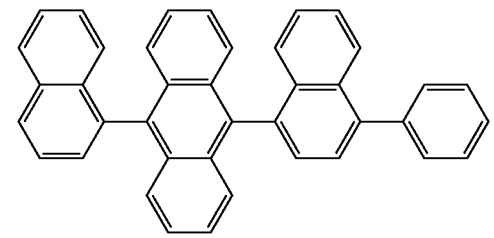
H14
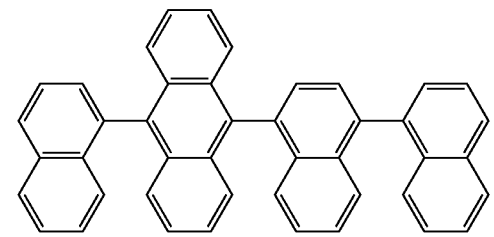
H15
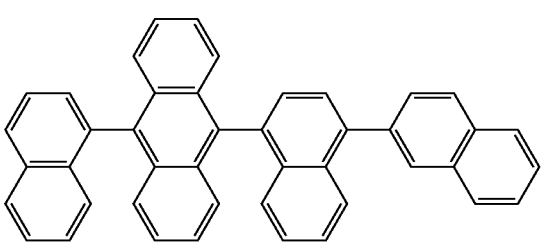
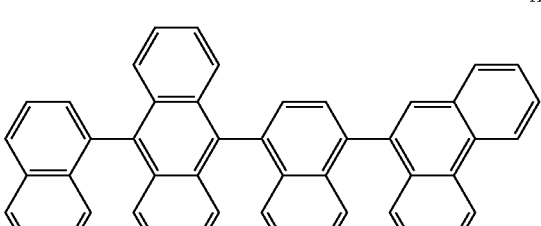
H16
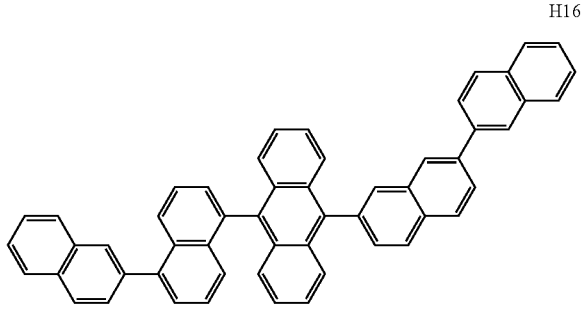
H17
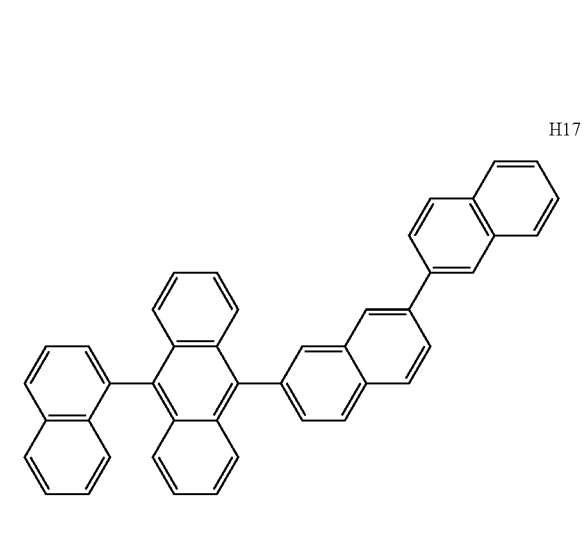
H18
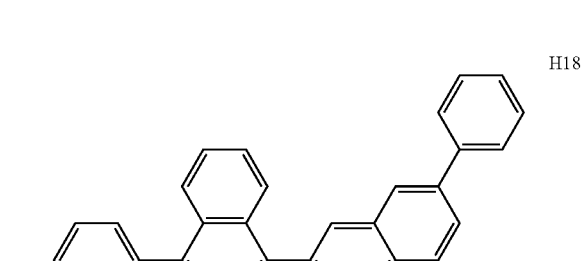
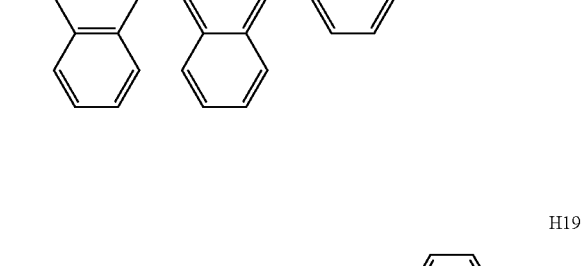
H19
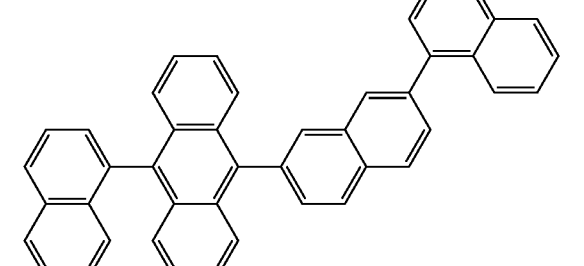

-continued
H20
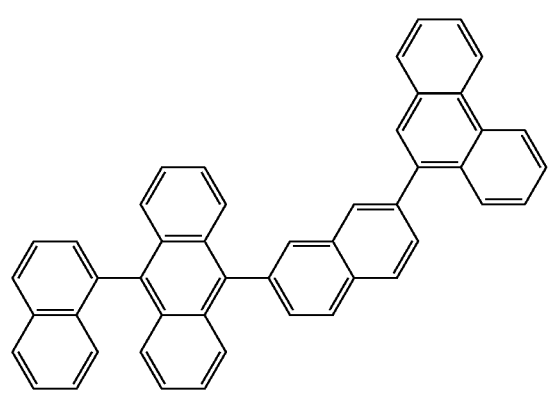
H21
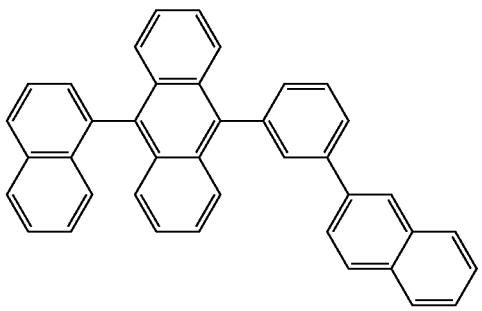
H22
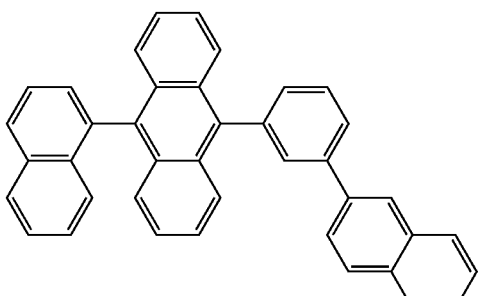
H23
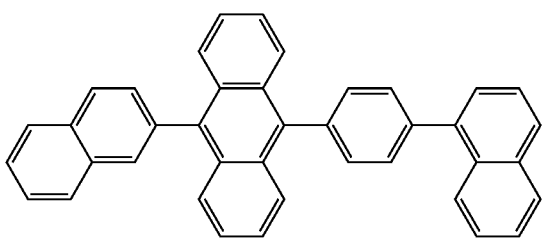
H24
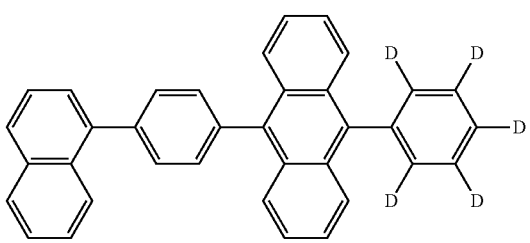
-continued
H25
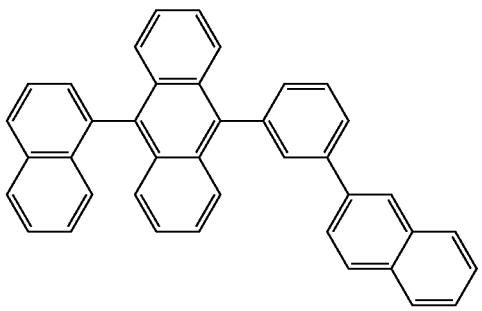
H26
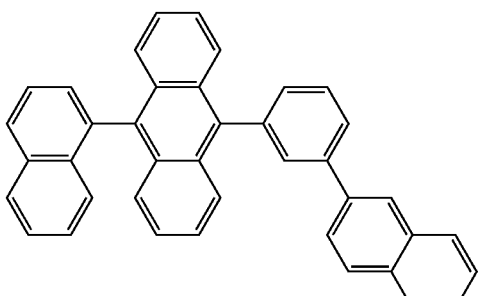
H27
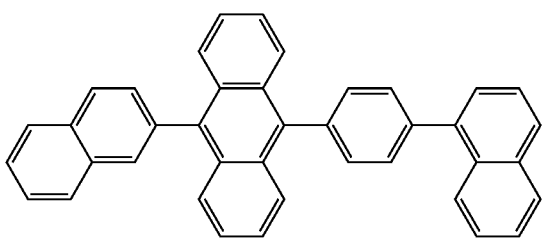
H28
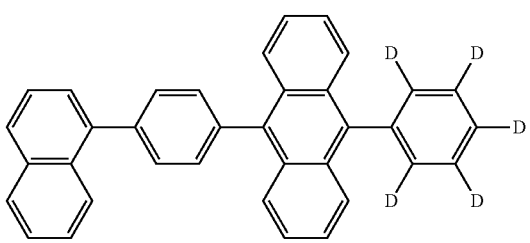
H29
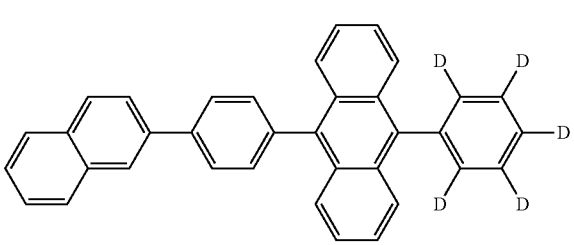
H30
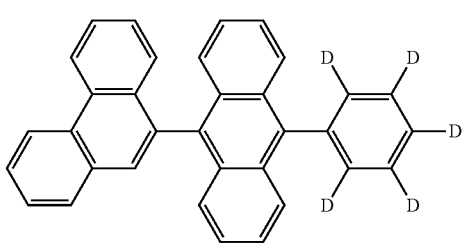

H31
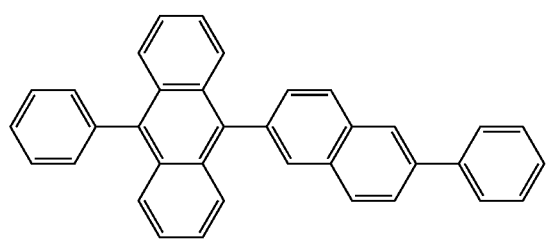
H32
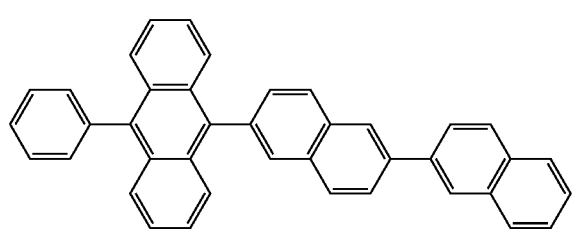
H33
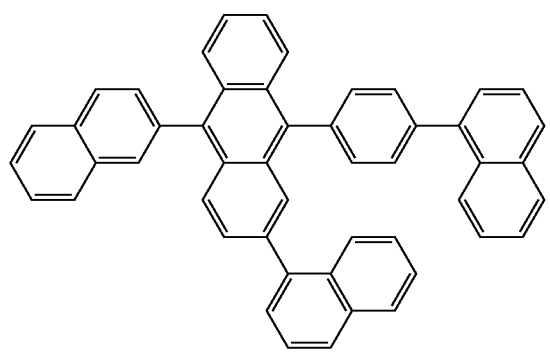
H34
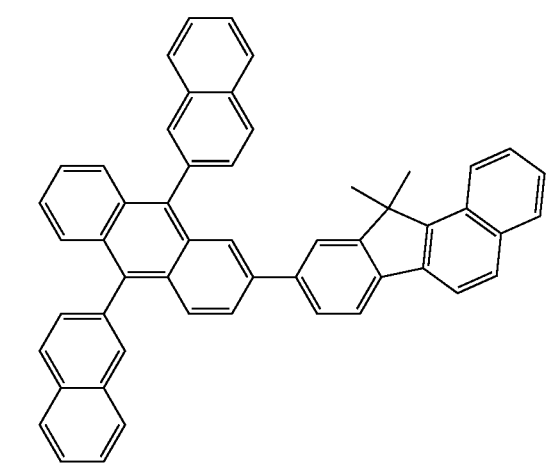
H35
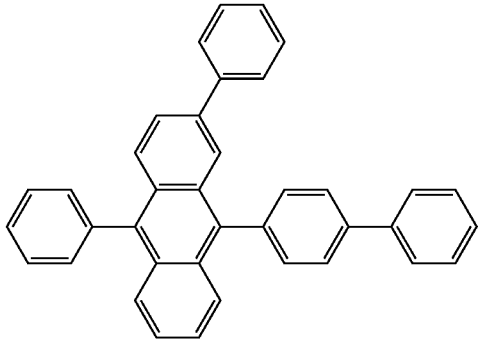
H36
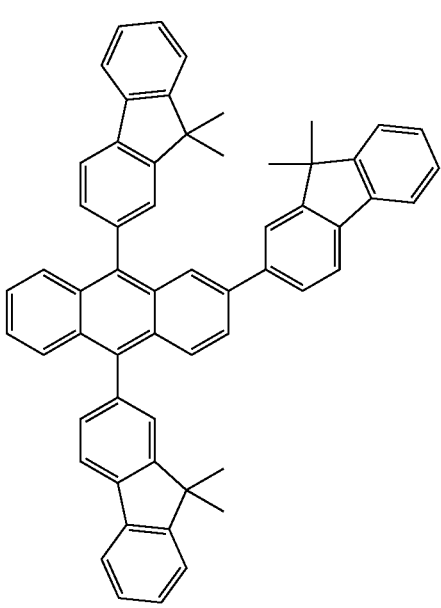
H37
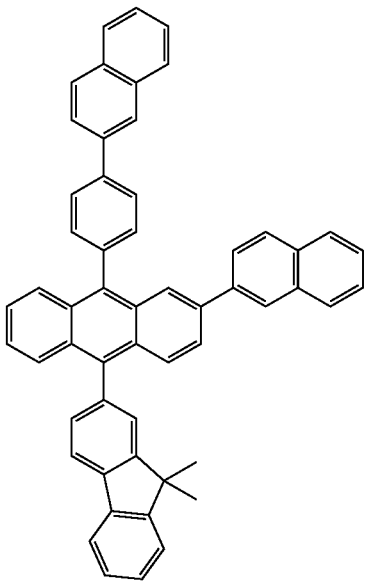

H38
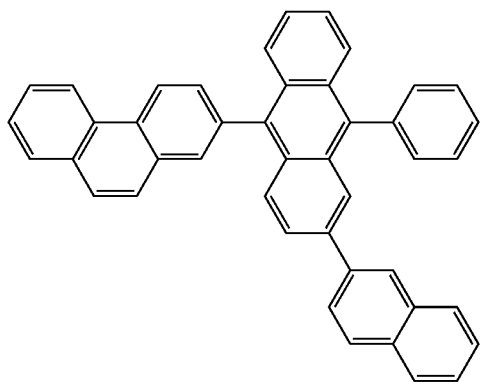
H39
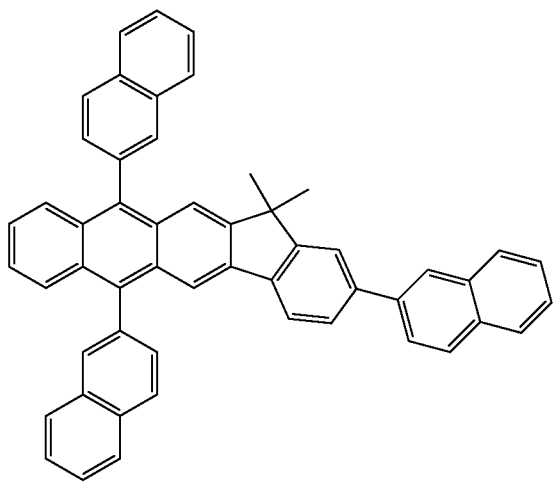
H40
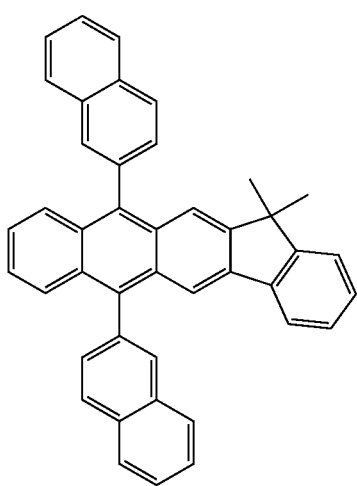
H41
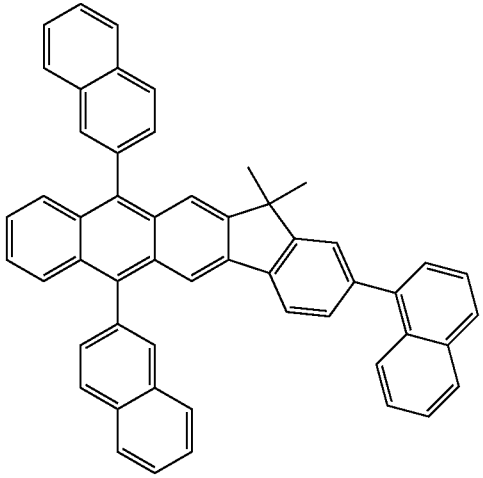
H42
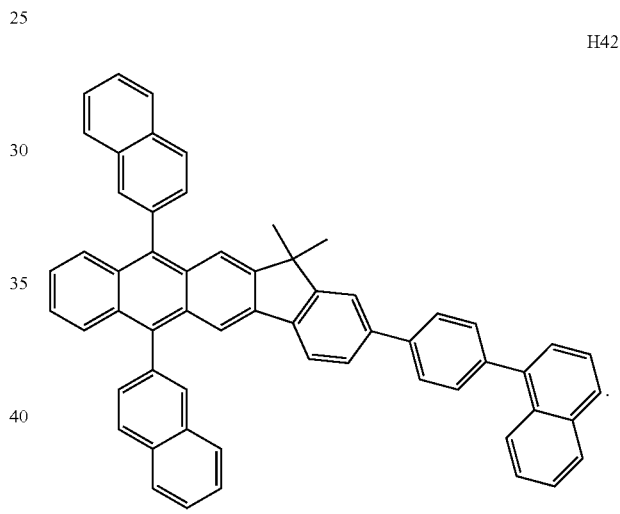
In some embodiments, the host may include at least one selected from Compounds H43 to H49, but embodiments of the present disclosure are not limited thereto:
H43
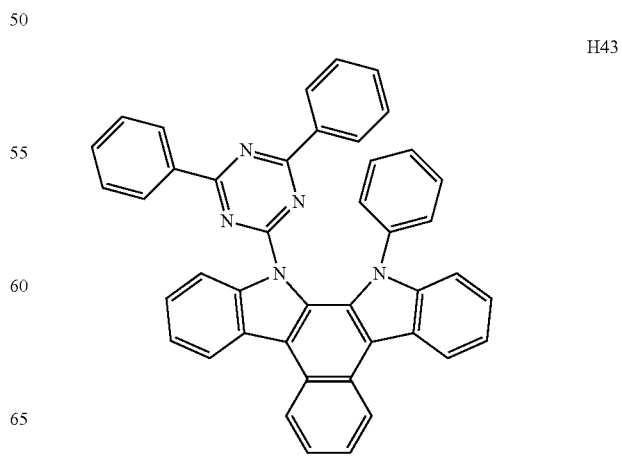

H44
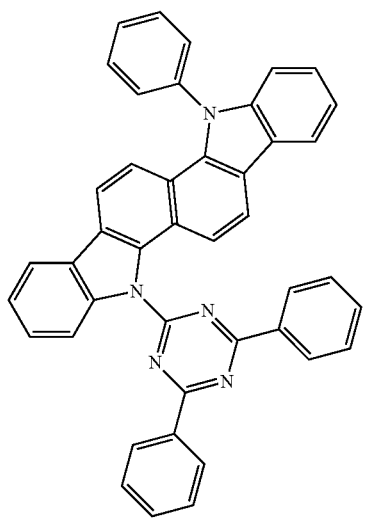
H45
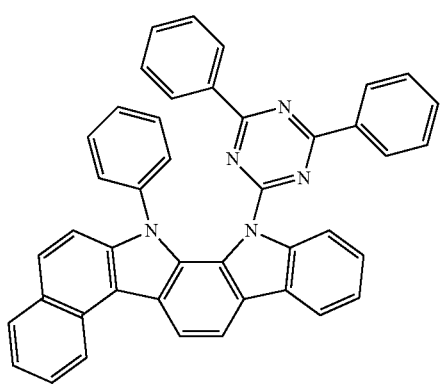
H46
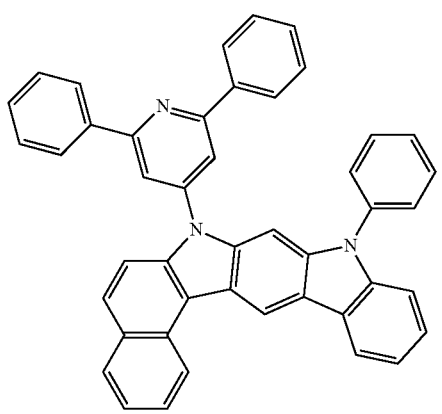
H47
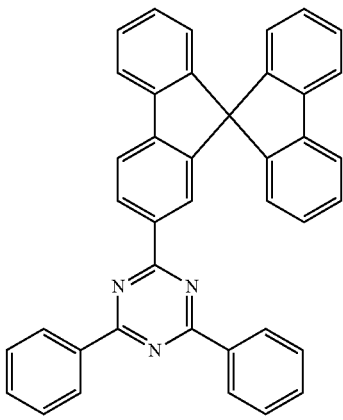
H48
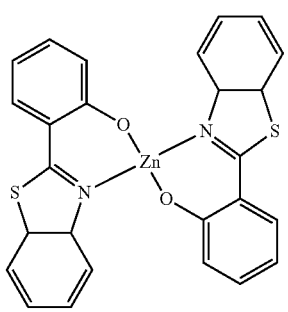
H49
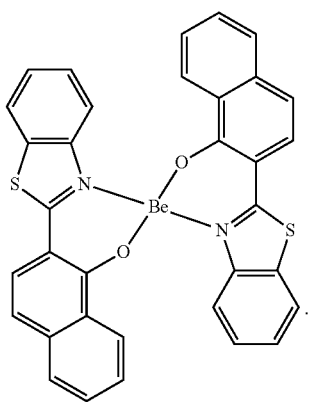
In some embodiments, the host may include at least one selected from TPBi, TBADN, ADN (also known as "DNA"), CBP, CDBP, TCP, and MADN:

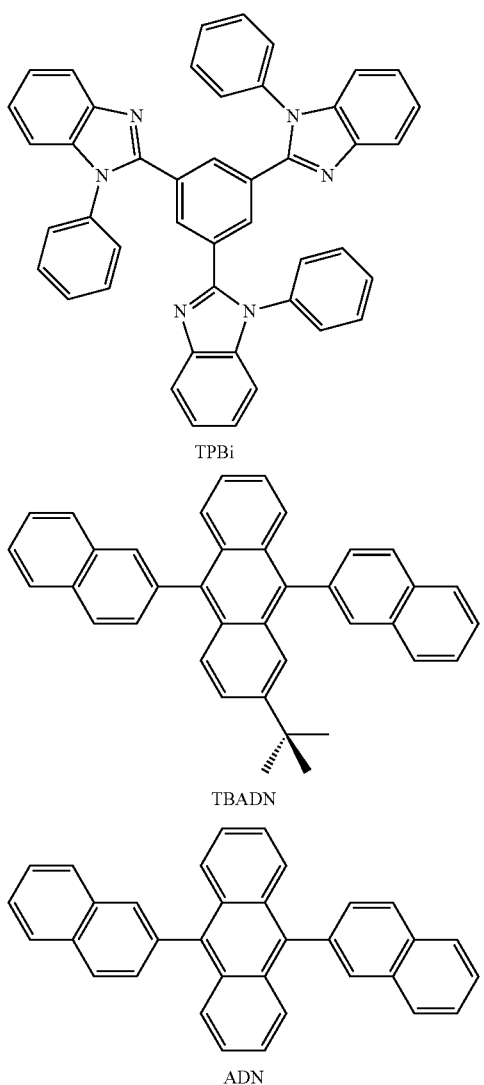

TPBi

TBADN

ADN

CBP

CDBP

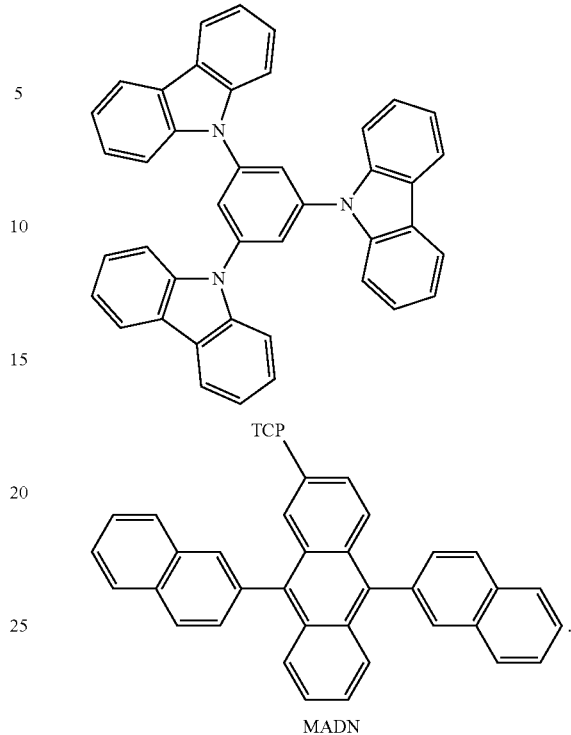

TCP

MADN

The dopant in the emission layer may include at least one selected from a fluorescent dopant and a phosphorescent dopant.

In some embodiments, the phosphorescent dopant may include an organometallic compound including at least one selected from iridium (Ir), platinum (Pt), osmium (Os), titanium (Ti), zirconium (Zr), hafnium (Hf), europium (Eu), terbium (Tb), thulium (Tm), rhodium (Rh), and copper (Cu).

In some embodiments, the phosphorescent dopant may include an organometallic complex represented by Formula 401:

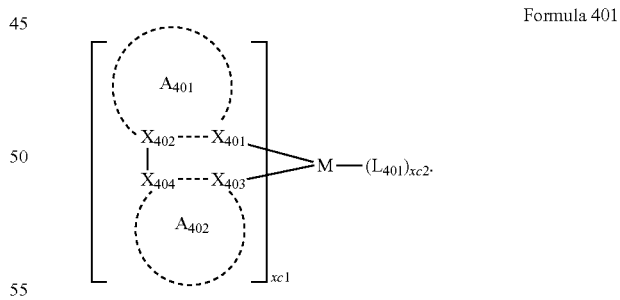

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may each independently be selected from nitrogen and carbon, $A_{401}$ and $A_{402}$ rings may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one substituent of the substituted benzene, substituted naphthalene, substituted fluorene, substituted spirofluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, $C_6$-$C_{60}$ arylthio group, $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), $L_{401}$ may be an organic ligand, xc1 may be selected from 1, 2, and 3, and xc2 may be selected from 0, 1, 2, and 3.

$Q_{401}$ to $Q_{407}$, $Q_{411}$ to $Q_{417}$, and $Q_{421}$ to $Q_{427}$ may be the same as described herein in connection with $Q_1$.

$L_{401}$ may be any suitable monovalent, divalent, and/or trivalent organic ligand. For example, $L_{401}$ may be selected from a halogen ligand (e.g., Cl and/or F), a diketone ligand (e.g., acetylacetonate, 1,3-diphenyl-1,3-propanedionate, 2,2,6,6-tetramethyl-3,5-heptanedionate, and/or hexafluoroacetonate), a carboxylic acid ligand (e.g., picolinate, dimethyl-3-pyrazolecarboxylate, and/or benzoate), a carbon monoxide ligand, an isonitrile ligand, a cyano ligand, and a phosphorous ligand (e.g., phosphine and/or phosphite), but embodiments of the present disclosure are not limited thereto.

When $A_{401}$ in Formula 401 includes a plurality of substituents, the plurality of substituents of $A_{401}$ may be bound (e.g., coupled) to each other to form a saturated or unsaturated ring.

When $A_{402}$ in Formula 401 includes a plurality of substituents, the plurality of substituents of $A_{402}$ may be bound (e.g., coupled) to each other to form a saturated or unsaturated ring.

When xc1 in Formula 401 is two or more, a plurality of ligands

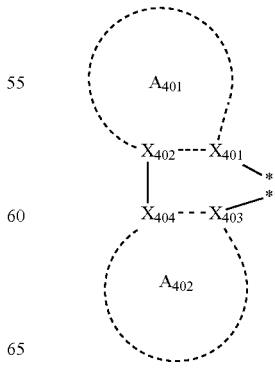

in Formula 401 may be identical to or different from each other. In Formula 401, when xc1 is 2 or more, $A_{401}$ and $A_{402}$ may each be directly connected (e.g., by a bond) and/or connected via a linking group (e.g., a $C_1$-$C_5$ alkylene group, —N(R')— (where R' may be a $C_1$-$C_{10}$ alkyl group and/or a $C_6$-$C_{20}$ aryl group), and/or —C(=O)—) to another adjacent ligand of $A_{401}$ and $A_{402}$, respectively.

The phosphorescent dopant may include at least one selected from Compounds PD1 to PD75, but embodiments of the present disclosure are not limited thereto:

PD1
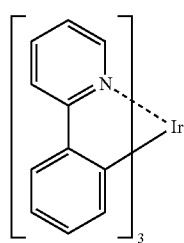

PD2
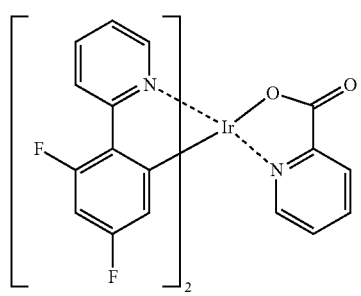

PD3
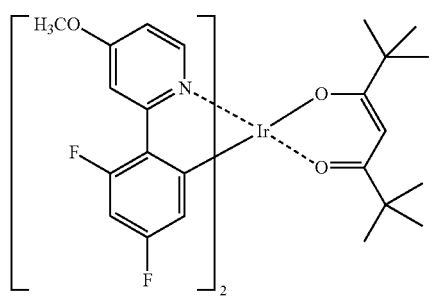

PD4
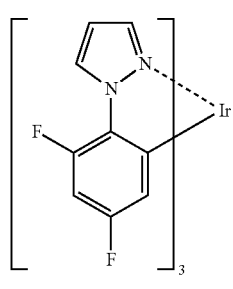

PD5
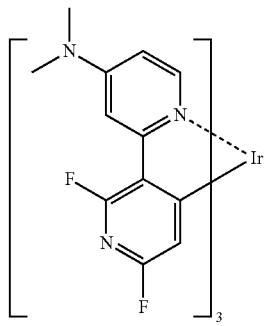

PD6
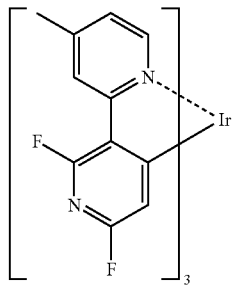

PD7
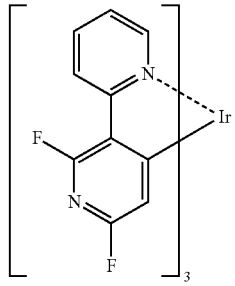

PD8
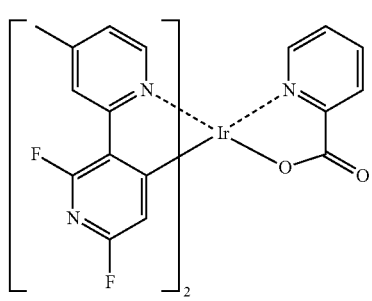

PD9
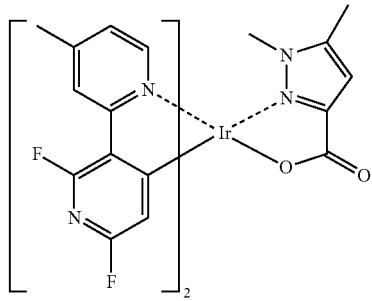

PD10 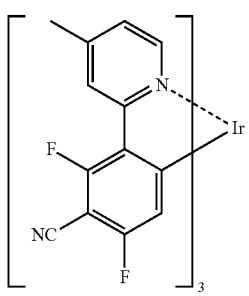
PD11 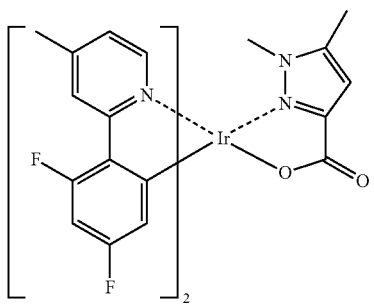
PD12 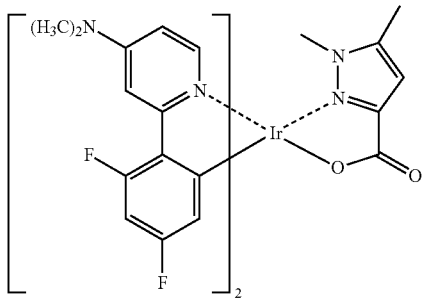
PD13 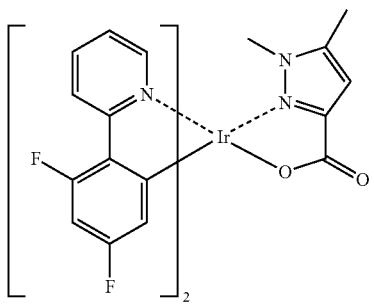
PD14 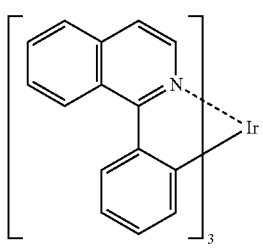
PD15 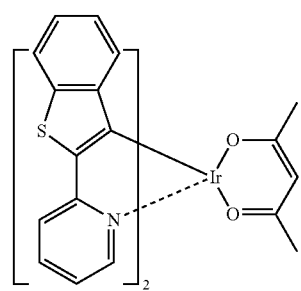
PD16 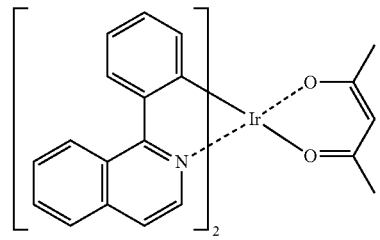
PD17 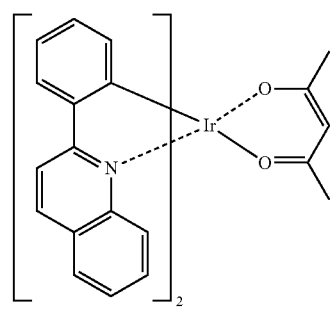
PD18 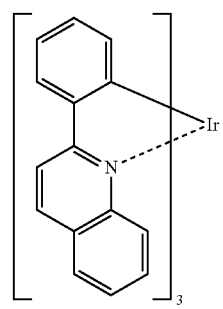
PD19 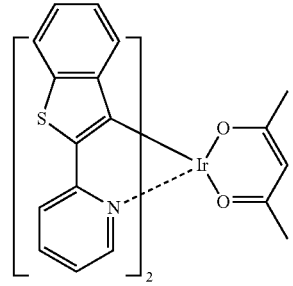

PD20
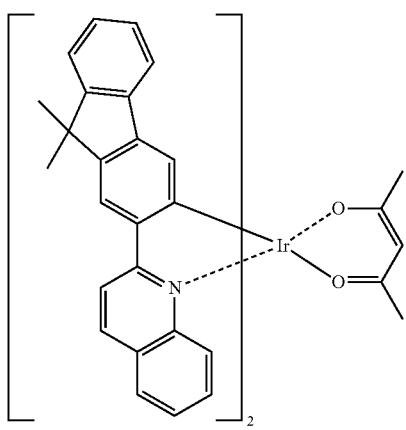
PD21
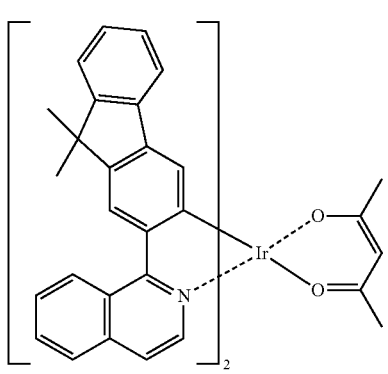
PD22
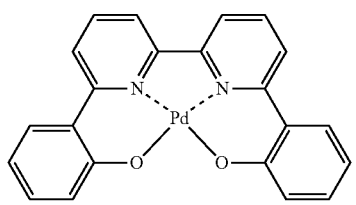
PD23
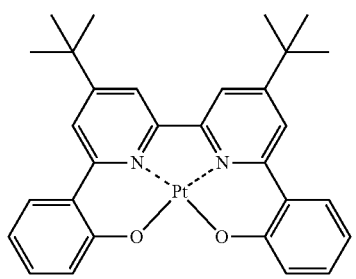
PD24
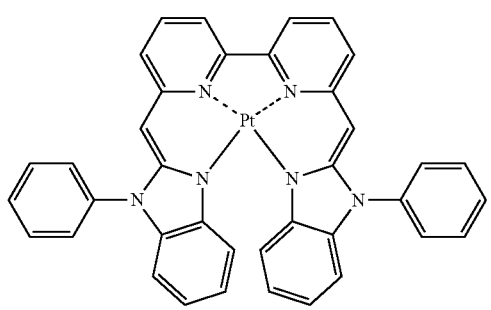
PD25
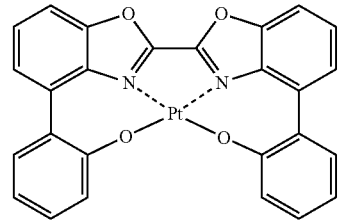
PD26
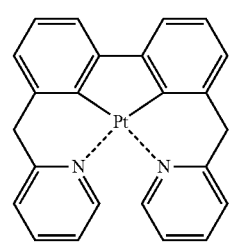
PD27
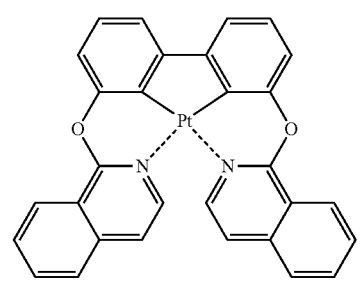
PD28
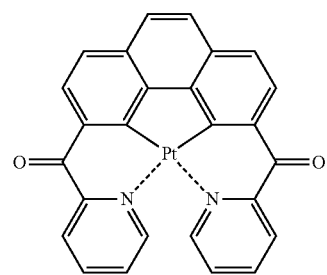
PD29
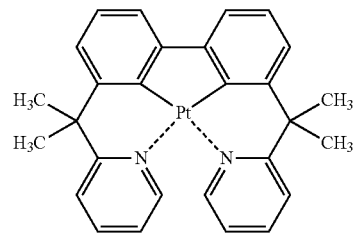
PD30
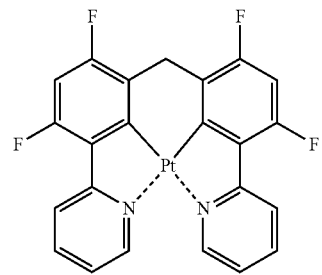

PD31 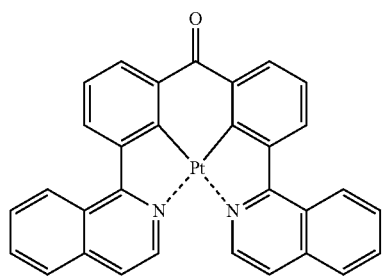
PD32 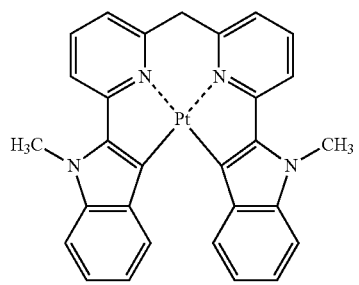
PD33 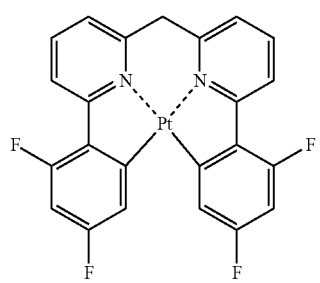
PD34 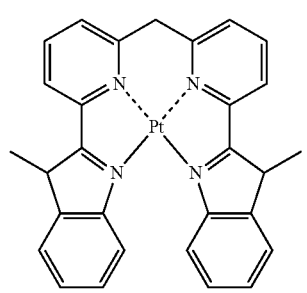
PD35 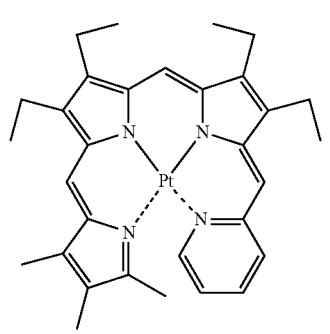
PD36 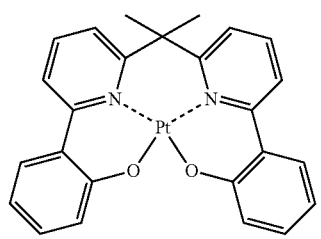
PD37 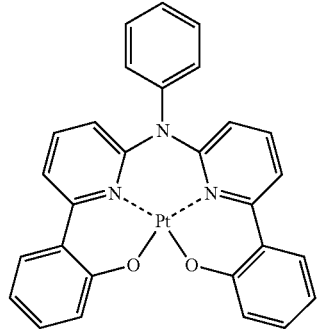
PD38 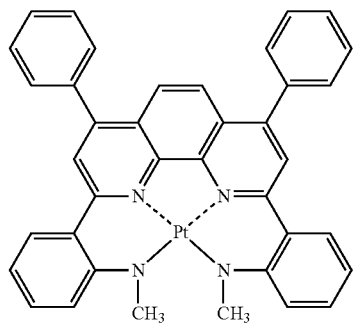
PD39 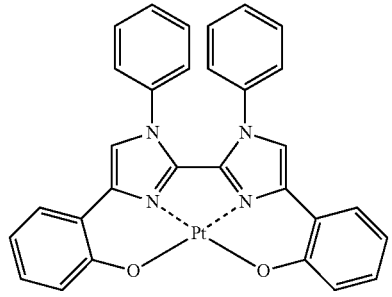
PD40 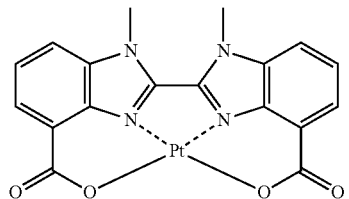
PD41 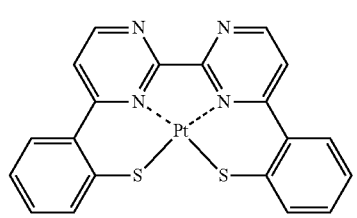

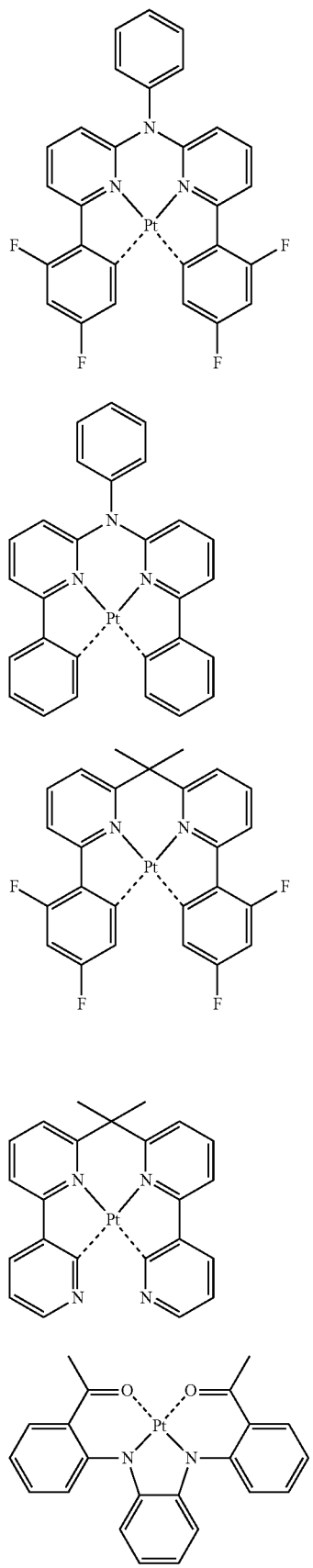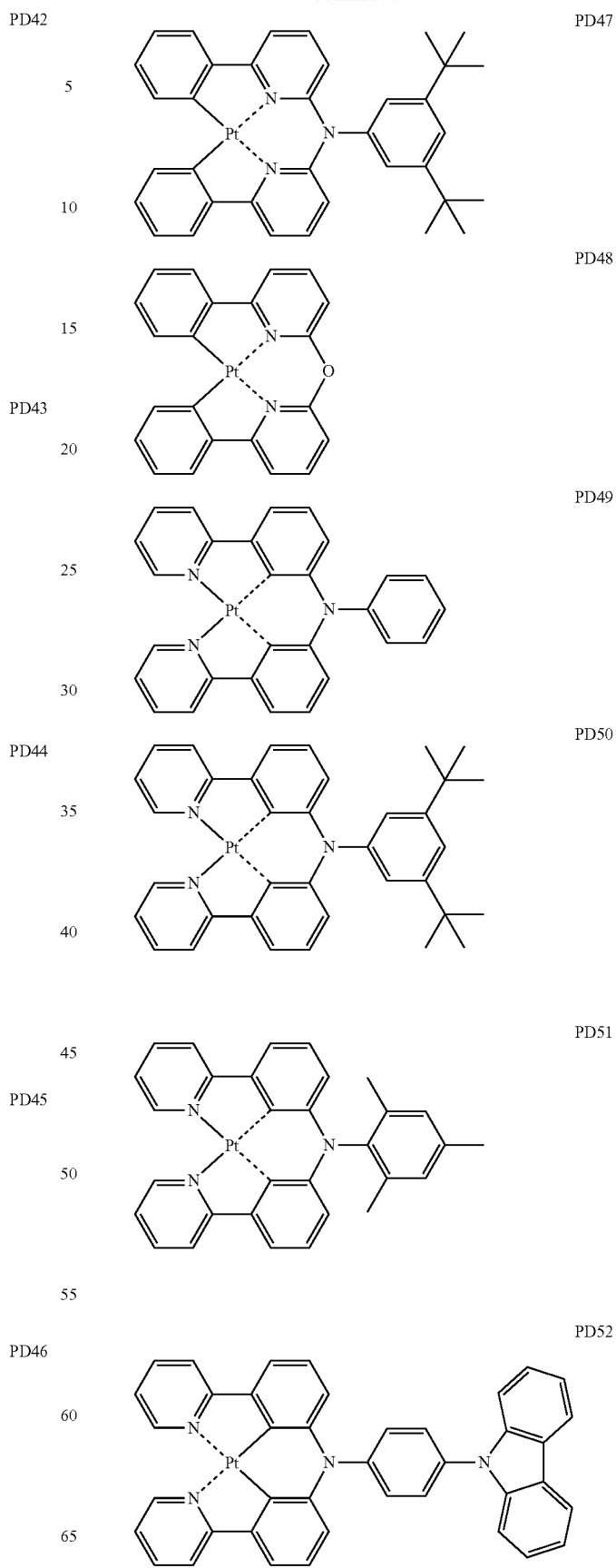

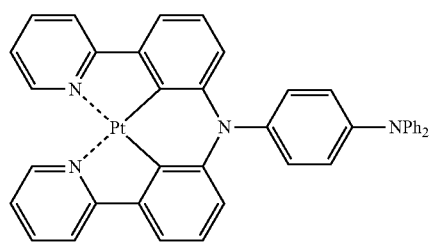
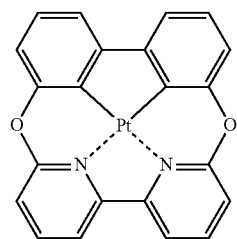
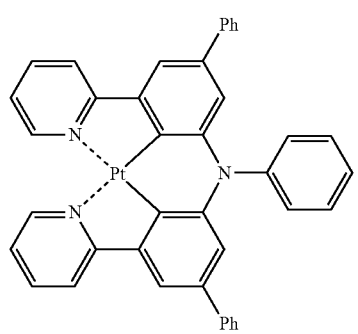
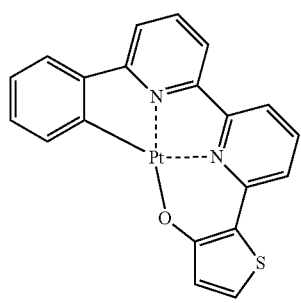
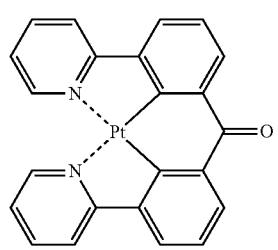
PD53
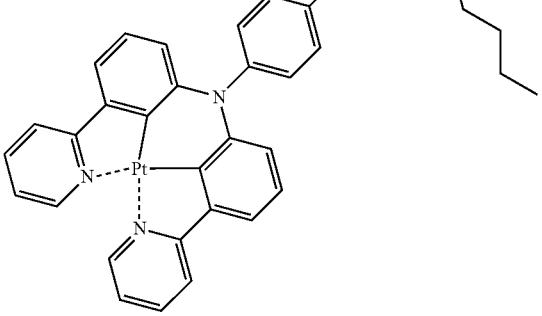
PD54
PD55
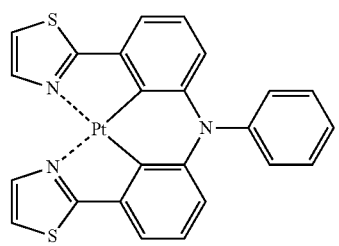
PD56
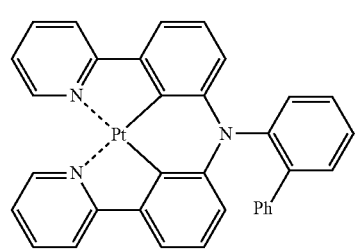
PD57
PD58
PD59
PD60
PD61
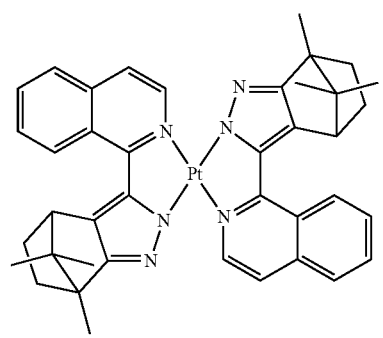
PD62
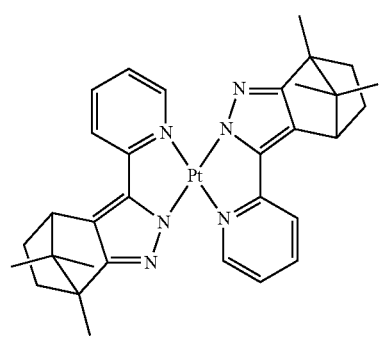

PD63 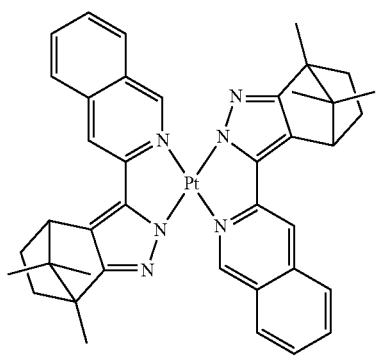
PD64 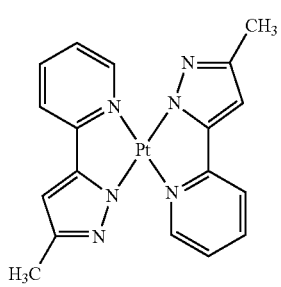
PD65 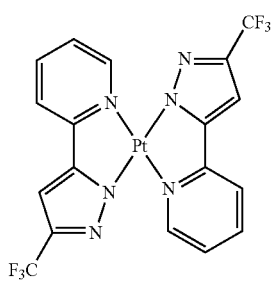
PD66 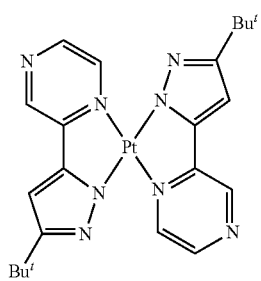
PD67 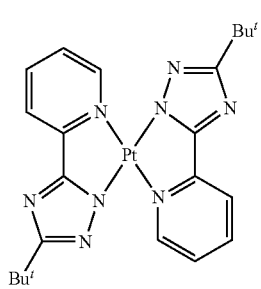
PD68 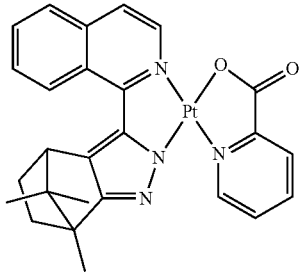
PD69 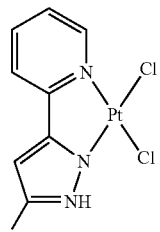
PD70 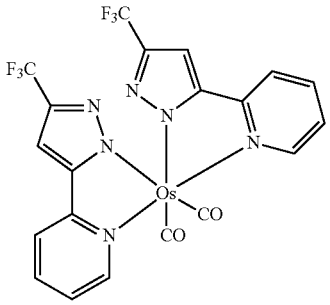
PD71 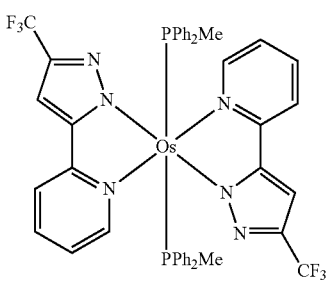
PD72 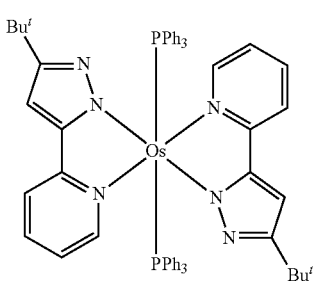

-continued
PD73 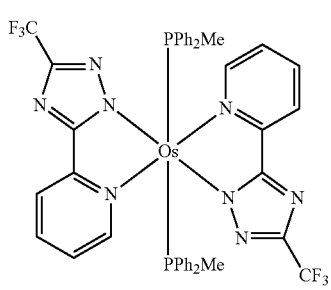
PD74 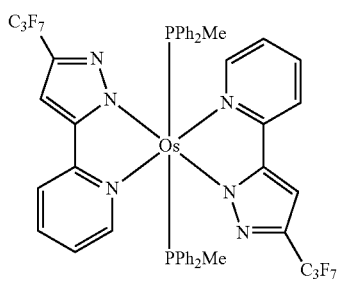
PD75 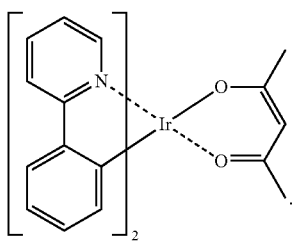
In some embodiments, the phosphorescent dopant may include PtOEP:
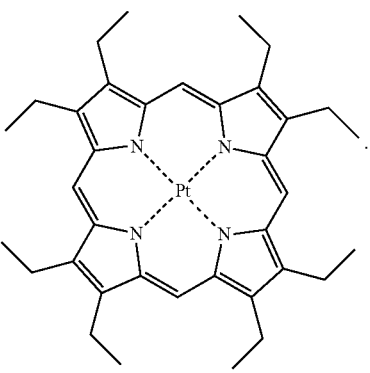
PtOEP
The fluorescent dopant may include at least one selected from DPVBi, DPAVBi, TBPe, DCM, DCJTB, Coumarin 6, and C545T:
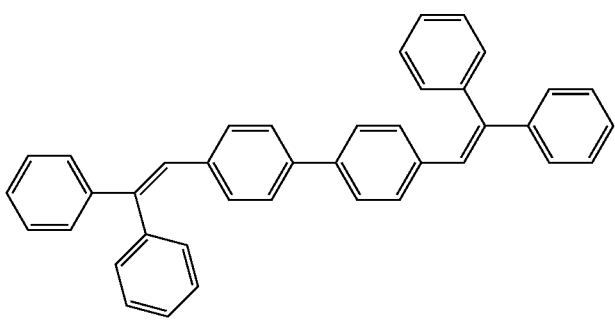
DPVBi
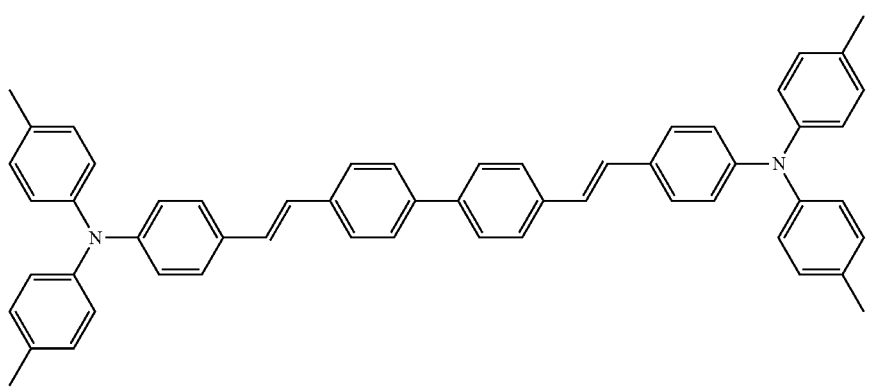
DPAVBi

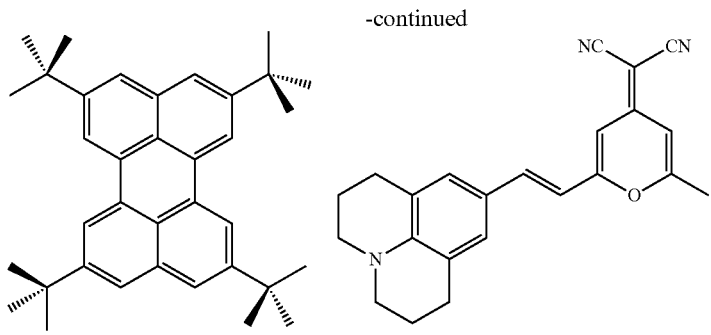

TBPe

DCM

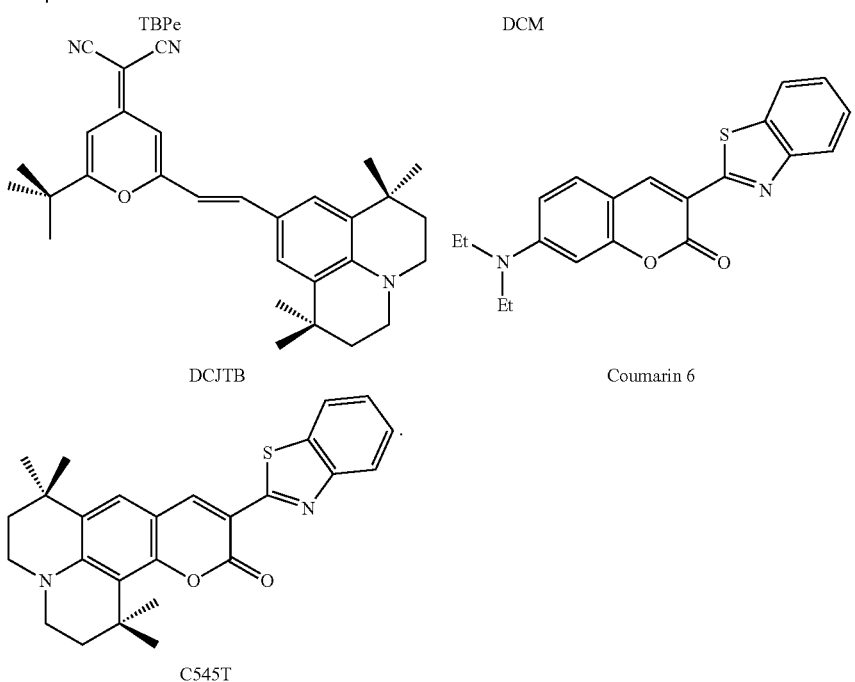

DCJTB

Coumarin 6

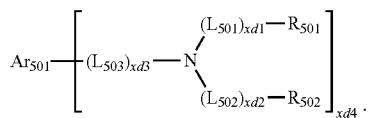

C545T

In some embodiments, the fluorescent dopant may include a compound represented by Formula 501:

Formula 501

$$Ar_{501}\!\!-\!\!\left[(L_{503})_{xd3}\!-\!N\!\!\begin{array}{c}(L_{501})_{xd1}\!-\!R_{501}\\ (L_{502})_{xd2}\!-\!R_{502}\end{array}\right]_{xd4}.$$

In Formula 501, $Ar_{501}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$), wherein $Q_{501}$ to $Q_{503}$ may be each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group, $L_{501}$ to $L_{503}$ may be the same as described herein in connection with $L_1$, $R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3, and xd4 may be selected from 1, 2, 3, and 4.

The fluorescent dopant may include at least one selected from compounds FD1 to FD9:

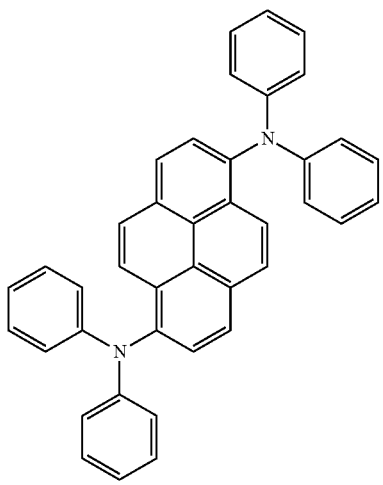

FD1

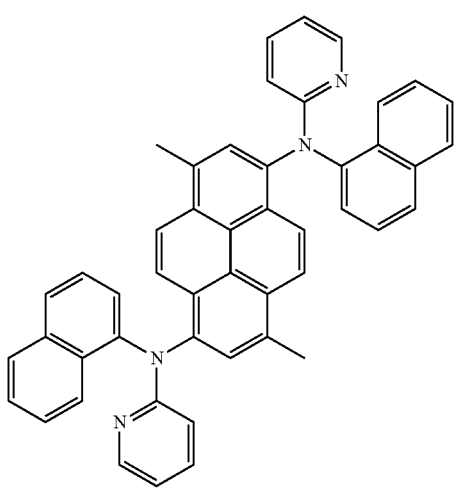

FD2

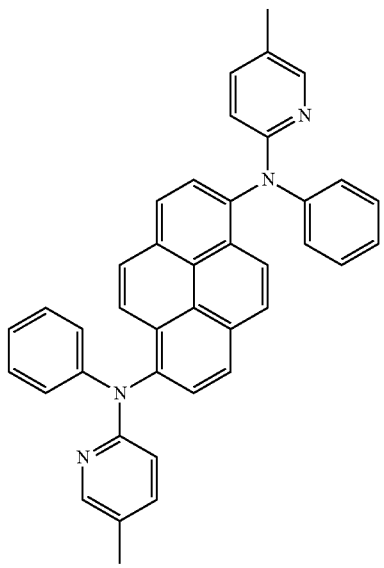

FD3

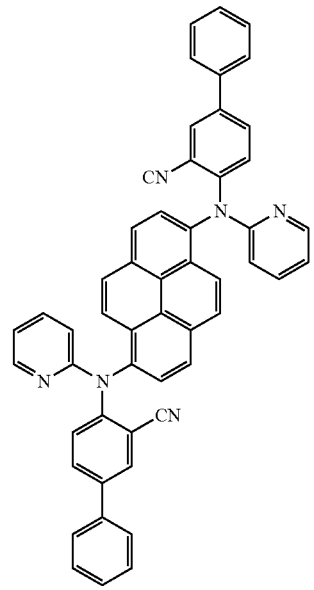

FD4

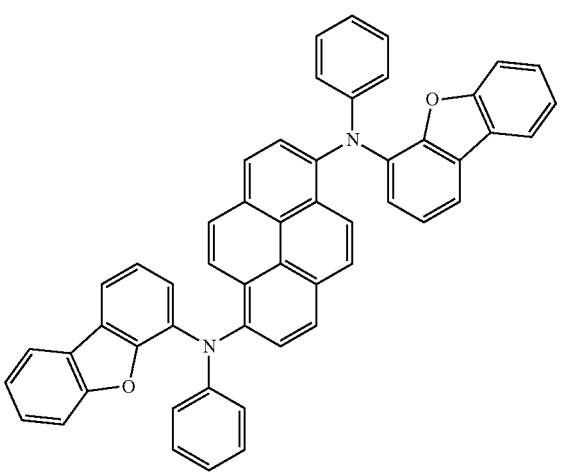

FD5

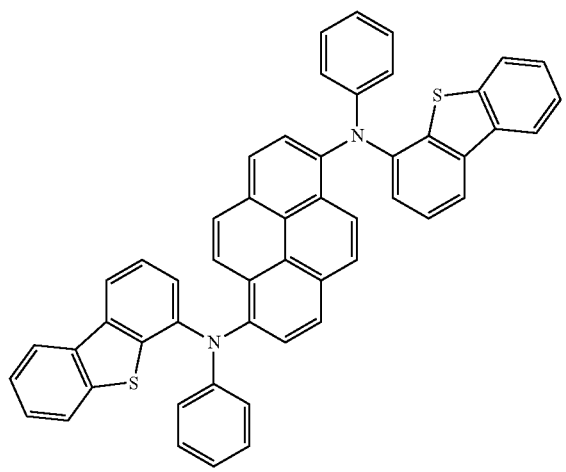
FD6

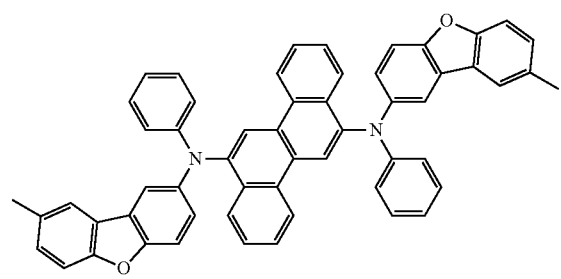
FD7

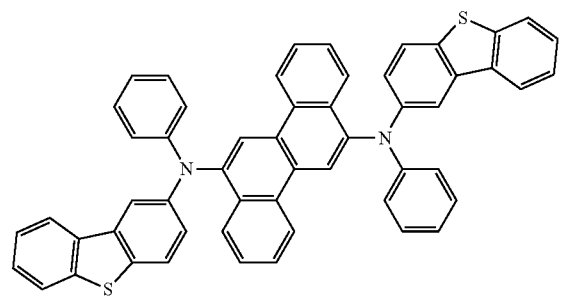
FD8

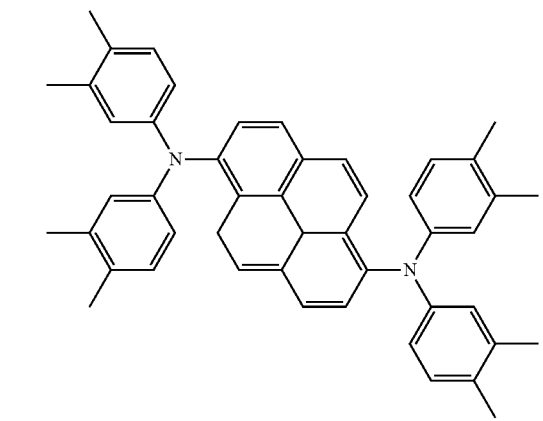
FD9

The amount of the dopant in the emission layer may be about 0.01 part by weight to about 15 parts by weight based on 100 parts by weight of the host, but embodiments of the present disclosure are not limited thereto.

The thickness of the emission layer may be about 100 Å to about 1,000 Å, and in some embodiments, about 200 Å to about 600 Å. When the thickness of the emission layer is within these ranges, excellent light-emission characteristics may be achieved without a substantial increase in driving voltage.

An electron transport region may be on the emission layer.

The electron transport region may include at least one selected from a hole blocking layer, an electron transport layer (ETL), and an electron injection layer, but embodiments of the present disclosure are not limited thereto.

In some embodiments, the electron transport region may have a structure of electron transport layer/electron injection layer and/or a structure of hole blocking layer/electron transport layer/electron injection layer, wherein layers of each structure are sequentially stacked on the emission layer in the stated order, but embodiments of the present disclosure are not limited thereto.

In some embodiments, the organic layer 150 of the organic light-emitting device 10 may include an electron transport region between the emission layer and the second electrode 190.

When the electron transport region includes a hole blocking layer, the hole blocking layer may be formed on the emission layer using one or more suitable methods, such as vacuum deposition, spin coating, casting, an LB method, ink-jet printing, laser printing, and/or LITI. When the hole blocking layer is formed by vacuum deposition and/or spin coating, deposition and coating conditions for the hole blocking layer may be determined by referring to the deposition and coating conditions for the hole injection layer.

The hole blocking layer may include, for example, at least one selected from BCP and Bphen, but embodiments of the present disclosure are not limited thereto:

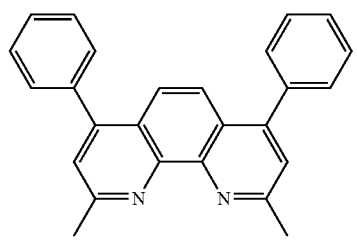
BCP

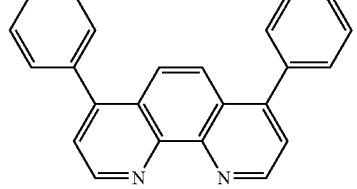
Bphen

The thickness of the hole blocking layer may be about 20 Å to about 1,000 Å, and in some embodiments, about 30 Å to about 300 Å. When the thickness of the hole blocking layer is within these ranges, excellent hole blocking characteristics may be achieved without a substantial increase in driving voltage.

The electron transport region may include an electron transport layer. The electron transport layer may be formed on the emission layer and/or the hole blocking layer using one or more suitable methods, such as vacuum deposition, spin coating, casting, an LB method, ink-jet printing, laser printing, and/or LITI. When the electron transport layer is formed by vacuum deposition and/or spin coating, the vacuum deposition and coating conditions used for the electron transport layer may be determined by referring to the vacuum deposition and coating conditions used for the hole injection layer.

In some embodiments, the electron transport layer may include at least one selected from a compound represented by Formula 601 and a compound represented by Formula 602:

$$Ar_{601}-[(L_{601})_{xe1}-E_{601}]_{xe2}. \quad \text{Formula 601}$$

In Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), wherein $Q_{301}$ to $Q_{303}$ may be each independently selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group, $L_{601}$ may be the same as described herein in connection with $L_1$, $E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, xe1 may be selected from 0, 1, 2, and 3, and xe2 may be selected from 1, 2, 3, and 4.

Formula 602

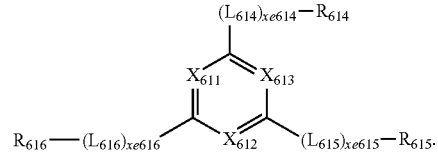

In Formula 602, $X_{611}$ may be selected from N and C-$(L_{611})_{xe611}$-$R_{611}$; $X_{612}$ may be selected from N and C-$(L_{612})_{xe612}$-$R_{612}$; $X_{613}$ may be selected from N and C-$(L_{613})_{xe613}$-$R_{613}$; and at least one selected from $X_{611}$ to $X_{613}$ may be N, L$_{611}$ to L$_{616}$ may each independently be selected from the same groups described herein in connection with L$_1$, R$_{611}$ to R$_{616}$ may each independently be selected from:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xe611 to xe616 may each independently be selected from 0, 1, 2, and 3.

The compound represented by Formula 601 and the compound represented by Formula 602 may each independently be selected from Compounds ET1 to ET15:

ET1

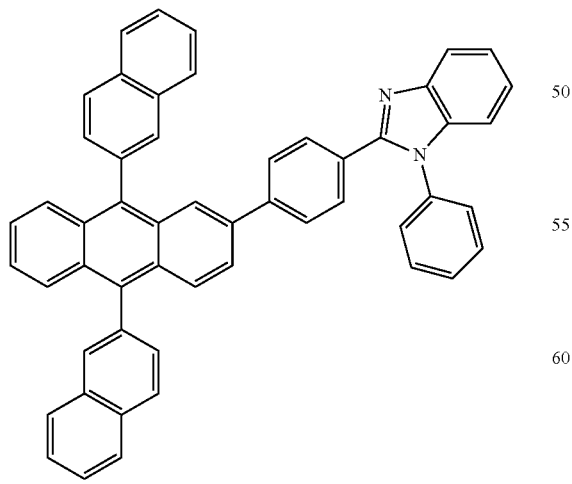

ET2

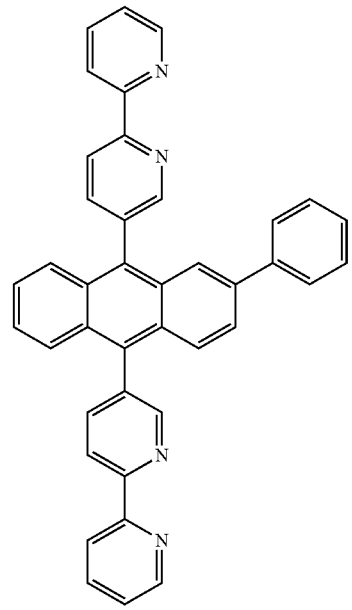

ET3

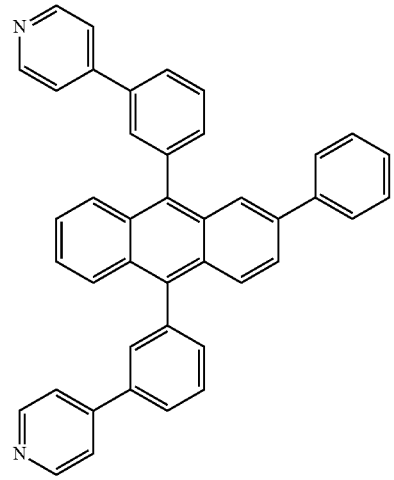

ET4

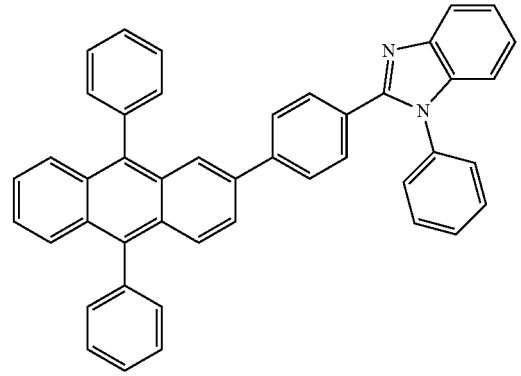

-continued
ET5
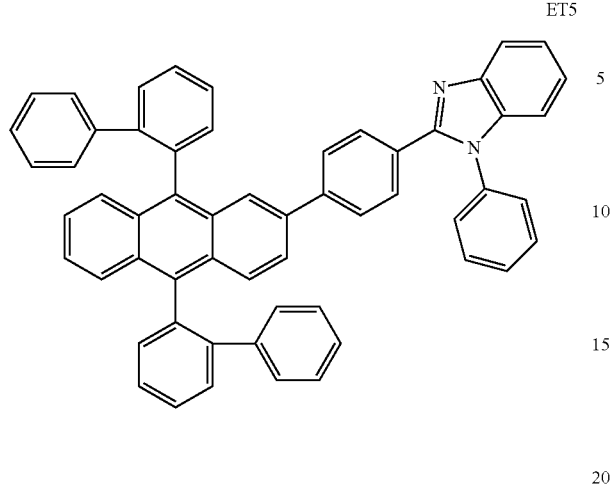
ET6
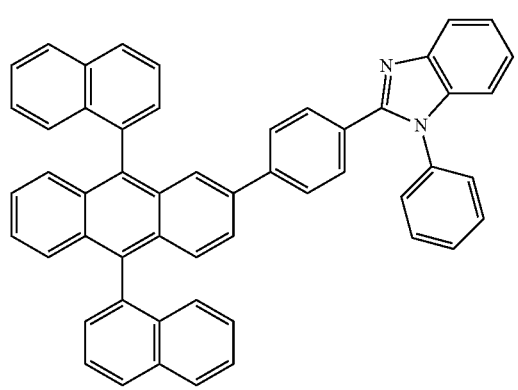
ET7
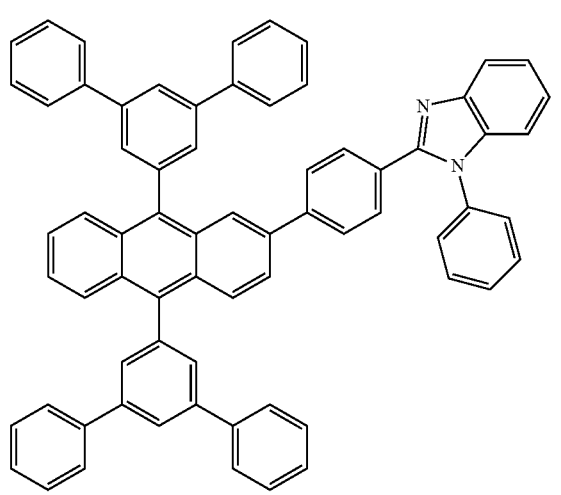
-continued
ET8
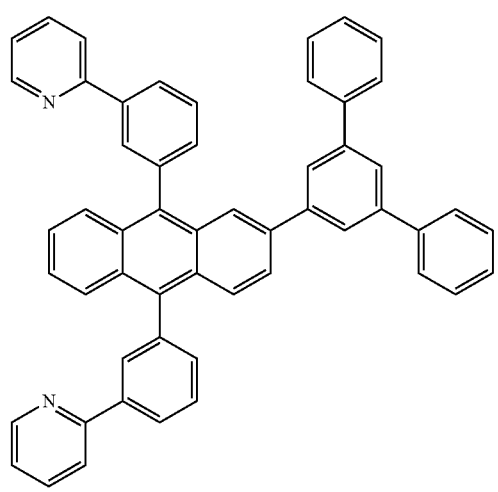
ET9
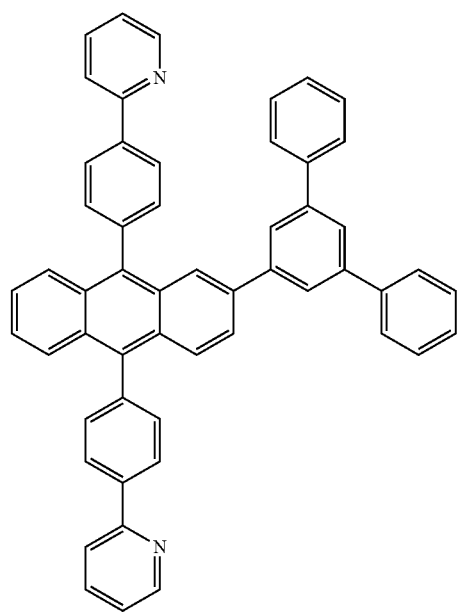

ET10
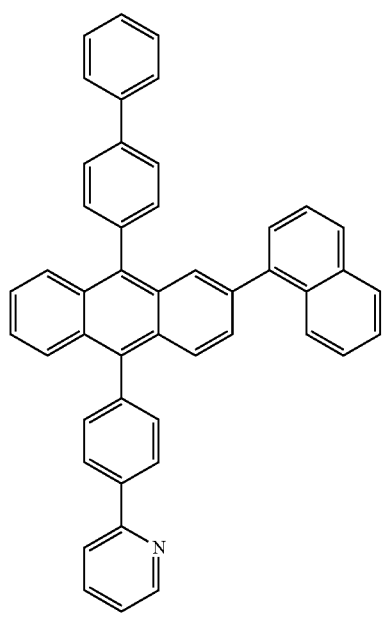
ET11
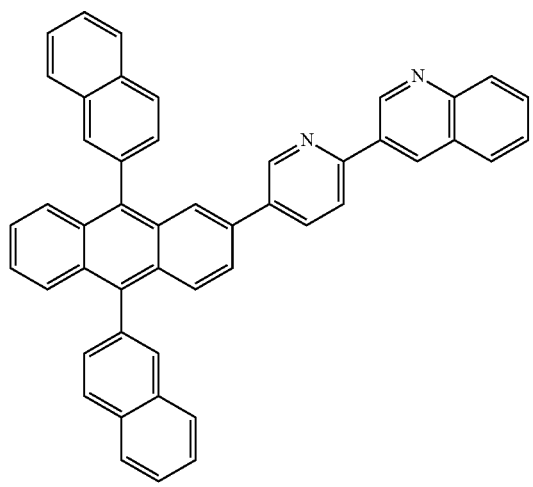
ET12
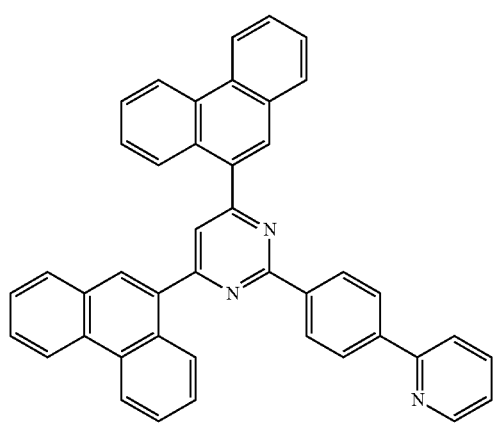
ET13
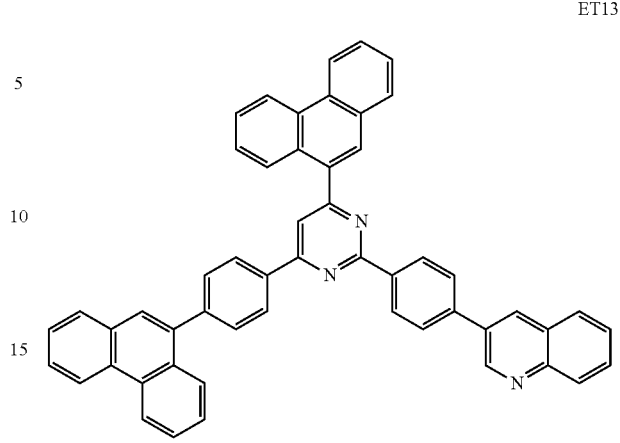
ET14
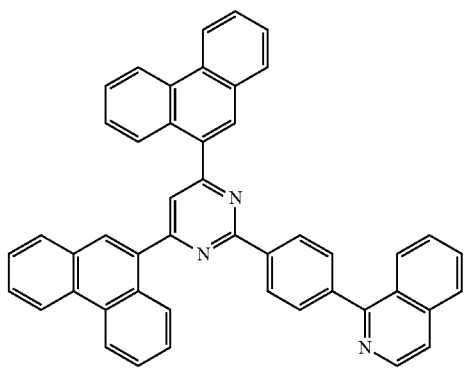
ET15
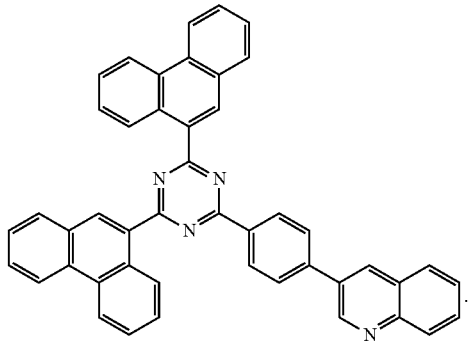
In some embodiments, the electron transport layer may include at least one selected from BCP, Bphen, Alq$_3$, BAlq, TAZ, and NTAZ.
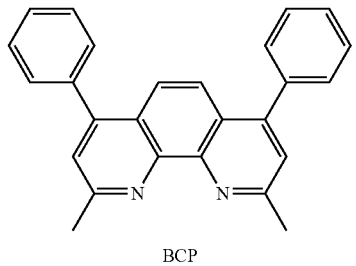
BCP -continued

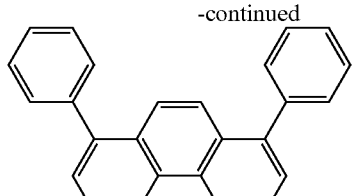
Bphen

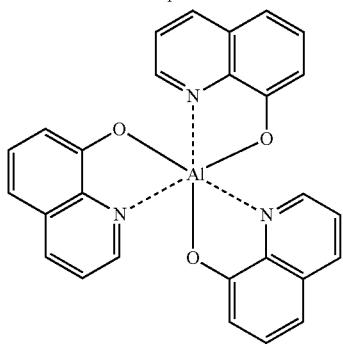
Alq₃

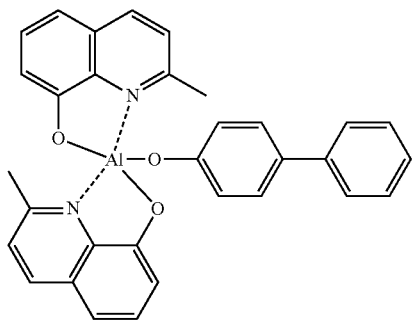
BAlq

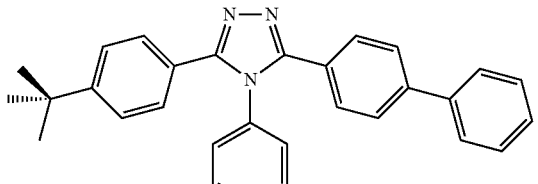
TAZ

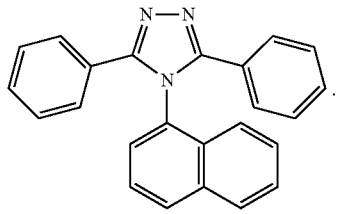
NTAZ

The thickness of the electron transport layer may be about 100 Å to about 1,000 Å, and in some embodiments, about 150 Å to about 500 Å. When the thickness of the electron transport layer is within these ranges, excellent electron transport characteristics may be achieved without a substantial increase in driving voltage.

The electron transport layer may further include a metal-containing material in addition to the materials described above.

The metal-containing material may include a Li complex. The Li complex may be selected from, e.g., Compound ET-D1 (lithium quinolate, LiQ) and ET-D2:

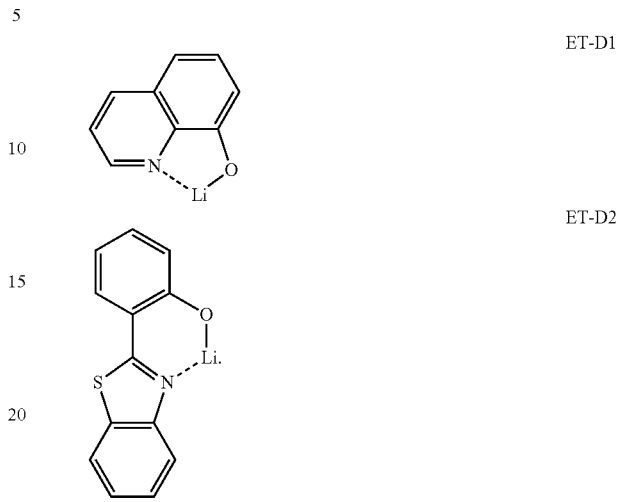

The electron transport region may include an electron injection layer that facilitates electron injection from the second electrode 190.

The electron injection layer may be formed on the electron transport layer using one or more suitable methods, such as vacuum deposition, spin coating, casting, an LB method, ink-jet printing, laser printing, and/or LITI. When the electron injection layer is formed by vacuum deposition and/or spin coating, the vacuum deposition and coating conditions used for the electron injection layer may be similar to the vacuum deposition and coating conditions used for the hole injection layer.

The electron injection layer may include at least one selected from LiF, NaCl, CsF, Li₂O, BaO, and LiQ.

The thickness of the electron injection layer may be about 1 Å to about 100 Å, and in some embodiments, about 3 Å to about 90 Å. When the thickness of the electron injection layer is within these ranges, excellent electron injection characteristics may be achieved without a substantial increase in driving voltage.

The second electrode 190 may be on the organic layer 150. The second electrode 190 may be a cathode that is an electron injection electrode. In this regard, a material for forming the second electrode 190 may be a material having a low work function, for example, a metal, an alloy, an electrically conductive compound, and/or a mixture thereof. Non-limiting examples of the material for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO and/or IZO. The second electrode 190 may be a semi-transmissive electrode and/or a transmissive electrode.

Hereinbefore the organic light-emitting device 10 has been described with reference to the drawing, but embodiments of the present disclosure are not limited thereto.

The term "$C_1$-$C_{60}$ alkyl group" as used herein refers to a linear or branched aliphatic hydrocarbon monovalent group having 1 to 60 carbon atoms. Non-limiting examples thereof may include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having substantially the same structure as the $C_1$-$C_{60}$ alkyl group.

The term "$C_1$-$C_{60}$ alkoxy group" as used herein refers to a monovalent group represented by —O-$A_{101}$ (where $A_{101}$ is the $C_1$-$C_{60}$ alkyl group). Non-limiting examples thereof may include a methoxy group, an ethoxy group, and an isopropyloxy group.

The term "$C_2$-$C_{60}$ alkenyl group" as used herein refers to a hydrocarbon group having at least one carbon-carbon double bond in the body (e.g., middle) or at the terminus of the $C_2$-$C_{60}$ alkyl group. Non-limiting examples thereof may include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a hydrocarbon group having at least one carbon-carbon triple bond in the body (e.g., middle) or at the terminus of the $C_2$-$C_{60}$ alkyl group. Non-limiting examples thereof may include an ethynyl group and a propynyl group. The term "$C_2$-$C_{60}$ alkynylene group" as used herein refers to a divalent group having substantially the same structure as the $C_2$-$C_{60}$ alkynyl group.

The term "$C_3$-$C_{10}$ cycloalkyl group" as used herein refers to a monovalent monocyclic saturated hydrocarbon group including 3 to 10 carbon atoms. Non-limiting examples thereof may include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent monocyclic group including at least one heteroatom selected from N, O, Si, P, and S as a ring-forming atom and 1 to 10 carbon atoms. Non-limiting examples thereof may include a tetrahydrofuranyl group and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in its ring, and is not aromatic. Non-limiting examples thereof may include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent monocyclic group including at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group may include a 2,3-hydrofuranyl group and a 2,3-hydrothiophenyl group. The term "$C_1$-$C_{10}$ heterocycloalkenylene group" as used herein refers to a divalent group having substantially the same structure as the $C_1$-$C_{10}$ heterocycloalkenyl group.

The term "$C_{60}$-$C_{60}$ aryl group" as used herein refers to a monovalent group having a carbocyclic aromatic system having 6 to 60 carbon atoms. The term "$C_{60}$-$C_{60}$ arylene group" as used herein refers to a divalent group having a carbocyclic aromatic system having 6 to 60 carbon atoms. Non-limiting examples of the $C_6$-$C_{60}$ aryl group may include a phenyl group, a biphenyl group, a terphenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the rings may be fused to each other.

The term "$C_1$-$C_{60}$ heteroaryl group" as used herein refers to a monovalent group having a carbocyclic aromatic system including at least one heteroatom selected from N, O, Si, P, and S as a ring-forming atom and 1 to 60 carbon atoms. The term "$C_1$-$C_{60}$ heteroarylene group" as used herein refers to a divalent group having a carbocyclic aromatic system including at least one heteroatom selected from N, O, P, and S as a ring-forming atom and 1 to 60 carbon atoms. Non-limiting examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the rings may be fused to each other.

The term "$C_6$-$C_{60}$ aryloxy group" as used herein refers to a group represented by —O-$A_{102}$ (where $A_{102}$ is the $C_6$-$C_{60}$ aryl group). The term "$C_6$-$C_{60}$ arylthio group" as used herein refers to a group represented by —S-$A_{103}$ (where $A_{103}$ is the $C_6$-$C_{60}$ aryl group).

The term "monovalent non-aromatic condensed polycyclic group" as used herein refers to a monovalent group that has two or more rings condensed (e.g., fused) to each other, and has only carbon atoms as ring-forming atoms (for example, the number of carbon atoms may be 8 to 60), wherein the molecular structure as a whole is non-aromatic. A non-limiting example of the monovalent non-aromatic condensed polycyclic group may include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more rings condensed (e.g., fused) to each other, has a heteroatom selected from N, O, Si, P, and S, in addition to carbon atoms as ring-forming atoms (for example, the number of carbon atoms may be 2 to 60), wherein the molecular structure as a whole is non-aromatic. A non-limiting example of the monovalent non-aromatic condensed heteropolycyclic group may include a carbazolyl group. The term "divalent non-aromatic condensed heteropolycyclic group" as used herein refers to a divalent group having substantially the same structure as the monovalent non-aromatic condensed hetero-polycyclic group.

In the present specification, at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The term "Ph" as used herein refers to a phenyl group. The term "Me" as used herein refers to a methyl group. The term "Et" as used herein refers to an ethyl group. The terms "ter-Bu", "t-Bu" and "But" as used herein refer to a tert-butyl group.

Hereinafter, an organic light-emitting device according to an example embodiment of the present disclosure will be described in more detail with reference to Synthesis Examples and Examples. The wording "B was used instead of A" used in describing Synthesis Examples means that a molar equivalent of A was substituted for a molar equivalent of B.

EXAMPLE

Synthesis Example

Synthesis Example 1

Synthesis of Compound 4

Compound 4 was synthesized following Reaction Scheme 1-1:

Reaction Scheme 1-1

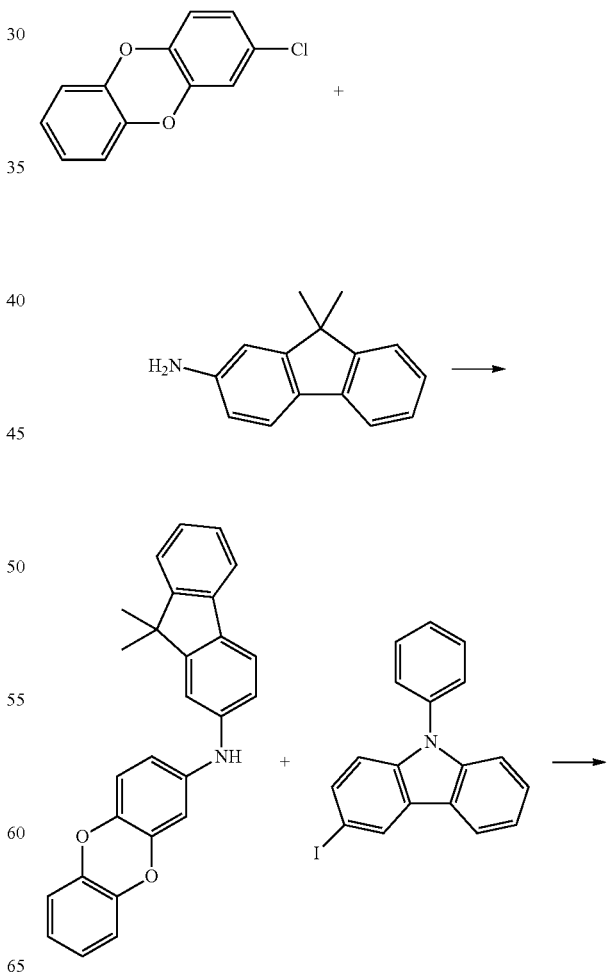

Intermediate A-1

-continued

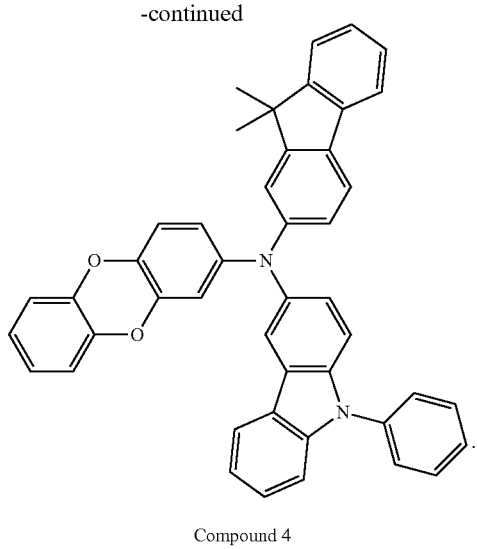

Compound 4

Synthesis of Intermediate A-1

2.18 g (10 mmol) of 2-chlorodibenzo[b,e][1,4]dioxane, 3.14 g (15 mmol) of 9,9-dimethyl-9H-fluoren-2-amine, 0.45 g (0.5 mmol) of Pd$_2$(dba)$_3$, 0.1 g (0.5 mmol) of P(tBu)$_3$, and 2.25 g (20.0 mmol) of KOtBu were dissolved in 250 mL, and the mixture was stirred at a temperature of about 85° C. for about 7 hours. The resulting mixture was cooled to room temperature, and an organic layer was extracted therefrom three times using 150 mL of water and 150 mL of diethyl ether. The obtained organic layer was dried using magnesium sulfate (MgSO$_4$), filtered, and the solvent was removed therefrom by evaporation. The obtained residue was separated and purified through silica gel chromatography to obtain 3.32 g of Intermediate A-1 (yield: 85%). The compound thus obtained was identified by liquid chromatography-mass spectrometry (LC-MS).

$C_{27}H_{21}NO_2$: M$^+$ 391.2

Synthesis of Compound 1

3.32 g (8.5 mmol) of Intermediate A-1, 4.98 g (13.5 mmol) of 3-iodo-9-phenyl-9H-carbazole, 0.45 g (0.5 mmol) of Pd$_2$(dba)$_3$, 0.1 g (0.5 mmol) of P(tBu)$_3$, and 2.25 g (20.0 mmol) of KOtBu were dissolved in 150 mL of toluene and stirred at a temperature of about 85° C. for 2 hours. The resulting mixture was cooled to room temperature, and an organic layer was extracted therefrom three times using 100 mL of water and 100 mL of diethyl ether. The obtained organic layer was dried using magnesium sulfate (MgSO$_4$), filtered, and the solvent was removed therefrom by evaporation. The obtained residue was separated and purified through silica gel chromatography to obtain 4.35 g of Compound 4 (yield: 81%). The obtained compound was identified by LC-MS.

$C_{45}H_{32}N_2O_2$: M$^+$ 632.4

Synthesis Example 2

Synthesis of Compound 18

Synthesis of Compound 18

3.58 g (yield: 75.6%) of Compound 18 was obtained in substantially the same manner used to synthesize Compound 4 in Synthesis Example 1, except that 3-bromo-dibenzo[b,d]furan was used instead of 3-iodo-9-phenyl-9H-carbazole.

The compound thus obtained was confirmed by LC-MS and nuclear magnetic resonance (NMR).

$C_{39}H_{27}NO_3$: M$^+$ 557.2

Synthesis Example 3

Synthesis of Compound 22

Compound 22 was synthesized following Reaction Scheme 1-2:

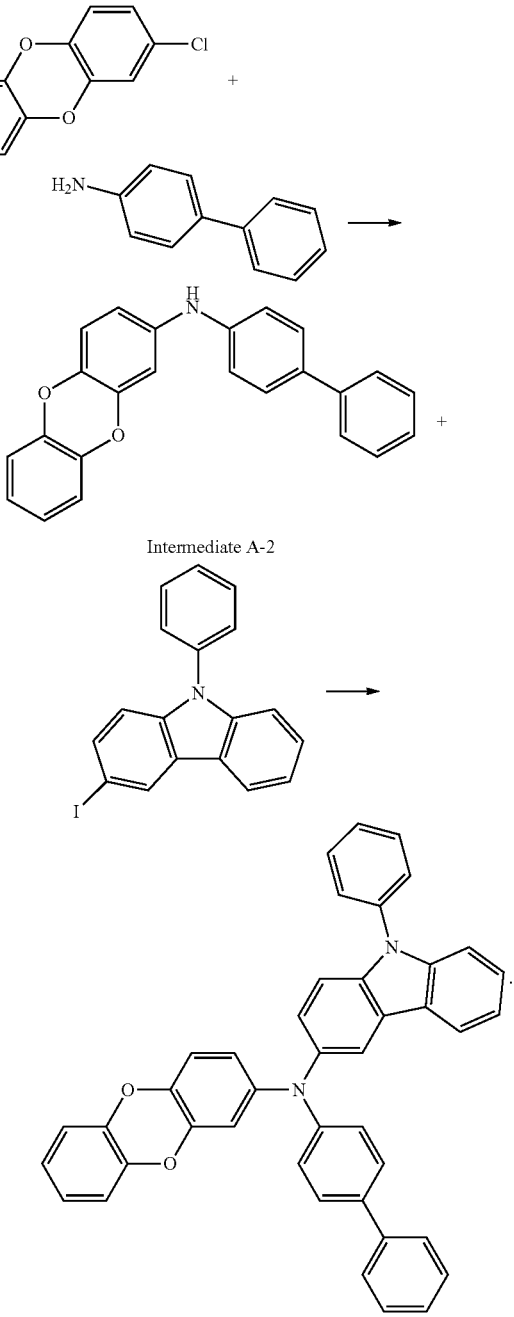

Reaction Scheme 1-2

Compound 22

Synthesis of Intermediate A-2

3.08 g (yield: 81%) of Intermediate A-2 was obtained in the same manner used to synthesize Intermediate A-1 in Synthesis Example 1, except that [1,1'-biphenyl]-4-amine was used instead of 9,9-dimethyl-9H-fluoren-2-amine. The compound thus obtained was identified by LC-MS.

$C_{24}H_{17}NO_2$: M$^+$ 351.1

Synthesis of Compound 22

3.42 g (yield: 84.1%) of Compound 22 was obtained in the same manner used to synthesize Compound 4 in Synthesis Example 1, except that Intermediate A-2 was used instead of Intermediate A-1. The compound thus obtained was confirmed by LC-MS and NMR.

$C_{42}H_{28}N_2O_2$: M$^+$ 592.3

Synthesis Example 4

Synthesis of Compound 29

Compound 29 was synthesized following Reaction Scheme 1-3:

Reaction Scheme 1-3

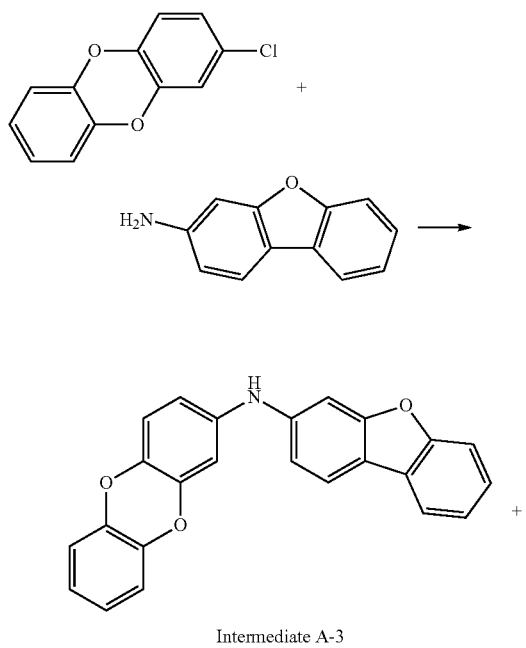

Intermediate A-3

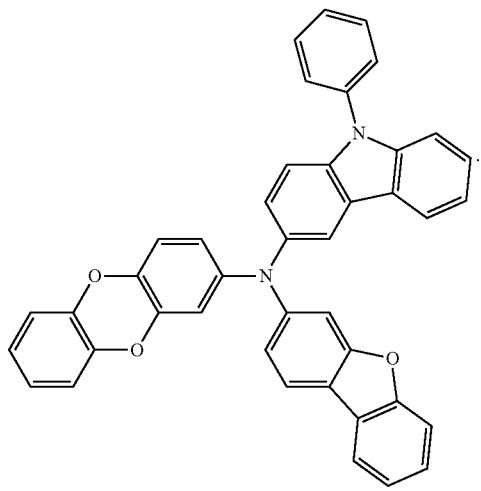

Compound 29

Synthesis of Intermediate A-3

3.17 g (yield: 78%) of Intermediate A-3 was obtained in substantially the same manner used to synthesize Intermediate A-1 in Synthesis Example 1, except that dibenzo[b,d]furan-3-amine was used instead of 9,9-dimethyl-9H-fluoren-2-amine. The compound thus obtained was identified by LC-MS.

$C_{24}H_{15}NO_3$: M$^+$ 365.1

Synthesis of Compound 29

3.87 g (yield: 87.3%) of Compound 29 was obtained in substantially the same manner used to synthesize Compound 4 in Synthesis Example 1, except that Intermediate A-3 was used instead of Intermediate A-1. The compound thus obtained was identified by LC-MS and NMR.

$C_{42}H_{26}N_2O_3$: M$^+$ 606.2

Synthesis Example 5

Synthesis of Compound 40

Reaction Scheme 1-4

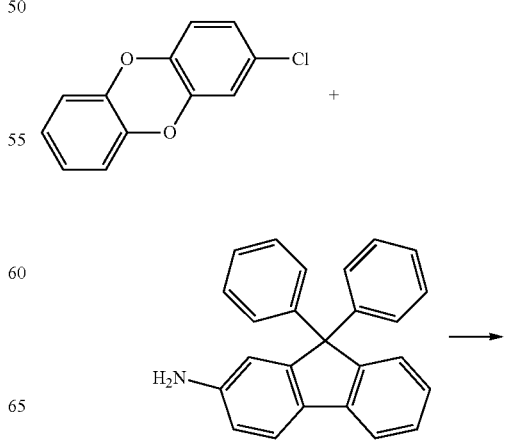

-continued

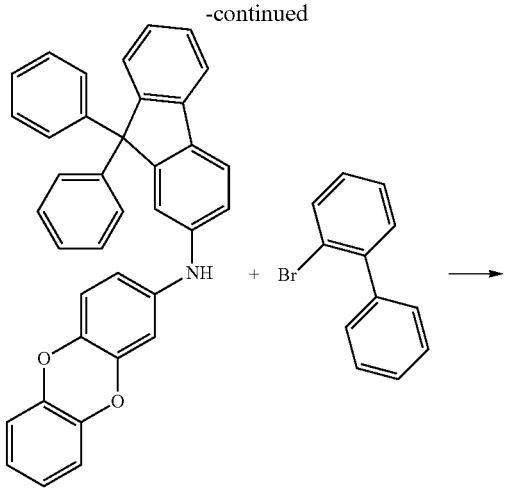

Intermediate A-4

Compound 40

Synthesis of Intermediate A-4

4.38 g (yield: 84%) of Intermediate A-4 was obtained in substantially the same manner used to synthesize Intermediate A-1 in Synthesis Example 1, except that 9,9-diphenyl-9H-fluoren-2-amine was used instead of 9,9-dimethyl-9H-fluoren-2-amine. The compound thus obtained was identified by LC-MS.

$C_{37}H_{25}NO_2$: M+ 515.2

Synthesis of Compound 40

2.49 g (yield: 64.2%) of Compound 40 was obtained in substantially the same manner used to synthesize Compound 4 in Synthesis Example 1, except that Intermediate A-4 was used instead of Intermediate A-1, and 2-bromo-1,1'-biphenyl was used instead of 3-iodo-9-phenyl-9H-carbazole. The compound thus obtained was confirmed by LC-MS and NMR.

$C_{49}H_{33}NO_2$: M+667.4

Synthesis Example 6

Synthesis of Compound 44

Synthesis of Compound 44

3.71 g (yield: 80.5%) of Compound 44 was obtained in substantially the same manner used to synthesize Compound 4 in Synthesis Example 1, except that Intermediate A-4 was used instead of Intermediate A-1, and 4-bromodibenzo[b,d]furan was used instead of 3-iodo-9-phenyl-9H-carbazole. The compound thus obtained was identified by LC-MS and NMR.

$C_{49}H_{31}NO_3$: M+ 681.2

Synthesis Example 7

Synthesis of Compound 50

Synthesis of Compound 50

3.02 g (yield: 71.4%) of Compound 50 was obtained in substantially the same manner used to synthesize Compound 4 in Synthesis Example 1, except that Intermediate A-3 was used instead of Intermediate A-1, and 9-(4-bromophenyl)-9H-carbazole was used instead of 3-iodo-9-phenyl-9H-carbazole. The compound thus obtained was identified by LC-MS and NMR.

$C_{42}H_{26}N_2O_3$: M+ 606.2

Synthesis Example 8

Synthesis of Compound 59

Synthesis of Compound 59

3.16 g (yield: 77.4%) of Compound 59 was obtained in substantially the same manner used to synthesize Compound 4 in Synthesis Example 1, except that 3-bromo-dibenzo[b,d]furan was used instead of 2-iodo-9-phenyl-9H-carbazole. The compound thus obtained was identified by LC-MS and NMR.

$C_{39}H_{27}NO_3$: M+ 557.2

Synthesis Example 9

Synthesis of Compound 69

Compound 69 was synthesized following Reaction Scheme 2-1:

Reaction Scheme 2-1

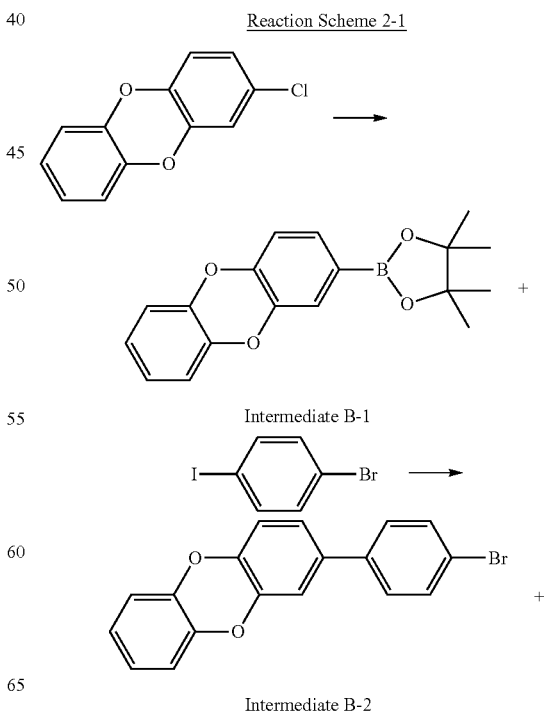

Intermediate B-1

Intermediate B-2

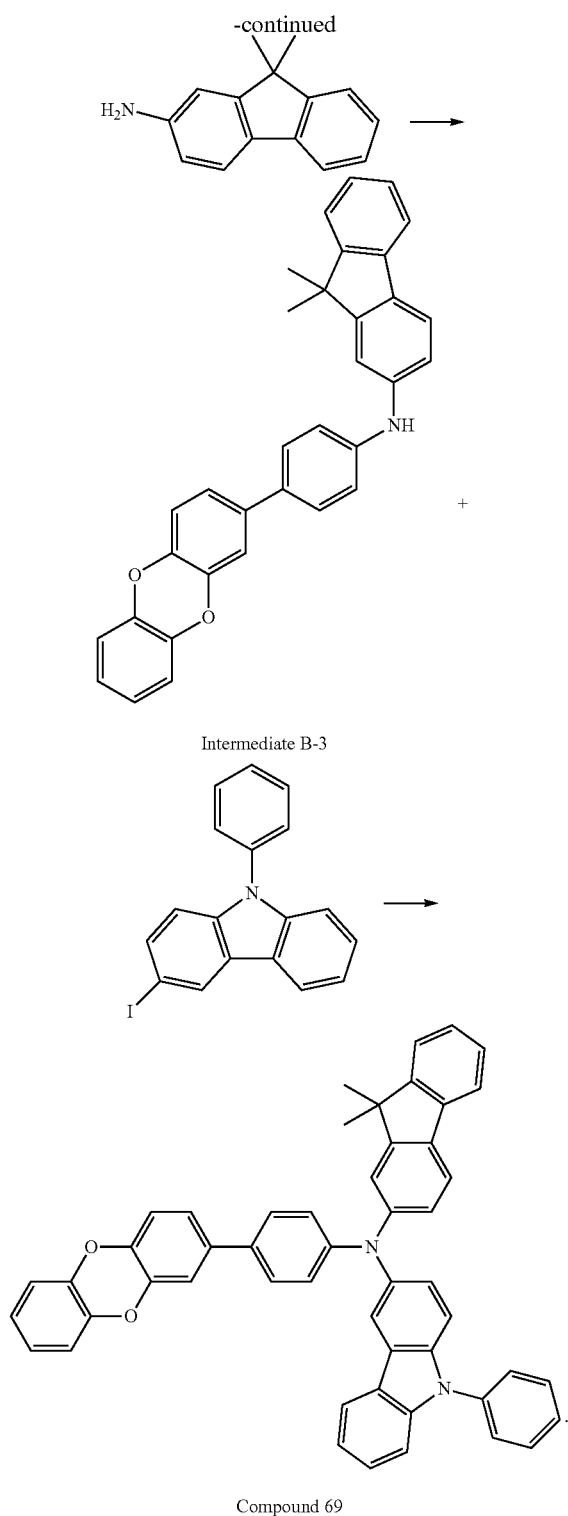

Intermediate B-3

Compound 69

Synthesis of Intermediate B-1

8.72 g (40.0 mmol) of 2-chlorodibenzo[b,e][1,4]dioxane, 20.2 g (80 mmol) of bis(pinacolato)diboron, 3.26 g (4 mmol) of [1,1'-bis(diphenylphosphino)ferrocene]dichloropalladium(II) complex, and 11.76 g (120 mmol) of potassium acetate were dissolved in 500 mL of toluene and stirred at a temperature of about 70° C. for about 5 hours. The resulting mixture was cooled to room temperature, and an organic layer was extracted therefrom three times using 300 mL of water and 300 mL of diethyl ether. The obtained organic layer was dried using MgSO$_4$, filtered, and the solvent was removed therefrom by evaporation. The obtained residue was separated and purified through silica gel chromatography to obtain 6.12 g of Intermediate B-1 (yield: 49.3%). The compound thus obtained was identified by LC-MS.

$C_{18}H_{19}BO_4$: M$^+$ 310.2

Synthesis of Intermediate B-2

6.12 g (19.7 mmol) of Intermediate B-1, 8.46 g (30 mmol) of 1-bromo-4-iodobenzene, 1.15 g (1 mmol) of tetrakis(triphenylphosphine)palladium (Pd(PPh$_3$)$_4$), and 4.15 g (30 mmol) of K$_2$CO$_3$ were dissolved in 300 mL of a mixture solution of THF/H$_2$O (at a volume ratio of 9:1), and stirred at 70° C. for 5 hours. The resulting mixture was cooled to room temperature, and an organic layer was extracted therefrom three times using 150 mL of water and 150 mL of diethyl ether. The obtained organic layer was dried using MgSO$_4$, filtered, and the solvent was removed therefrom by evaporation. The obtained residue was separated and purified through silica gel chromatography to obtain 4.64 g of Intermediate B-2 (yield: 69.6%). The compound thus obtained was identified by LC-MS.

$C_{18}H_{11}BrO_2$: M$^+$ 338.0

Synthesis of Intermediate B-3

3.35 g (9.5 mmol) of Intermediate B-2, 3.14 g (15 mmol) of 9,9-dimethyl-9H-fluoren-2-amine, 0.45 g (0.5 mmol) of Pd$_2$(dba)$_3$, 0.1 g (0.5 mmol) of P(tBu)$_3$, and 2.25 g (20.0 mmol) of KOtBu were dissolved in 250 mL of toluene and stirred at a temperature of about 85° C. for 7 hours. The resulting mixture was cooled to room temperature, and an organic layer was extracted therefrom three times using 150 mL of water and 150 mL of diethyl ether. The obtained organic layer was dried using MgSO$_4$, filtered, and the solvent was removed therefrom by evaporation. The obtained residue was separated and purified through silica gel chromatography to obtain 3.59 g of Intermediate B-3 (yield: 80.9%). The compound thus obtained was identified by LC-MS.

$C_{33}H_{25}NO_2$: M$^+$ 467.2

Synthesis of Compound 69

4.08 g (yield: 74.9%) of Compound 69 was obtained in substantially the same manner used to synthesize Compound 4 in Synthesis Example 1, except that Intermediate B-3 was used instead of Intermediate A-1. The compound thus obtained was identified by LC-MS and NMR.

$C_{51}H_{36}N_2O_2$: M$^+$ 708.3

Synthesis Example 10

Synthesis of Compound 71

Synthesis of Compound 71

2.97 g (yield: 61.7%) of Compound 71 was obtained in substantially the same manner used to synthesize Compound 4 in Synthesis Example 1, except that Intermediate B-3 was used instead of Intermediate A-1, and 4-bromo-4'-fluoro-1,1'-biphenyl was used instead of 3-iodo-9-phenyl-9H-carbazole. The compound thus obtained was identified by LC-MS and NMR.

$C_{45}H_{32}FNO_2$: M$^+$ 637.2

Synthesis Example 11

Synthesis of Compound 76

Compound 22 was synthesized following Reaction Scheme 2-2:

Reaction Scheme 2-2

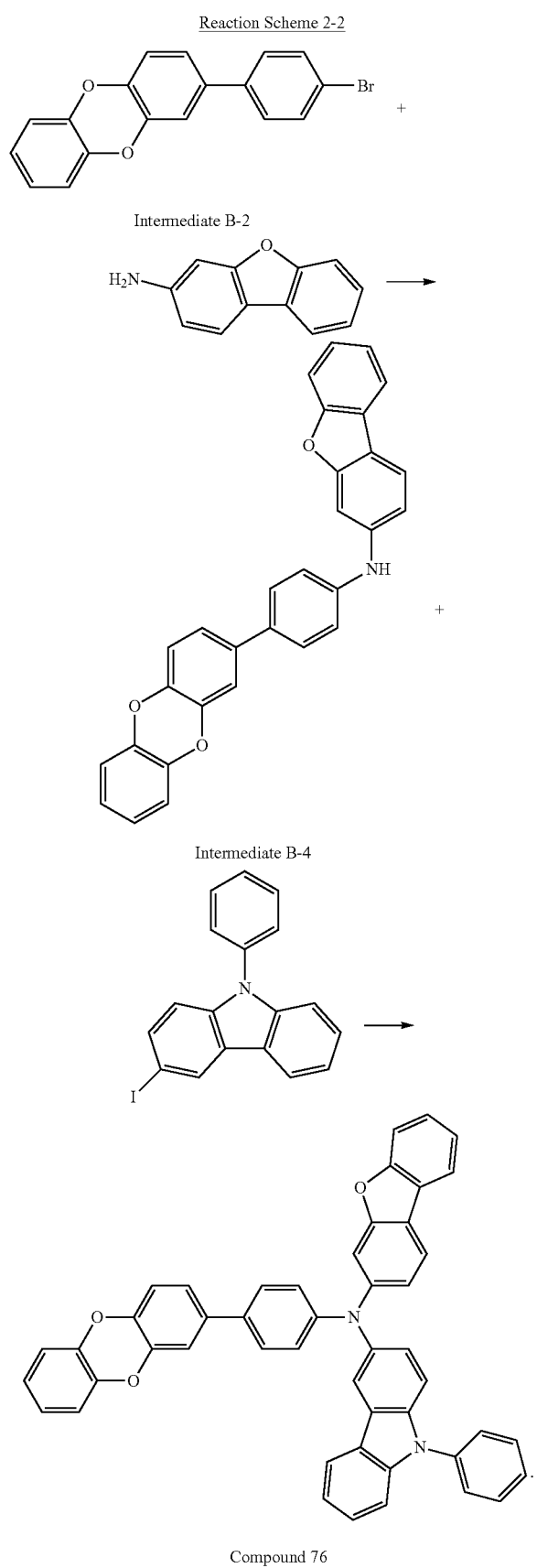

Synthesis of Intermediate B-4

3.71 g (yield: 78%) of Intermediate B-4 was obtained in substantially the same manner used to synthesize Intermediate B-3 in Synthesis Example 9 except that dibenzo[b,d]furan-3-amine was used instead of 9,9-dimethyl-9H-fluoren-2-amine. The compound thus obtained was identified by LC-MS.

$C_{30}H_{19}NO_3$: M⁺ 441.2

Synthesis of Compound 76

2.98 g (yield: 71.8%) of Compound 76 was obtained in substantially the same manner used to synthesize Compound 4 in Synthesis Example 1, except that Intermediate B-4 was used instead of Intermediate A-1. The compound thus obtained was identified by LC-MS and NMR.

$C_{48}H_{30}N_2O_3$: M⁺ 682.2

Synthesis Example 12

Synthesis of Compound 81

Compound 81 was synthesized following Reaction Scheme 2-3:

Reaction Scheme 2-3

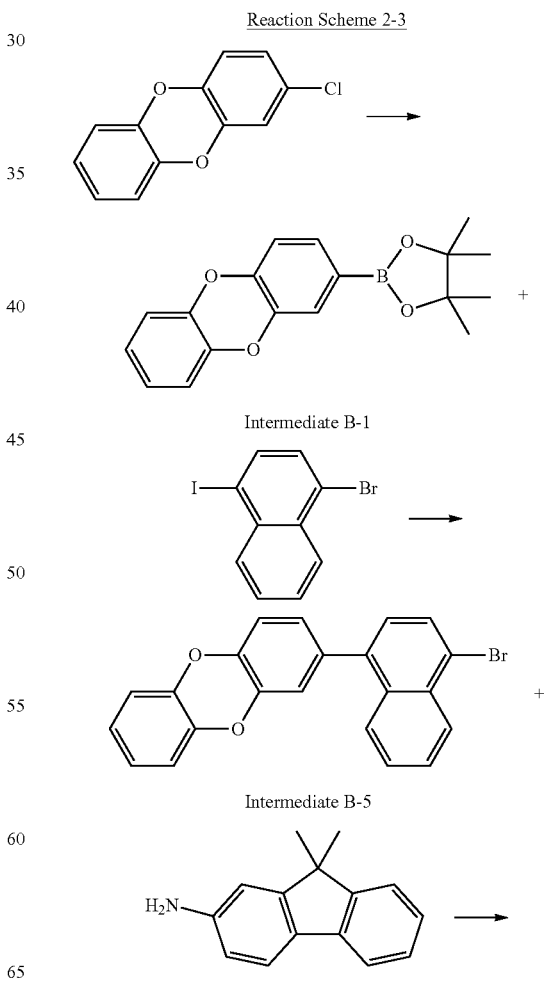

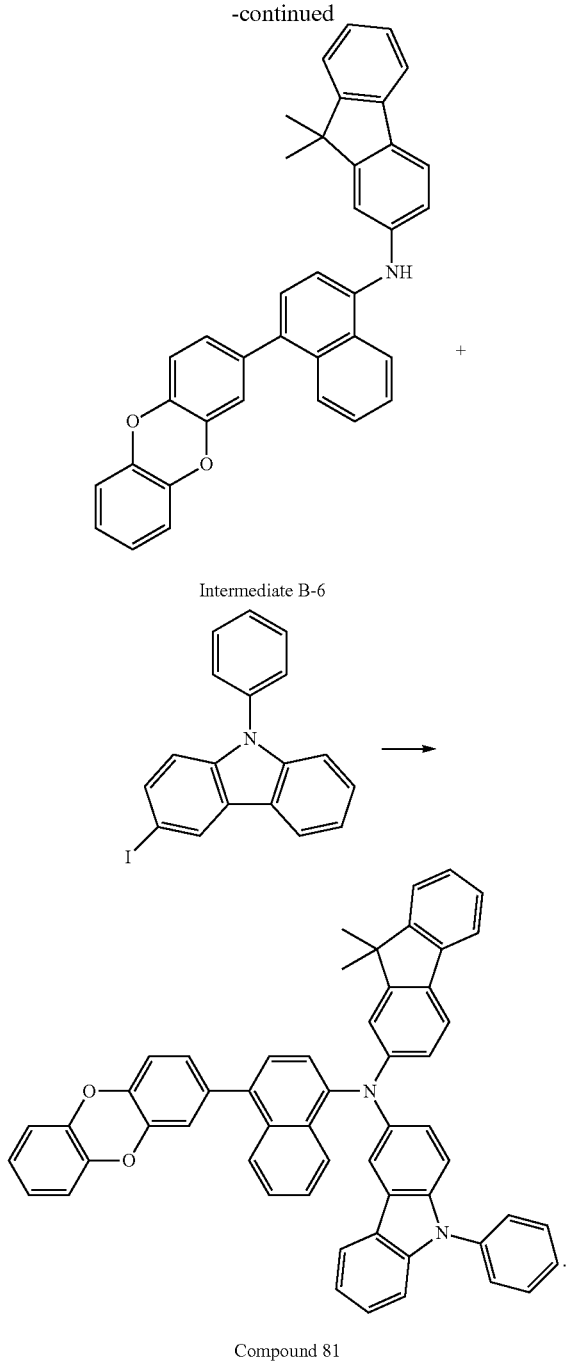

Intermediate B-6

Compound 81

Synthesis of Intermediate B-5

4.73 g (yield: 67%) of Intermediate B-5 was obtained in substantially the same manner used to synthesize Intermediate B-2 in Synthesis Example 9, except that 1,4-bibromonaphthalene was used instead of 1-bromo-4-iodobenzene. The compound thus obtained was identified by LC-MS.

$C_{22}H_{13}BrO_2$: M⁺ 338.0

Synthesis of Intermediate B-6

4.04 g (yield: 87%) of Intermediate B-6 was obtained in substantially the same manner used to synthesize Intermediate B-3 in Synthesis Example 9, except that Intermediate B-5 was used instead of Intermediate B-2. The compound thus obtained was identified by LC-MS.

$C_{37}H_{27}NO_2$: M⁺ 517.2

Synthesis of Compound 81

3.39 g (yield: 78.1%) of Compound 81 was obtained in substantially the same manner used to synthesize Compound 4 in Synthesis Example 1, except that Intermediate B-6 was used instead of Intermediate A-1. The compound thus obtained was identified by LC-MS and NMR.

$C_{55}H_{38}N_2O_2$: M⁺ 758.3

Synthesis Example 13

Synthesis of Compound 86

Compound 86 was synthesized following Reaction Scheme 2-4:

Reaction Scheme 2-4

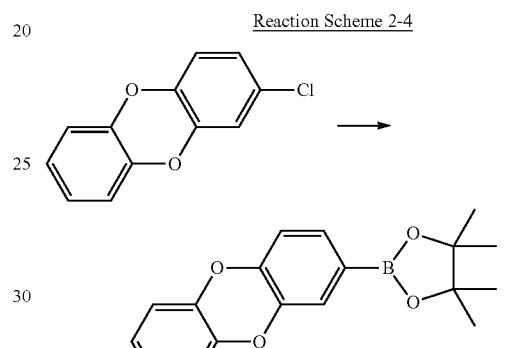

Intermediate B-1

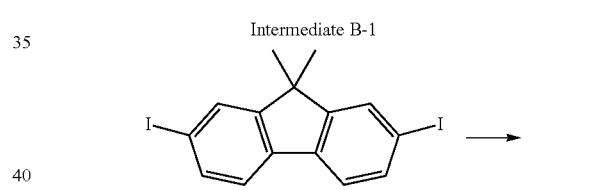

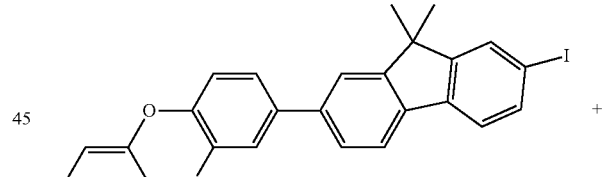

Intermediate B-7

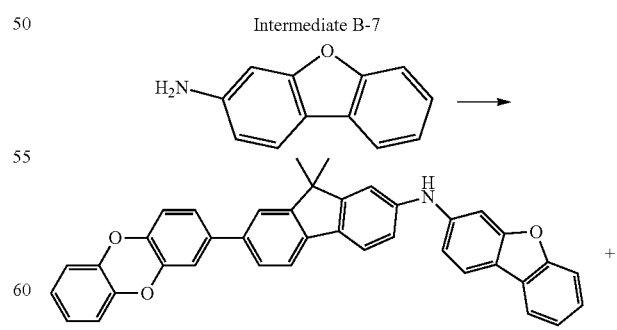

Intermediate B-8

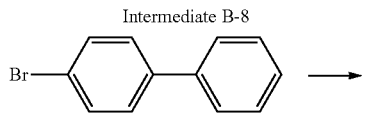

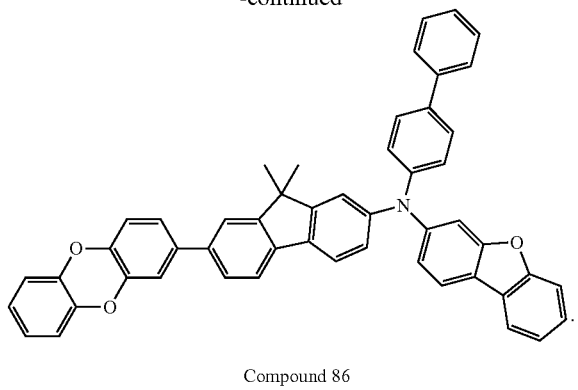

Compound 86

Synthesis of Intermediate B-7

4.25 g (yield: 70%) of Intermediate B-7 was obtained in substantially the same manner used to synthesize Intermediate B-2 in Synthesis Example 9, except that 2,7-diiodo-9,9-dimethyl-9H-fluorene was used instead of 1-bromo-4-iodobenzene. The compound thus obtained was identified by LC-MS.

$C_{27}H_{19}IO_2$: $M^+$ 502.1

Synthesis of Intermediate B-8

4.20 g (yield: 89%) of Intermediate B-8 was obtained in substantially the same manner used to synthesize Intermediate B-3 in Synthesis Example 9 except that Intermediate B-7 was used instead of Intermediate B-2, and dibenzo[b,d]furan-3-amine was used instead of 9,9-dimethyl-9H-fluoren-2-amine. The compound thus obtained was identified by LC-MS.

$C_{39}H_{27}NO_3$: $M^+$ 557.2

Synthesis of Compound 86

3.39 g (yield: 78.1%) of Compound 86 was obtained in substantially the same manner used to synthesize Compound 4 in Synthesis Example 1, except that Intermediate B-8 was used instead of Intermediate A-1, and 4-bromo-1,1'-biphenyl was used instead of 3-iodo-9-phenyl-9H-carbazole. The compound thus obtained was identified by LC-MS and NMR.

$C_{55}H_{38}N_2O_2$: $M^+$ 709.3

Synthesis Example 14

Synthesis of Compound 88

Compound 88 was synthesized following Reaction Scheme 3-1:

Reaction Scheme 3-1

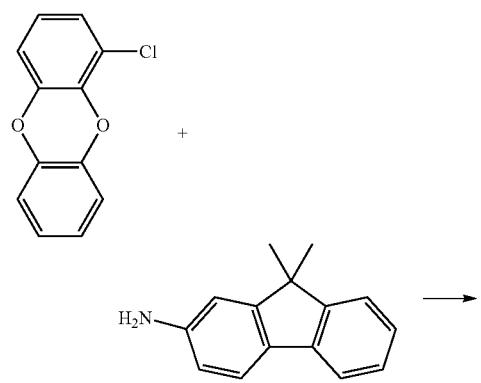

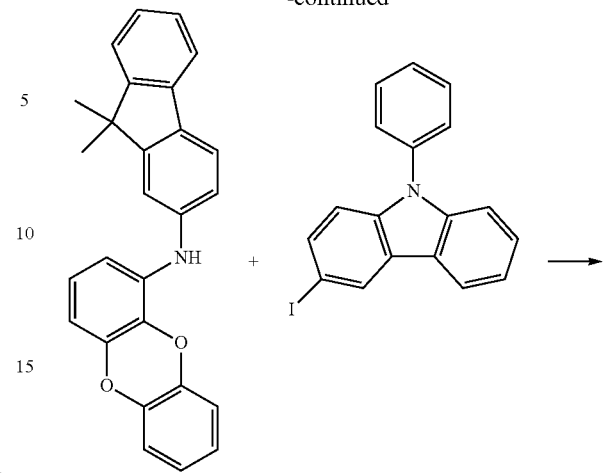

Intermediate C-1

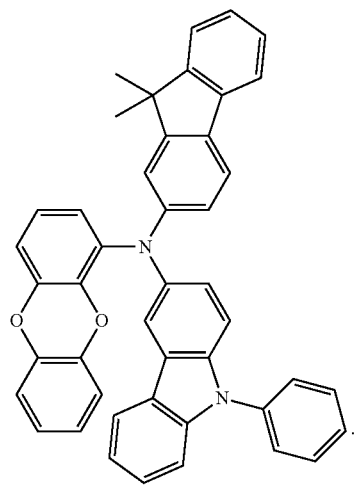

Compound 88

Synthesis of Intermediate C-1

3.14 g (yield: 70%) of Intermediate C-1 was obtained in substantially the same manner used to synthesize Intermediate A-1 in Synthesis Example 1, except that 1-chlorodibenzo[b,e][1,4]dioxane was used instead of 2-chlorodibenzo[b,e][1,4]dioxane. The compound thus obtained was identified by LC-MS.

$C_{27}H_{21}NO_2$: $M^+$ 391.2

Synthesis of Compound 88

3.81 g (yield: 83.7%) of Compound 88 was obtained in substantially the same manner used to synthesize Compound 4 in Synthesis Example 1, except that Intermediate C-1 was used instead of Intermediate A-1. The compound thus obtained was identified by LC-MS and NMR.

$C_{45}H_{32}N_2O_2$: $M^+$632.3

Synthesis Example 15

Synthesis of Compound 95

Compound 95 was synthesized following Reaction Scheme 3-2:

Reaction Scheme 3-2

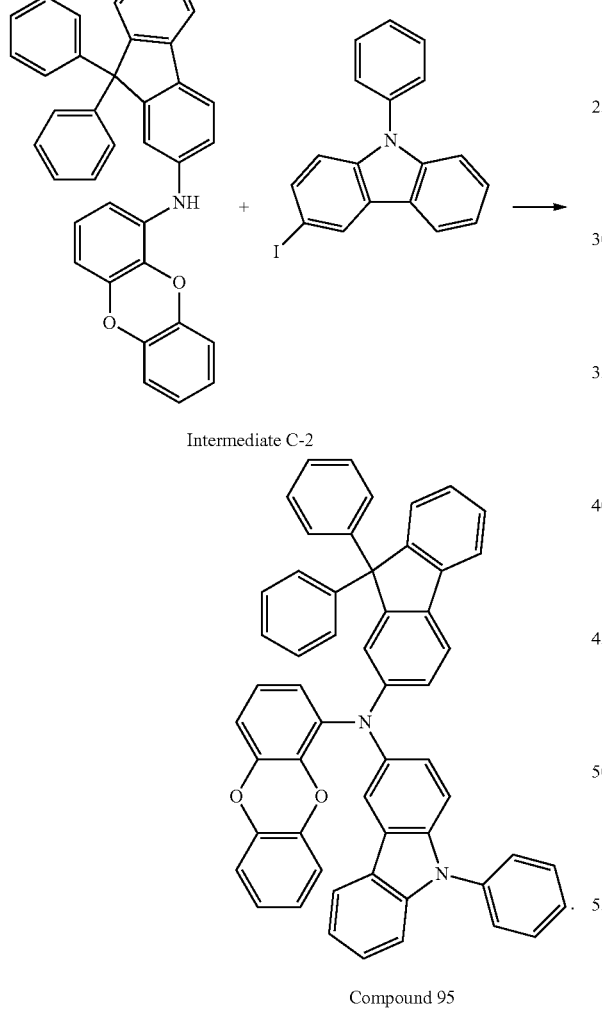

Intermediate C-2

Compound 95

Synthesis of Intermediate C-2

3.91 g (yield: 73%) of Intermediate C-2 was obtained in substantially the same manner used to synthesize Intermediate A-1 in Synthesis Example 1, except that 1-chlorodibenzo[b,e][1,4]dioxane was used instead of 2-chlorodibenzo[b,e][1,4]dioxane, and 9,9-diphenyl-9H-fluoren-2-amine was used instead of 9,9-dimethyl-9H-fluoren-2-amine. The compound thus obtained was identified by LC-MS.

$C_{37}H_{25}NO_2$: M⁺ 515.2

Synthesis of Compound 95

4.18 g (yield: 82.1%) of Compound 95 was obtained in substantially the same manner used to synthesize Compound 4 in Synthesis Example 1, except that Intermediate C-2 was used instead of Intermediate A-1. The compound thus obtained was identified by LC-MS and NMR.

$C_{55}H_{36}N_2O_2$: M⁺ 756.3

Synthesis Example 16

Synthesis of Compound 108

Compound 108 was synthesized following Reaction Scheme 4-1:

Reaction Scheme 4-1

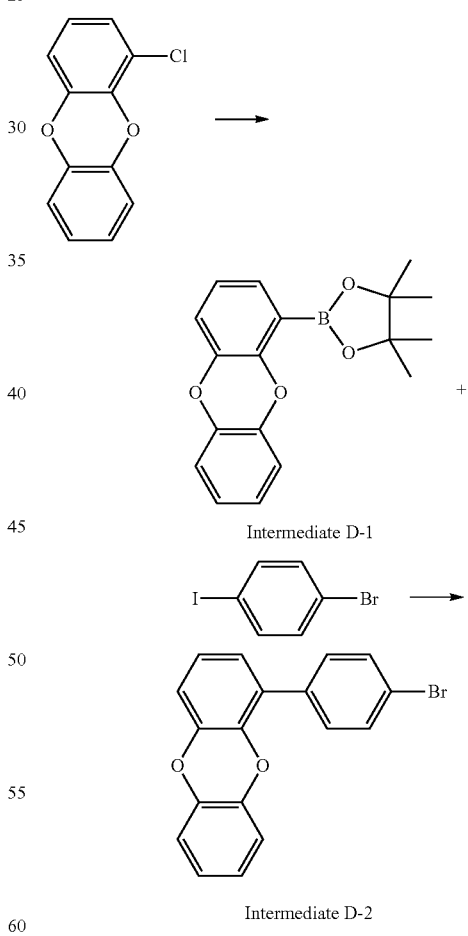

Intermediate D-1

Intermediate D-2

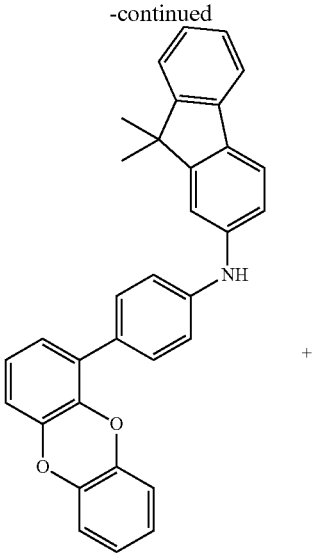

Intermediate D-3

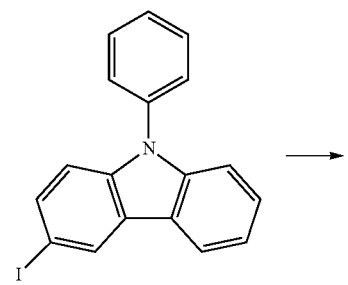

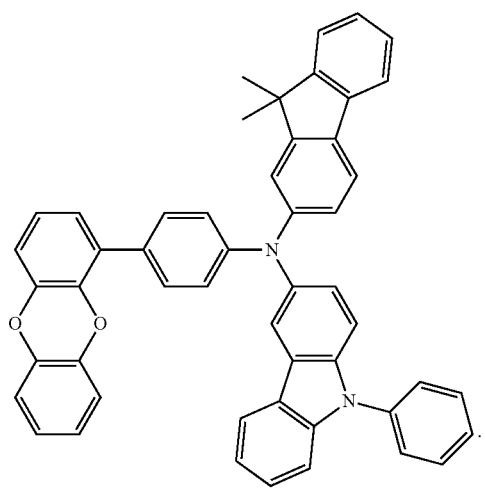

Compound 108

Synthesis of Intermediate D-1

4.36 g (20.0 mmol) of 1-chlorodibenzo[b,e][1,4]dioxane, 10.1 g (40 mmol) of bis(pinacolato) diboron, 1.63 g (2 mmol) of [1,1'-bis(diphenylphosphino)ferrocene]dichloropalladium(II) complex, and 5.88 g (60 mmol) of potassium acetate were dissolved in 300 mL of toluene and stirred at a temperature of about 70° C. for about 5 hours. The resulting mixture was cooled to room temperature, and an organic layer was extracted therefrom three times using 200 mL of water and 200 mL of diethyl ether. The obtained organic layer was dried using $MgSO_4$, filtered, and the solvent was removed therefrom by evaporation. The obtained residue was separated and purified through silica gel chromatography to obtain 3.17 g of Intermediate D-1 (yield: 51%). The compound thus obtained was identified by LC-MS.

$C_{18}H_{19}BO_4$: $M^+$ 310.1

Synthesis of Intermediate D-2

3.17 g (10.2 mmol) of Intermediate D-1, 4.23 g (15 mmol) of 1-bromo-4-iodobenzene, 1.15 g (1 mmol) of tetrakis(triphenylphosphine)palladium ($Pd(PPh_3)_4$), and 2.76 g (20 mmol) of $K_2CO_3$ were dissolved in 200 mL of a mixture of $THF/H_2O$ (at a volume ratio of 9:1), and stirred at 70° C. for 5 hours. The resulting mixture was cooled to room temperature, and an organic layer was extracted therefrom three times using 80 mL of water and 80 mL of diethyl ether. The obtained organic layer was dried by using $MgSO_4$, filtered, and the solvent was removed therefrom by evaporation. The obtained residue was separated and purified through silica gel chromatography to obtain 2.28 g of Intermediate D-2 (yield: 66%). The compound thus obtained was identified by LC-MS.

$C_{18}H_{11}BrO_2$: $M^+$ 338.0

Synthesis of Intermediate D-3

2.28 g (6.7 mmol) of Intermediate D-2, 2.1 g (10 mmol) of 9,9-dimethyl-9H-fluoren-2-amine, 0.45 g (0.5 mmol) of $Pd_2(dba)_3$, 0.1 g (0.5 mmol) of $P(tBu)_3$, and 2.25 g (20.0 mmol) of KOtBu were dissolved in 250 mL of toluene and stirred at a temperature of about 85° C. for 7 hours. The result mixture was cooled to room temperature, and an organic layer was extracted therefrom three times using 150 mL of water and 150 mL of diethyl ether. The obtained organic layer was dried by using $MgSO_4$, filtered, and the solvent was removed therefrom by evaporation. The obtained residue was separated and purified through silica gel chromatography to obtain 2.61 g of Intermediate D-3 (yield: 83%). The compound thus obtained was identified by LC-MS.

$C_{33}H_{27}NO_2$: $M^+$ 469.2

Synthesis of Compound 108

3.13 g (yield: 79.4%) of Compound 108 was obtained in the same manner used to synthesize Compound 4 in Synthesis Example 1, except that Intermediate D-3 was used instead of Intermediate A-1. The compound thus obtained was identified by LC-MS and NMR.

$C_{51}H_{36}N_2O_2$: $M^+$ 708.3

TABLE 1

| Compound | ¹H NMR (CDCl₃, 400 MHz) | LC-MS found | LC-MS calc. |
|---|---|---|---|
| 4 | δ = 7.79 (d, 1H), 7.44 (d, 1H), 7.38 (d, 1H), 7.16-7.10 (m, 5H), 7.05-6.88 (m, 6H), 6.80-6.55 (m, 8H), 6.52 (d, 1H), 6.35 (dd, 1H), 6.29 (d, 1H), 6.22 (d, 1H), 1.72 (s, 6H) | 632.4 | 632.73 |
| 8 | δ = 7.52 (t, 2H), 7.45 (d, 1H), 7.24 (d, 1H), 7.18 (d, 1H), 7.10 (d, 1H), 7.05 (dd, 1H), 6.96 (t, 1H), 6.84 (dd, 2H), 6.78-6.55 (m, 8H), 6.43 (d, 1H), 6.34 (dd, 2H), 1.67 (s, 6H) | 557.2 | 557.65 |
| 22 | δ = 7.91 (d, 1H), 7.32 (dd, 2H), 7.25-7.19 (m, 8H), 7.15-7.00 (m, 7H), 6.81-6.64 (m, 4H), 6.60-6.55 (m, 3H), 6.42 (d, 1H), 6.36 (d, 1H), 6.28 (d, 1H) | 592.3 | 592.7 |
| 29 | δ = 7.93 (d, 1H), 7.57 (dd, 2H), 7.30-7.22 (m, 5H), 7.16-6.99 (m, 8H), 6.93 (d, 1H), 6.83-6.60 (m, 6H), 6.49 (d, 1H), 6.37 (dd, 2H) | 606.2 | 606.68 |
| 40 | δ = 7.66 (d, 1H), 7.40 (dd, 2H), 7.34-7.22 (m, 5H), 7.13-6.99 (m, 12H), 6.91-6.59 (m, 9H), 6.49 (d, 1H), 6.44 (d, 1H), 6.35 (dd, 2H) | 667.4 | 667.81 |
| 44 | δ = 7.69 (d, 1H), 7.66 (d, 1H), 7.52 (d, 1H), 7.50 (d, 1H), 7.35-7.23 (m, 3H), 7.15-7.01 (m, 12H), 6.90-6.66 (m, 9H), 6.53 (dd, 1H), 6.42 (d, 1H), 6.38 (d, 1H) | 681.2 | 681.79 |
| 50 | δ = 7.94 (dd, 2H), 7.65 (dd, 2H), 7.36 (d, 1H), 7.25-7.05 (m, 10H), 6.98-6.66 (m, 7H), 6.56-6.50 (m, 3H), 6.41 (d, 1H) | 606.2 | 606.68 |
| 59 | δ = 7.57 (dd, 1H), 7.50 (d, 1H), 7.42 (d, 1H), 7.31-7.07 (m, 6H), 6.92-6.60 (m, 9H), 6.46 (dd, 1H), 6.40 (d, 1H), 6.31 (d, 1H), 1.69 (s, 6H) | 557.2 | 557.65 |
| 69 | δ = 8.07 (d, 1H), 7.63 (dd, 2H), 7.39-7.10 (m, 15H), 7.02-6.97 (m, 3H), 6.93-6.75 (m, 5H), 6.64 (dd, 1H), 6.49 (dd, 2H), 6.41 (d, 1H), 1.62 (s, 6H) | 708.3 | 708.86 |
| 71 | δ = 7.70 (d, 1H), 7.47-7.17 (m, 10H), 7.10-7.05 (m, 3H), 7.01-6.82 (m, 6H), 6.66 (dd, 1H), 6.55-6.47 (m, 4H), 6.38 (d, 1H), 1.66 (s, 6H), | 637.2 | 637.75 |
| 76 | δ = 8.10 (d, 1H), 7.71 (dd, 2H), 7.44 (d, 1H), 7.41-7.37 (m, 4H), 7.32-7.12 (m, 12H), 7.05 (dd, 1H), 6.98-6.78 (m, 6H), 6.68 (dd, 2H), 6.51 (d, 1H) | 682.2 | 682.78 |
| 81 | δ = 8.01 (d, 1H), 7.76 (d, 1H), 7.56 (dd, 2H), 7.42 (dd, 1H), 7.37 (d, 1H), 7.31-7.04 (m, 16H), 6.98-6.93 (m, 3H), 6.84-6.70 (m, 4H), 6.64 (d, 1H), 6.50 (d, 1H), 6.31 (d, 1H), 1.65 (s, 6H) | 758.3 | 758.92 |
| 86 | δ = 7.61 (dd, 2H), 7.43 (d, 1H), 7.38 (dd, 2H), 7.34 (d, 1H), 7.29-7.16 (m, 8H), 7.06-6.99 (m, 5H), 6.87-6.70 (m, 7H), 6.49 (dd, 2H), 6.36 (d, 1H), 1.69 (s, 6H) | 709.3 | 709.85 |
| 88 | δ = 8.02 (d, 1H), 7.63 (d, 1H), 7.58 (d, 1H), 7.34-7.29 (m, 5H), 7.23-7.08 (m, 6H), 6.96-6.69 (m, 9H), 6.40 (d, 1H), 6.29 (dd, 1H), 6.14 (t, 1H), 1.67 (s, 6H) | 632.3 | 632.76 |
| 95 | δ = 7.97 (d, 1H), 7.64 (d, 1H), 7.33-6.98 (m, 23H), 6.90-6.76 (m, 5H), 6.67 (d, 1H), 6.58 (dd, 1H), 6.46 (d, 1H), 6.39 (dd, 1H), 6.32 (d, 1H), 6.16 (t, 1H) | 756.3 | 756.91 |
| 108 | δ = 7.99 (d, 1H), 7.55 (m, 2H), 7.31-7.05 (m, 13H), 6.97-6.70 (m, 10H), 6.58 (d, 1H), 6.48 (dd, 2H), 6.35 (d, 1H), 1.64 (s, 6H), | 708.3 | 708.86 |

Example 1

A 15 Ohms per square centimeter (Ω/cm²) (1,200 Å) ITO glass substrate (available from Corning Co., Ltd) was cut to a size of 50 millimeters (mm)×50 mm×0.7 mm, sonicated in isopropyl alcohol and pure water for 5 minutes in each solvent, cleaned with ultraviolet rays for 30 minutes, treated with ozone, and was then mounted on a vacuum deposition apparatus.

2-TNATA was vacuum-deposited on the ITO anode of the glass substrate to form a hole injection layer having a thickness of about 600 Å. Compound 4 was then vacuum-deposited on the hole injection layer to form a hole transport layer having a thickness of about 300 Å, thereby forming a hole transport region.

On the hole transport region, 9,10-di(naphthalen-2-yl)anthracene (ADN) (host) and N,N,N',N'-tetraphenyl-pyrene-1,6-diamine (TPD) (dopant) were co-deposited at a weight ratio of about 98:2 to form an emission layer having a thickness of about 300 Å.

Alq₃ was vacuum-deposited on the emission layer to form an electron transport layer having a thickness of about 300 Å. Then, LiF was vacuum-deposited on the electron transport layer to form an electron injection layer having a thickness of about 10 Å, thereby forming an electron transport region.

Aluminum was vacuum-deposited on the electron transport region to form a cathode having a thickness of about 3,000 Å, thereby completing the manufacture of an organic light-emitting device.

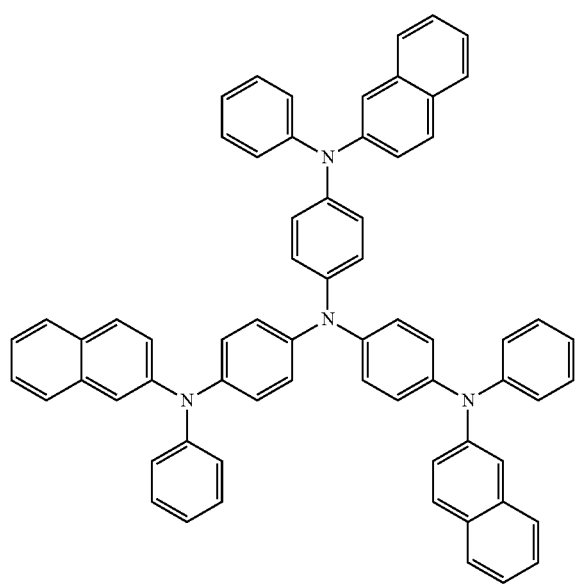

2-TNATA

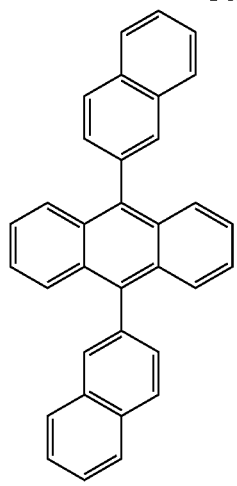

ADN

-continued

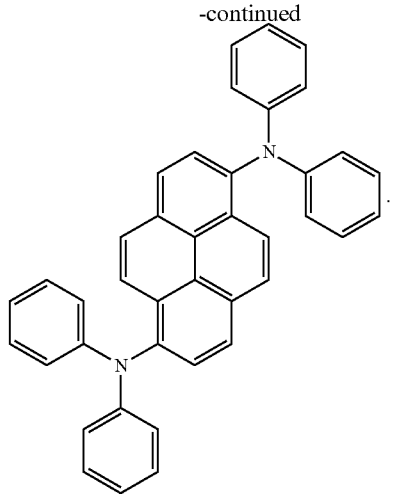

TPD

Examples 2 to 16 and Comparative Examples 1 to 3

Organic light-emitting devices were manufactured in the same manner as in Example 1, except that the compounds listed in Table 2 were used instead of Compound 4 in the formation of a hole transport layer.

Evaluation Example 1

Driving voltages, current densities, luminances, emission colors, efficiencies, and half-lifespans (@100 mA/cm²) of the organic light-emitting devices prepared in Examples 1 to 16 and Comparative Examples 1 to 3 were evaluated using a PR650 Spectroscan Source Measurement Unit. (available from PhotoResearch). The evaluation results are shown in Table 2.

TABLE 2

|  | Hole transport layer | Driving voltage (V) | Current density (mA/cm$^2$) | Luminance (cd/m$^2$) | Efficiency (cd/A) | Emission color | Half lifespan (hr @100 mA/cm$^2$) |
| --- | --- | --- | --- | --- | --- | --- | --- |
| Example 1 | Compound 4 | 5.29 | 50 | 3435 | 6.87 | blue | 382 |
| Example 2 | Compound 18 | 5.36 | 50 | 3135 | 6.27 | blue | 358 |
| Example 3 | Compound 22 | 5.44 | 50 | 3160 | 6.32 | blue | 345 |
| Example 4 | Compound 29 | 5.32 | 50 | 3285 | 6.57 | blue | 354 |
| Example 5 | Compound 40 | 5.83 | 50 | 3095 | 6.19 | blue | 319 |
| Example 6 | Compound 44 | 5.74 | 50 | 3115 | 6.23 | blue | 337 |
| Example 7 | Compound 50 | 6.17 | 50 | 3025 | 6.05 | blue | 323 |
| Example 8 | Compound 59 | 5.27 | 50 | 3095 | 6.19 | blue | 349 |
| Example 9 | Compound 69 | 5.38 | 50 | 3305 | 6.61 | blue | 347 |
| Example 10 | Compound 71 | 5.46 | 50 | 3215 | 6.43 | blue | 352 |

TABLE 2-continued

| | Hole transport layer | Driving voltage (V) | Current density (mA/cm²) | Luminance (cd/m²) | Efficiency (cd/A) | Emission color | Half lifespan (hr @100 mA/cm²) |
|---|---|---|---|---|---|---|---|
| Example 11 | Compound 76 | 5.57 | 50 | 3145 | 6.29 | blue | 317 |
| Example 12 | Compound 81 | 5.84 | 50 | 3065 | 6.13 | blue | 297 |
| Example 13 | Compound 86 | 5.95 | 50 | 3035 | 6.07 | blue | 311 |
| Example 14 | Compound 88 | 5.39 | 50 | 2935 | 5.87 | blue | 304 |
| Example 15 | Compound 95 | 5.63 | 50 | 3190 | 6.38 | blue | 332 |
| Example 16 | Compound 108 | 5.43 | 50 | 3280 | 6.56 | blue | 347 |
| Comparative Example 1 | NPB | 7.07 | 50 | 2545 | 5.09 | blue | 268 |
| Comparative Example 2 | Compound A | 6.76 | 50 | 2130 | 4.26 | blue | 280 |
| Comparative Example 3 | Compound B | 9.48 | 50 | 1305 | 2.61 | blue | 163 |

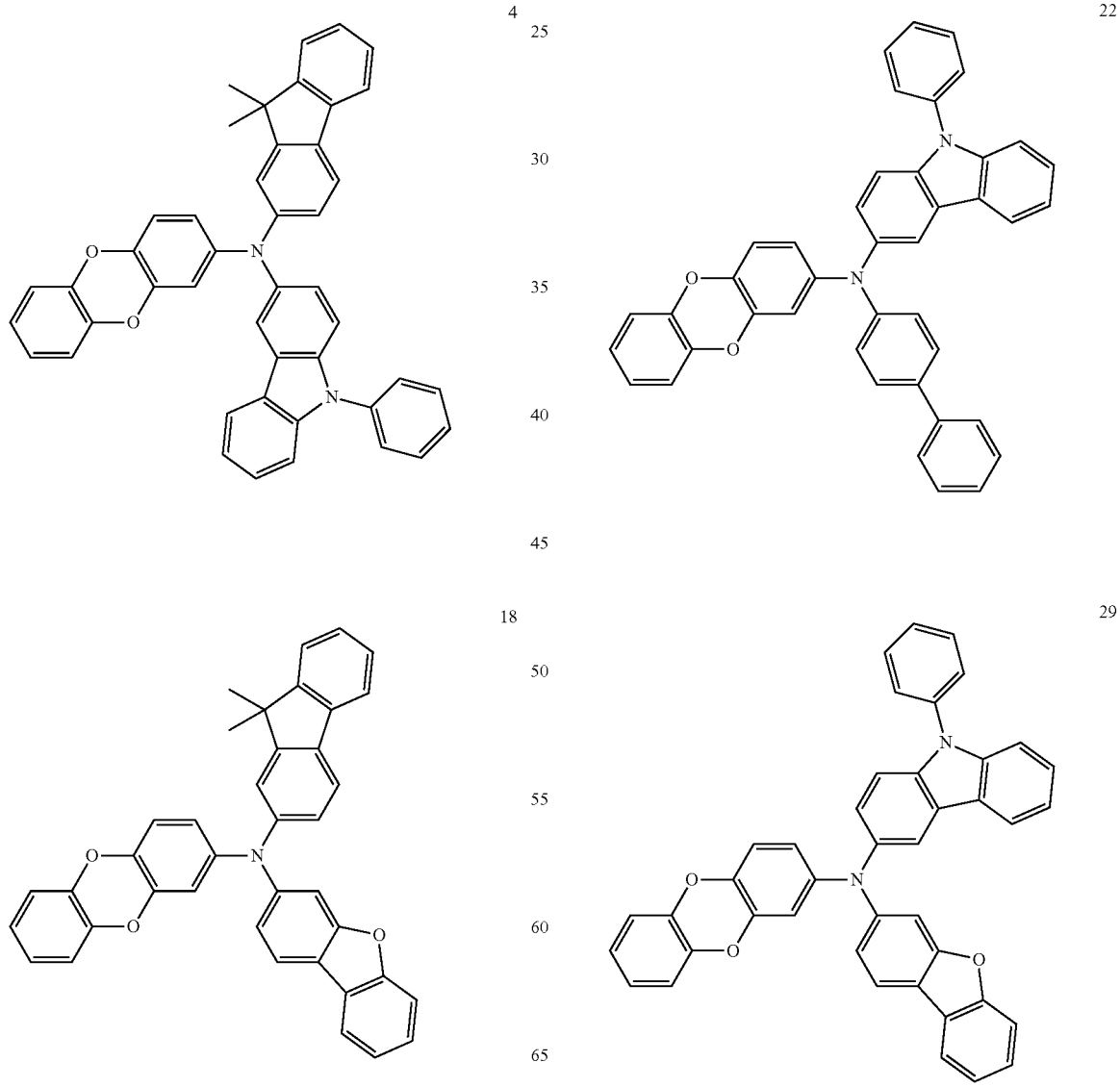

-continued
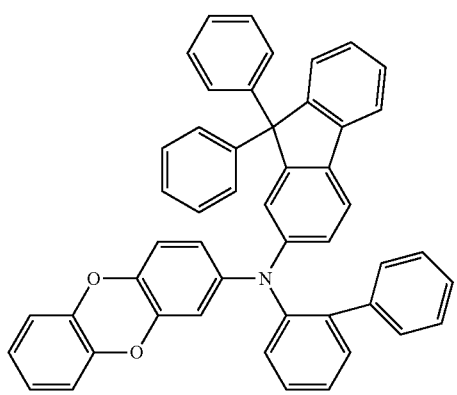
40
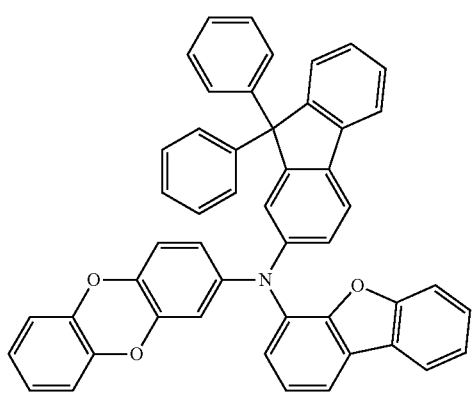
44
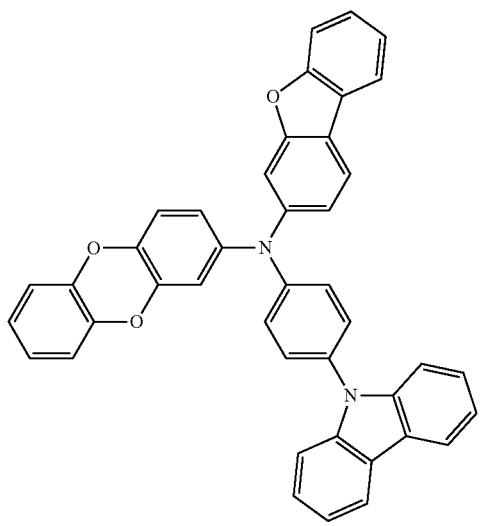
50
-continued
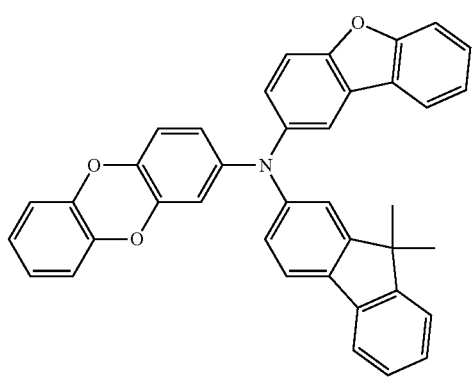
59
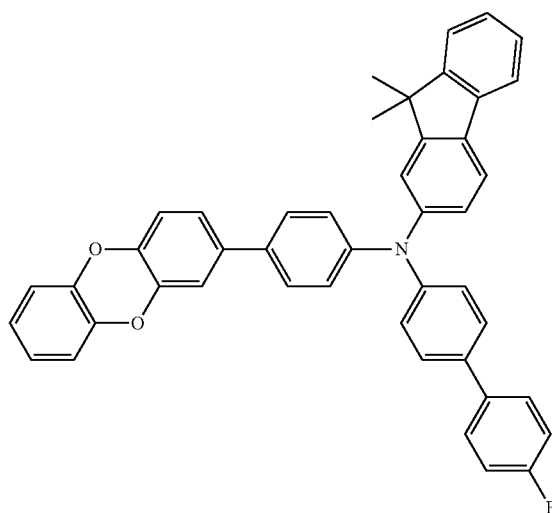
71

76
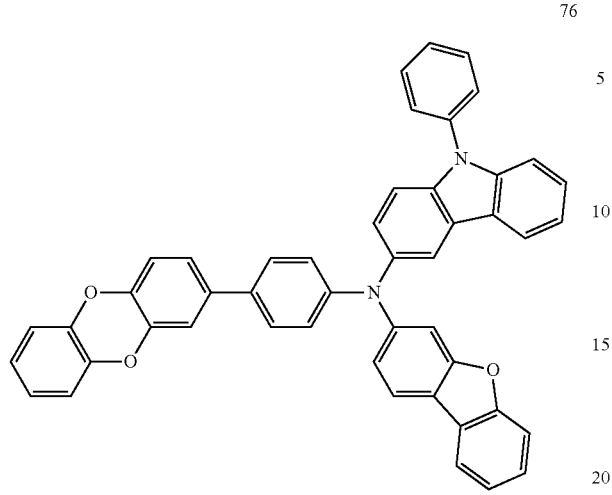
88
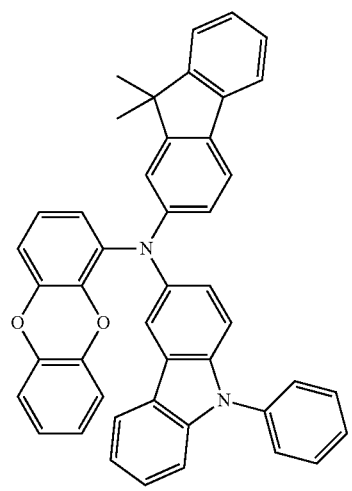
81
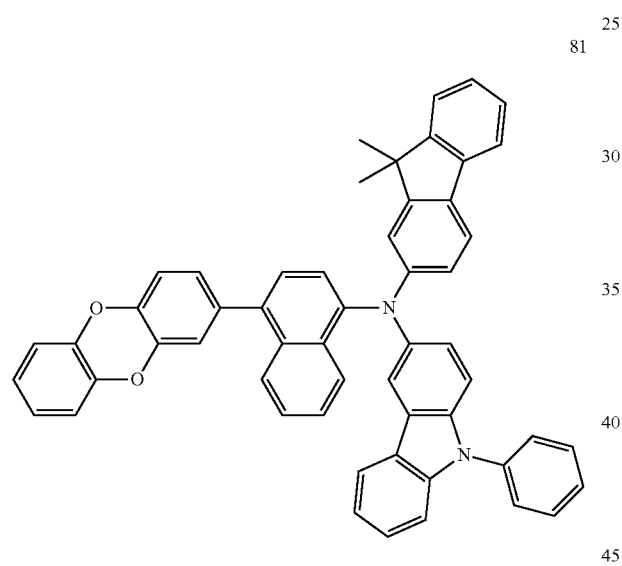
95
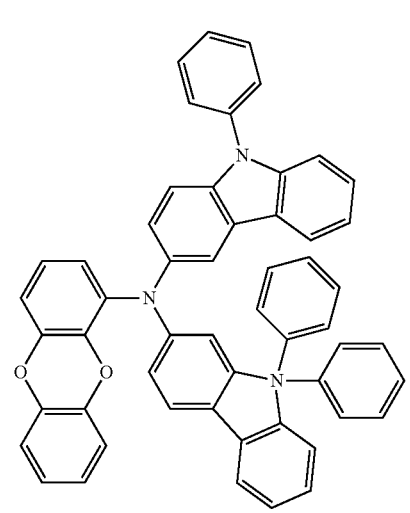
86
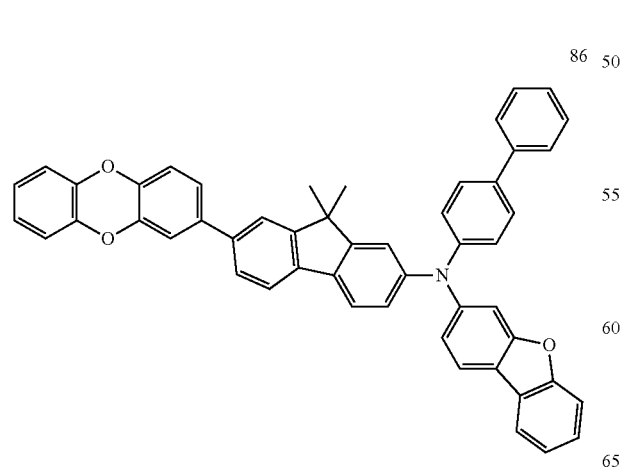
108
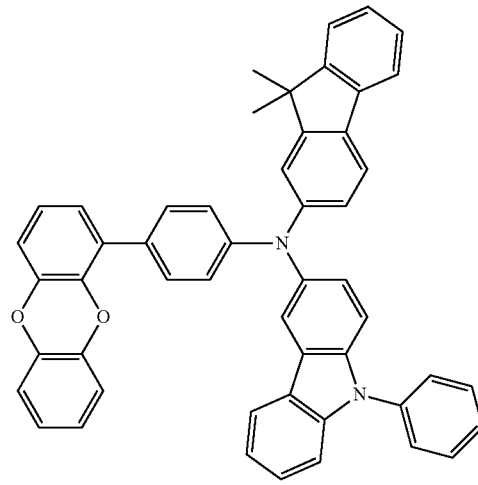

Compound A

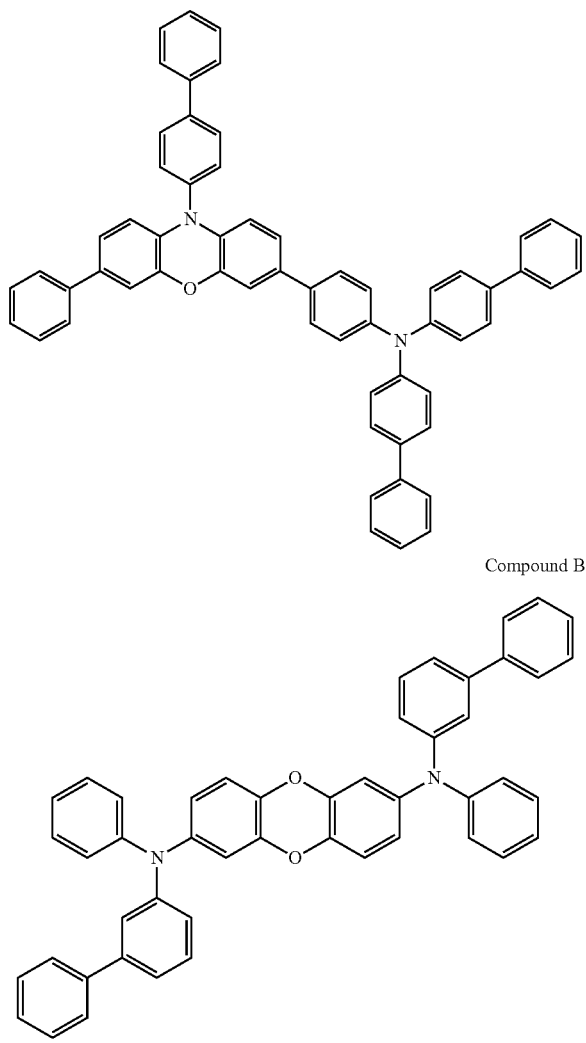

Compound B

According to Table 2, it was found that the organic light-emitting devices prepared in Examples 1 to 16 had low driving voltages, high luminances, high efficiencies, and long lifespans compared to the organic light-emitting devices prepared in Comparative Examples 1 to 3.

As described above, according to one or more example embodiments, the organic light-emitting device including the condensed-cyclic compound may have a low driving voltage, improved efficiency, improved luminance, and long lifespan.

It should be understood that example embodiments described herein should be considered in a descriptive sense only and not for purposes of limitation. Descriptions of features or aspects within each example embodiment should typically be considered as available for other similar features or aspects in other example embodiments.

As used herein, the terms "use", "using", and "used" may be considered synonymous with the terms "utilize", "utilizing", and "utilized", respectively. Further, the use of "may" when describing embodiments of the present disclosure refers to "one or more embodiments of the present disclosure".

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more example embodiments have been described with reference to the drawing, it will be understood by those of ordinary skill in the art that various changes in form and details may be made therein without departing from the spirit and scope as defined by the following claims and equivalents thereof.

What is claimed is:

1. A condensed-cyclic compound represented by one of Formulae 1A and 1B:

Formula 1A

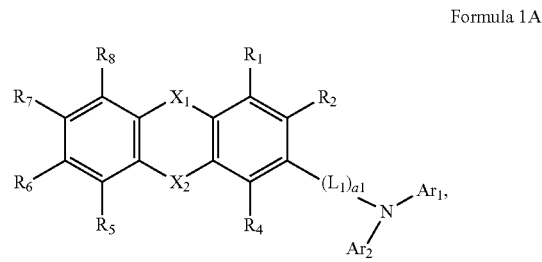

Formula 1B

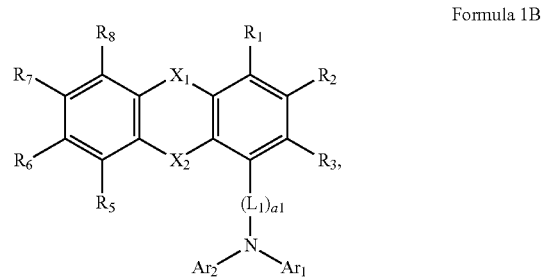

wherein, in Formulae 1A and 1B,
$X_1$ and $X_2$ are each O,
$L_1$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 is an integer selected from 0 to 3, and when a1 is 2 or more, each $L_1$ moiety is independently selected from the above described groups, $Ar_1$ is selected from the groups represented by Formulae 6-1 to 6-54, and $Ar_2$ is selected from the groups represented by Formulae 6-11, 6-12, 6-14, 6-19, 6-20, 6-24 to 6-27, 6-30, 6-31, 6-42, 6-43, and 6-52 to 6-54:

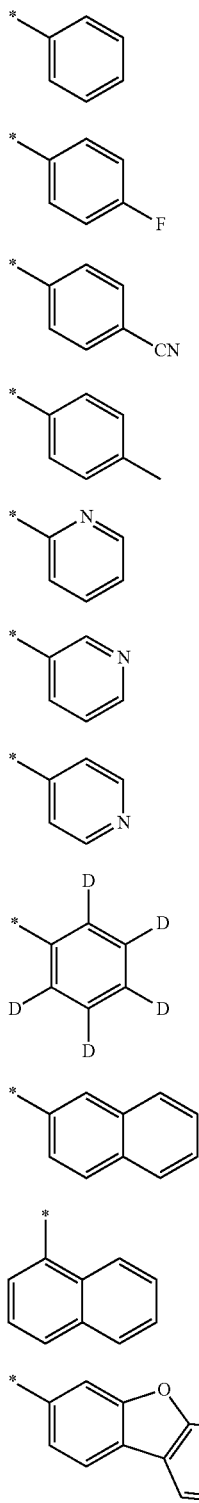

Formula 6-1
Formula 6-2
Formula 6-3
Formula 6-4
Formula 6-5
Formula 6-6
Formula 6-7
Formula 6-8
Formula 6-9
Formula 6-10
Formula 6-11

-continued

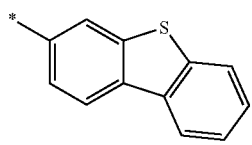

Formula 6-12

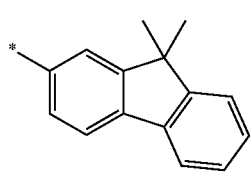

Formula 6-13

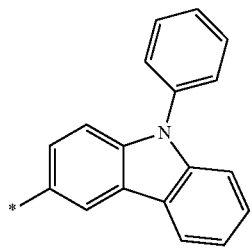

Formula 6-14

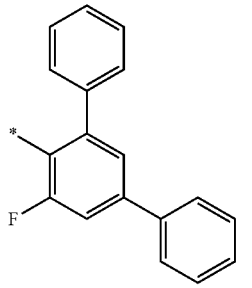

Formula 6-15

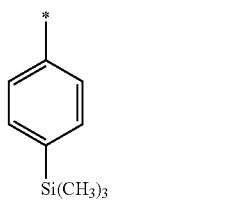

Formula 6-16

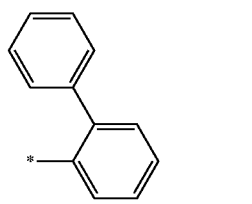

Formula 6-17

Formula 6-18

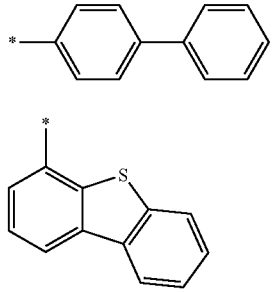

Formula 6-19

-continued
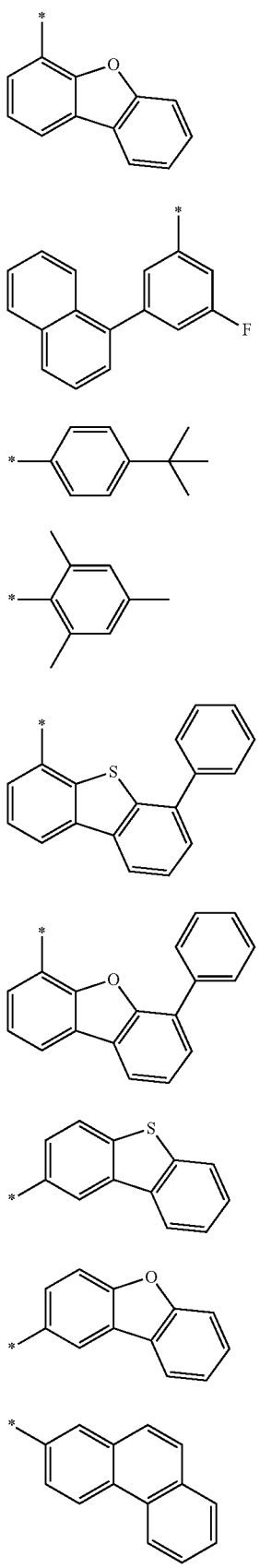
Formula 6-20
Formula 6-21
Formula 6-22
Formula 6-23
Formula 6-24
Formula 6-25
Formula 6-26
Formula 6-27
Formula 6-28
-continued
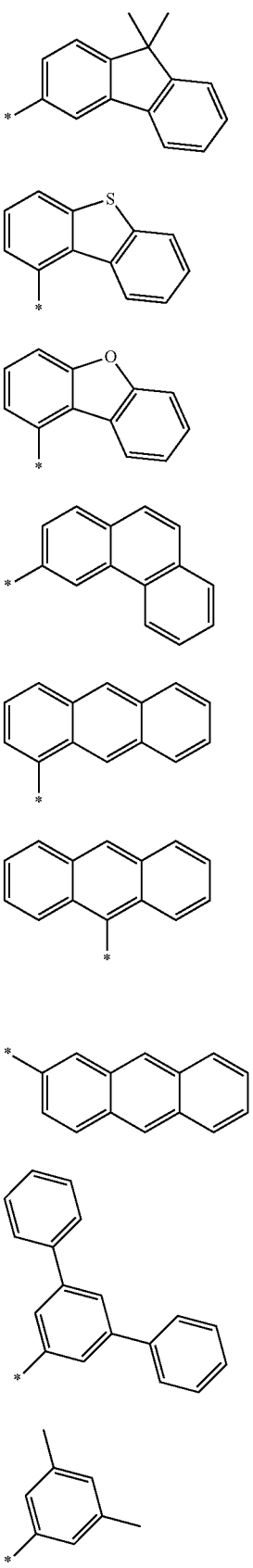
Formula 6-29
Formula 6-30
Formula 6-31
Formula 6-32
Formula 6-33
Formula 6-34
Formula 6-35
Formula 6-36
Formula 6-37

-continued

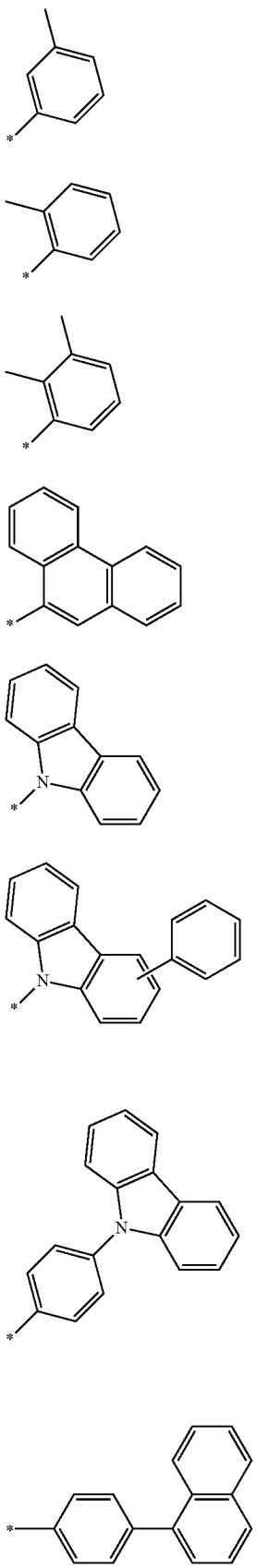

Formula 6-38

Formula 6-39

Formula 6-40

Formula 6-41

Formula 6-42

Formula 6-43

Formula 6-44

Formula 6-45

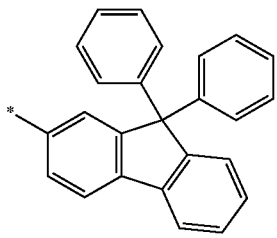
Formula 6-46

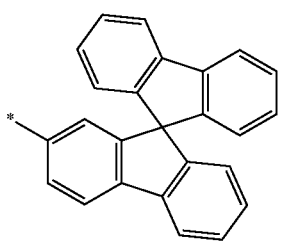
Formula 6-47

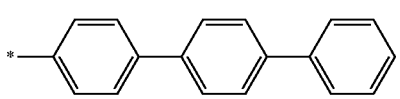
Formula 6-48

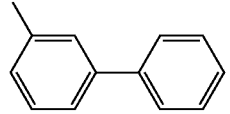
Formula 6-49

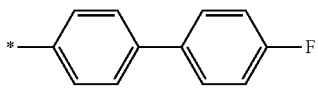
Formula 6-50

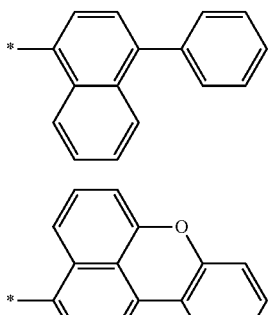
Formula 6-51

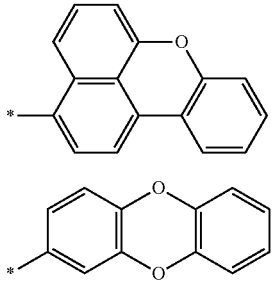
Formula 6-52

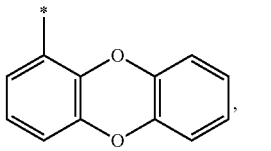
Formula 6-53

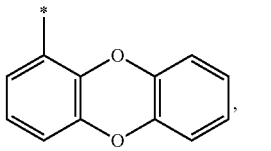
Formula 6-54 wherein, in Formulae 6-1 to 6-54, * indicates a binding site to an adjacent atom, $R_1$, $R_2$, $R_4$, and $R_5$ to $R_8$ in Formula 1A and $R_1$ to $R_3$ and $R_5$ to $R_8$ in Formula 1B are each independently selected from hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$), and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed-cyclic compound of claim 1, wherein $L_1$ is selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed-cyclic compound of claim 1, wherein $L_1$ is selected from the group represented by Formulae 3-1 to 3-41:

Formula 3-1

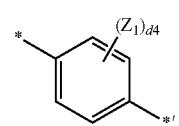

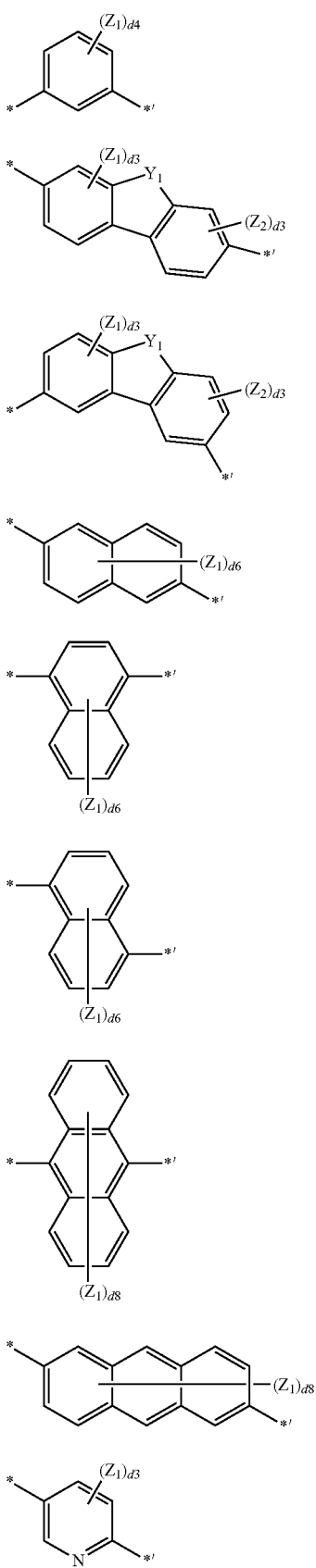
Formula 3-2
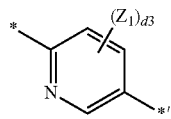
Formula 3-11
Formula 3-3
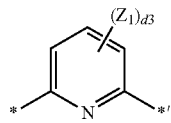
Formula 3-12
Formula 3-4
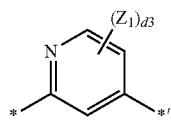
Formula 3-13
Formula 3-5
Formula 3-14
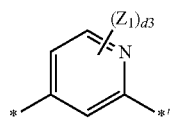
Formula 3-15
Formula 3-6
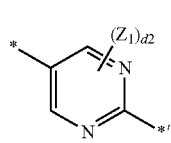
Formula 3-16
Formula 3-7
Formula 3-17
Formula 3-8
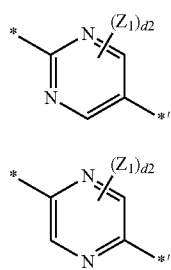
Formula 3-18
Formula 3-19
Formula 3-20
Formula 3-9
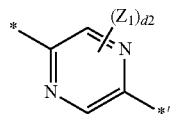
Formula 3-21
Formula 3-10
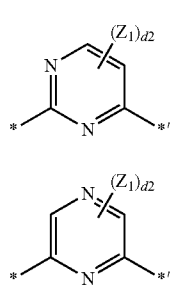
Formula 3-22
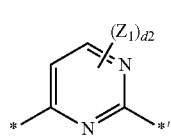

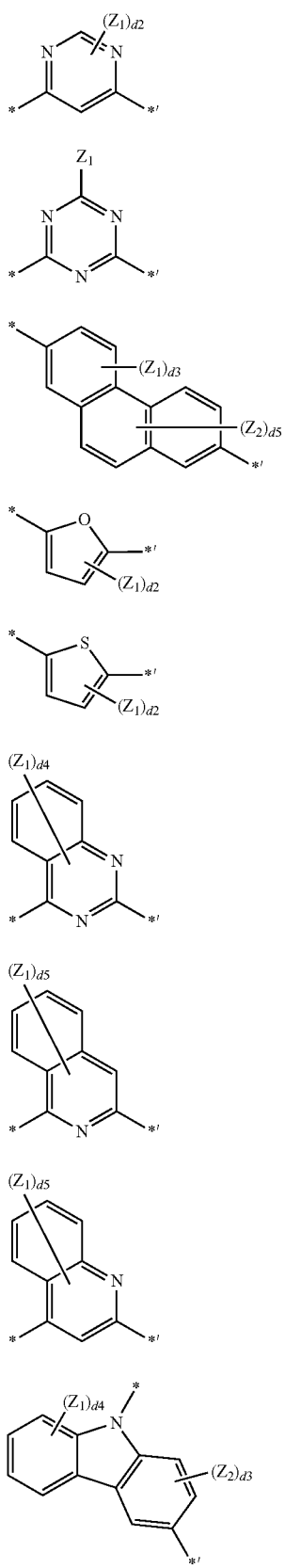
Formula 3-23
Formula 3-24
Formula 3-25
Formula 3-26
Formula 3-27
Formula 3-28
Formula 3-29
Formula 3-30
Formula 3-31
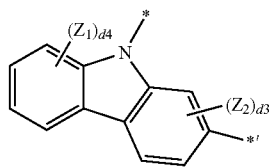
Formula 3-32
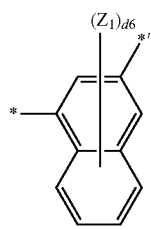
Formula 3-33
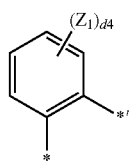
Formula 3-34
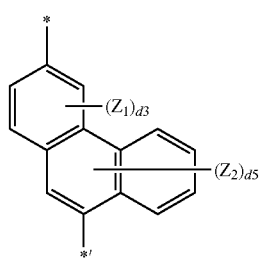
Formula 3-35
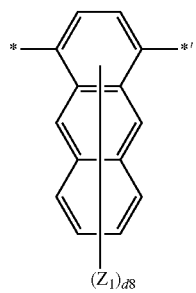
Formula 3-36
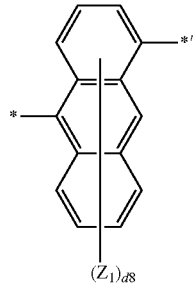
Formula 3-37

Formula 3-38

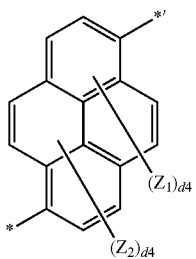

Formula 3-39

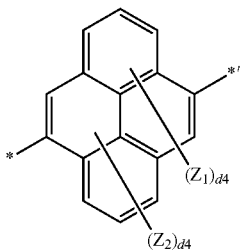

Formula 3-40

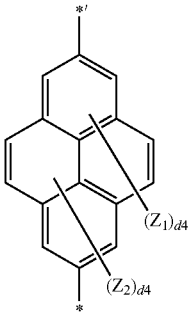

Formula 3-41

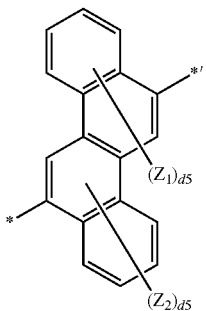

wherein, in Formulae 3-1 to 3-41, $Y_1$ is O, S, $C(Z_3)(Z_4)$, $N(Z_5)$, or $Si(Z_6)(Z_7)$, and $Z_1$ to $Z_7$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, a biphenyl group, a terphenyl group, and a naphthyl group, d2 is an integer selected from 1 and 2, d3 is an integer selected from 1 to 3, d4 is an integer selected from 1 to 4, d5 is an integer selected from 1 to 5, d6 is an integer selected from 1 to 6, d8 is an integer selected from 1 to 8, and

* and *' each indicate a binding site to an adjacent atom.

4. The condensed-cyclic compound of claim 1, wherein a1 is 0, 1, or 2.

5. The condensed-cyclic compound of claim 1, wherein *-$(L_1)_{a1}$-*' is selected from a single bond and the group represented by Formulae 4-1 to 4-36:

Formula 4-1

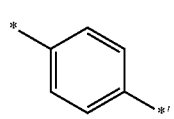

Formula 4-2

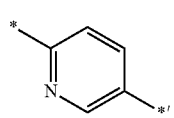

Formula 4-3

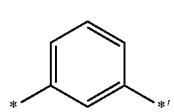

Formula 4-4

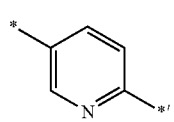

Formula 4-5

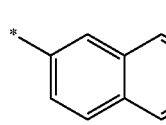

Formula 4-6

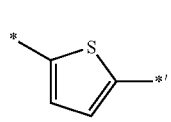

Formula 4-7

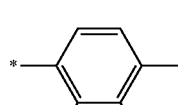

Formula 4-8

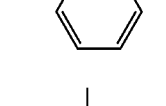

191
-continued
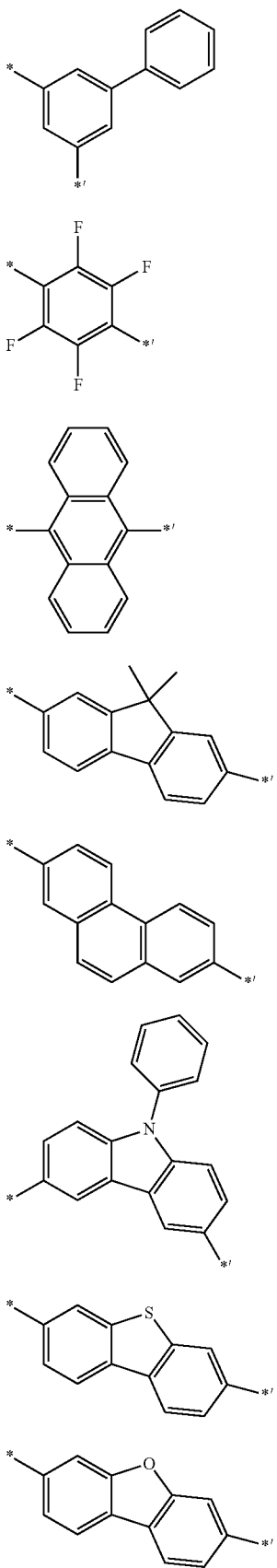
192
-continued
Formula 4-9
Formula 4-10
Formula 4-11
Formula 4-12
Formula 4-13
Formula 4-14
Formula 4-15
Formula 4-16
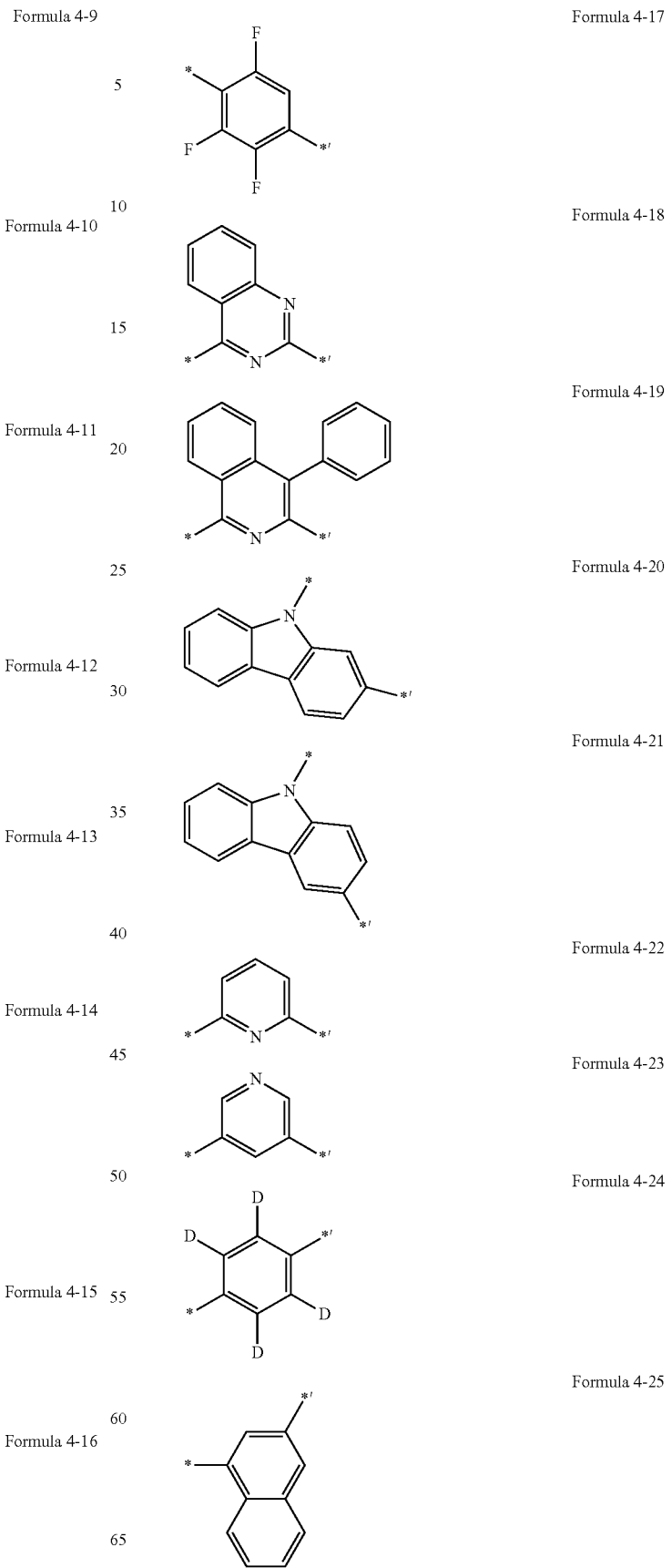
Formula 4-17
Formula 4-18
Formula 4-19
Formula 4-20
Formula 4-21
Formula 4-22
Formula 4-23
Formula 4-24
Formula 4-25

-continued

Formula 4-26
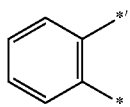

Formula 4-27
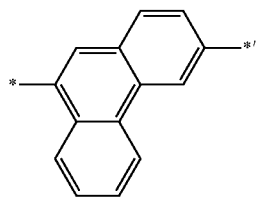

Formula 4-28
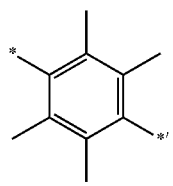

Formula 4-29
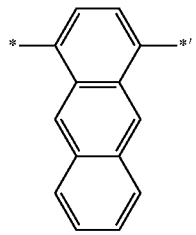

Formula 4-30
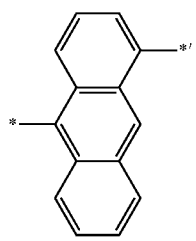

Formula 4-31
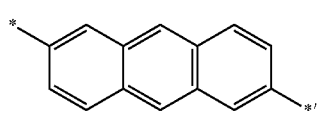

Formula 4-32
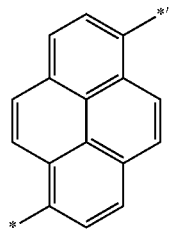

Formula 4-33
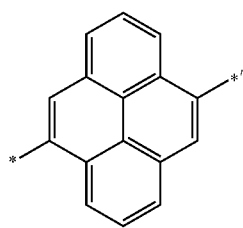

Formula 4-34
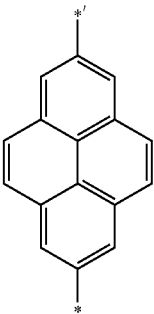

Formula 4-35
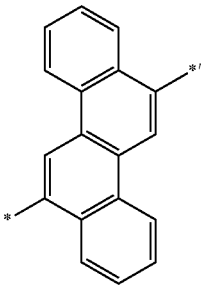

Formula 4-36 wherein, in Formulae 4-1 to 4-36, * and *' each indicate a binding site to an adjacent atom.

6. The condensed-cyclic compound of claim 1, wherein $R_1$ to $R_8$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

7. The condensed-cyclic compound of claim 1, wherein $R_1$ to $R_8$ are each independently selected from:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

8. The condensed-cyclic compound of claim 1, wherein $R_1$ to $R_8$ are each independently selected from:
hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;
a phenyl group, a biphenyl group, a terphenyl group, a naphthyl group, a pyridinyl group, a pyrimidinyl group, and a triazinyl group;
a phenyl group, a naphthyl group, a pyridinyl group, a pyrimidinyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

9. The condensed-cyclic compound of claim 1, wherein $R_1$, $R_2$, and $R_5$ to $R_8$ are hydrogen.

10. The condensed-cyclic compound of claim 1, wherein:

$R_1$, $R_2$, $R_4$, and $R_5$ to $R_8$ in Formula 1A and $R_1$ to $R_3$ and $R_5$ to $R_8$ in Formula 1B are each hydrogen, and

*-$(L_1)_{a1}$-*' is a single bond or selected from the group represented by Formulae 4-1 to 4-36:

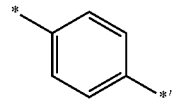

Formula 4-1

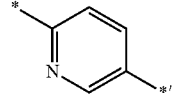

Formula 4-2

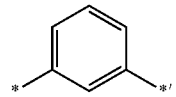

Formula 4-3

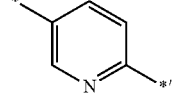

Formula 4-4

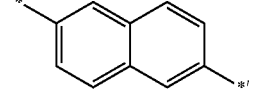

Formula 4-5

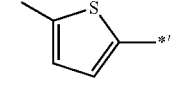

Formula 4-6

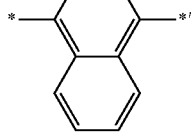

Formula 4-7

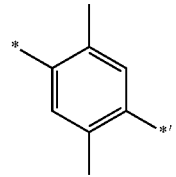

Formula 4-8

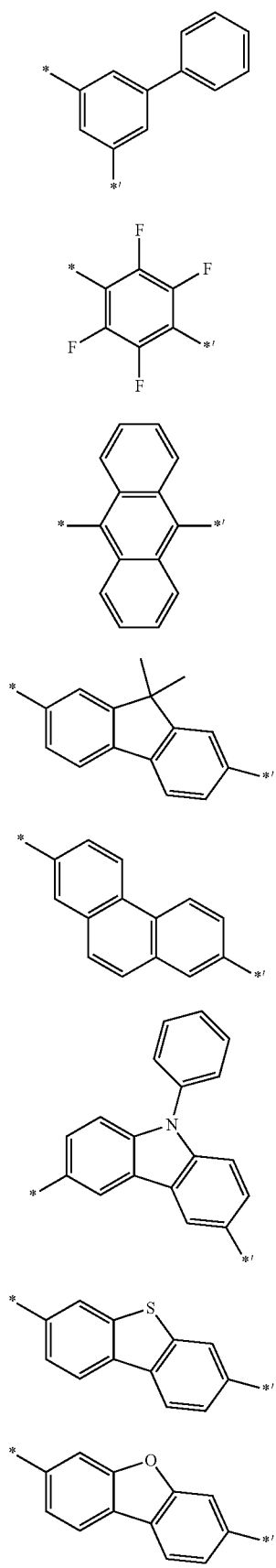
Formula 4-9
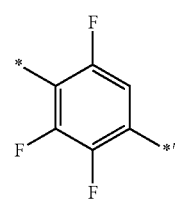
Formula 4-10
Formula 4-11
Formula 4-12
Formula 4-13
Formula 4-14
Formula 4-15
Formula 4-16
Formula 4-17
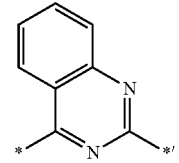
Formula 4-18
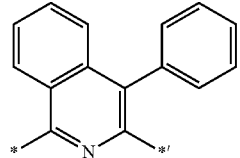
Formula 4-19
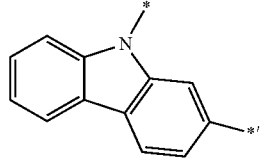
Formula 4-20
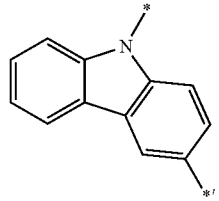
Formula 4-21
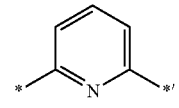
Formula 4-22
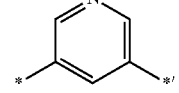
Formula 4-23
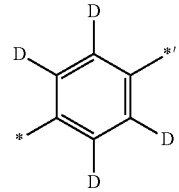
Formula 4-24
Formula 4-25
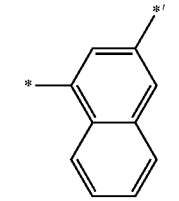

Formula 4-26 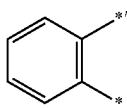
Formula 4-27 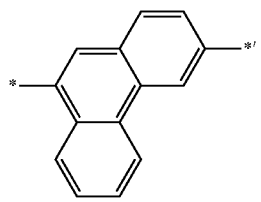
Formula 4-28 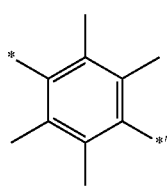
Formula 4-29 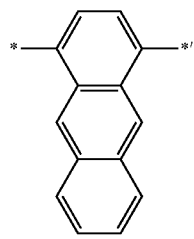
Formula 4-30 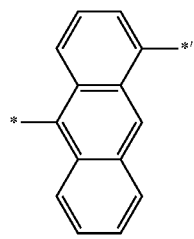
Formula 4-31 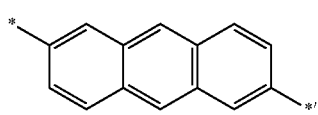
Formula 4-32 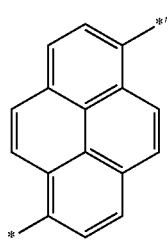
Formula 4-33 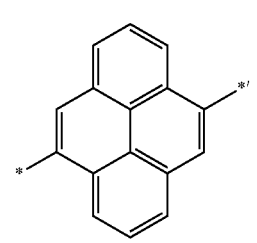
Formula 4-34 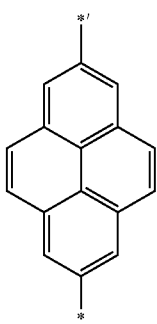
Formula 4-35 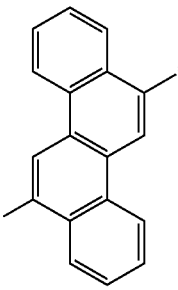
Formula 4-36 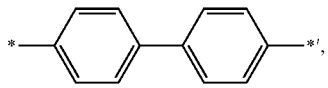
wherein, in Formulae 4-1 to 4-36, * and *' each indicate a binding site to an adjacent atom.
11. A condensed-cyclic compound represented by one of Compounds 4, 14 to 18, 21 to 29, 35, 36, 43 to 46, 48 to 69, 72 to 76, 79 to 81, 84 to 86, 88, 90, 91, 93 to 96, 98, 101 to 104, 107, 108, and 110 to 117:
4
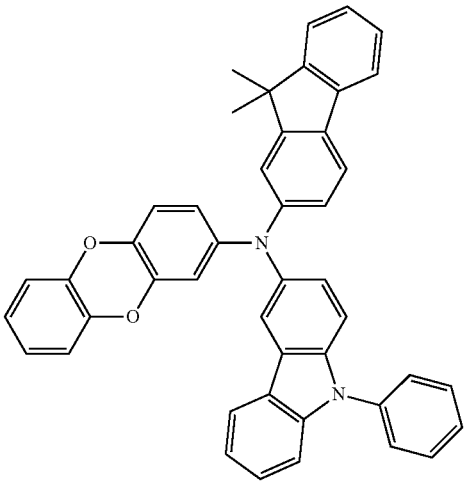

14
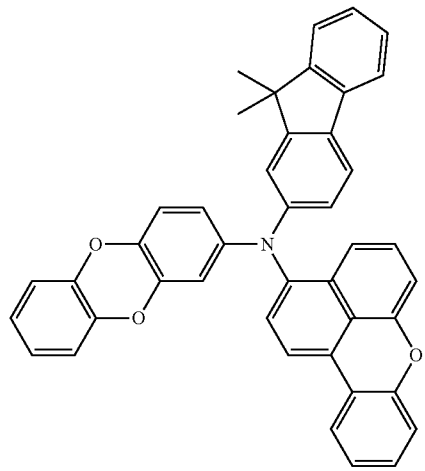
15
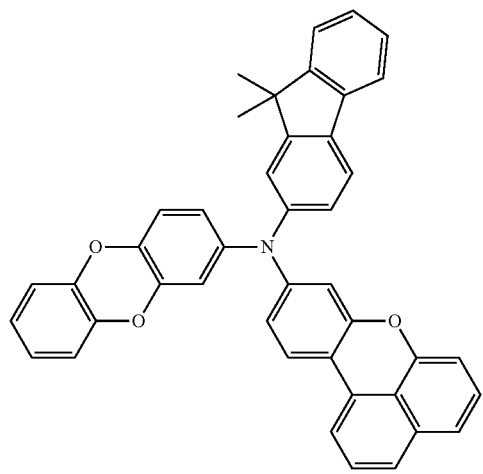
16
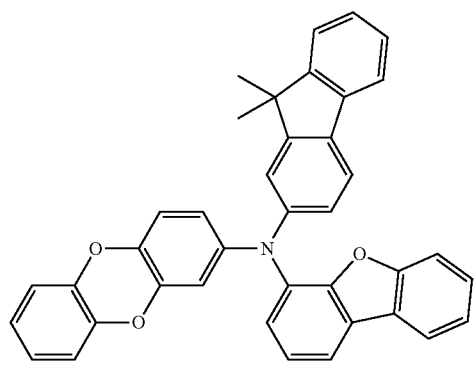
17
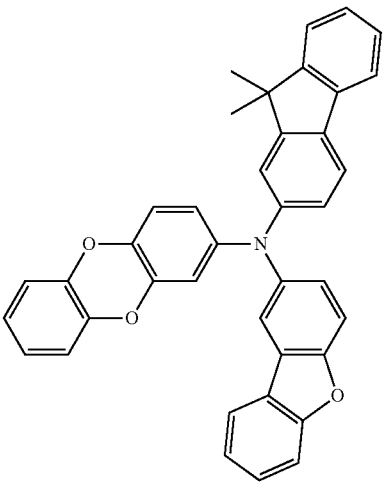
18
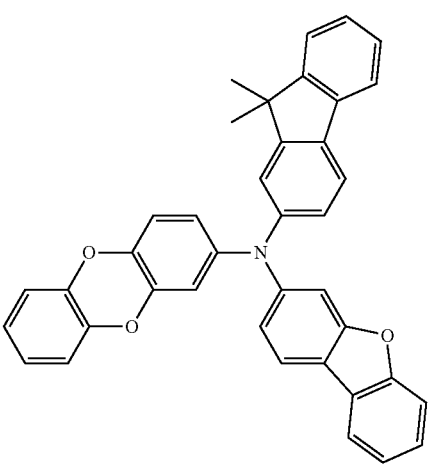
21
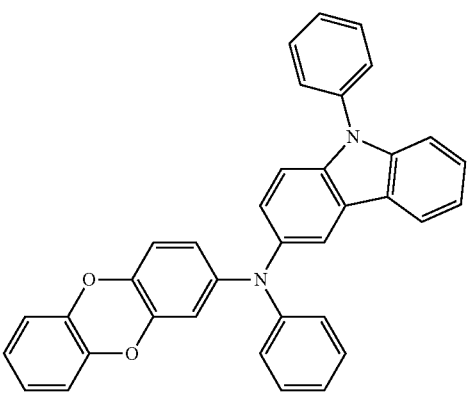

203
-continued
22
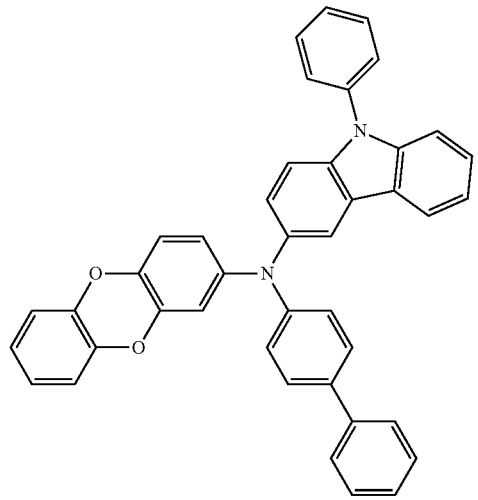
23
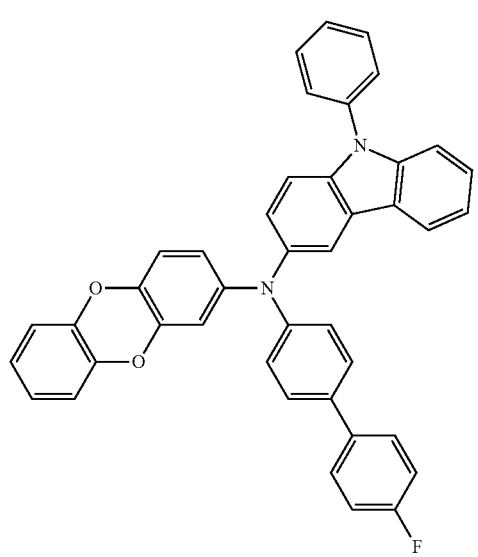
24
-continued
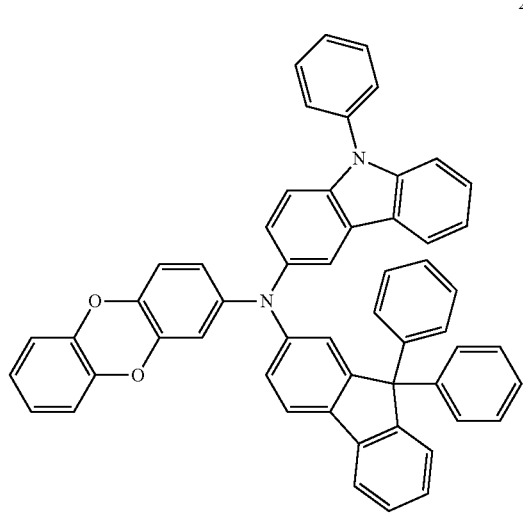
25
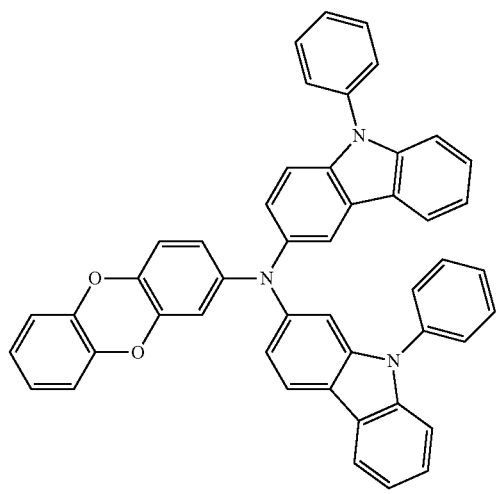
26
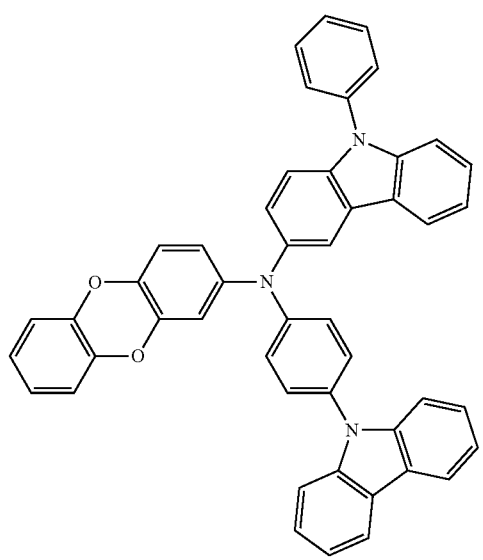

205
-continued
27
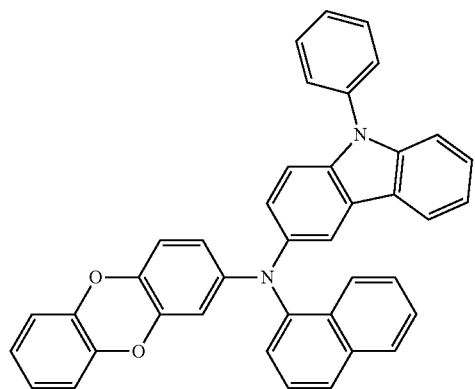
28
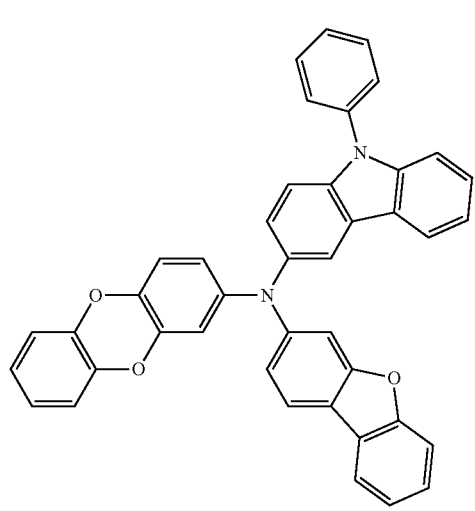
29
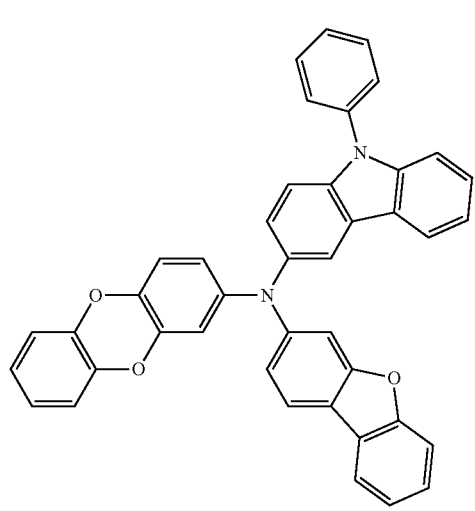
206
-continued
33
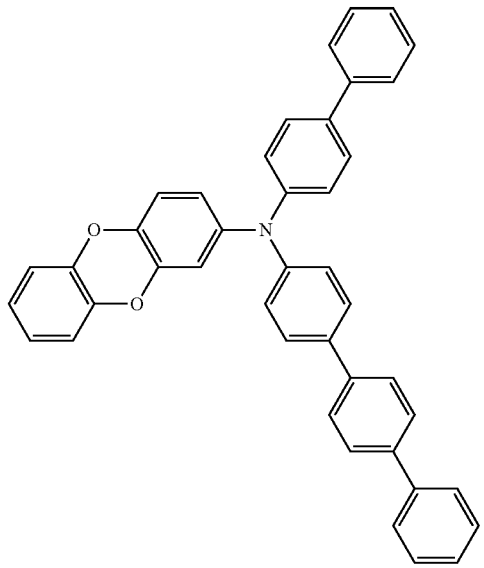
34
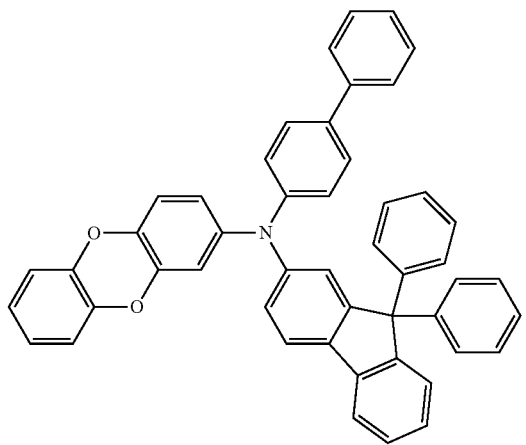
38
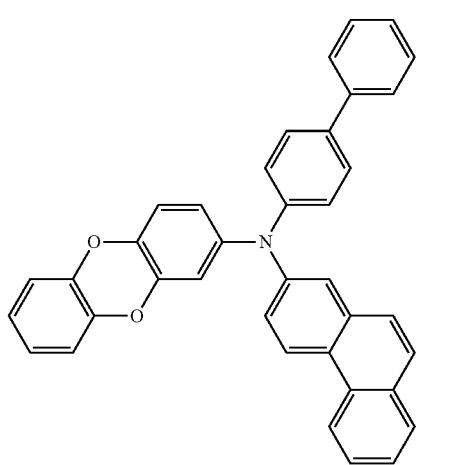

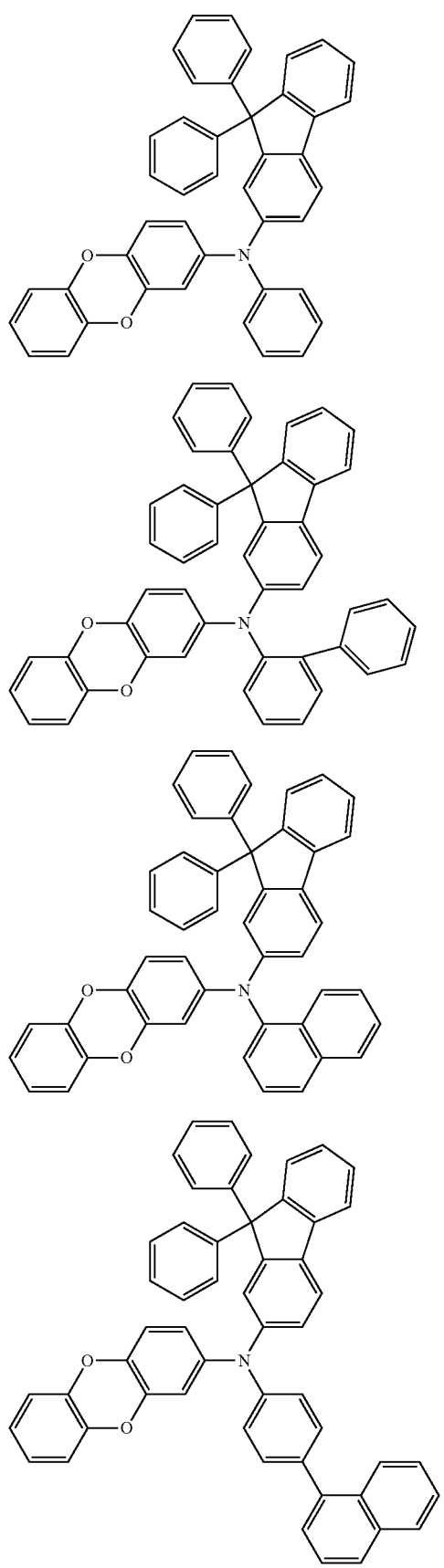
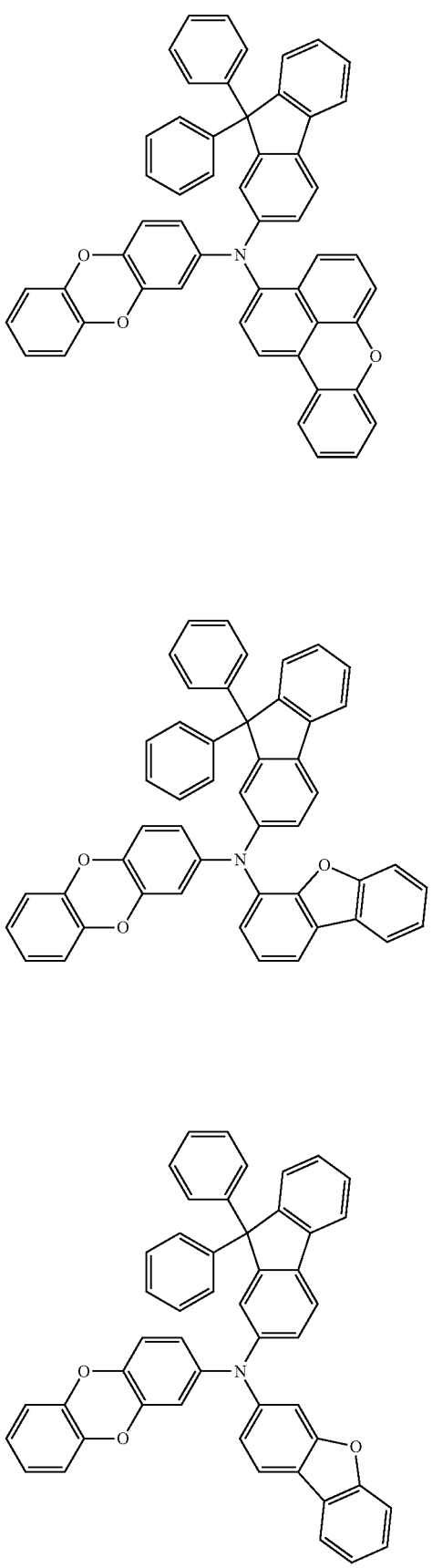

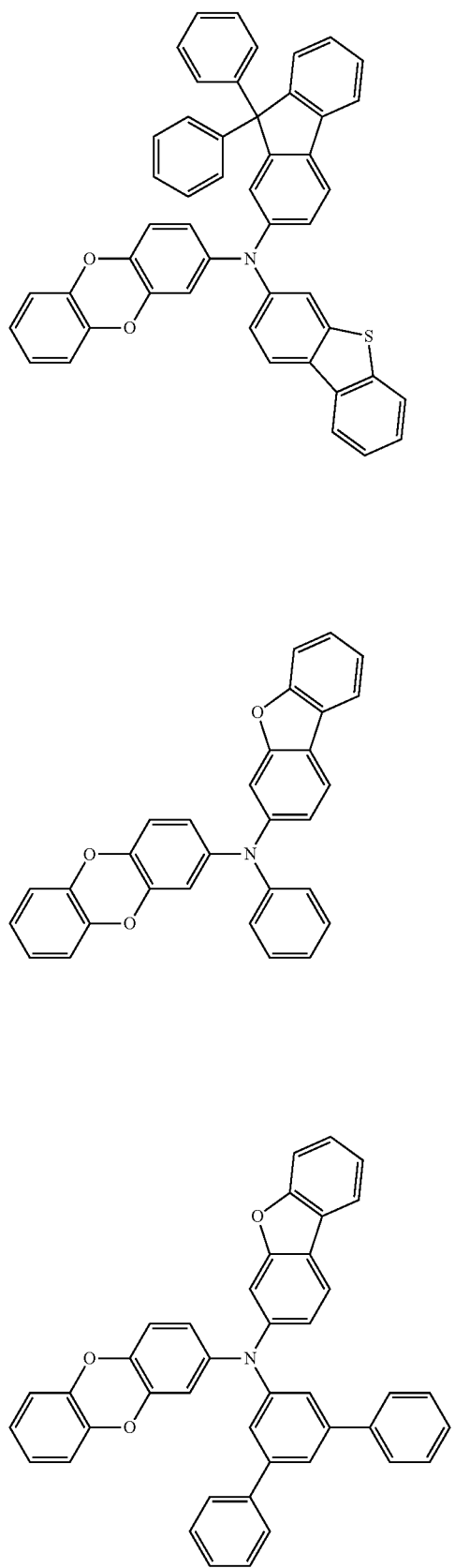
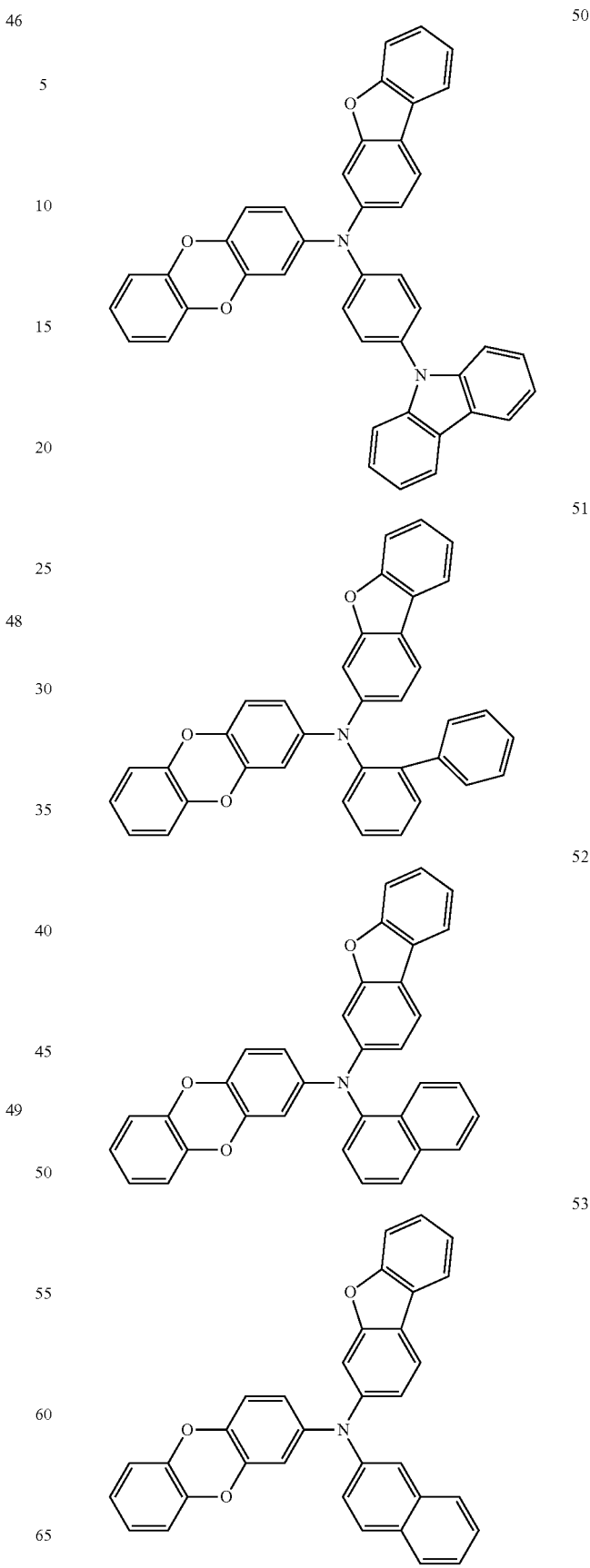

211
-continued
54
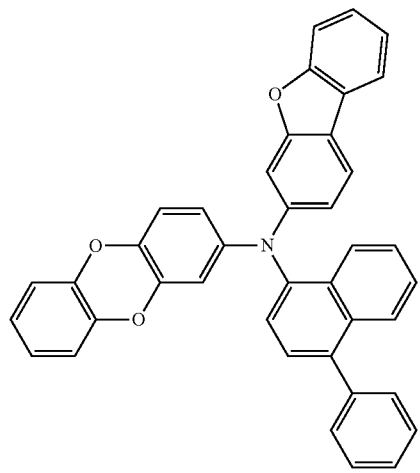
55
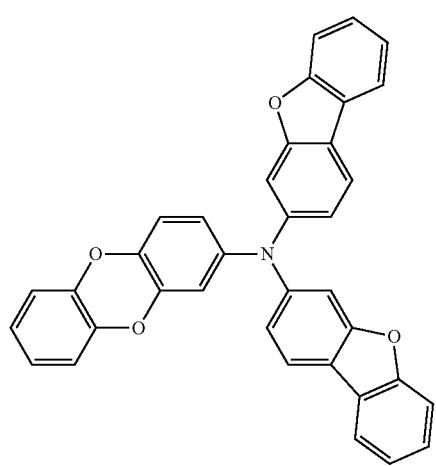
56
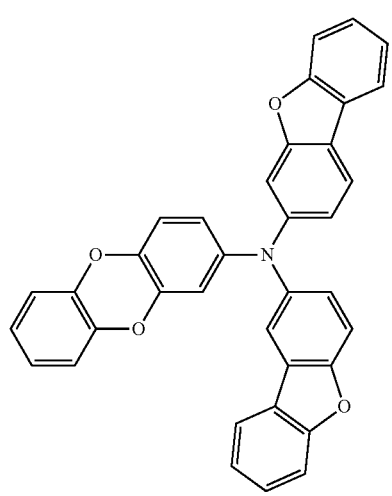
212
-continued
57
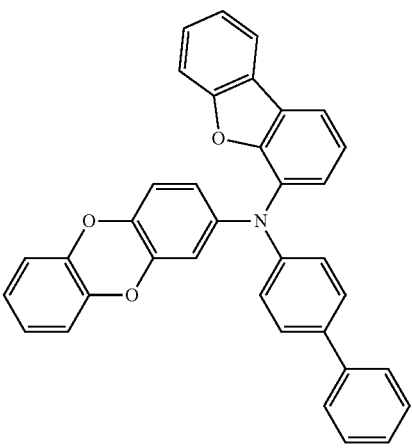
58
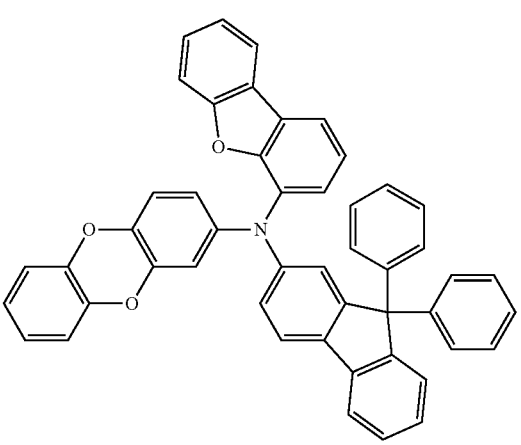
59
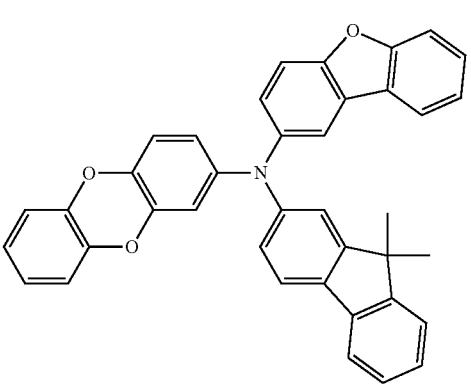

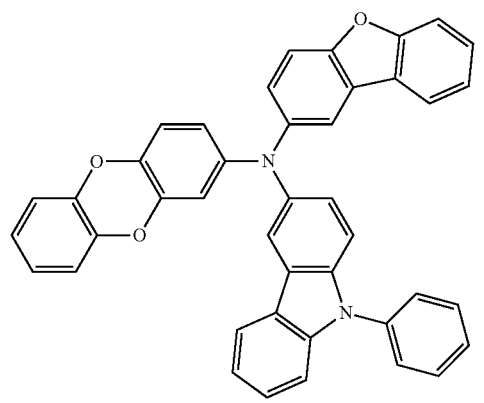
60
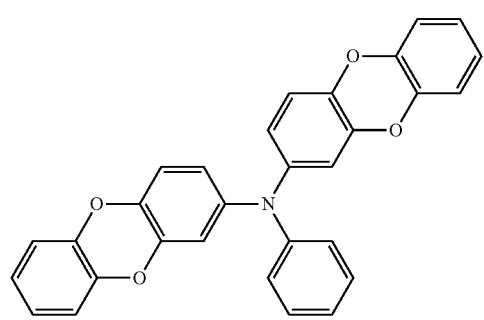
61
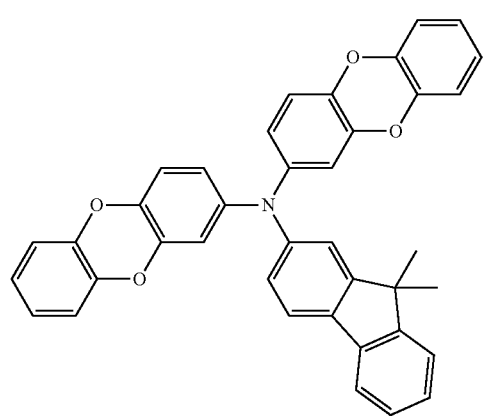
62
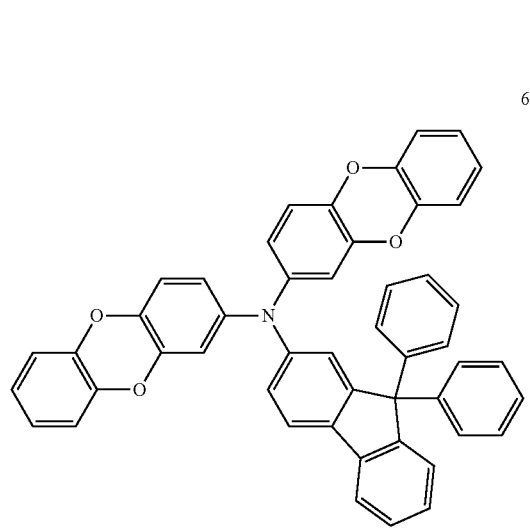
63
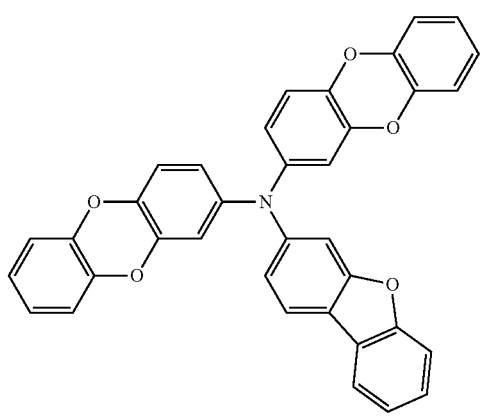
64
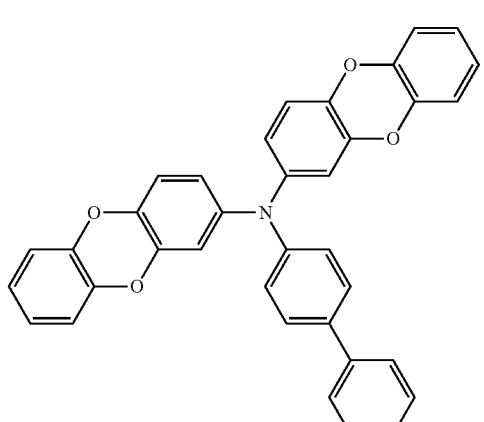
65
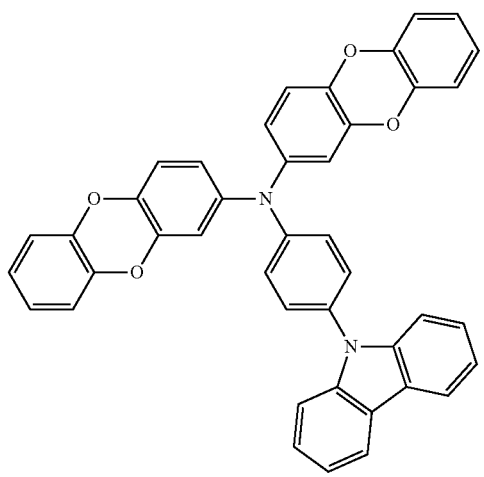
66

67
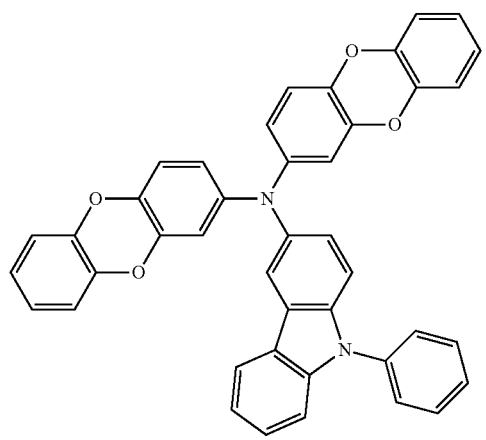
68
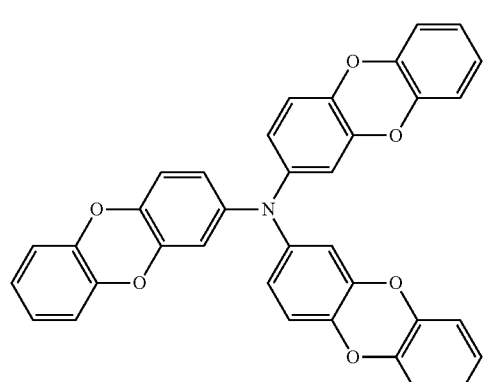
69
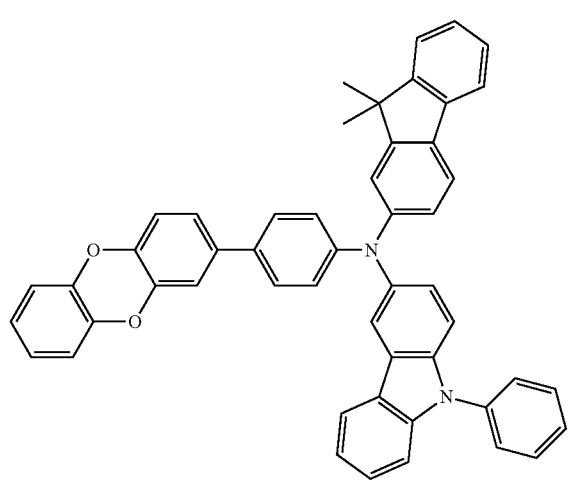
72
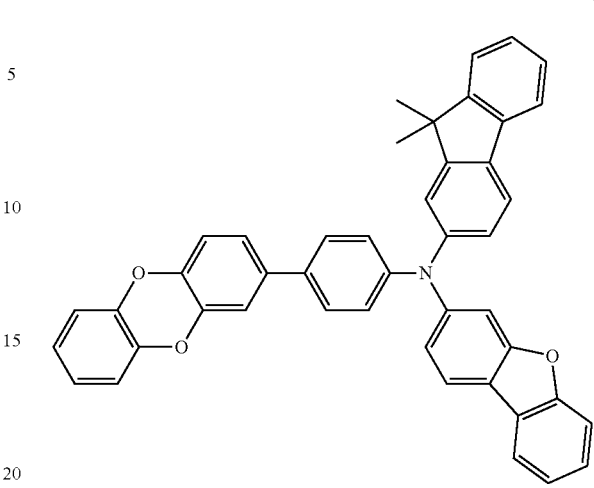
73
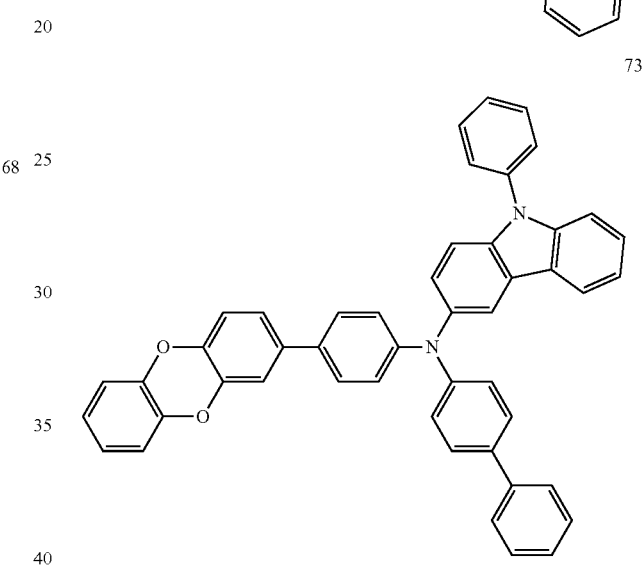
74
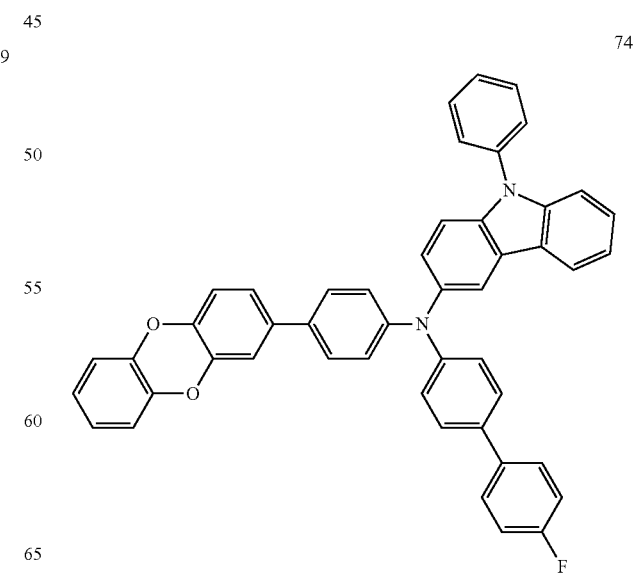

217
-continued
75
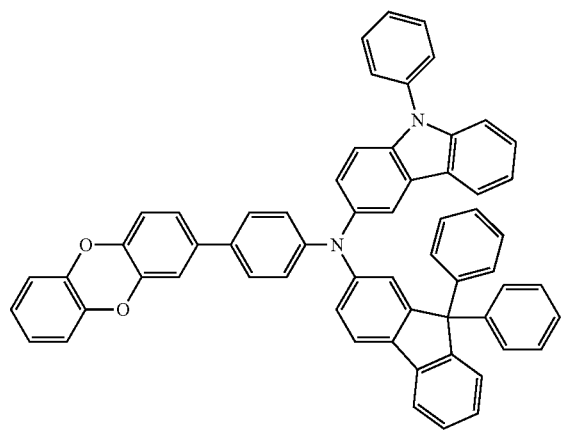
76
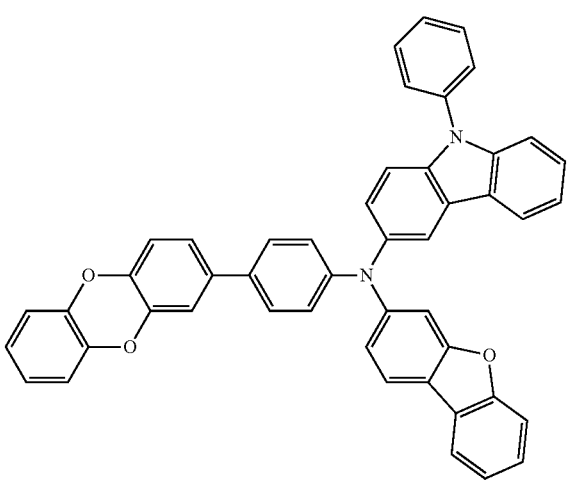
79
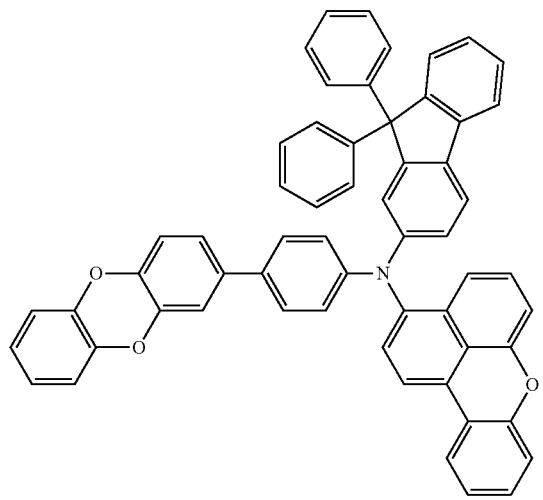
218
-continued
80
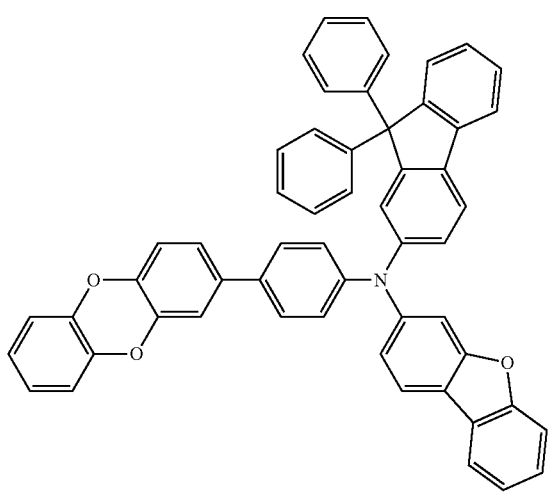
81
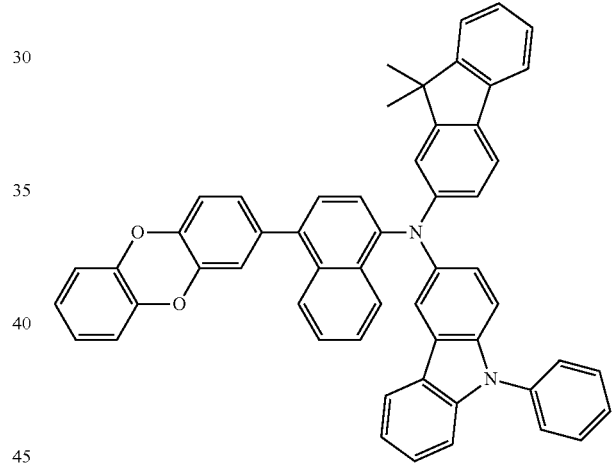
84
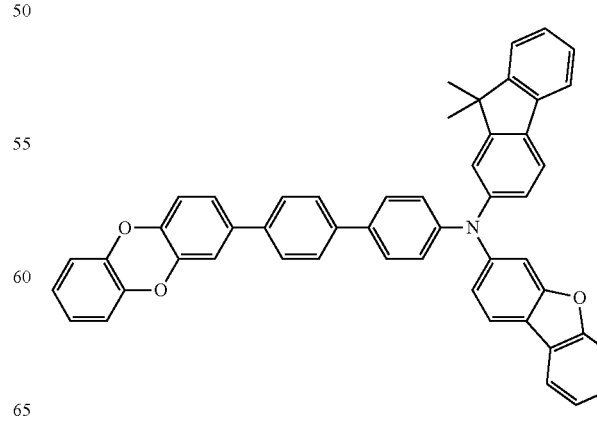

219
-continued
85
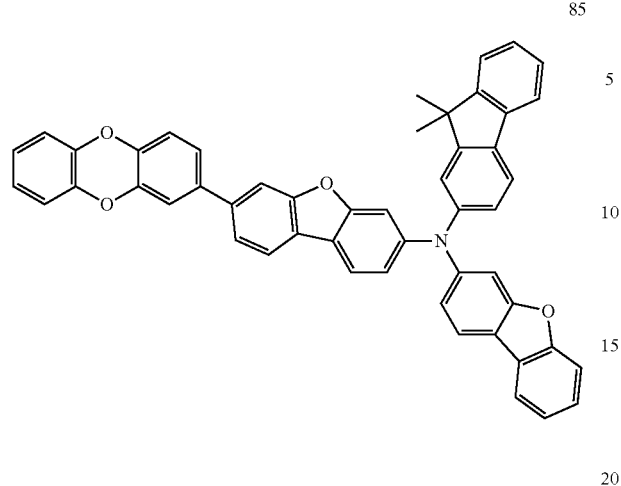
86
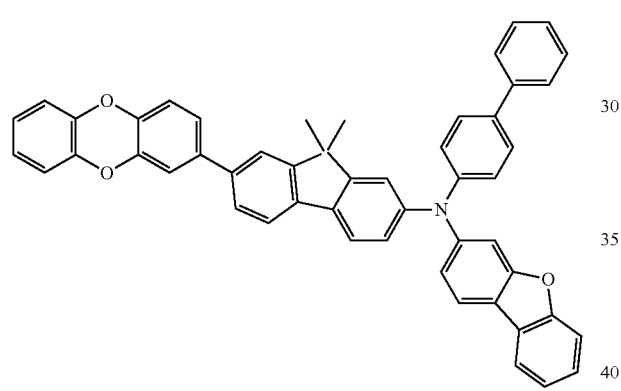
88
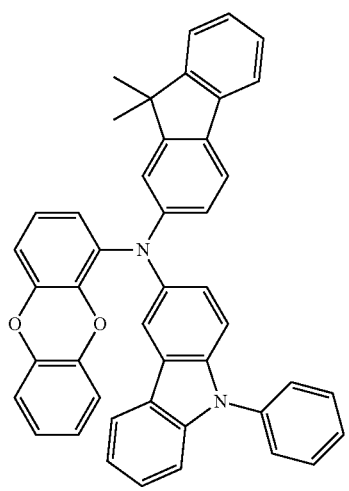
220
-continued
90
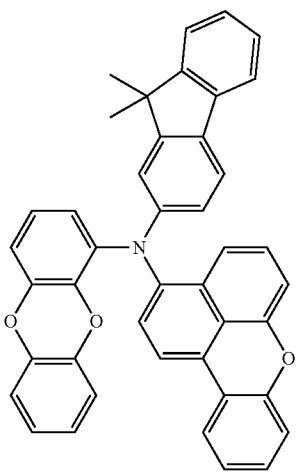
91
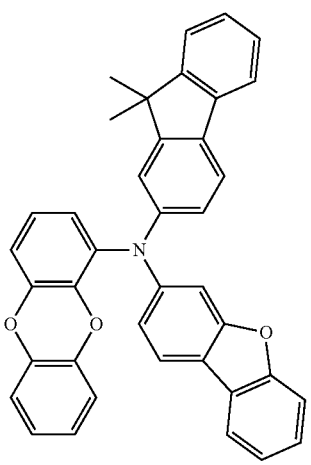
93
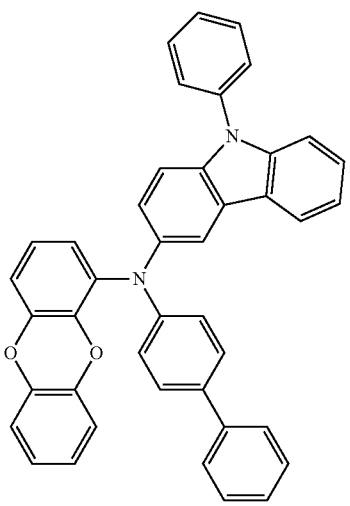

221
-continued
94
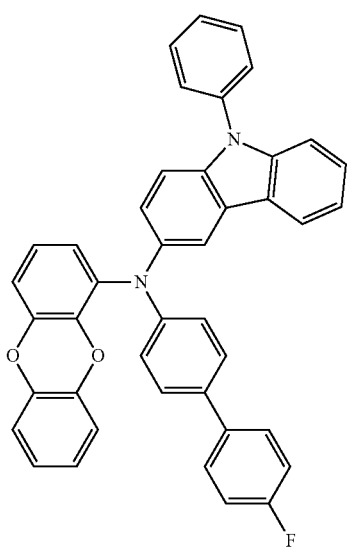
95
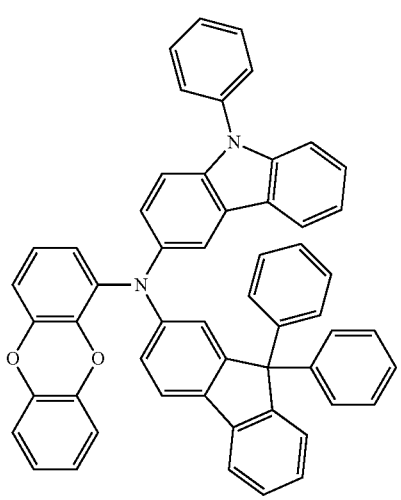
96
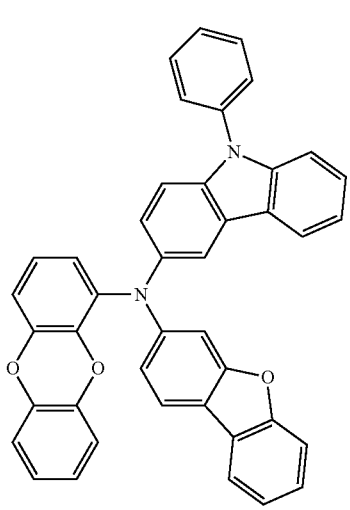
222
-continued
98
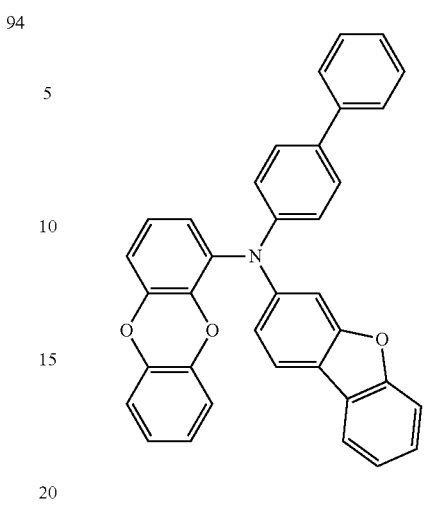
101
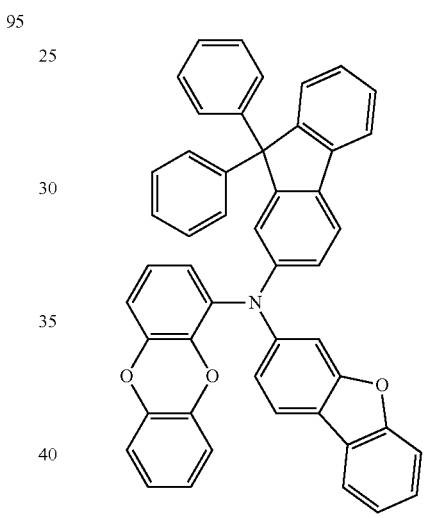
102
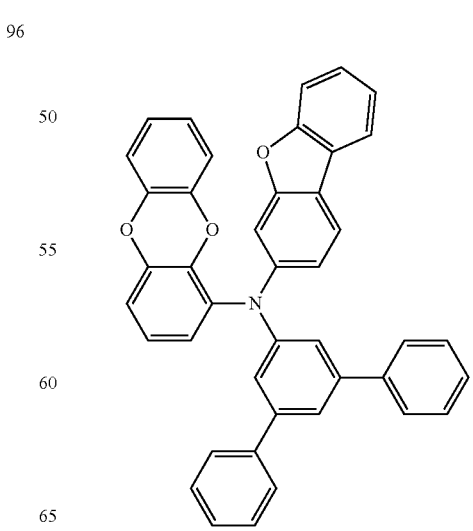

-continued
103 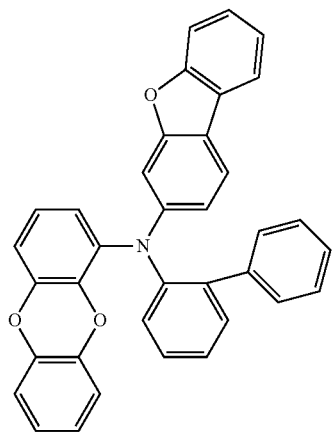
104 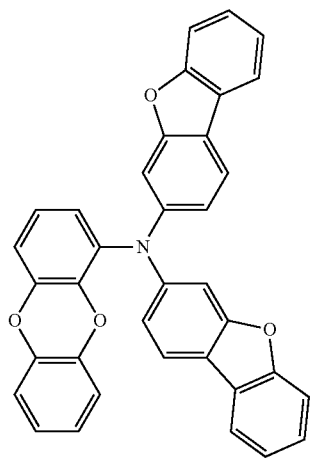
107 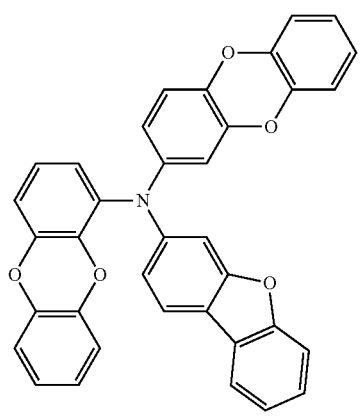
-continued
108 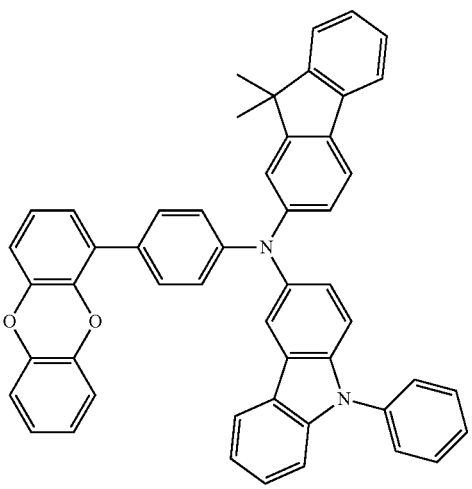
110 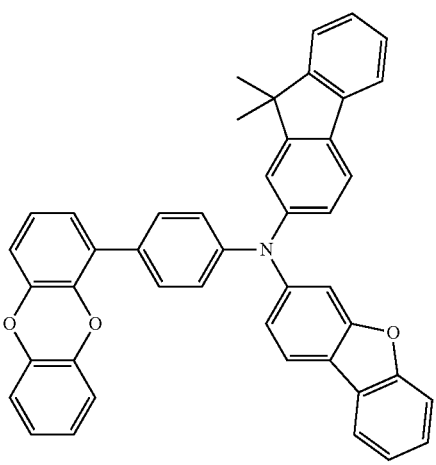
111 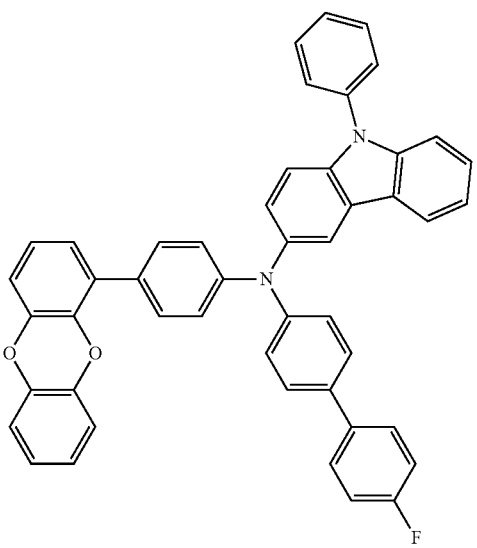

112
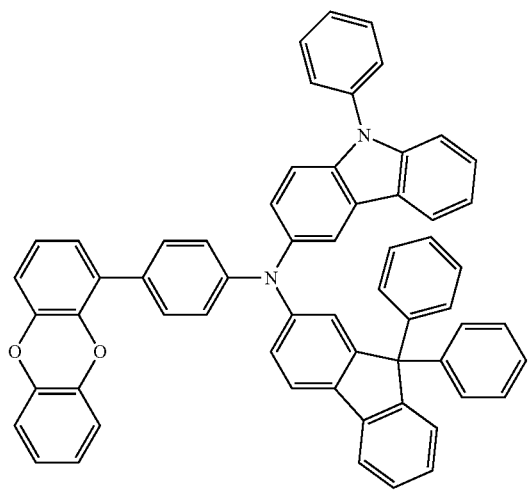
113
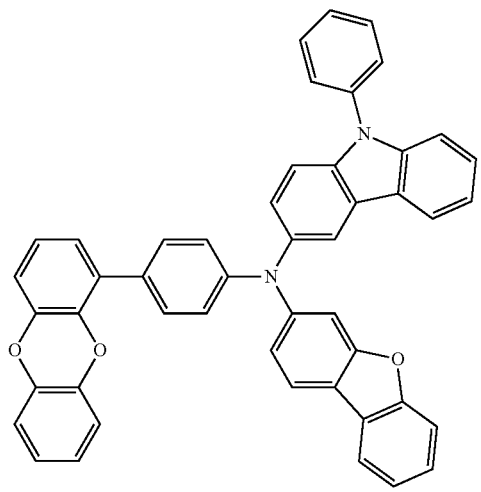
114
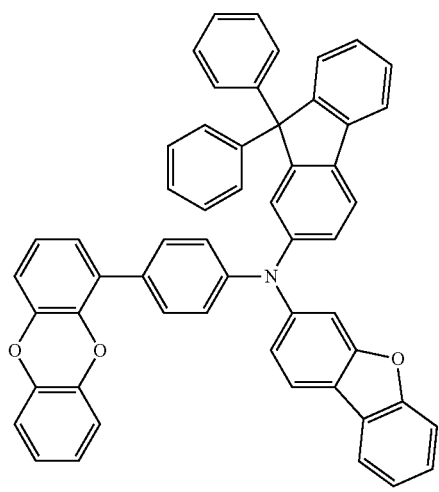
115
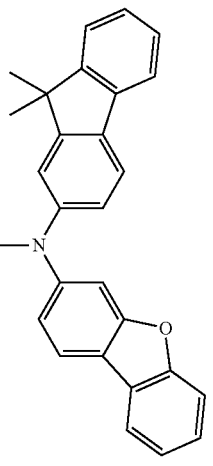
116
117
12. An organic light-emitting device comprising:
a first electrode;
a second electrode facing the first electrode; and
an organic layer between the first electrode and the second electrode,
wherein the organic layer comprises an emission layer and the condensed-cyclic compound of claim 1.

13. The organic light-emitting device of claim 12, wherein:
the first electrode is an anode,
the second electrode is a cathode, and
the organic layer comprises i) a hole transport region that is between the first electrode and the emission layer and comprises at least one selected from a hole injection layer, a hole transport layer, a buffer layer, and an electron blocking layer, and ii) an electron transport region that is between the emission layer and the second electrode and comprises at least one selected from a hole blocking layer, an electron transport layer, and an electron injection layer.

14. The organic light-emitting device of claim 13, wherein the hole transport region comprises the condensed-cyclic compound.

15. The organic light-emitting device of claim 14, wherein the hole transport region further comprises a charge-generating material.

* * * * *